US011085055B2

United States Patent
Mallol Dominguez et al.

(10) Patent No.: US 11,085,055 B2
(45) Date of Patent: Aug. 10, 2021

(54) VIRAL VECTORS FOR THE TREATMENT OF DIABETES

(71) Applicant: UNIVERSITAT AUTONOMA DE BARCELONA, Barcelona (ES)

(72) Inventors: Cristina Mallol Dominguez, Cerdanyola del Valles (ES); Fatima Bosch Tubert, Cerdanyola del Valles (ES); Veronica Jimenez Cenzano, Cerdanyola del Valles (ES)

( * ) Notice: Subject to any disclaimer, the term of this patent is extended or adjusted under 35 U.S.C. 154(b) by 0 days.

(21) Appl. No.: 15/532,958

(22) PCT Filed: Dec. 7, 2015

(86) PCT No.: PCT/EP2015/078878
§ 371 (c)(1),
(2) Date: Jun. 2, 2017

(87) PCT Pub. No.: WO2016/087678
PCT Pub. Date: Jun. 9, 2016

(65) Prior Publication Data
US 2018/0265893 A1 Sep. 20, 2018

(30) Foreign Application Priority Data
Dec. 5, 2014 (EP) .................................. 14196536

(51) Int. Cl.
*C12N 15/86* (2006.01)
*A61P 3/10* (2006.01)
(Continued)

(52) U.S. Cl.
CPC .......... *C12N 15/86* (2013.01); *A61K 48/0058* (2013.01); *A61P 3/10* (2018.01);
(Continued)

(58) Field of Classification Search
CPC ....... A61K 48/0058; A61P 3/10; C07K 14/65; C12N 15/111; C12N 15/1136; C12N 15/86; C12N 15/864; C12N 15/8645
See application file for complete search history.

(56) References Cited

U.S. PATENT DOCUMENTS

| 2010/0216709 A1* | 8/2010 | Scheule | A61K 38/30 514/1.1 |
| 2014/0045923 A1* | 2/2014 | Anguela Martinez | A61K 48/005 514/44 R |

FOREIGN PATENT DOCUMENTS

| EP | 2394667 A1 | 12/2011 |
| EP | 2453019 A1 | 5/2012 |

(Continued)

OTHER PUBLICATIONS

Lagos-Quintana et al, Current Biology 12: 735-739, 2002.*
(Continued)

*Primary Examiner* — Kevin K Hill
(74) *Attorney, Agent, or Firm* — Sterne, Kessler, Goldstein & Fox P.L.L.C.

(57) ABSTRACT

They are provided gene constructs comprising a nucleotide sequence encoding the Insulin-like growth factor 1 (IGF-1) of a mammal; and target sequences of a microRNA of a tissue where the expression of IGF-1 is wanted to be prevented, wherein the sequences (a) and (b) are operationally linked to a promoter of ubiquitous expression. Also provided are expression vectors comprising the gene construct and pharmaceutical compositions comprising them. They are useful in the treatment and/or prevention of diabetes mellitus in mammals, wherein a dysfunction and/or a loss of the beta-cells of the islets of Langerhans is present.

1 Claim, 23 Drawing Sheets
Specification includes a Sequence Listing.

(51) Int. Cl.
    C07K 14/65    (2006.01)
    A61K 48/00    (2006.01)
    C12N 15/11    (2006.01)
    C12N 15/864   (2006.01)
    C12N 15/113   (2010.01)
(52) U.S. Cl.
    CPC ............ *C07K 14/65* (2013.01); *C12N 15/111* (2013.01); *C12N 15/1136* (2013.01); *C12N 15/864* (2013.01); *C12N 15/8645* (2013.01); *C12N 2310/141* (2013.01); *C12N 2320/30* (2013.01); *C12N 2320/32* (2013.01); *C12N 2330/51* (2013.01); *C12N 2750/14143* (2013.01); *C12N 2750/14145* (2013.01)

(56) References Cited

FOREIGN PATENT DOCUMENTS

| | | | |
|---|---|---|---|
| EP | 2492347 A1 | 8/2012 | |
| EP | 3101125 A1 | 12/2016 | |
| WO | 2007-000668 A2 | 1/2007 | |
| WO | 2008-071959 A1 | 6/2008 | |
| WO | WO 08/071959 | * | 6/2008 |
| WO | WO 11/004051 | * | 1/2011 |
| WO | WO2011/154520 A1 | 12/2011 | |
| WO | 2014-012025 A2 | 1/2014 | |
| WO | WO 14/012025 | * | 1/2014 |
| WO | 2014-020149 A1 | 2/2014 | |
| WO | WO2015173308 A1 | 11/2015 | |
| WO | WO2016193431 A1 | 12/2016 | |
| WO | WO2018/060097 A1 | 4/2018 | |

OTHER PUBLICATIONS

Collaco et al, BMC Physiol. 3(8): epub Aug. 19, 2003, abstract only.*
Kim et al (GenBank NP_001104746.1; Dec. 2007).*
Kelly et al, Mol. Therapy 17(3): 409-416, 2009.*
Xie et al, Mol. Therapy 19(3): 526-535, 2011.*
GenBank AC139754, Mar. 2005, first two pages only.*
NCBI NM_00I111276, version 1 of 18 May 2014.*
Vinod et al, Am. J. Physiol. Endocrinol. Metabl. 311: E175-E185, May 24, 2016.*
Wang et al, Diabetes 55: 875-884, 2006.*
Anguela et al, Diabetes 62(2): 551-560, 2013; available Feb. 2013.*
Jimenez et al, Diabetologia 54: 1075-1086, 2011.*
Bostick et al, Gene Therapy 14: 1605-1609, 2007.*
Borel, F., et al., "Recombinant AAV as a Platform for Translating the Therapeutic Potential of RNA Interference," Molecular Therapy, vol. 22, No. 4, pp. 692-701 (Apr. 2014).
George, M., et al., "β Cell Expression of IGF-I Leads to Recovery from Type 1 Diabetes," The Journal of Clinical Investigation, vol. 109, No. 9, pp. 1153-1163 (May 1, 2002).
Jimenez, V., et al., "In vivo Genetic Engineering of Murine Pancreatic Beta Cells Mediated by Single-Stranded Adeno-Associated Viral Vectors of Serotypes 6, 8 and 9," Diabetologia, vol. 54, pp. 1075-1086 (Feb. 11, 2011).
Kim, Joseph., et al., "Combined Expression of miR-122a, miR-1, and miR-200b Can Differentiate Degraded RNA Samples from Liver, Pancreas, and Stomach," Pathology International, vol. 61, pp. 67-72 (Feb. 2011).
Xie, Jun., et al., "MicroRNA-Regulated, Systemically Delivered rAAV9: A Step Closer to CNS-restricted Transgene Expression," Molecular Therapy, vol. 19, No. 3, pp. 526-535 (Mar. 2011).
International Search Report of PCT/EP2015/078878 dated Mar. 15, 2016.
Agudo, J., et al.. "IGF-I mediates regeneration of 5 endocrine pancreas by increasing beta cell replication through cell cycle protein modulation in mice." Diabetologia 51: 1862-1872, Springer Science, Germany (2008).

Alexopoulou, A.N., "The CMV early enhancer/chicken beta actin (CAG) promoter can be used to drive transgene expression during the differentiation of murine embryonic stem cells into vascular progenitors." BMC Cell Biol. 9.1: 2, Springer Publishing, United States (2008).
Altschul, S.F., et al. "Gapped BLAST and PSI-BLAST: a new generation of protein database search programs." Nucleic Acids Res. 25: 3389-3402, Oxford University Press, England (1997).
American Diabetes Association. Diagnosis and Classification of Diabetes 15 Mellitus, Diabetes Care, vol. 33, Suppl. S62-69. (2010).
American Diabetes Association. Diagnosis and classification of diabetes mellitus. Diabetes Care 37 Suppl, S81-S90. (2014).
Anguela, X.M., et al. "Nonviral-mediated hepatic expression ofiGF-I increases Treg levels and suppresses autoimmune diabetes in mice." Diabetes 62: 551-560, American Diabetes Association, United States (2013).
Ayuso, E., et al. "Production, purification and characterization of adeno-associated vectors." Curr. Gene Ther. 10: 423-436, Bentham Science Publishers, United Arab Emirates (2010).
Bartel, D.P. MicroRNAs: genomics, biogenesis, mechanism, and function. Cell 116(2):281-297, Elsevier, Netherlands (2004).
Bergerot, I., et al., "Insulin-like growth factor-1 (IGF-1) protects NOD mice from insulitis and diabetes." Clin. Exp. Immunol. 102: 335-340, British Society for Immunology, England (1995).
Bergerot, I., et al., "Effects of insulin like grmvth factor-1 and insulin on effector T cells generating autoimmune diabetes." Diabetes Metab. 22: 235-239, Elsevier, Netherlands (1996); (Abstract only).
Birnboim, H. C., et al., "A rapid alkaline extraction procedure for screening recombinant plasmid DNA." Nucleic Acids Res. 7: 1513-1523, Oxford University Press, England (1979).
Brown, B.D., et al., "Exploiting and antagonizing microRNA regulation for therapeutic and experimental applications." Nat. Rev. Genet. 10: 578-585, Nature Research, England (2009).
Carter, P.J., et al., "Adeno-associated viral vectors as gene delivery vehicles." Int. J. Mol. Med. 6: 17-27, Springer Science+Business Media, Germany (2000).
Casellas, A., et al., "Expression of IGF-I in pancreatic islets prevents lymphocytic infiltration and protects mice from type 1 diabetes." Diabetes 55: 3246-3255, American Diabetes Association, United States (2006).
Cheetham, T.D., et al., "The effects of repeated daily recombinant human insulin-like growth factor I administration in adolescents with type 1 diabetes." Diabet. Med. 12: 885-892, John Wiley & Sons, United States (1995).
Chen, S., et al., "Efficient gene delivery to pancreatic islets with ultrasonic microbubble destruction technology." Proceedings of the National Academy of Sciences of the United States of America, 103(22): 8469-74, United States National Academy of Sciences (2006).
Ebert, M.S., et al., "MicroRNA sponges: competitive inhibitors of small RNAs in mammalian cells." Nat. Methods 4: 721-726, Nature Publishing Germany (2007).
Esau, C., et al. "miR-122 regulation of lipid metabolism revealed by in vivo antisense targeting." Cell Metab. 3: 87-98, Cell Press, United States (2006).
Gao, G., et al., "Clades of Adena-associated viruses are widely disseminated in human tissues." J. Virol. 78: 6381-6388, American Society for Microbiology, United States (2004).
Geisler, A., et al., "microRNA122-regulated transgene expression increases specificity of cardiac gene transfer upon intravenous delivery of AA V9 vectors." Gene Therapy 18(2): 199-209, Nature Publishing, Germany (2011).
Hendrick, L.M., et al., "Utilization Of resource leveling to optimize ERCP efficiency." Ir. J. Med. Sci. 180: 143-148, Springer Science+Business Media, Ireland (2011).
Hill, D.J., and Hogg, J. "Expression of insulin-like growth factors (IGFs) and their binding proteins (IGF BPs) during pancreatic development in rat, and modulation of iGF actions on rat islet DNA synthesis by IGF BPs." Adv. Exp. Med. Biol. 321: 113-122, Springer Publishing, United States (1992).

(56) References Cited

OTHER PUBLICATIONS

Jabri, N., et al., "Adverse effects of recombinant human insulin-like growth factor I in obese insulin-resistant type II diabetic patients." Diabetes 43: 369-374, American Diabetes Association (1994)

Jimenez, V., et al., "In vivo adeno-associated viral vectormediated genetic engineering of white and brown adipose tissue in adult mice." Diabetes 62: 4012-4022, American Diabetes Association (2013).

Kaino, Y., et al., Insulin-like growth factor I (IGF-I) delays the onset of diabetes in non-obese diabetic (NOD) mice. Diabetes Res. Clin. Pract. 34: 7-11, Elsevier, Netherlands (1996).

Kang, W. J., et al., Dual optical biosensors for imaging microRNA-1 during myogenesis. Biomaterials 33(27): 6430-7, Elsevier, Netherlands (2012).

Kulkarni, R.N., et al., "Beta-cell-specific deletion of the Igf1 receptor leads to hyperinsulinemia and glucose intolerance but does not alter beta-cell mass." Nat. Genet. 31: 111-115, Nature Publishing, England (2002).

Liu, F., et al., "Hydrodynamics-based transfection in animals by systemic administration of plasmid DNA." Gene Ther. 6: 1258-1266, Nature Publishing, England. (1999).

Livak, K.J., et al., "Analysis of relative gene expression data using real-time quantitative PCR and the 2(-Delta Delta C(T)) method." Methods 25: 402-408, Elsevier, Netherlands (2001).

Lock, M., et al., "Characterization of a recombinant adeno-associated virus type 2 Reference Standard Material." Hum. Gene Ther. 21: 1273-1285, Mary Ann Liebert, United States (2010).

Loiler, S.A., et al. "Localized gene expression following administration of adeno-associated viral vectors via pancreatic ducts." Mol. Ther. 12: 519-527, Cell Press, United States (2005).

Lu, Y., et al., Pancreatic-specific inactivation of IGF-1 gene causes enlarged pancreatic islets and significant resistance to diabetes. Diabetes 53: 3131-3141, American Diabetes Association, United States (2004).

Mingozzi F, High KA. "Therapeutic in vivo gene transfer for genetic disease using AAV: progress and challenges." Nat Rev Genet. 12(5):341-55. Nature Publishing, Germany (2011).

Rehman, K. K., et al. "Efficient gene delivery to human and rodent islets with doublestranded (ds) AAV-based vectors." Gene Therapy 12(17): 1313-23, Nature, England (2005).

Savage, M.O., et al., "Therapeutic applications of the insulin-like growth factors." Growth Horm. IGF Res. 14: 301-308. Elsevier, Netherlands (2004).

Sherry, N., et al. Teplizumab for treatment of type 1 diabetes (Protege study): 1-year results from a randomised, placebo-controlled trial. Lancet 378: 487-497, Elsevier, Netherlands (2011).

Smith, T.J. "Insulin-like growth factor-I regulation of immune function: a potential therapeutic target in autoimmune diseases?" Pharmacol. Rev. 62: 199-236, American Society for Pharmacology and Experimental Therapeutics, United States (2010).

Tsai, W.-C., et al. "MicroRNA-122 plays a critical role in liver homeostasis and hepatocarcinogenesis." J. Clin. Invest. 122: 2884-2897. American Society for Clinical Investigation, United States (2012).

Pescovitz, M.D., et al. "B-lymphocyte depletion with rituximab and f)-cell function: two-year results." Diabetes Care 37: 453-459. (Feb. 2014).

\* cited by examiner

AAV8-CAG-IGF1-dmiRT

AAV8-CAG-IGF1

AAV8-CAG-NULL

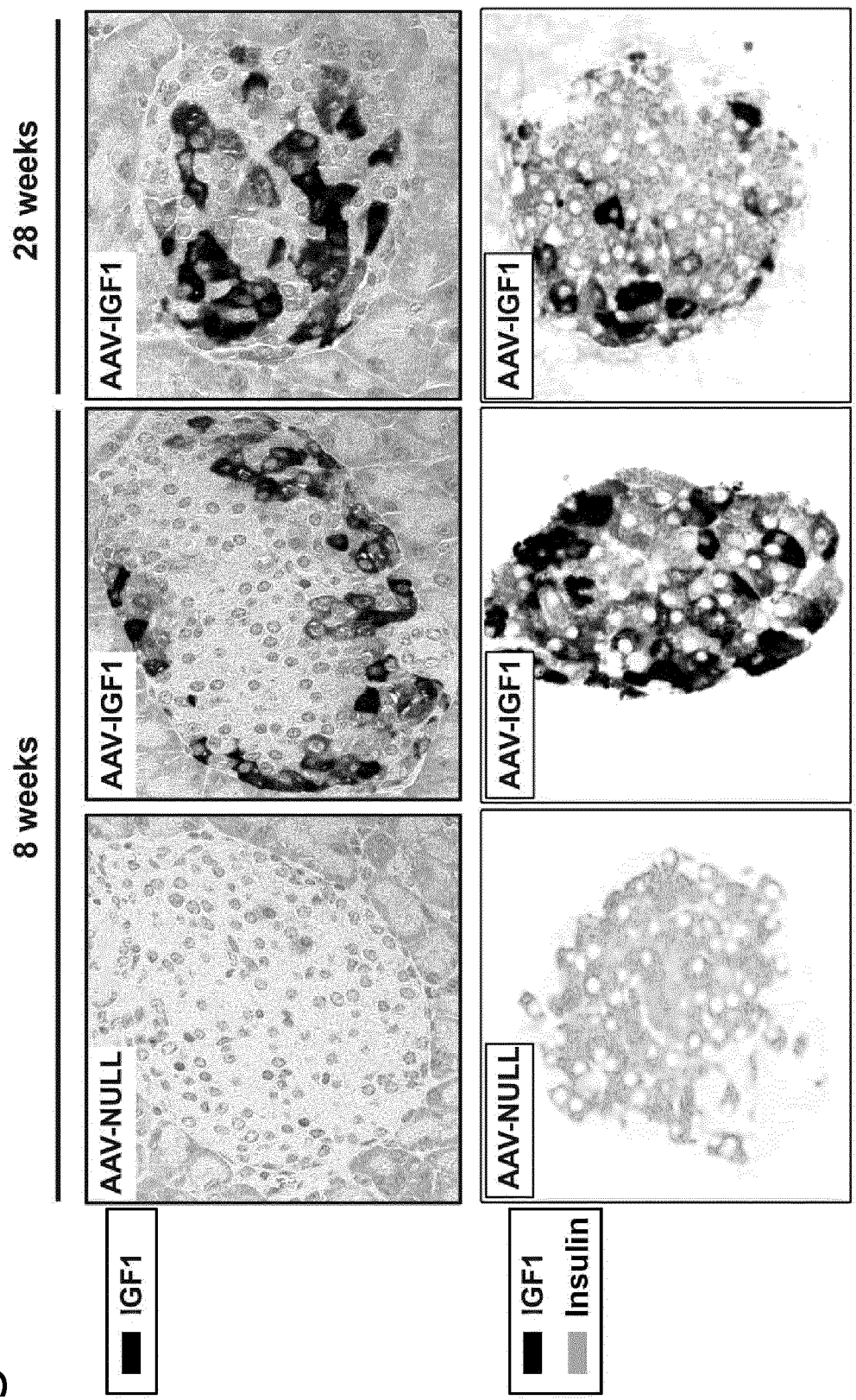

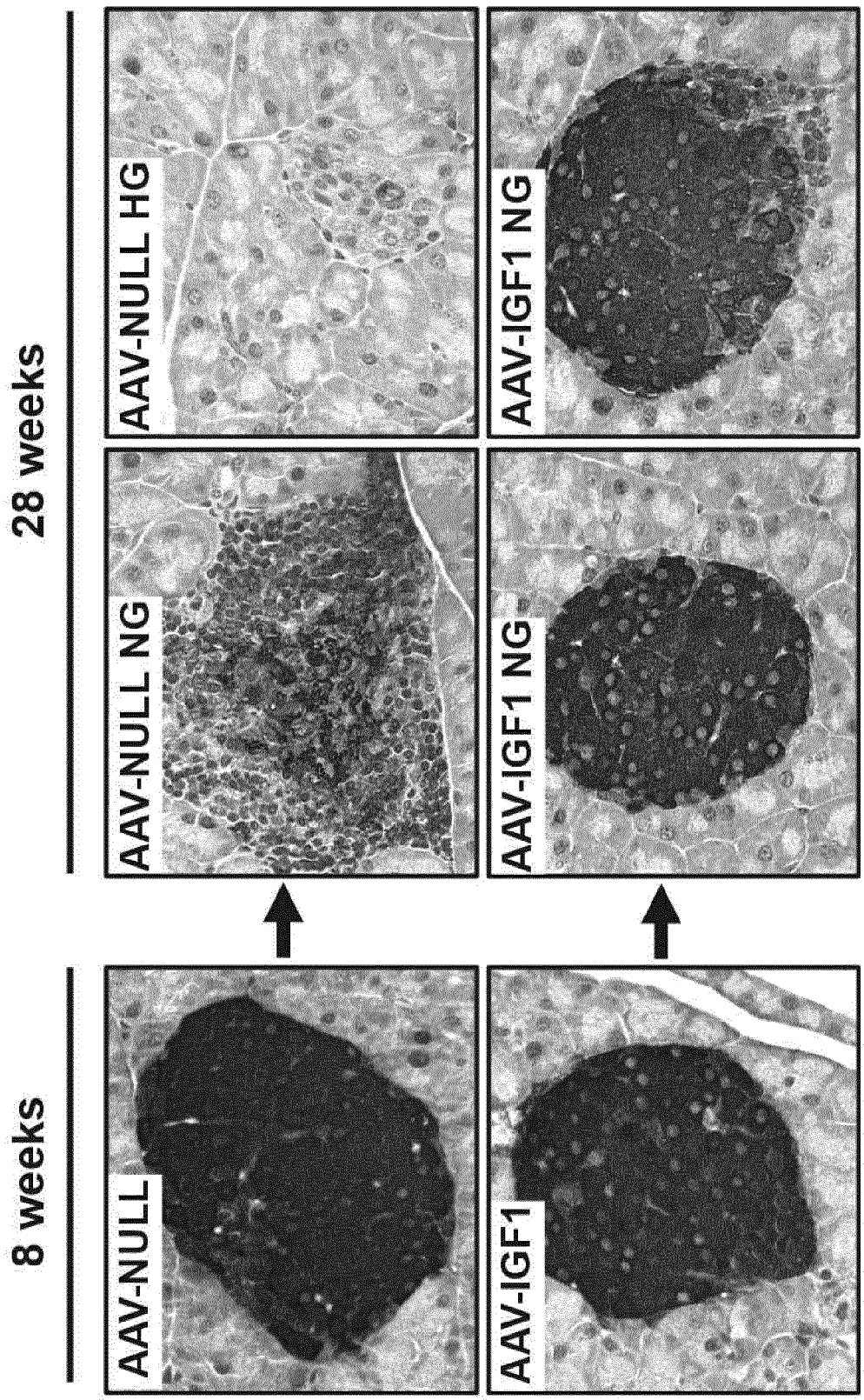

VIRAL VECTORS FOR THE TREATMENT OF DIABETES

CROSS REFERENCE TO RELATED APPLICATIONS

The present application is the 35 U.S.C. 371 National Stage of International Application Number PCT/EP2015/078878, filed Dec. 7, 2015, which claims priority from European patent application 14196536.8, filed Dec. 5, 2014, the contents of which are incorporated herein by reference.

Sequence Listing Submission Via EFS-Web

A computer readable text file, entitled "031902-5026-US-Sequence-Listing.txt", created on or about Jun. 2, 2017, with a file size of about 161 KB contains the sequence listing for this application and is hereby incorporated by reference in its entirety.

FIELD OF THE INVENTION

The present invention relates to the fields of medicine and gene therapy and, particularly, to gene constructs and expression vectors for the treatment and/or prevention of diabetes mellitus in mammals.

BACKGROUND ART

Diabetes

Diabetes comprises a group of metabolic diseases characterized by the presence of hyperglycemia as a result of defects in insulin secretion, in insulin action, or both. The chronic hyperglycemia of diabetes is associated with long-term damage, such as dysfunction and failure of various organs and especially the eyes, kidneys, nerves, heart and blood vessels. Currently it is estimated to exist in the world more than 380 million of people with diabetes and it is expected that this number will be increased to over 590 million by 2035 (International Diabetes Federation). Most cases of diabetes fall into two broad categories: type 1 and type 2 diabetes. Type 1 diabetes is caused by autoimmune destruction of pancreatic β cells. In contrast, type 2 diabetes is caused by insulin resistance in peripheral tissues (mainly muscle, liver and adipose tissue) and by an inadequate secretion of the hormone insulin. Defects in insulin secretion observed in type 2 diabetes are probably caused by the combination of both cellular dysfunction and reduction in β-cell mass. Thus, in both type 1 diabetes and type 2 diabetes, ultimately, there is an insufficient functional β-cell mass (American Diabetes Association, 2014).

Type 1 Diabetes

Type 1 diabetes (T1D) represents 5-10% of diabetic patients and generally develops in childhood or adolescence individuals. T1D results from the autoimmune destruction of pancreatic β-cells, which leads to insulin deficiency and hyperglycemia. The spontaneous onset of T1D in humans is preceded by a progressive leukocytic infiltration into the islets (insulitis), which persists for a relatively long period of time before the massive destruction of cells. This disease becomes clinically apparent after a preclinical period of variable duration during which the autoimmune destruction reduces the β-cells mass in pancreatic islet so that glucose levels in blood cannot be maintained at physiological range. The lack of insulin leads to hyperglycemia and ketoacidosis, which can end up causing a coma and sometimes the death of the patient. T1D patients are diagnosed after loosing almost the entire mass of β-cells, and require replacement therapy with insulin to survive. Therefore, interventions aimed to stop the immune attack on the islets and to promote β-cell survival are of great interest for the treatment of diabetes.

Current Treatments for Type 1 Diabetes

Current treatments for T1D are based on insulin replacement therapies, which are required throughout the life of the patient to reduce blood glucose levels. However, these treatments do not prevent the development of secondary complications arising from long-term chronic hyperglycemia, which are the main cause of death of patients with T1D. In addition, patients are exposed to episodes of hypoglycemia, with risk of death, because this therapy does not allow reaching the sophisticated level of physiological regulation. Pancreas or islet transplant also offers a therapeutic option for T1D since they provide a source of physiologically regulated endogenous insulin. However, the eventual failure of most transplanted islets after recurrent autoimmune destruction, the shortage of donors, the immune rejection and the need of immunosuppression make these alternatives very limited.

On the other hand, therapies exist based on immunomodulators, which would delay the onset of T1D and/or would protect the residual β-cells from the autoimmune attack thus maintaining endogenous insulin production. The first of these treatments showed limited efficacy but new approaches are being developed For example, there are anti-CD3 antibodies which reduce the number of circulating T lymphocytes in the patient.

However, Phase III clinical trials with these monoclonal antibodies did not get the expected initial objectives (Sherry et al., 2011). Another antibody, anti-CD20, against B lymphocytes, is being tested on diabetics patients. After a year of treatment with anti-CD20 patients had improved function of β cells and needed lower insulin doses compared to controls during the first six months, but afterwards, the treated group had finally lost the µ cell mass (Pescovitz et al., 2014).

Another area under development is the study of embryonic stem cells (ESC) and induced pluripotent cells (iPS), which through different strategies can be differentiated or reprogrammed to cells producing insulin and in the future could become a potential cellular therapy for T1D. It has been possible to reprogram adult fibroblasts from diabetic patients to insulin-producing cells by inserting only three transcription factors: octamer-binding transcription factor 4 (Oct-4), SRY (Sex Determining Region Y)-box 2 (Sox-2) and Kruppel-like factor 4 (KLF-4). There are many groups that are moving towards differentiating ESC and iPS cells to PDX-1+ capable of producing insulin or secreting peptide C. However, the biggest challenge in reprogramming is to get a fully differentiated state of β alike cells so that they can produce insulin in a finely regulated way and, even so, the reprogrammed cells would not be protected from autoimmune destruction. In addition, studies are still needed to assess the risks of autoimmune destruction of transplanted iPS- or ESC-derived cells and the tumorigenic potential of such cells.

Therefore there is a need to develop new therapeutic strategies to counteract type 1 diabetes.

Gene therapy offers a new treatment tool with great potential. For example it can counteract the autoimmune attack against β cells and/or to regenerate β cell mass. Among possible candidate genes for the treatment of diabetes, insulin-like growth factor 1 (IGF-1) is known for its immunomodulatory properties (Smith, 2010) and its control over the proliferation and survival of β-cells (Hill and Hogg, 1992).

Insulin-Like Growth Factor 1 (IGF-1)

IGF-1 is a major mediator of both pre-natal and post-natal growth and has shown an important role in the development of the pancreas as it stimulates the proliferation and differentiation of β-cells. Additional, IGF-1 is considered to be one of the main interplayers of the endocrine and immune system crosstalk.

Approaches with Recombinant Protein Igf-1

Since IGF-1 and insulin share the same cell signaling pathway, factor IGF-1 has been used to try to treat diabetes showing benefits (Cheetham et al., 1995; Savage et al., 2004). The intravenous administration of recombinant protein IGF-1 in patients with marked insulin resistance produces similar effects to insulin, improving glycemic control and other metabolic parameters. However, the increase in circulating levels of IGF-1 involves the development of undesired side effects (Jabri et al., 1994).

Moreover, it was observed that daily subcutaneous administration of IGF-1 recombinant protein in pre-diabetic NOD mice reduced the severity of insulitis in the islets and the incidence of T1D (Bergerot et al., 1995; Kaino et al., 1996). Furthermore, the administration of IGF-1 alone or in complex with IGFBP-3 protected islets of insulitis and delayed the onset of T1D in NOD mouse. Similarly, the transfer of autoreactive T cells to NOD mice treated with IGF-1 reduced the incidence of diabetes due to a reduction in insulitis and to alterations in the activation of T cells of the immune system (Bergerot et al., 1996). Finally, it was observed that the plasmid-derived IGF-1 expression in the non-parenchymal liver cells was able to preserve β-cell mass and prevent the development of autoimmune diabetes in transgenic mice for IFN-β treated with Streptozotocin. This prevention was also due to an increase in regulatory T cells in the pancreas of these mice (Anguela et al., 2013).

Transgenic Animals Expressing IGF-1

It has been reported that local overexpression of IGF-1 in the β-cell is able to prevent infiltration of the islet and β-cell death in transgenic mouse RIP-1/IFN-β, a model of lymphocyte infiltration of the islets with increased susceptibility to the development of diabetes (Casellas et al., 2006). In addition, the transgenic expression of IGF-1 into β-cells of diabetic mice induced by treatment with multiple doses of Streptozotocin (STZ, 5×50 mg/kg) was able to regenerate the endocrine pancreas (Agudo et al., 2008; George et al., 2002). However, these models are far from becoming feasible therapies for the treatment of diabetes and do not demonstrate whether the local expression of IGF-1 in pancreatic β-cells is also able to prevent or counteract T1D in a model of spontaneous onset of the disease.

Although existing treatments for both type 1 and type 2 diabetes have significantly improved the quality of life of patients, these therapies have certain drawbacks and are not able to cure the disease. Because T1D patients require insulin therapy throughout their lives and have a high risk of secondary complications, new preventive and curative therapies are needed.

"Adeno-associated viral (AAV) vectors have emerged as very safe and effective delivery vehicles to mediate long-term transgene expression of therapeutic genes in a wide range of tissues in vivo both in adult animal models and in humans (Mingozzi & High 2011). Promising results have been obtained using AAV vectors administered directly into the pancreatic duct to achieve widespread pancreas transduction in mice (Jimenez et al 2011). Additionally, recent progress has shown that endogen microRNA target sequences (miRTs) can be included in the AAV expression cassette to efficiently control transgene expression (Brown & Naldini, 2009) which opens the door to new approaches of sophisticated regulation of vector tropism."

SUMMARY OF THE INVENTION

One problem to be solved by the present invention may be seen as related to the provision of a therapeutical approach for the treatment and/or prevention of diabetes in mammals, preferably diabetes mellitus in mammals. The solution is based on the provision of a gene construct encoding Insulin-like growth factor 1 (IGF-1) and expression vectors for being used in gene therapy.

The inventors have developed a gene therapy strategy directed to pancreas to counteract diabetes in the NOD mouse, which has many similarities with human T1D as will be seen below. An AAV8 vector expressing IGF-1 under the control of the ubiquitous CAG promoter was generated. In order to restrict the expression of IGF-1 in pancreas, the target sequences of microRNA-122A (expressed mainly in the liver, see FIG. 4) and microRNA-1 (expressed mainly in the heart, see FIG. 5) were linked to the construct at the 3'-UTR region. The construct contained four copies of the target sequence of miRNA-122A and four copies of the target sequence of miRNA-1 in the 3'-UTR region (AAV8-CAG-IGF1-dmiRT), in both cases fully complementary to miRNA-122A or miRNA-1.

It has been observed that intraductal administration of this vector was able to prevent the onset of hyperglycemia in NOD mouse. Thus, most of the animals administered with the vector encoding IGF-1 remained normoglycemic throughout the 28 weeks of follow-up and the incidence of diabetes was significantly reduced. Therefore, gene transfer of IGF-1 in the pancreas using AAV vectors represents a new gene therapy approach for diabetes, and particularly type 1 diabetes. The intraductal administration of vectors AAV8-CAG-IGF1-dmiRT precluded liver and heart IGF-1 overexpression as shown by similar IGF-1 expression levels to those observed in the control group in contrast to animals administered with vector without the target sequences of microRNAs (AAV8-CAG-IGF1). In the context of the invention the "precluding effect" of the vector or gene construct could be replaced by reduction of IGF-1 expression as later defined herein. However, the expression in the pancreas was not altered by the presence of these sequences. The levels of expression of microRNAs were maintained regardless of the diabetic stage of animals indicating that the precluding effect of the AAV construct in the liver or heart NOD animals was not lost even during the diabetic process. In the case of the liver, the precluding effect was even more sustained due to increased levels of expression of microRNA-122A in hyperglycemic NOD individuals.

The main advantages achieved by the gene construct and vector of the invention are:

1) The intraductal administration of the vector to NOD mice resulted in an efficient transduction of exocrine and endocrine pancreas. Pancreatic islets were transduced mainly in the periphery but also core cells were genetically engineered. The transduction of β cells on the periphery of the islets is important to combat the autoimmune destruction in T1D, because the autoimmune attack by infiltrating lymphocytes actively takes place in the periphery of the islets. Moreover, the administration (preferably pancreatic administration) of AAV8 vectors with an ubiquitous expression promoter makes possible the expression of IGF-1 in beta-cells of the islets as well as maximizing the number of acinar cells providing IGF-1 to not transduced beta-cells. Thus, in front of an autoimmune attack and of the selective destruction of a percentage of the beta-cells in the NOD islets, the exocrine pancreas would continue providing the therapeutic IGF-1 to the remaining cells.

2) NOD mice showed high levels of expression of microRNA-122A in liver and of microRNA-1 in heart, regardless of the diabetic stage. Furthermore, the expression of these microRNAs was not detectable in the pancreas of NOD mice. Remarkably, it is believed that this is the first time that the target sequences of the miRNAs 122a and 1 are used with success in NOD mice. In an embodiment, these target sequences are used to decrease, reduce or even preclude transgene expression in liver and/or heart.

3) Overexpression (preferably pancreatic overexpression) of IGF-1 mediated by the pancreas intraductal administration of the AAV8-CAG-IGF-1-dmiRT vectors, protected NOD mice of developing spontaneous diabetes and reduced the incidence of diabetes. NOD mice were also protected against lymphocytic infiltration of the islets and preserved beta-cell mass over time.

Moreover, the long-term and effective expression provided by a single administration of the vectors of the invention represents a significant advantage over other therapies. For example, due to the short half-life of IGF-1 in circulation, treatment with recombinant protein IGF-1 requires a constant and repeated administration and, moreover, its effects have a limited duration once treatment is interrupted. Furthermore, the intraductal administration can potentially be applied to larger animals and humans, through a non-surgical and less invasive clinical process called endoscopic retrograde cholangiopancreatography (ERCP) (Hendrick et al, 2011).

Thus, a first aspect of the invention is related to a gene or expression construct comprising:
(a) a nucleotide sequence encoding the Insulin-like growth factor 1 (IGF-1) of a mammal; and (b) at least one target sequence of a microRNA of a tissue where the expression of IGF-1 is wanted to be prevented; wherein the sequences (a) and (b) are operationally linked to a promoter of ubiquitous expression.

A second aspect of the invention is an expression vector comprising the gene or expression construct as defined above.

A third aspect of the invention is the vector and/or the gene construct as defined previously, for use as a medicament.

A fourth aspect of the invention is the vector and/or the gene construct as defined previously, for use in treatment and/or prevention of diabetes mellitus in mammals, wherein a dysfunction and/or a loss of the beta-cells of the islets of Langerhans is present.

Finally, a fifth aspect of the invention relates to a pharmaceutical composition comprising a therapeutically effective amount of a gene construct and/or of a vector as defined previously, together with one or more pharmaceutically acceptable excipients or vehicles.

The detailed description and examples shown below are presented for the purposes of providing those skilled in the art with a sufficiently clear and complete explanation of this invention, but should not be considered limitations on the essential aspects contemplated therein, as presented in earlier sections of this description.

DETAILED DESCRIPTION OF THE INVENTION

First Aspect of the Invention: Gene Construct

The first aspect of the invention is related to a gene construct comprising: (a) a nucleotide sequence encoding the Insulin-like growth factor 1 (IGF-1) of a mammal; and (b) at least one target sequence of a microRNA of a tissue where the expression of IGF-1 is wanted to be prevented; wherein the sequences (a) and (b) are operationally linked to a promoter of ubiquitous expression.

A gene construct according to the invention can also be called "expression cassette" or "expression construct" and refers to a gene or a group of genes, including the gene that encodes a protein of interest, which is operatively linked to a promoter that controls its expression. Being "operationally linked" should be understood, as the sequence of the gene is placed after the promoter sequence or relatively close in the event that restriction fragments or elements that provide stability to the construction are included. The construction can also comprise small gene fragments with useful sequences in order to adapt it to the desired expression systems, which the skilled in art will know. The general part of this application entitled "general definitions" comprises more detail as to said "gene construct".

The gene construct of the invention allows to express preferably, when it is placed in a suitable vector, IGF-1 of a mammal in a tissue of interest, preventing its expression in other tissues where the expression is wanted to be prevented. For this reason, the construct comprises target sequences of microRNAs that are specific to those tissues where the expression is not of interest. In a preferred embodiment, these microRNAs are expressed in those tissues where IGF-1 over expression is not of interest. IGF-1 expression may not be of interest for example when non-desired side-effects are expected. For example liver-overexpression may mediate increased circulating levels of IGF-1 which may lead to non-desired side effects (Jabri et al 1994).

As will be seen below, in the present invention, the expression (preferably the over-expression) of IGF-1 in mammals in heart and/or liver tissues, (preferably liver) should be prevented. The skilled person will understand that endogenous expression of IGF-1 may still occur. The present invention prevents expression (preferably over-expression) of IGF-1 in heart and/or liver tissues resulting from the gene construct or expression vector of the invention. In other words, the present invention prevents expression, preferably over-expression of IGF-1 in heart and/or liver tissues. They are tissues that are also transduced when an intraductal injection is performed to the biliar duct in order to achieve specific expression in the pancreas (Jimenez et al 2011). For this reason, in a particular embodiment, the target sequence of a microRNA of the gene construct is selected from those target sequences that bind to microRNAs expressed in heart and/or liver of the mammal.

The IGF-1 molecule is preferably expressed even more preferably over-expressed in the pancreatic tissue, more preferably solely in the pancreatic tissue and/or preferably the expression, (even more preferably the over-expression) of the IGF-1 molecule is to be prevented in non-pancreatic tissue.

In this context, the wording "non-pancreatic tissue" is preferably the liver or the heart. In this context, the wording "non-pancreatic tissue" is more preferably the liver or the heart when the vector is administered via intraductal injection.

In this context, "prevented" could be replaced by decreased or inhibited or precluded. The IGF-1 expression preferably over-expression is said to have been prevented in a non-pancreatic tissue/cell (i.e. preferably the liver and/or the heart when the vector is administered via intraductal injection) when the IGF-1 expression, preferably over-expression level in a given non-pancreatic tissue/cell is at least 30%, 40%, 50%, 60%, 70%, 80%, 90%, 95%, 99% lower (or more preferably not detectable) than the expression preferably over-expression level of IGF-1 in the same non-pancreatic tissue/cell when a corresponding control vector without the target sequence of a microRNA is being administered. The skilled person may assess the expression level in a cell derived from said tissue. IGF-1 expression may be assessed at the transcript level via PCR or at the protein level via Western blotting. The skilled person knows which cells could be used. Preferred cells are derived from a subject and are hepatocytes for the liver tissue and cardiomyocytes for the heart tissue. Cell lines may also be used as Hub7 (human liver cell line) (Geisler 2011) and differentiated C2C12 (mouse myoblast) (Kang 2012).

Within the context of the invention, a target sequence that binds miRNAs that are specific to those tissues whose expression is not of interest could be replaced by a target sequence that binds miRNAs that are expressed in those tissues in which IGF-1 expression is to be prevented. The skilled person understands that such miRNA may be expressed in other tissues. For example miRNA-1 is expressed in brown adipose tissues. In an embodiment, when the vector is administered by intraductal injection, the target sequence preferably binds a miRNA that is expressed in the heart and/or the liver (preferably the liver). The skilled person is well aware of techniques allowing the identification of miRNAs specifically expressed in these tissues. Preferred miRNAs and associated target sequences are defined later herein. In the context of the invention, a target sequence of a miRNA preferably means at least one. It therefore means that one, two, three, four or at least one, at least two, at least three, at least four target sequence of a miRNA are present in said construct. The same holds for each target sequence of one miRNA as defined herein. Depending on the expression level of the miRNA used, the skilled person may have to fine tune the optimal number of target sequence to obtain a prevention of the expression, preferably over-expression of IGF-1 in the tissue concerned as earlier defined herein (i.e. IGF-1 expression preferably over-expression level in a given non-pancreatic tissue/cell is at least 30%, 40%, 50%, 60%, 70%, 80%, 90%, 95%, 99% lower (or more preferably not detectable) than the expression preferably over-expression level of IGF-1 in the same non-pancreatic tissue/cell when a corresponding control vector without the target sequence of a microRNA is being administered).

In a particular embodiment, the nucleotide sequence encoding the IGF-1 is selected from a nucleotide sequence encoding the human IGF-1 protein, which comprises an amino acid sequence selected from the group consisting of sequences SEQ ID NOs: 23 to 27; and a nucleotide sequence encoding the murine IGF-1 protein, which comprises an amino acid sequence selected from the group consisting of sequences SEQ ID NOs: 28 to 29, and 44 to 47.

SEQ ID NO: 23 corresponds to the human protein of 137 amino acids with accession number at the Protein database from NCBI NP_001104754, version 1 of 25 May 2014. It is the form known as preproIGF-1, isoform 2 (isoform of IGF-1a).

SEQ ID NO: 24 corresponds to the human protein of 195 amino acids with accession number at the Protein database from NCBI NP_001104755, version 1 of 25 May 2014. It is the form known as preproIGF-1, isoform 3 (isoform of IGF-1b). This human isoform does not have any murine counterpart.

SEQ ID NO: 25 corresponds to the human protein of 158 amino acids with accession number at the Protein database from NCBI NP_001104753, version 1 of 25 May 2014. It is the form known as preproIGF-1, isoform 1 (isoform of IGF-1c/MGF). This human isoform is the equivalent of murine IGF-1b. It is also named MGF (Mechano Growth Factor).

SEQ ID NO: 26 corresponds to the human protein of 153 amino acids with accession number at the Protein database from NCBI NP_000609, version 1 of 25 May 2014. It is the form known as preproIGF-1, isoform 4 (isoform of IGF-1c/MGF).

SEQ ID NO: 27 corresponds to the human protein of 179 amino acids with accession number at the Protein database from NCBI XP_005268892, version 1 of 3 Feb. 2014. It is the form known as IGF-1, isoform X1. No isoform type has been attributed to this sequence.

SEQ ID NO: 28 corresponds to the murine protein of 137 amino acids with accession number at the Protein database from NCBI NP_001104746, version 1 of 18 May 2014. It is the form known as preproIGF-1, isoform 5 (isoform of IGF-1a).

SEQ ID NO: 29 corresponds to the murine protein of 133 amino acids with accession number at the Protein database from NCBI AAH12409, version 1 of 15 Jul. 2006 (isoform of IGF-1b/MGF).

SEQ ID NO: 44 corresponds to the murine protein of 159 amino acids with accession number at the Protein database from NCBI NP_034642, version 2 of 18 May 2014. It is the form known as transcription variant 1 (isoform of IGF-1b/MGF).

SEQ ID NO: 45 corresponds to the murine protein of 165 amino acids with accession number at the Protein database from NCBI NP_908941, version 1 of 18 May 2014. It is the form known as transcription variant 2. No isoform type has been attributed to this sequence.

SEQ ID NO: 46 corresponds to the murine protein of 143 amino acids with accession number at the Protein database from NCBI NP_001104744, version 1 of 18 May 2014. It is the form known as transcription variant 3 (isoform of IGF-1b/MGF).

SEQ ID NO: 47 corresponds to the murine protein of 153 amino acids with accession number at the Protein database from NCBI NP_001104745, version 1 of 18 May 2014. It is the form known as transcription variant 4 (isoform of IGF-1a).

In another particular embodiment, the gene construct according to the invention comprises a nucleotide sequence encoding the IGF-1 of a mammal, which is selected from the group consisting of sequences SEQ ID NOs: 1 to 7, and 48 to 51.

SEQ ID NO: 1 corresponds to the murine nucleotide sequence with accession number at the Nucleotide database from NCBI NM_001111276, version 1 of 18 May 2014. It encodes the amino acid sequence NP_001104746 (SEQ ID NO: 28) above mentioned.

SEQ ID NO: 2 corresponds to the murine nucleotide sequence with accession number at the Nucleotide database from NCBI BC012409, version 1 of 15 Jul. 2006. It encodes the amino acid sequence AAH12409 (SEQ ID NO: 29) above mentioned.

SEQ ID NO: 48 corresponds to the murine nucleotide sequence with accession number at the Nucleotide database from NCBI NM_010512, version 4 of 18 May 2014. It encodes the amino acid sequence NP_034642 (SEQ ID NO: 44) above mentioned.

SEQ ID NO: 49 corresponds to the murine nucleotide sequence with accession number at the Nucleotide database from NCBI NM_184052.3, version 3 of 18 May 2014. It encodes the amino acid sequence NP_908941 (SEQ ID NO: 45) above mentioned.

SEQ ID NO: 50 corresponds to the murine nucleotide sequence with accession number at the Nucleotide database from NCBI NM_001111274, version 1 of 18 May 2014. It encodes the amino acid sequence NP_001104744 (SEQ ID NO: 46) above mentioned.

SEQ ID NO: 51 corresponds to the murine nucleotide sequence with accession number at the Nucleotide database from NCBI NM_001111275, version 1 of 18 May 2014. It encodes the amino acid sequence NP_001104745 (SEQ ID NO: 47) above mentioned.

SEQ ID NO: 3 corresponds to the human nucleotide sequence with accession number at the Nucleotide database from NCBI NM_001111284, version 1 of 25 May 2014. It encodes the amino acid sequence NP_001104754 (SEQ ID NO: 23) above mentioned.

SEQ ID NO: 4 corresponds to the human nucleotide sequence with accession number at the Nucleotide database from NCBI NM_001111285, version 1 of 25 May 2014. It encodes the amino acid sequence NP_001104755 (SEQ ID NO: 24) above mentioned.

SEQ ID NO: 5 corresponds to the human nucleotide sequence with accession number at the Nucleotide database from NCBI NM_001111283, version 1 of 25 May 2014. It encodes the amino acid sequence NP_001104753 (SEQ ID NO: 25) above mentioned.

SEQ ID NO: 6 corresponds to the human nucleotide sequence with accession number at the Nucleotide database from NCBI NM_000618, version 3 of 25 May 2014. It encodes the amino acid sequence NP_000609 (SEQ ID NO: 26) above mentioned. SEQ ID NO: 7 corresponds to the human nucleotide sequence with accession number at the Nucleotide database from NCBI XM_005268835, version 1 of 3 Feb. 2014. It encodes the amino acid sequence XP_005268892 (SEQ ID NO: 27) above mentioned.

The expert will understand that the invention comprises those variants of the nucleotide sequences encoding the proteins of interest and which have a percentage of identity with the sequences listed of at least 60%, at least 65%, at least 70%, at least 80%, at least 90%, at least 95%, at least 96%, at least 97%, at least 98% or at least 99% so that the proteins expressed have the same or similar activity to the IGF-1 of mammals. The same or similar activity means that at least one activity of IGF-1 is maintained to at least some extent in said variant. "At least one activity of IGF-1" means at least one anti-diabetic activity as later defined herein. "At least some extent" usually means at least 50%, 60%, 70%, 80%, 90% of the activity is maintained. The invention therefore contemplates the degeneracy of the genetic code and also includes nucleotide sequences with nucleotide variations that lead to silent or conservative mutations at protein level. Also included are amino acid mutations that do not affect the activity of the protein. The identity between two amino acid sequences is preferably determined by the algorithm Blastp, described in Altschul, S. F., et. al. 1997, and NCBI ncbi.nlm.nih.gov/BLAST. The invention encompasses variants of nucleic acids represented by nucleotide sequences encoding a protein and protein variants represented by an amino acid sequence. A more detailed explanation of the term variant is provided in the section entitled "general definition".

In another particular embodiment, optionally in combination with any of the embodiments above or below indicated, the gene construct comprises a target sequence of a microRNA, wherein the target is selected from a group consisting of sequences SEQ ID NOs: 8 to 22, 93, 94, 95 and/or combinations thereof:

This target sequence is preferably located in the 3'UTR region of the gene or expression construct. 3'UTR region could be replaced with 3'UTR end of said construct.

SEQ ID NO: 8
(5'caaacaccattgtcacactcca3'), target for the microRNA 122a (Accession Number to the miRBase database MI0000442);

SEQ ID NO: 9
(5'AGTCACGTACTGTCTTGAACC3'), target for the microRNA 152 (MI0000462);

SEQ ID NO: 10
(5'GGGTCACAAGTCTGATGGACAAG3'), target for the microRNA 199a-5p (MI0000242);

SEQ ID NO: 11
(5'TGTCATCAGACGTGTAACCAAT3'), target for the microRNA 99a-3p (MI0000101);

SEQ ID NO: 12
(5' TACTGGATACTTAACTGTCTG3'),target for the microRNA 215 (MI0000291);

SEQ ID NO: 13
(5'ggctgtcaattcataggtcag3'), target for the microRNA 192 (MI0000234);

SEQ ID NO: 14
(5'ACATTGTCGTTGAGGTACACCT3'), target for the microRNA 194 (MI0000488);

SEQ ID NO: 15
(5'ttacatacttctttacattcca3'), target for the microRNA 1 (MI0000651);

SEQ ID NO: 16
(5'AGTCACGTGATGTCTTGAAACA3'), target for the microRNA 148 (MI0000253);

SEQ ID NO: 17
(5'AAACCAGGGGAAGTTGGTCGAC3'), target for the microRNA 133a (MI0000450);

SEQ ID NO: 18
(5'ACCTTACATTCCTTCACACACC3'), target for the microRNA 206 (MI0000490);

SEQ ID NO: 19
(5'ATTCCGTGCGCCACTTACGG3'), target for the microRNA 124 (MI0000443);

SEQ ID NO: 20
(5'AGGGACTCTGGGAAATTGGACACT3'), target for the microRNA 125 (MI0000469);

SEQ ID NO: 21
(5'ATTAGAGTCGACCGTTGACACT3'), target for the microRNA 216 (MI0000292);

SEQ ID NO: 22
(5'GTCACGTTACAATTTTCCCGTA3') target for the microRNA 130 (MI0000448) (mirbase.org/, version 21 Jun. 2014).

SEQ ID NO: 93
(5' TGTCATCAGACGTGTAACCAAT3'), target for the microRNA 199a-3p (MI0000242);

-continued

SEQ ID NO: 94
(5'TATTCTGCTCGTTTTTCGAACA3'), target for the
microRNA 208 (MI0000251);
and SEQ ID NO: 95
(5' ATGTCATGACACTATTGACTT3'), target for the
microRNA 101 (MI0000103) (mirbase.org/,
version 4 Dec. 2015).

In an embodiment, the gene construct comprises at least one, at least two, at least three, or at least four copies or one or two or three or four copies of a target sequence of a microRNA which is selected from a group consisting of nucleotide sequences SEQ ID NO: 8 to 22, 93, 94, 95 and/or combinations thereof.

The skilled person will understand that a target of any new miRNA expressed in the tissues wherein the over-expression of IGF-1 needs to be prevented is also encompassed within the present invention.

In an embodiment, the gene construct does not comprise as target sequence SEQ ID NO:21.

In a preferred embodiment, the gene construct comprises at least one, at least two, at least three, or at least four copies or one or two or three or four copies of a target sequence of a microRNA which is selected from a group consisting of nucleotide sequences selected from SEQ ID NO: 8 to 20, 22, 93, 94 and 95 and/or combinations thereof.

In a preferred embodiment, the gene construct comprises at least one, at least two, at least three, or at least four copies or one or two or three or four copies of a target sequence of a microRNA which is expressed in the liver (preferably selected from SEQ ID NO: 8-14, 16, 93, 95) and at least one, at least two, at least three, or at least four copies or one or two or three or four copies of a target sequence of a microRNA which is expressed in the heart (preferably selected from SEQ ID NO:15, 17, 18 and 94).

In a more particular embodiment, the gene construct comprises a target sequence of a microRNA, which is selected from a group consisting of nucleotide sequences SEQ ID NO: 8 and SEQ ID NO: 15, which are target of microRNA 122 and miR1, respectively.

In another particular embodiment, optionally in combination with any of the embodiments above or below indicated, the gene construct comprises at least one target sequence of the microRNA 122a and at least one target sequence of the microRNA 1. In a preferred embodiment, the gene construct comprises four copies of the target sequence of the microRNA 122a and four copies of the target sequence of the microRNA 1. In another preferred embodiment, the gene construct comprises at least one, at least two, at least three, at least four or one, two, three or four copies of the target sequence of the microRNA 122a and at least one, at least two, at least three, at least four or one, two, three or four copies of the target sequence of the microRNA 1.

As for the IGF-1 molecule and coding sequence, the invention is not limited to the specific target sequence of a miRNA as identified herein. The skilled person may identify variants of said target sequence that is still able to bind said miRNA to some extent. In this context, "some extent" means that the target sequence preferably retains at least 50%, 60%, 70%, 80%, 90%, 99% of the binding of the initial target sequence as assessed using an EMSA (Electrophoretic Mobility Shift Assay) and/or is still able to reduce, decrease, prevent or preclude the IGF-1 expression, preferably over-expression in the context of the gene construct or expression vector of the invention to at least 50%, 60%, 70%, 80%, 90%, 99% of the reduction of expression obtained using the initial target sequence in a similar gene construct or expression vector, preferably assessed in a cell as earlier explained herein. In this context a variant of a binding sequence may have at least 85%, at least 90%, at least 95%, at least 96%, at least 97%, at least 98%, at least 99% identity with the specific binding sequence identified herein. Other particular embodiments of the invention are gene constructs comprising microRNA target sequences with homology or identity of at least 85% to 99% with the target of sequences SEQ ID NO: 8 to 22, 93, 94 and 95, preferably 8 to 20, 22, 93, 94 and 95 listed above. More particularly, the target sequences have a percentage of 85% homology with sequences SEQ ID NO:8 to 22, more preferably with SEQ ID NO:8 to 20, 22, 93, 94 and 95.

"MicroR" or "miRNA" or "microRNA" or "miR" as used herein, are small (~22 nucleotides) sequences evolutionarily conserved of regulatory RNAs involved in gene silencing of RNA at post-transcriptional level (See Bartel D P. 2004). Through the base pairing with complementary regions (most often in the untranslated region 3'(3'UTR) of the cellular messenger RNA (mRNA)), miRNAs may act to suppress mRNA translation or cause catalytic degradation of mRNA. Due to the differential expression among tissues, many cellular miRNAs can be exploited to mediate the differential expression of gene therapy vectors. Having multiple copies of target elements complementary to these tissue specific miRNAs (miRT) in vectors or viral vectors, the expression of the transgene (or gene from another species of interest) in an unwanted tissue can be efficiently inhibited. The complementarity of the miRNA target sequences may be complete or partial. In any case, while it is able to match with the miRNA is sufficient to prevent the expression of the transgene placed in a viral vector.

In another particular embodiment, optionally in combination with any of the embodiments above or below indicated, the gene construct comprises a constitutive and/or an ubiquitous promoter. In a preferred embodiment the promoter is an ubiquitous and constitutive promoter. The expression "a promoter of ubiquitous expression" could be replaced with "an ubiquitous promoter". Preferably, it comprises the CAG promoter, which is an ubiquitous promoter, which means that it can drive the expression in any or in many tissue(s) of a nucleotide sequence operatively linked to it. The CAG promoter refers to the combination based on the cytomegalovirus early enhancer element and the chicken beta actin promoter (see Alexopoulou A, et al, 2008). A preferred CAG promoter is represented by SEQ ID NO:52. A variant of said promoter (preferably represented by a sequence having at least 60% identity with SEQ ID NO:52) may also be used as long as said variant is said to be an active promoter as defined later herein.

A "constitutive" promoter is a promoter that is active under most physiological and developmental conditions. An "inducible" promoter is a promoter that is preferably regulated depending on physiological or developmental conditions. An inducible promoter may be active after drug delivery or light exposure. A "constitutive" promoter therefore is not regulated in the sense of an "inducible" promoter. A "tissue specific" promoter is preferably active in specific types of cells/tissues. As opposed to a "tissue-specific" promoter, the promoter used in the context of the invention is an "ubiquitous" promoter. An ubiquitous promoter may be defined as a promoter that is active in many or in any different tissue(s). Usually, "many" in this context may mean more than 5 or at least 6, 10, 15, 20 or in 5, 6, 7, 8, 9, 10, 11, 12, 13, 14, 15, 16, 17, 18, 19, 20 different tissues. In a preferred embodiment, a promoter as used in the construct of the invention is ubiquitous and/or constitutive. In a more preferred embodiment, said promoter is ubiquitous and constitutive. In another preferred embodiment, the promoter as used herein is non-pancreas specific and not an ubiquitous promoter. It means it is not only or not solely or not exclusively active in pancreas. It may also be active in at least 1, 2, 3, 4, or 5 or more different tissues.

For "promoter" must be understood a nucleic acid fragment that functions to control the transcription of one or more polynucleotides, which is placed 5' upstream of the polynucleotide sequence(s), and which is structurally identified by the presence of a binding site for RNA dependent DNA polymerase, transcription initiation sites and, but not limited to, binding sites for transcription factors, repressors, and any other nucleotide sequences known in the art to act directly or indirectly to regulate the amount of transcription from the promoter.

A promoter is said to be active or is said to drive the expression of a nucleotide sequence operatively linked to it when it can initiate transcription of said nucleotide sequence in an expression system using a gene construct comprising said promoter operably linked to a nucleotide sequence of interest using a suitable assay such a RT-qPCR or Northern blotting (detection of the transcript). The activity of said promoter may also be assessed at the protein level using a suitable assay for the encoded protein such as Western blotting or an ELISA. A promoter is said to be capable to initiate transcription if a transcript can be detected or if an increase in a transcript or protein level is found of at least 5%, 10%, 15%, 20%, 30%, 40%, 50%, 60%, 70%, 80%, 90%, 100%, 200%, 300%, 500%, 1000%, 1500% or 2000% as compared to transcription using a construct which only differs in that it is free of said promoter.

The term "polynucleotide" as used herein, refers to a nucleic acid molecule, either DNA or RNA, which contains deoxyribonucleotides or ribonucleotides. The nucleic acid may be double stranded, single stranded, or contain portions of both double stranded or single strand sequences. The term "polynucleotide" includes, but is not limited to, nucleic acid sequences with the ability to encode a polypeptide and nucleic acid sequences partially or completely complementary to a polynucleotide endogenous of the cell or of the subject administered with it so that, after the transcription of the same, generates a RNA molecule (e.g., microRNA, shRNA, siRNA) able to hybridize and inhibit the expression of the endogenous polynucleotide.

In another particular embodiment, optionally in combination with any of the embodiments listed below or above, the nucleotide sequence comprises a sequence that encodes any of the isoforms of IGF-1 of a mammal, particularly human, murine, dog or cat; the CAG promoter sequence and four copies of at least two targets of microRNA, particularly, four copies of the target sequence of miR122 and four copies of the target sequence of miR1.

The expert will know how to switch the nucleotide sequences encoding the murine protein IGF-1 in any of its isoforms, to the corresponding nucleotide sequences that encode the protein iso forms of human, canine (dog) or feline (cat) IGF-1. Within the context of the invention an IGF-1 or Igf1 refers to the nucleotide sequence encoding preproIGF-1a unless otherwise indicated. The invention is not limited to the use of preproIGF-1a. Some embodiments of the invention relate to the use of mechano growth factor (MGF), which corresponds to murine preproIGF-1b and human preproIGF1c. Other embodiments relate to the use of human preproIGF-1b. Preferred IGF-1a proteins are represented by SEQ ID NO: 23, 28 and 47 or variants thereof. Preferred corresponding IGF-1a nucleic acid are represented by SEQ ID NO: 1, 51 and 3 or variants thereof. Preferred MGF proteins are represented by SEQ ID NO: 25, 26, 29, 44 and 46 or variants thereof. Preferred corresponding MGF nucleic acid are represented by SEQ ID NO: 2, 48, 50, 5 and 6 or variants thereof.

Second Aspect of the Invention: Expression Vector

These gene constructs are placed in expression vectors. Thus, another aspect of the invention is an expression vector comprising the gene construct as defined in any of the preceding embodiments. The section entitled "general definitions" provides more detailed information as to the expression vector of the invention.

In a particular embodiment, the vector is characterized for being a viral vector, more preferably a viral vector selected from the group consisting of adenoviral vectors, adeno associated vectors or adeno associated viral vectors, retroviral vectors, and lentiviral vectors. These vectors are also known as adenovirus derived vector, adeno associated derived vector, retrovirus derived vector and lentivirus derived vector.

In a more particular embodiment, the vector is a viral adeno associated vector or adeno associated viral vector selected from the group consisting of adeno associated viral vector of serotype 6, adeno associated viral vector of serotype 7, adeno associated viral vector of serotype 8, adeno associated viral vector of serotype 9, adeno associated viral vector of serotype 10, adeno associated viral vector of serotype 11, adeno associated viral vector of serotype rh8, and adeno associated viral vector of serotype rh10. In a preferred embodiment, the vector is a adeno associated viral vector of serotype 8 (abbreviated AAV8). These serotypes of adeno associated viral vectors are known for their tropism in the pancreas.

The terms "adeno associated virus", "AAV virus", "AAV virion," "AAV viral particle" and "AAV particle", used as synonyms herein, refer to a viral particle composed of at least one capsid protein of AAV (preferably composed of all capsid protein of a particular AAV serotype) and an encapsulated polynucleotide of the AAV genome. If the particle comprises a heterologous polynucleotide (i.e. a polynucleotide different from a wild-type AAV genome, such as a transgene to be delivered to a mammalian cell) flanked by AAV inverted terminal repeats, then they are typically known as a "AAV vector particle" or "AAV viral vector" or "AAV vector". AAV refers to a virus that belongs to the genus Dependovirus family Parvoviridae. The AAV genome is approximately 4.7 Kb in length and it consists of single strand deoxyribonucleic acid (ssDNA) that can be positive or negative detected. The invention also encompasses the use of double stranded AAV also called dsAAV or scAAV. The genome includes inverted terminal repeats (ITR) at both ends of the DNA strand, and two open reading frames (ORFs): rep and cap. The frame rep is made of four overlapping genes that encode proteins Rep necessary for AAV lifecycle. The frame cap contains nucleotide sequences overlapping with capsid proteins: VP1, VP2 and VP3, which interact to form a capsid of icosahedral symmetry (see Carter and Samulski., 2000, and Gao et al, 2004). More information is provided as to this type of virus, viral particle or viral vector in the section entitled "general definitions".

In a particular embodiment, the expression vector comprises a sequence selected among sequences SEQ ID NOs: 30 and 31.

SEQ ID NO: 30 comprises 7264 nucleotides and is named herein as pAAV-CAG-preproIGF1a-double mirT122a-mirT1. It is used to express in pancreas the murine preproIGF-1 (isoform 5, SEQ ID NO: 28). The CAG promoter is located at bases 180 to 1824; the sequence encoding the murine preproIGF-1 is located at nucleotides 2112-2525 (signal peptide: nucleotides 2112-2197; mature IGF1: 2198-2417 nucleotides, peptide Ea: nucleotides 2418 to 2525); at nucleotides 2942-3460 there is the polyadenylation signal (PolyA, poliadenines) of the rabbit beta globin; the four copies of the target sequence of miR122a and four copies of the target sequence of miR1 (herein called as doublemiRT122a-miRT1, also called herein dmiRT) are at nucleotides 2592-2852 of the gene construct; and the inverted terminal repeat sequences (ITR) from the serotype 2 adeno associated virus (AAV2) are located at nucleotides 2-143 (AAV2 5' ITR) and at nucleotides 3519-3651 (AAV2 3' ITR).

The expression cassette comprised within SEQ ID NO: 30 consists of SEQ ID NO:96: CAG promoter: 180-1824 bp, Mouse preproIGF1a: 2112-2525 bp (signal peptide: 2112-2197 bp; mature IGF1: 2198-2417 bp; Ea peptide: 2418-2525 bp), doblemiRT122a-mirT1 (4 copies of the mirT122a and 4 copies of the mirT1): 2592-2852 bp, Rabbit β-Globin polyA signal: 2942-3460 bp.

The viral vector comprised within SEQ ID NO:30 consists of SEQ ID NO: 97: AAV2 5' ITR: 2-143 bp, CAG promoter: 180-1824 bp, Mouse preproIGF1a: 2112-2525 bp (signal peptide: 2112-2197 bp; mature IGF1: 2198-2417 bp; Ea peptide: 2418-2525 bp), doblemiRT122a-mirT1 (4 copies of the mirT122a and 4 copies of the mirT1): 2592-2852 bp, Rabbit β-Globin polyA signal: 2942-3460 bp, AAV2 3' ITR: 3519-3651 bp.

SEQ ID NO: 31 comprises 7200 nucleotides and is also called herein pAAV-CAG-preproIGF1b-double miRT122a-mirT1. It is used to express in pancreas the murine preproIGF-1 (SEQ ID NO: 29). The CAG promoter is located at bases 180 to 1824; the sequence encoding the murine preproIGF-1 is located at nucleotides 2036 to 2434 (signal peptide: nucleotides 2036-2101; mature IGF1: nucleotides 2102-2311, peptide Eb: nucleotides 2312-2434); at nucleotides 2878-3396 there is the polyadenylation signal (PolyA, poliadenines) of the rabbit beta globin; the four copies of the target sequence of miR122a and the four copies of the target sequence of miR1 (herein called as doblemiRT122a-miRT1) are at nucleotides 2528-2788 of the gene construction; and the inverted terminal repeat sequences from the serotype 2 adeno associated virus (AAV2) are located at nucleotides 2-143 (AAV2 5 'ITR) and at nucleotides 3455 to 3587 (AAV2 3' ITR).

The expression cassette comprised within SEQ ID NO: 31 consists of SEQ ID NO:98: CAG promoter: 180-1824 bp, Mouse preproIGF1b (MGF): 2036-2434 bp (signal peptide: 2036-2101 bp; mature IGF1: 2102-2311 bp; Eb peptide: 2312-2434 bp), doblemiRT122a-mirT1 (4 copies of the mirT122a and 4 copies of the mirT1): 2528-2788 bp, Rabbit β-Globin polyA signal: 2878-3396 bp.

The viral vector comprised within SEQ ID NO:31 consists of SEQ ID NO: 99: AAV2 5' ITR: 2-143 bp, CAG promoter: 180-1824 bp, Mouse preproIGF1b (MGF): 2036-2434 bp (signal peptide: 2036-2101 bp; mature IGF1: 2102-2311 bp; Eb peptide: 2312-2434 bp), doblemiRT122a-mirT1 (4 copies of the mirT122a and 4 copies of the mirT1): 2528-2788 bp, Rabbit β-Globin polyA signal: 2878-3396 bp AAV2 3' ITR: 3455-3587 bp.

As can be seen throughout the description, the vectors of the invention are preferably for the expression of the gene construct in mammalian pancreas, preferably human or murine pancreas.

The expression vectors of the invention can be obtained by methods known to the expert. The invention also comprises methods of obtaining vectors comprising the steps of:

(a) providing a cell with: (i) a gene construct as defined above, flanked by adeno associated virus ITRs; (ii) cap and rep proteins of adeno associated virus; and (iii) adequate viral proteins for the replication of AAV;

(b) cultivating the cell in suitable conditions to produce the AAV assembly; and (c) purifying AAV vector produced by the cell.

More detail is provided in the section entitled "general definitions".

In a particular embodiment of the method of obtaining the expression vectors, rep proteins of the adeno associated virus are of 2 serotype 2 (AAV2) and cap proteins derive from an AVV serotype selected from a group consisting of adeno associated viral vector of serotype 6, adeno associated viral vector of serotype 7, adeno associated viral vector of serotype 8, adeno associated viral vector of serotype 9, adeno associated viral vector of serotype 10, adeno associated viral vector of serotype 11, adeno associated viral vector of serotype rh8, and adeno associated viral vector of serotype rh10.

Third, Fourth and Fifth Aspects of the Invention: Therapeutic Applications and Pharmaceutical Compositions Another aspect of the invention refers to the gene construct and/or the expression vector, both as defined above, for use as a medicament. This aspect may also be formulated as the use of the vector and/or of the gene construct in medicine.

Alternatively, it refers to a method of treatment and/or prevention of a subject in need thereof, wherein the treatment comprises administering a therapeutically effective amount of the vector or of the gene construct as described previously.

In a particular embodiment, the vector and/or the gene construct are used in treatment and/or prevention of diabetes in mammals, preferably diabetes mellitus in mammals, wherein a dysfunction and/or a loss of the beta-cells of the Langerhans islets is present. In a more particular embodiment, diabetes is type 1 diabetes mellitus in mammal (T1D). "Dysfunction" should be understood as the cells do not work properly even though the number of cells per volume of islet is maintained. "Loss" means that the number of cells is lower than that associated with a pancreas without diabetes. Lower may mean 10% lower, 20% lower, 30% lower, 40% lower, 50% lower, 60% lower, 70% lower, 80% lower or more.

During the autoimmune process characteristic of T1D, two stages can be clearly distinguished: a clinically occult phase, characterized by the generation of antibodies directed against a variety of antigens of β cells together with a gradual infiltration of autoreactive T lymphocytes and other inflammatory cells in the islets, called insulitis; and an open phase of diabetes where the destruction of β cells is extensive causing a deficiency in production of insulin and finally hyperglycemia. The period of time between the onset of T1D biomarkers and the onset of clinical symptoms is highly variable and can take several years before clinical disease occurs. Not until there is a loss of 70-80% of the β cell mass that occurs the onset of elevated blood glucose values and T1D is diagnosed.

In this regard, the vector and/or the gene construct are used in treatment and/or prevention of diabetes, both the asymptomatic and the symptomatic phase. Within the context of the invention the "treatment" and the "prevention" of diabetes encompasses the prevention, the regression, the delay and/or curing diabetes. The vector and/or the gene construct as used herein preferably exhibit an anti-diabetes effect as later defined herein.

In even a more particular embodiment, the vector or the gene construct is for use in the treatment and/or prevention of T1D in a mammal selected from human, murine, feline (cats) and canine (dogs), preferably in humans.

These embodiments can also be formulated as the use of the vector and/or of the gene construct described above for the preparation of a medicament for the treatment and/or prevention of diabetes mellitus, in which there is dysfunction and/or loss of beta-cells of the islets of Langerhans. More preferably, they are used to prepare a medicament for the treatment of T1D in mammals, especially murine, humans, cats and dogs. Alternatively, these embodiments relate to methods for therapeutic and/or prophylactic treatment of diabetes mellitus, particularly T1D, comprising administering a therapeutically or prophylactically effective amount of the vector or of the gene construct as described previously in a subject (particularly a human) in need thereof.

In the context of the present invention is to be understood by "therapeutically effective amount" the amount of a compound (herein the vector or the gene construct) which, when administered, is sufficient to prevent the development of or alleviate to some extent one or more symptoms of the disease to which is directed (diabetes). The particular dose of the compound to be administered according to this invention will be determined by considering the particular circumstances surrounding the case, including the route of administration, the particular condition that it is treated and other similar considerations that the expert will know how to interpret.

An object of the present invention is a pharmaceutical composition comprising a gene construct as defined previously and/or of a vector as defined previously, together with one or more pharmaceutically acceptable excipients or vehicles.

Another object of the present invention is a pharmaceutical composition comprising a therapeutically effective amount of a gene construct as defined previously and/or of a vector as defined previously, together with one or more pharmaceutically acceptable excipients or vehicles.

In the context of the present invention, the term "pharmaceutically acceptable excipients or vehicles" refers to pharmaceutically acceptable materials, compositions or vehicles. Each component should be pharmaceutically acceptable in the sense that it must be compatible with the other ingredients of the pharmaceutical composition. It should also be suitable for use in contact with the tissue or organ of humans and animals without excessive toxicity, irritation, allergic response, immunogenicity, or other problems or complications put into context with a reasonable relation benefit/risk. Such pharmaceutically acceptable excipients or vehicles may be pharmaceutically acceptable carrier, filler, preservative, solubilizer, diluent. They may for instance be found in Remington: The Science and Practice of Pharmacy, 20th Edition. Baltimore, Md.: Lippincott Williams & Wilkins, 2000.

A gene construct and/or an expression vector and/or a pharmaceutical composition of the invention comprising a gene construct and/or an expression vector is preferably said to be able to be used for preventing, delaying, reverting, curing and/or treating a diabetes, when said gene construct, expression vector and/or composition are able to exhibit an anti-diabetic effect in a treated individual. An anti-diabetic effect may be reached when glucose disposal is increased and/or when glucose tolerance is improved and/or circulating insulin is increased and/or hyperglycemia is delayed. Glucose and insulin circulating levels in blood/serum and glucose tolerance could be assessed using techniques known to the skilled person or as done in the experimental part. For humans, it is accepted that in fasting conditions (fasting is defined as no calorie intake for at least 8 h) in healthy human subjects, glucose is usually ranged from 70-125 mg/dl and insulin from 5-20 mcU/ml. Values of fasting plasma glucose (FPG) of 126 mg/dl or higher are criteria of diagnosis of Diabetes (ADA, 2010). In healthy mice, glucose is usually ranged from 60-180 mg/dl and insulin from 0.3 to 10 ng/ml. In this context, "increase" (respectively "improvement") means at least a detectable increase (respectively a detectable improvement) using an assay known to the skilled person or using assays as carried out in the experimental part. In this context, "decrease" means at least a detectable decrease using an assay known to the skilled person or using assays as carried out in the experimental part. A detectable decrease may be a decrease of at least 5%, 10%, 20%, 30%, 40%, 50%, 60%, 70%, 80%, 90%, 100% or more by comparison to the corresponding level before treatment or to the corresponding level in a control subject.

The anti-diabetic effect may be assessed on a sample from a treated individual such as blood.

The expression "glucose disposal is increased" may mean increased glucose uptake by peripheral tissues (mainly liver, skeletal muscle and adipose tissue) resulting in decreased circulating levels of glucose. The expression "glucose tolerance is improved" may mean that circulating levels of glucose are decreased after glucose overload.

The expression "the hyperglycemia is delayed" preferably means that the delay may be of at least 1, 2, 3, 4, 5, 6, 7, 8, 9, 10 days or at least 1, 2, 3, 4, 5, 6, 7 weeks or at least 1, 2, 3, 4, 5, 6, 7, months or at least 1, 2, 3, 4, 5, 6, 7, years. Hyperglycemia is typically defined when circulating levels of glucose are higher than the ones defined above. In this context, "higher" means at least 10%, 20%, 30%, 40%, 50%, 60%, 70%, 80%, 90% or even 100% higher.

An anti-diabetic effect may also be observed when the progression of a typical symptom (i.e. insulitis, beta cell loss, . . . ) has been slowed down as assessed by a physician. A decrease of a typical symptom may mean a slow down in progression of symptom development or a complete disappearance of symptoms. Symptoms, and thus also a decrease in symptoms, can be assessed using a variety of methods, to a large extent the same methods as used in diagnosis of diabetes, including clinical examination and routine laboratory tests. Such methods include both macroscopic and microscopic methods, as well as molecular methods, X-rays, biochemical, immunohistochemical and others.

A medicament as defined herein (gene construct, expression vector, composition) is preferably able to alleviate one symptom or one characteristic of a patient or of a cell, tissue or organ of said patient if after at least one week, one month, six month, one year or more of treatment using an expression vector or a composition of the invention, said symptom or characteristic is no longer detectable. A preferred organ is the pancreas and a preferred cell is a beta-cell of the pancreas.

A gene construct or an expression vector or a composition as defined herein for use according to the invention may be suitable for administration to a cell, tissue and/or an organ in vivo of individuals affected by or at risk of developing a diabetes, and may be administered in vivo, ex vivo or in vitro. Said gene construct or expression vector or composition may be directly or indirectly administrated to a cell, tissue and/or an organ in vivo of an individual affected by or at risk of developing a diabetes, and may be administered directly or indirectly in vivo, ex vivo or in vitro. A preferred administration mode is intraductal as later defined herein.

A gene construct or an expression vector or a composition of the invention may be directly or indirectly administered using suitable means known in the art. Improvements in means for providing an individual or a cell, tissue, organ of said individual with a gene construct or an expression vector or a composition of the invention are anticipated, considering the progress that has already thus far been achieved. Such future improvements may of course be incorporated to achieve the mentioned effect of the invention. A gene construct or an expression vector or a composition can be delivered as is to an individual, a cell, tissue or organ of said individual. Depending on the disease or condition, a cell, tissue or organ of said individual may be as earlier defined herein. When administering a gene construct or an expression vector or a composition of the invention, it is preferred that such gene construct or vector or composition is dissolved in a solution that is compatible with the delivery method. For intravenous, subcutaneous, intramuscular, intrathecal, intraarticular and/or intraventricular administration it is preferred that the solution is a physiological salt solution.

As encompassed herein, a therapeutically effective dose of a gene construct, vector or composition as mentioned above is preferably administered in a single and unique dose hence avoiding repeated periodical administration.

A further compound may be present in a composition of the invention. Said compound may help in delivery of the composition. Below is provided a list of suitable compounds: compounds capable of forming complexes, nanoparticles, micelles and/or liposomes that deliver each constituent as defined herein, complexed or trapped in a vesicle or liposome through a cell membrane. Many of these compounds are known in the art. Suitable compounds comprise polyethylenimine (PEI), or similar cationic polymers, including polypropyleneimine or polyethylenimine copolymers (PECs) and derivatives, synthetic amphiphiles (SAINT-18), Lipofectin™, DOTAP.

Depending on their identity, the skilled person will know which type of formulation is the most appropriate for the composition as defined herein.

In this context a further compound may be insulin that could be regularly injected.

In a further aspect there is provided a method for preventing, delaying, reverting, curing and/or treating a diabetes wherein a gene construct or expression vector or composition as defined herein as defined herein is being used.

Such a method is preferably for alleviating one or more symptom(s) of diabetes in an individual, in a cell, tissue or organ of said individual or alleviate one or more characteristic(s) or symptom(s) of a cell, tissue or organ of said individual, the method comprising administering to said individual an expression construct or vector (preferably a viral expression construct or a viral vector) or a composition as defined herein.

In a further aspect there is provided a use of a gene construct or vector or a composition as defined herein for the manufacture of a medicament for preventing, delaying, reverting, curing and/or treating a diabetes.

Diabetes and the type of subject treated have been earlier defined herein.

In a preferred embodiment, a treatment in a use or in a method according to the invention does not have to be repeated. Alternatively in a use or a method according to the invention said administration of the gene construct or of said composition may be repeated each year or each 2, 3, 4, 5, 6, 7, 8, 9, 10, 11, 12, 13, 14, 15 years. The gene construct and/or the vector and/or the pharmaceutical compositions that comprise them, can be used in the treatment of diabetes, via systemic or local. In a preferred embodiment, they are used in the treatment by local intraductal administration via or through by the bile duct. The intraductal administration can potentially be applied to larger animals and humans, through a non-surgical and less invasive clinical process called endoscopic retrograde cholangiopancreatography (ERCP) (Hendrick et al., 2011).

Other Aspects of the Invention

The invention also has the object of methods for in vitro or ex vivo transduction of mammalian cells, where the methods comprise providing mammalian cells, particularly cells of murine, pig and human pancreas, with an expression vector or gene construct, as described above. Ex-vivo gene therapy delivering AAV vectors to mammalian cells may be carried out as described in Rehman K et al 2005.

The invention also has the object of in vitro methods of transduction of mammalian cells, wherein the methods comprise contacting the mammalian cell, particularly cells of murine, pig and human pancreas, with an expression vector as described above and/or a construction gene as described above.

In a particular embodiment, the gene construct and/or expression vector used in the method of transduction is an adeno associated viral vector, and the cell is a beta-cell from the islet of Langerhans or the complete islet of Langerhans of the pancreas of the mammal, preferably human.

Another object of the invention is, therefore, a mammalian cell transduced or a complete islet transduced. In a particular embodiment, the cell is a pancreatic cell, preferably a beta-cell of the islet of Langerhans or a complete islet of Langerhans.

Within the context of the invention a beta-cell could be replaced by a beta-cell of the islet of Langerhans or by a β-cell or by a β cell.

Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein. The following examples and drawings are provided herein for illustrative purposes, and without intending to be limiting to the present invention. In addition, this invention covers all possible combinations of particular and preferred embodiments herein indicated.

General Definitions

Expression Construct

An expression construct or gene construct carries a genome that is able to stabilize and remain episomal in a cell. However, an expression construct for gene construct may also integrate into the genome of the cell. Within the context of the invention, a cell may mean to encompass a cell used to make the construct or a cell wherein the construct will be administered. Alternatively a construct is capable of integrating into a cell's genome, e.g. through homologous recombination or otherwise. A particularly preferred expression construct is one wherein a nucleotide sequence encoding an IGF-1 as defined herein, is operably linked to a promoter and a target sequence of a miRNA as defined herein. An expression construct, preferably a viral expression construct is intended to be used in gene therapy. Expression construct may be used to introduce DNA/gene of interest to the pancreas via microbubble treatment with ultrasound (Chen et al., 2006). A viral expression construct is designed to comprise part of a viral genome as later defined herein.

Expression constructs disclosed herein could be prepared using recombinant techniques in which nucleotide sequences encoding said IGF-1 are expressed in a suitable cell, e.g. cultured cells or cells of a multicellular organism, such as described in Ausubel et al., "Current Protocols in Molecular Biology", Greene Publishing and Wiley-Interscience, New York (1987) and in Sambrook and Russell (2001, supra); both of which are incorporated herein by reference in their entirety. Also see, Kunkel (1985) Proc. Natl. Acad. Sci. 82:488 (describing site directed mutagenesis) and Roberts et al. (1987) Nature 328:731-734 or Wells, J. A., et al. (1985) Gene 34: 315 (describing cassette mutagenesis).

Typically, a nucleic acid or nucleotide sequence encoding an IGF-1 is used in an expression construct or gene construct. The phrase "expression construct" generally refers to a nucleotide sequence that is capable of effecting expression of a gene in a host compatible with such sequences. These expression constructs typically include at least suitable promoter sequences and optionally, transcription termination signals. An additional factor necessary or helpful in effecting expression can also be used as described herein. A nucleic acid or DNA or nucleotide sequence encoding an IGF-1 is incorporated into a DNA construct capable of introduction into and expression in an in vitro cell culture. Specifically, a DNA construct is suitable for replication in a prokaryotic host, such as bacteria, e.g., *E. coli*, or can be introduced into a cultured mammalian, plant, insect, (e.g., Sf9), yeast, fungi or other eukaryotic cell lines.

A DNA construct or gene construct or expression construct prepared for introduction into a particular host may include a replication system recognized by the host, an intended DNA segment encoding a desired polypeptide, and transcriptional and translational initiation and termination regulatory sequences operably linked to the polypeptide-encoding segment. The term "operably linked" has already been defined herein. For example, a promoter or enhancer is operably linked to a coding sequence if it stimulates the transcription of the sequence. A promoter has also already been defined herein. DNA for a signal sequence is operably linked to DNA encoding a polypeptide if it is expressed as a preprotein that participates in the secretion of a polypeptide. Generally, a DNA sequence that is operably linked are contiguous, and, in the case of a signal sequence, both contiguous and in reading frame. However, enhancers need not be contiguous with a coding sequence whose transcription they control. Linking is accomplished by ligation at convenient restriction sites or at adapters or linkers inserted in lieu thereof, or by gene synthesis.

The selection of an appropriate promoter sequence generally depends upon the host cell selected for the expression of a DNA segment. Examples of suitable promoter sequences include prokaryotic, and eukaryotic promoters well known in the art (see, e.g. Sambrook and Russell, 2001, supra). A transcriptional regulatory sequence typically includes a heterologous enhancer or promoter that is recognised by the host. The selection of an appropriate promoter depends upon the host, but promoters such as the trp, lac and phage promoters, tRNA promoters and glycolytic enzyme promoters are known and available (see, e.g. Sambrook and Russell, 2001, supra). An expression construct or gene construct or expression vector includes the replication system and transcriptional and translational regulatory sequences together with the insertion site for the polypeptide encoding segment can be employed. In most cases, the replication system is only functional in the cell that is used to make the vector (bacterial cell as *E. Coli*). Most plasmids and vectors do not replicate in the cells infected with the vector. Examples of workable combinations of cell lines and expression vectors are described in Sambrook and Russell (2001, supra) and in Metzger et al. (1988) Nature 334: 31-36. For example, suitable expression vectors can be expressed in, yeast, e.g. *S. cerevisiae*, e.g., insect cells, e.g., Sf9 cells, mammalian cells, e.g., CHO cells and bacterial cells, e.g., *E. coli*. A cell may thus be a prokaryotic or eukaryotic host cell. A cell may be a cell that is suitable for culture in liquid or on solid media.

Alternatively, a host cell is a cell that is part of a multicellular organism such as a transgenic plant or animal. An animal is preferably a mammal.

Viral Vector, Expression Vector

An expression vector is preferably a viral vector or a gene therapy vector. Such a viral vector is a vector that comprises a viral expression construct as defined above.

A vector (preferably a viral vector) is preferably a gene therapy vector. A gene therapy vector is a vector that is suitable for gene therapy. Vectors that are suitable for gene therapy are described in Anderson 1998, Nature 392: 25-30; Walther and Stein, 2000, Drugs 60: 249-71; Kay et al., 2001, Nat. Med. 7: 33-40; Russell, 2000, J. Gen. Virol. 81: 2573-604; Amado and Chen, 1999, Science 285: 674-6; Federico, 1999, Curr. Opin. Biotechnol. 10: 448-53; Vigna and Naldini, 2000, J. Gene Med. 2: 308-16; Marin et al., 1997, Mol. Med. Today 3: 396-403; Peng and Russell, 1999, Curr. Opin. Biotechnol. 10: 454-7; Sommerfelt, 1999, J. Gen. Virol. 80: 3049-64; Reiser, 2000, Gene Ther. 7: 910-3; and references cited therein.

A particularly suitable gene therapy vector includes an Adenoviral and Adeno-associated virus (AAV) vector. These vectors infect a wide number of dividing and non-dividing cell types including synovial cells and liver cells. The episomal nature of the adenoviral and AAV vectors after cell entry makes these vectors suited for therapeutic applications. (Russell, 2000, J. Gen. Virol. 81: 2573-2604; Goncalves, 2005, Virol J. 2(1):43) as indicated above. AAV vectors are even more preferred since they are known to result in very stable long term expression of transgene expression (up to 9 years in dog (Niemeyer et al, Blood. 2009 Jan. 22; 113(4):797-806) and ~2 years in human (Nathwani et al, N Engl J Med. 2011 Dec. 22; 365(25): 2357-65, Simonelli et al, Mol Ther. 2010 March; 18(3):643-50. Epub 2009 Dec. 1.)). Preferred adenoviral vectors are modified to reduce the host response as reviewed by Russell (2000, supra). Method for gene therapy using AAV vectors are described by Wang et al., 2005, J Gene Med. March 9 (Epub ahead of print), Mandel et al., 2004, Curr Opin Mol Ther. 6(5):482-90, and Martin et al., 2004, Eye 18(11):1049-55, Nathwani et al, N Engl J Med. 2011 Dec. 22; 365(25): 2357-65, Apparailly et al, Hum Gene Ther. 2005 April; 16(4):426-34.

Another suitable gene therapy vector includes a retroviral vector. A preferred retroviral vector for application in the present invention is a lentiviral based expression construct. Lentiviral vectors have the ability to infect and to stably integrate into the genome of dividing and non-dividing cells (Amado and Chen, 1999 Science 285: 674-6). Methods for the construction and use of lentiviral based expression constructs are described in U.S. Pat. Nos. 6,165,782, 6,207,455, 6,218,181, 6,277,633 and 6,323,031 and in Federico (1999, Curr Opin Biotechnol 10: 448-53) and Vigna et al. (2000, J Gene Med 2000; 2: 308-16).

Other suitable gene therapy vectors include a herpes virus vector, a polyoma virus vector or a vaccinia virus vector.

A gene therapy vector comprises a nucleotide sequence encoding an IGF-1 to be expressed, whereby said nucleotide sequence is operably linked to the appropriate regulatory sequences. Such regulatory sequence will at least comprise a promoter sequence. Suitable promoters for expression of a nucleotide sequence encoding an IGF-1 from gene therapy vectors include e.g. cytomegalovirus (CMV) intermediate early promoter, viral long terminal repeat promoters (LTRs), such as those from murine moloney leukaemia virus (MMLV) rous sarcoma virus, or HTLV-1, the simian virus 40 (SV 40) early promoter and the herpes simplex virus thymidine kinase promoter. Suitable promoters are described below.

Several inducible promoter systems have been described that may be induced by the administration of small organic or inorganic compounds. Such inducible promoters include those controlled by heavy metals, such as the metallothionine promoter (Brinster et al. 1982 Nature 296: 39-42; Mayo et al. 1982 Cell 29: 99-108), RU-486 (a progesterone antagonist) (Wang et al. 1994 Proc. Natl. Acad. Sci. USA 91: 8180-8184), steroids (Mader and White, 1993 Proc. Natl. Acad. Sci. USA 90: 5603-5607), tetracycline (Gossen and Bujard 1992 Proc. Natl. Acad. Sci. USA 89: 5547-5551; U.S. Pat. No. 5,464,758; Furth et al. 1994 Proc. Natl. Acad. Sci. USA 91: 9302-9306; Howe et al. 1995 J. Biol. Chem. 270: 14168-14174; Resnitzky et al. 1994 Mol. Cell. Biol. 14: 1669-1679; Shockett et al. 1995 Proc. Natl. Acad. Sci. USA 92: 6522-6526) and the tTAER system that is based on the multi-chimeric transactivator composed of a tetR polypeptide, as activation domain of VP16, and a ligand binding domain of an estrogen receptor (Yee et al., 2002, U.S. Pat. No. 6,432,705).

A gene therapy vector may optionally comprise a further nucleotide sequence coding for a further polypeptide. A further polypeptide may be a (selectable) marker polypeptide that allows for the identification, selection and/or screening for cells containing the expression construct. Suitable marker proteins for this purpose are e.g. the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) "Molecular Cloning: A Laboratory Manual ($3^{rd}$ edition), Cold Spring Harbor Laboratory, Cold Spring Harbor Laboratory Press, New York.

A gene therapy vector is preferably formulated in a pharmaceutical composition as defined herein. In this context, a pharmaceutical composition may comprise a suitable pharmaceutical carrier as earlier defined herein.

Adeno-Associated Virus Vector (AAV Vector)

A preferred viral vector or a preferred gene therapy vector is an AAV vector. An AAV vector as used herein preferably comprises a recombinant AAV vector (rAAV). A "rAAV vector" as used herein refers to a recombinant vector comprising part of an AAV genome encapsidated in a protein shell of capsid protein derived from an AAV serotype as explained herein. Part of an AAV genome may contain the inverted terminal repeats (ITR) derived from an adeno-associated virus serotype, such as AAV1, AAV2, AAV3, AAV4, AAV5, AAV6, AAV7, AAV8, AAV9, AAV10, AAV11, AAV rh8, AAV rh10 and others. Preferred ITR are derived from an AAV2. Protein shell comprised of capsid protein may be derived from an AAV serotype such as AAV1, 2, 3, 4, 5, 6, 8, 9, 10, 11, rh8, rh10 and others. A preferred AAV capsid is a AAV1, AAV2, AAV3, AAV4, AAV5, AAV6, AAV7, AAV8, AAV9, AAV10, AAV11, AAV rh8, AAV rh10 capsid. Any capsid with a tropism for pancreas is preferably used in the context of the invention even if this capsid has not yet been discovered. The invention therefore also encompasses the use of viral vector encapsidated in a capsid protein with a tropism for pancreas. A preferred ITR is from the AAV2, AAV3, AAV4, AAV5, AAV6, AAV7, AAV8, AAV9, AAV10, AAV11, AAV rh8, AAV rh10. Preferred ITR are derived from an AAV2. A protein shell may also be named a capsid protein shell. rAAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the present invention a capsid protein shell may be of a different serotype than the rAAV vector genome ITR.

A nucleic acid molecule represented by a nucleic acid sequence of choice is preferably inserted between the rAAV genome or ITR sequences as identified above, for example an expression construct comprising an expression regulatory element operably linked to a coding sequence and a 3' termination sequence. Said nucleic acid molecule may also be called a transgene.

"AAV helper functions" generally refers to the corresponding AAV functions required for rAAV replication and packaging supplied to the rAAV vector in trans. AAV helper functions complement the AAV functions which are missing in the rAAV vector, but they lack AAV ITRs (which are provided by the rAAV vector genome). AAV helper functions include the two major ORFs of AAV, namely the rep coding region and the cap coding region or functional substantially identical sequences thereof. Rep and Cap regions are well known in the art, see e.g. Chiorini et al. (1999, J. of Virology, Vol 73(2): 1309-1319) or U.S. Pat. No. 5,139,941, incorporated herein by reference. The AAV helper functions can be supplied on a AAV helper construct. Introduction of the helper construct into the host cell can occur e.g. by transformation, transfection, or transduction prior to or concurrently with the introduction of the rAAV genome present in the rAAV vector as identified herein. The AAV helper constructs of the invention may thus be chosen such that they produce the desired combination of serotypes for the rAAV vector's capsid protein shell on the one hand and for the rAAV genome present in said rAAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 incorporated herein by reference.

A "transgene" is herein defined as a gene or a nucleic acid molecule (i.e. a molecule encoding an IGF-1) that has been newly introduced into a cell, i.e. a gene that may be present but may normally not be expressed or expressed at an insufficient level in a cell. In this context, "insufficient" means that although said IGF-1 is expressed in a cell, a condition and/or disease as defined herein could still be developed. In this case, the invention allows the overexpression of an IGF-1. The transgene may comprise sequences that are native to the cell, sequences that naturally do not occur in the cell and it may comprise combinations of both. A transgene may contain sequences coding for an IGF-1 and/or additional proteins as earlier identified herein that may be operably linked to appropriate regulatory sequences for expression of the sequences coding for an IGF-1 in the cell. Preferably, the transgene is not integrated into the host cell's genome.

"Transduction" refers to the delivery of an IGF-1 into a recipient host cell by a vector, preferably a viral vector. For example, transduction of a target cell by a rAAV vector of the invention leads to transfer of the rAAV genome contained in that vector into the transduced cell. "Host cell" or "target cell" refers to the cell into which the DNA delivery takes place, such as the muscle cells of a subject. AAV vectors are able to transduce both dividing and non-dividing cells.

Production of an AAV Vector

The recombinant AAV vector, including all combinations of AAV serotype capsid and AAV genome ITRs, is produced using methods known in the art, as described in Pan et al. (J. of Virology 1999, Vol 73(4):3410-3417) and Clark et al. (Human Gene Therapy, 1999, 10:1031-1039), incorporated herein by reference. In short, the methods generally involve (a) the introduction of the rAAV genome into a host cell, (b) the introduction of an AAV helper construct into the host cell, wherein the helper construct comprises the viral functions missing from the rAAV genome and (c) introducing a helper virus or a helper plasmid into the host cell. All functions for rAAV vector replication and packaging need to be present, to achieve replication and packaging of the rAAV genome into rAAV vectors. The AAV vector may also be produced in baculovirus system. The introduction into the host cell can be carried out using standard virological techniques and can be simultaneously or sequentially. Finally, the host cells are cultured to produce rAAV vectors and are purified using standard techniques such as CsCl gradients (Xiao et al. 1996, J. Virol. 70: 8098-8108). Residual helper virus activity can be inactivated using known methods, such as for example heat inactivation. If helper activity has been provided using a plasmid, no inactivation is needed. The purified rAAV vector is preferably dialyzed to eliminate CsCl traces. The purified rAAV vector is then ready for use in the methods. High titres of more than $10^{12}$ particles per ml and high purity (free of detectable helper and wild type viruses) can be achieved (Clark et al. supra and Flotte et al. 1995, Gene Ther. 2: 29-37).

The rAAV genome present in a rAAV vector comprises at least the nucleotide sequences of the inverted terminal repeat regions (ITR) of one of the AAV serotypes (preferably the ones of serotype AAV2, AAV3, AAV4, AAV5, AAV6, AAV7, AAV8, AAV9, AAV10, AAV11, AAV rh8, AAV rh10), or nucleotide sequences substantially identical thereto, and nucleotide sequence encoding an IGF-1 (under control of a suitable regulatory element) inserted between the two ITRs. Preferred ITR are derived from an AAV2. A vector genome requires the use of flanking 5' and a 3' ITR sequences to allow for efficient packaging of the vector genome into the rAAV capsid.

The complete genome of several AAV serotypes and corresponding ITR has been sequenced (Chiorini et al. 1999, J. of Virology Vol. 73, No. 2, p 1309-1319). They can be either cloned or made by chemical synthesis as known in the art, using for example an oligonucleotide synthesizer as supplied e.g. by Applied Biosystems Inc. (Fosters, Calif., USA) or by standard molecular biology techniques. The ITRs can be cloned from the AAV viral genome or excised from a vector comprising the AAV ITRs. The ITR nucleotide sequences can be either ligated at either end to the nucleotide sequence encoding one or more therapeutic proteins using standard molecular biology techniques, or the wild type AAV sequence between the ITRs can be replaced with the desired nucleotide sequence.

Preferably, the rAAV genome as present in a rAAV vector does not comprise any nucleotide sequences encoding viral proteins, such as the rep (replication) or cap (capsid) genes of AAV. This rAAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

The rAAV genome as present in said rAAV vector further comprises a promoter sequence operably linked to the nucleotide sequence encoding an IGF-1. Preferred promoter sequences have already been defined herein.

A suitable 3' untranslated sequence may also be operably linked to the nucleotide sequence encoding an IGF-1. Suitable 3' untranslated regions may be those naturally associated with the nucleotide sequence or may be derived from different genes such as those disclosed herein (i.e. target sequence of a miRNA).

Optionally, additional nucleotide sequences may be operably linked to the nucleotide sequence(s) encoding an IGF-1, such as nucleotide sequences encoding signal sequences, nuclear localization signals, expression enhancers, and the like.

Variants

In the context of the invention, a protein is represented by an amino acid sequence. In the context of this invention a preferred protein is an IGF-1.

In the context of the invention, a nucleic acid molecule as a nucleic acid molecule encoding an IGF-1 is represented by a nucleic acid or nucleotide sequence which encodes a protein or a polypeptide or a protein fragment or a peptide or a derived peptide. A nucleic acid molecule may comprise a regulatory region.

It is to be understood that each nucleic acid molecule or protein or protein fragment or peptide or derived peptide or polypeptide as identified herein by a given Sequence Identity Number (SEQ ID NO) is not limited to this specific sequence as disclosed.

Each gene sequence or nucleotide sequence or nucleic acid sequence as identified herein encodes a given protein or polypeptide or protein fragment or peptide or derived peptide. Throughout this application, each time one refers to a specific nucleotide sequence SEQ ID NO (take SEQ ID NO: X as example) encoding a given polypeptide, one may replace it by:
  i. a nucleotide sequence comprising a nucleotide sequence that has at least 60% sequence identity or similarity with SEQ ID NO: X;
  ii. a nucleotide sequences the complementary strand of which hybridizes to a nucleic acid molecule of sequence of (i);
  iii. a nucleotide sequence the sequence of which differs from the sequence of a nucleic acid molecule of (i) or (ii) due to the degeneracy of the genetic code; or,
  iv. a nucleotide sequence that encodes an amino acid sequence that has at least 60% amino acid identity or similarity with an amino acid sequence encoded by a nucleotide sequence SEQ ID NO: X.

Throughout this application, each time one refers to a specific amino acid sequence SEQ ID NO (take SEQ ID NO: Y as example), one may replace it by: a polypeptide comprising an amino acid sequence that has at least 60% sequence identity or similarity with amino acid sequence SEQ ID NO: Y.

Each nucleotide sequence or amino acid sequence described herein by virtue of its identity or similarity percentage (at least 60%) with a given nucleotide sequence or amino acid sequence respectively has in a further preferred embodiment an identity or a similarity of at least 65%, 70%, 75%, 80%, 85%, 90%, 95%, 97%, 98%, 99% or more identity or similarity with the given nucleotide or amino acid sequence respectively. In a preferred embodiment, sequence identity or similarity is determined by comparing the whole length of the sequences as identified herein. Unless otherwise indicated herein, identity or similarity with a given SEQ ID NO means identity or similarity based on the full length of said sequence (i.e. over its whole length or as a whole).

Each non-coding nucleotide sequence (i.e. of a promoter) could be replaced by a nucleotide sequence comprising a nucleotide sequence that has at least 60% sequence identity or similarity with SEQ ID NO: A. A preferred nucleotide sequence has at least 60%, 65%, 70%, 75%, 80%, 85%, 90%, 95%, 99%, 100% identity with SEQ ID NO:A.

Identity may be assessed over the whole SEQ ID NO or over part thereof as explained herein.

"Sequence identity" or "sequence homology" is herein defined as a relationship between two or more amino acid (polypeptide or protein) sequences or two or more nucleic acid (polynucleotide) sequences, as determined by comparing the sequences. In a preferred embodiment, sequence identity is calculated based on the full length of two given SEQ ID NO or on part thereof. Part thereof preferably means at least 10%, 20%, 30%, 40%, 50%, 60%, 70%, 80%, 90%, or 100% of both SEQ ID NO. In the art, "identity" also means the degree of sequence relatedness between amino acid or nucleic acid sequences, as the case may be, as determined by the match between strings of such sequences.

"Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu;

Met to Leu or Ile; Phe to Met, Leu or Tyr; Ser to Thr; Thr to Ser; Trp to Tyr; Tyr to Trp or Phe; and, Val to Ile or Leu.

The NOD Mouse

NOD mice (Non-obese Diabetic) represent the main spontaneous mouse model to study the disease. This mouse model is characterized to develop diabetes without obesity, which is very similar to human T1D. The incidence of diabetes in NOD strain presents a marked difference depending on gender. At 30 weeks of age, the cumulative incidence of diabetic individuals is 60-80% in females and 20-30% in males NOD. The onset of diabetes occurs abruptly in both sexes, and usually begins after the age of 12-14 weeks, although it can occur at older ages. Diabetic symptoms are characterized biochemically by polyuria, polydipsia, hyperglycemia, hypercholesterolemia and glycosuria accompanied by a rapid loss of body weight. In no case a remission has been observed. However, the daily administration of insulin leads to increase body weight and prolongs the life of diabetic mice. The pathological examination of the pancreas shows a high frequency of infiltration of lymphocytes in the islets of Langerhans. Insulitis is present in both genders even in pre-diabetic stages (after 5 weeks) and progresses with age.

Multiple loci control genetic susceptibility to the development of diabetes in the NOD mouse. These mice show a unique haplotype for MHC, called H-$2^{g^7}$, which is the main genetic contribution to disease susceptibility. This MHC haplotype presents a series of defects that substantially alter the repertoire of peptides that can bind and be presented by MHC encoded by this allele. Surprisingly, a similar genetic alteration is also observed in genetic susceptibility loci to T1D of the MHC in humans. Besides MHC locus, many other loci contribute to the development of the disease, and they are called locus Idd.

In the NOD mouse, the antigen presenting cells against the islet appear first in the pancreatic lymph nodes at 2-4 weeks of age. Effector T cells present in nodules are activated and begin the process of autoimmunity against islets. At 4-6 weeks of age it can be observed a peri-vascular and peri-ductal accumulation of lymphocytes, and finally, at 6-8 weeks it appears infiltration to the islet perimeter (peri-insulitis). First, neurons and Schwann cells surrounding the islet are destroyed. T cells synthesize cytokines, particularly IFN-γ and propagate autoimmune reaction that intensifies the destruction of these cells until it breaks up the basal membrane of the islet. The infiltrating lymphocytes specifically destroy insulin-producing beta-cells.

Mononuclear cells present in the infiltrated islet in the NOD mouse, as in humans, are CD4+ and CD8+ autoreactive (dendritic cells, macrophages, NK, B cells). In the early stages of activation of autoimmune response macrophages and dendritic cells are predominant. During the peri-insulitis, islets are infiltrated mostly by CD4+ cells, whereas CD8+ cells are recruited at a later stage, when the mononuclear infiltrate penetrates the interior of the islet. The inflammation produced by this process culminates with the progressive destruction of beta-cells. When the mass of destroyed beta-cell reaches values around 80%, it is produced the clinical manifestation of diabetes. At this stage, the islets are characterized by having completely lost its component of beta-cells and for the regression of insulitis.

BRIEF DESCRIPTION OF THE DRAWINGS

Otherwise indicated IGF-1 refers to IGF-1a.

Figure 10A:
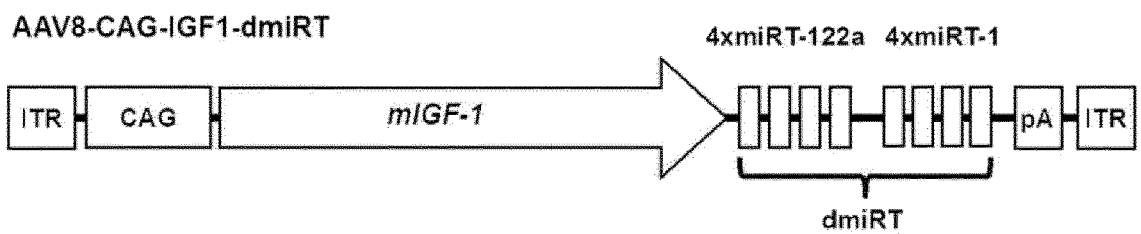
Figure 10B:
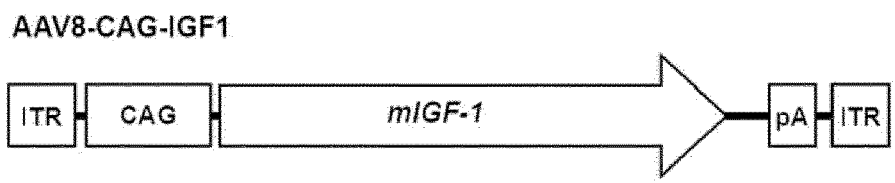
Figure 10C:

FIG. 10. Schematic diagram of the AAV8 vectors generated. (A) AAV8-CAG-IGF-1-dmiRT. Genome of the AAV8 vector expressing Igf-1 and the target sequences for the microRNA-122a and -1 (dmiRT). (B) AAV8-CAG-IGF-1. Genome of the AAV8 vector expressing Igf-1 without the dmiRT fragment. (C) AAV8-CAG-NULL. Genome of the AAV8 vector that does not encode any transgene. All the viral vectors contain the CAG promoter (hybrid cytomegalovirus enhancer/chicken (3-actin constitutive promoter) and the signal of polyadenylation (pA) flanked by the ITRs. The schematic representation is not to scale.

Figure 11:
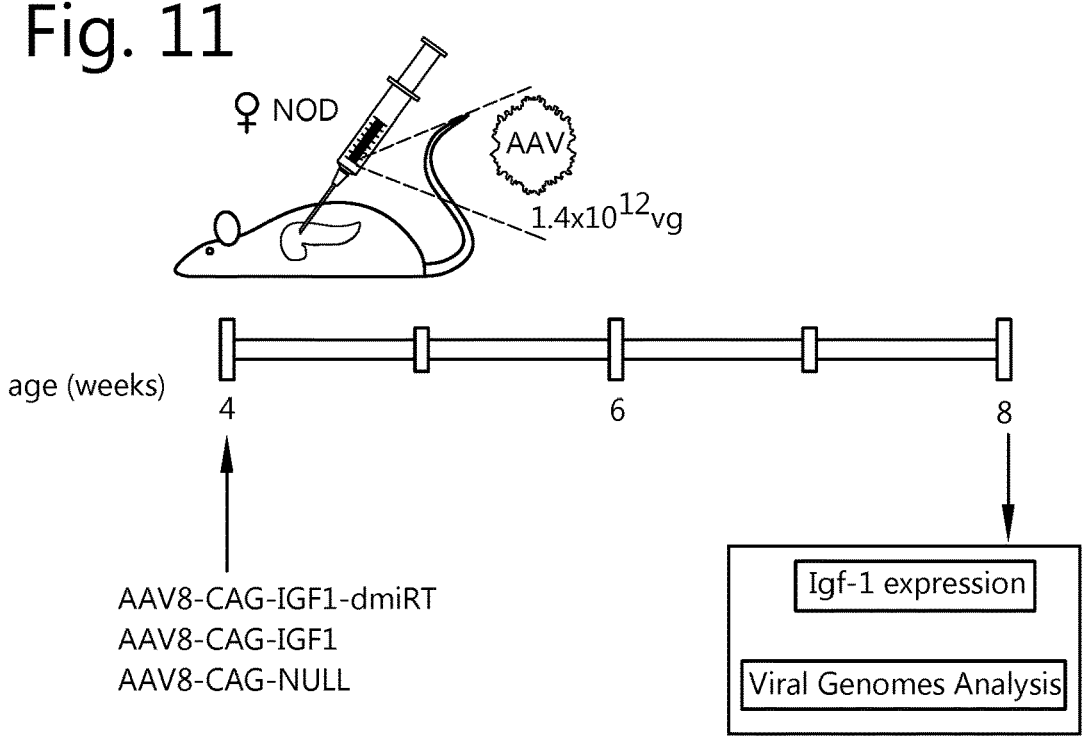

FIG. 11. Experimental design. Intraductal administration of AAV8-CAG-IGF-1-dmiRT, AAV8-CAG-IGF-1 and AAV8-CAG-NULL viral vectors in 4-week-old female NOD mice at a dose of $1.4 \times 10^{12}$ vg. The animals were killed 1 month post-injection and the expression of Igf-1 and viral genomes were analyzed.

Figure 12:
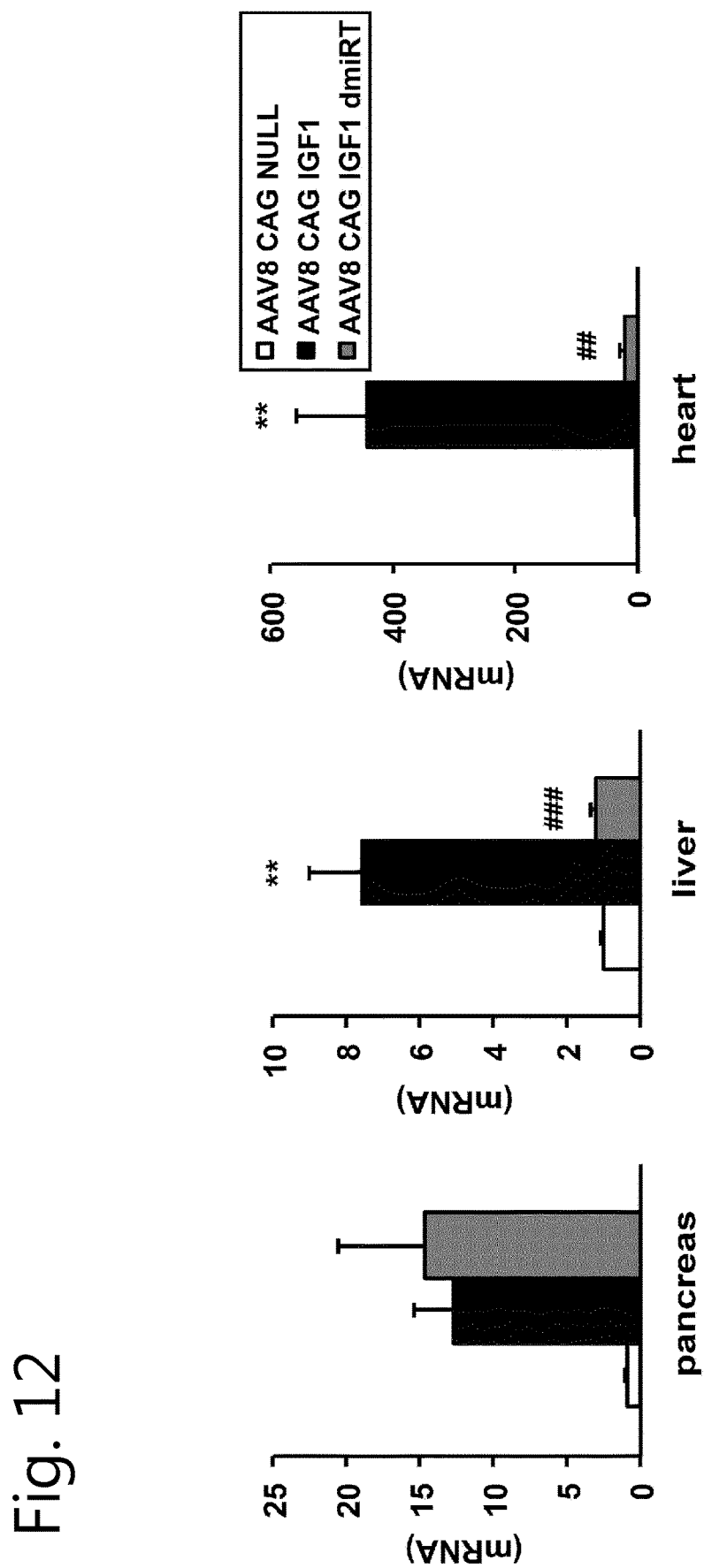

FIG. 12. In vivo testing of the AAV8-CAG-IGF-1-dmiRT viral vectors infectivity by intraductal administration in NOD mice. Igf-1 expression levels were quantified in pancreas, liver and heart RNA samples from NOD mice 1-month post-intraductal administration of $1.4 \times 10^{12}$ vg per mouse. Values are expressed in arbitrary units normalized for the Rplp0 gene and relative to AAV8-CAG-NULL group. Results are expressed as mean±SEM, n=4-5 animals per group. **p<0.01 vs. AAV8 CAG NULL; ##p<0.01 vs. AAV8 CAG IGF-1; ###p<0.001 vs. AAV8 CAG IGF-1.

Figure 13:
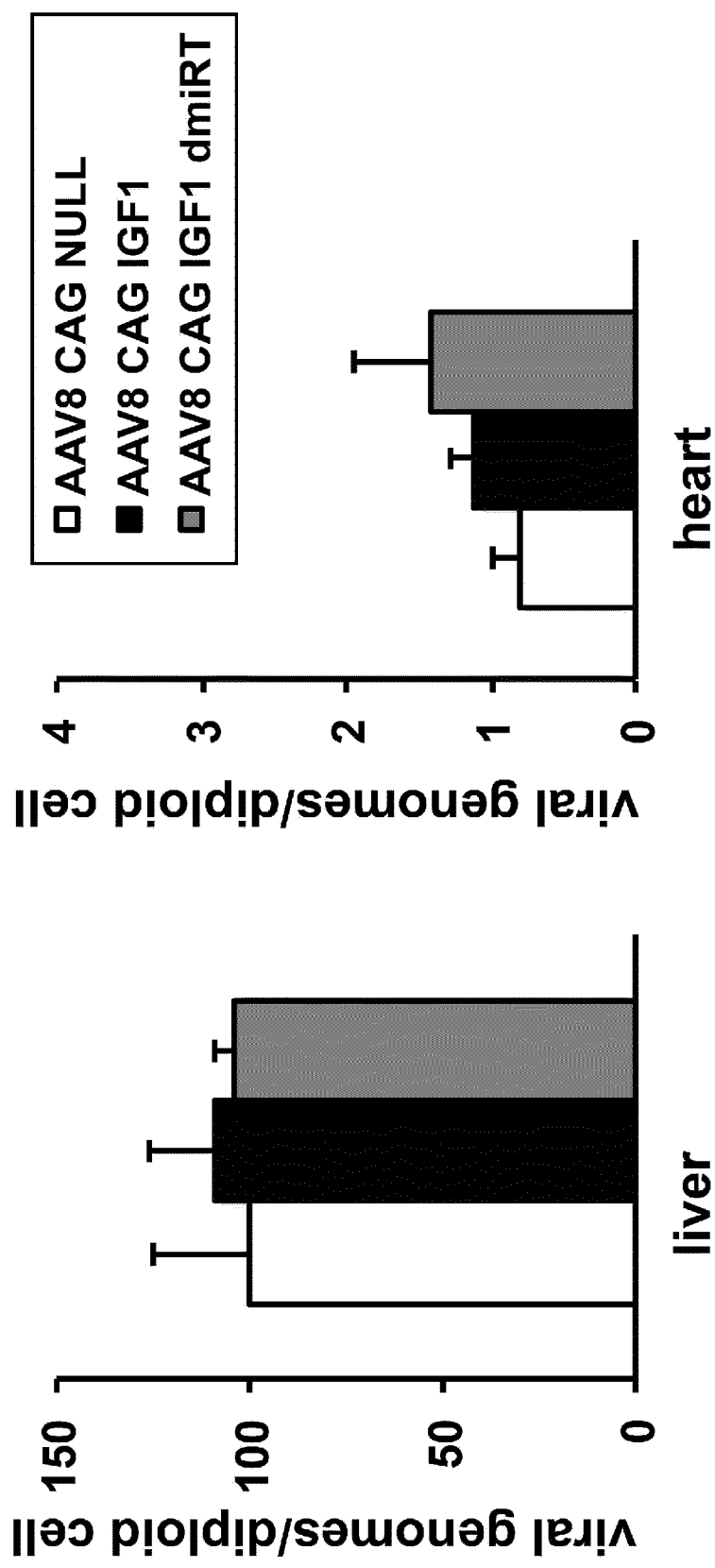

FIG. 13. Viral genome quantification in liver and heart. Viral genomes corresponding to AAV8-CAG-NULL, AAV8-CAG-IGF-1 and AAV8-CAG-IGF-1-dmiRT vectors were quantified by qPCR in liver and heart samples of NOD mice 1-month post-intraductal administration of $1.4 \times 10^{12}$ vg per mouse. Results are expressed as mean±SEM, n=4-5 animals per group.

Figure 14:
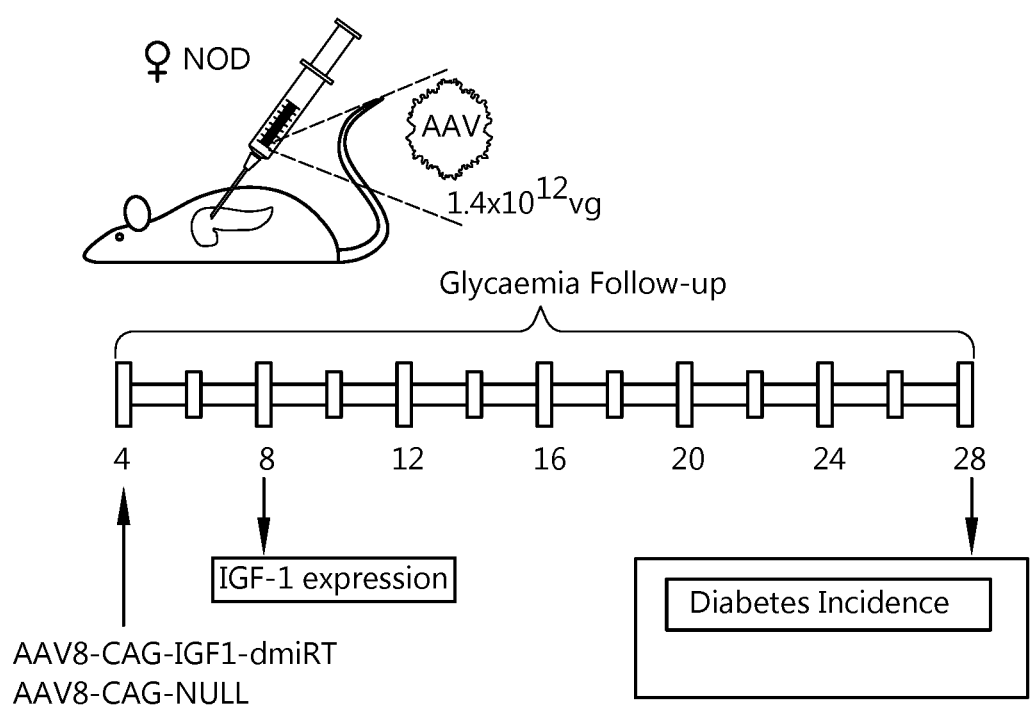

FIG. 14. Experimental design. Intraductal administration of AAV8-CAG-IGF-1-dmiRT and AAV8-CAG-NULL viral vectors in 4-week-old female NOD mice at a dose of $1.4 \times 10^{12}$ vg. Glycaemia was followed-up in treated mice until 28 weeks of age and diabetes incidence was determined.

Figure 15A:
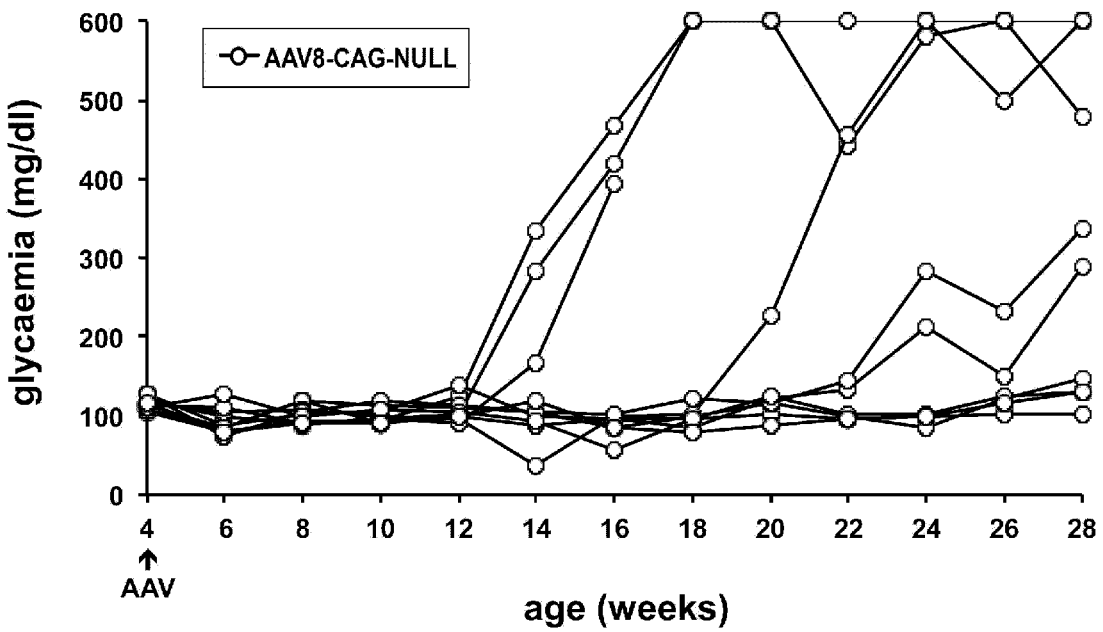
Figure 15B:
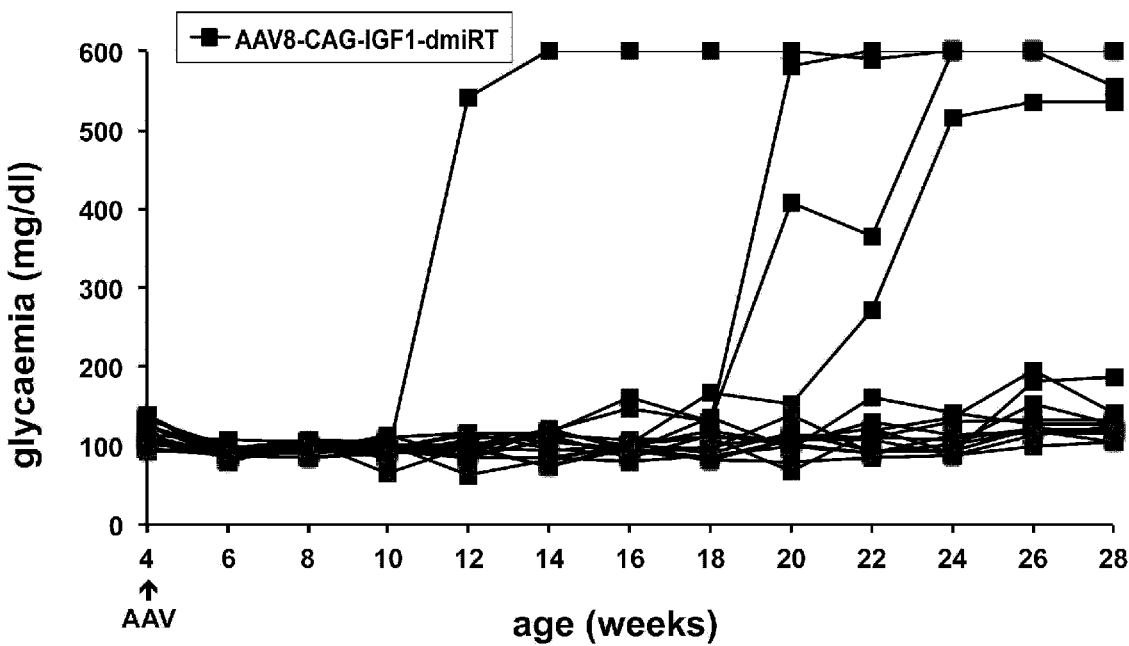

FIG. 15. Individual glycemic profiles in female NOD mice intraductally administered with AAV8 vectors. (A) Glycaemia follow-up in AAV8-CAG-NULL treated NOD mice. n=10. Due to the death of one hyperglycemic mouse, one of the blood glucose monitoring lines is discontinued from 16 weeks of age onwards. (B) Glycaemia follow-up in AAV8-CAG-IGF-1-dmiRT treated mice. n=16. The arrow indicates the age at which the corresponding viral vectors were administered (4 weeks). Results are expressed as mean±SEM.

Figure 16:
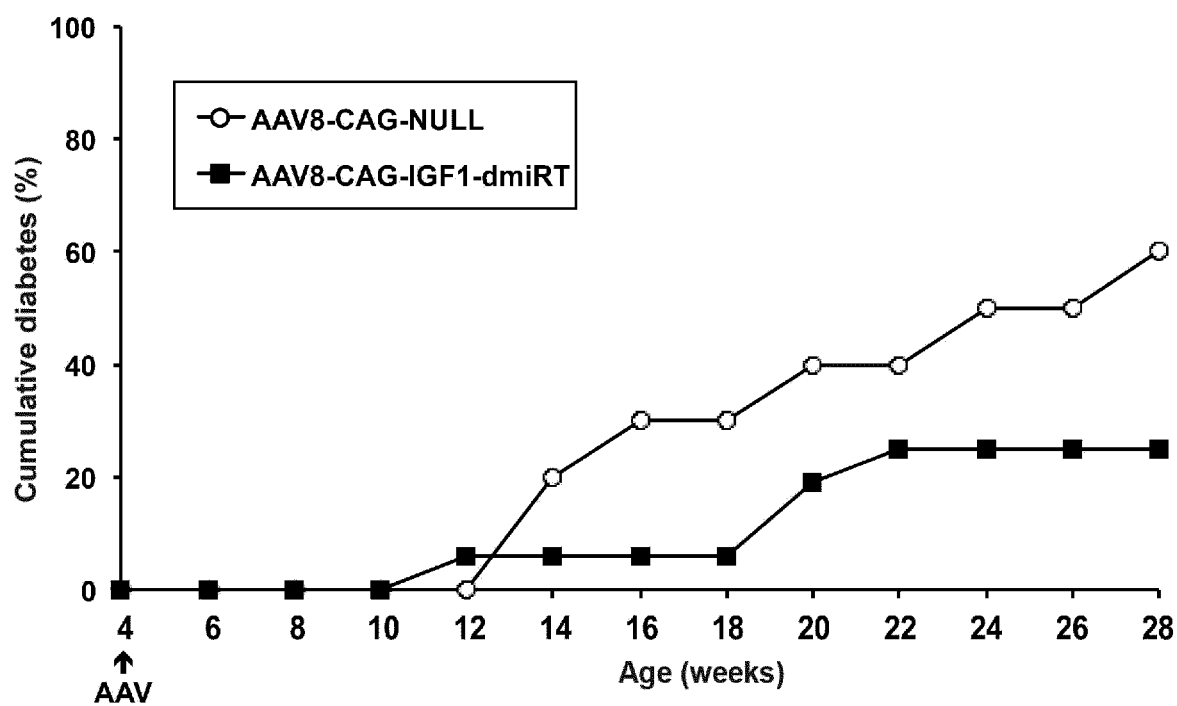

FIG. 16. Diabetes incidence in female NOD mice intraductally administered with AAV8 vectors. Mice were considered diabetic after two consecutives measurements of blood glucose ≥250 mg/dl. n=10 (AAV8-CAG-NULL); n=16 (AAV8-CAG-IGF-1-dmiRT). The arrow indicates the age at which the corresponding viral vectors were administered (4 weeks).

Figure 17B:
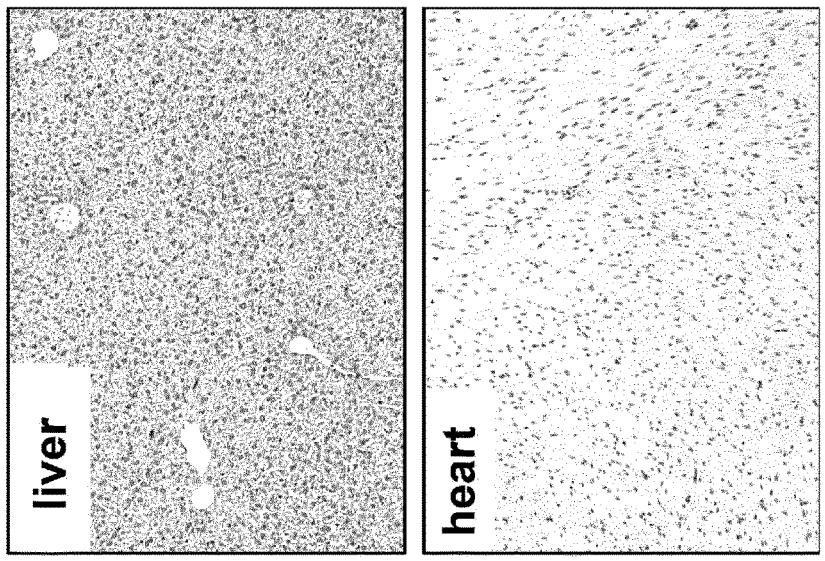
Figure 17A:
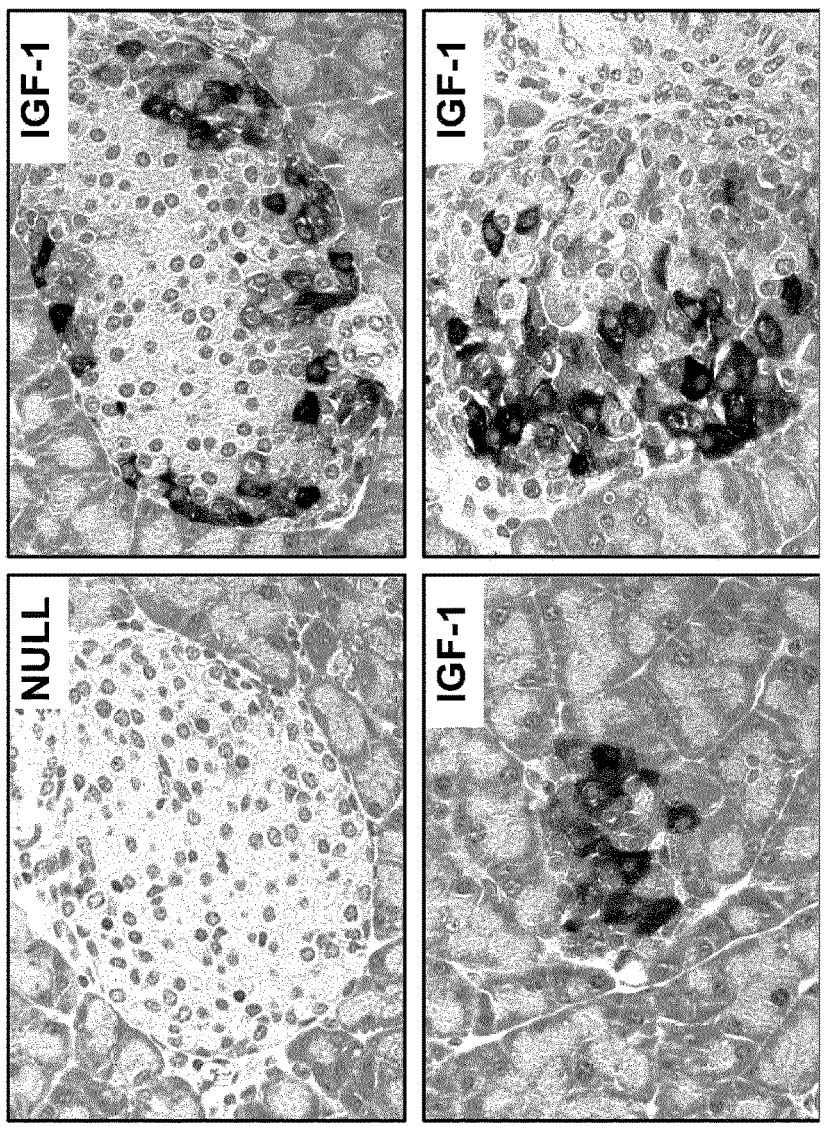

FIG. 17. Pancreas transduction in female NOD mice intraductally administered with the AAV8-CAG-IGF1-dmiRT vector. (A,B) Pancreas, liver and heart immunohistochemistry against IGF-1 in samples from NOD mice intraductally injected at 4 weeks of age with $1.4 \times 10^{12}$ vg and killed 1 month later. (A) Pancreatic islets transduction. NULL: AAV8-CAG-NULL; IGF-1: AAV8-CAG-IGF-1-dmiRT. Original magnification ×400. (B) Liver and heart representative image of AAV8-CAG-IGF1-dmiRT administered mice. Original magnification ×100.

FIG. 18. Intraductal delivery of AAV8-CAG-IGF-1a-dmiRT vectors protects NOD mice from autoimmune diabetes. (A) Immunohistochemical detection of IGF-1 (black) (upper panel) and double immunostaining of insulin (grey) and IGF-1 (black) (lower panel) in islets at 8 and 28 weeks of age; Original magnification ×400. (B-C) Igf1a gene expression was analyzed in isolated islets (B) and total pancreas (C) at 28 weeks of age (n=4-6). (D) Serum IGF-1 circulating levels at 28 weeks of age (n=8-10). Results are expressed as mean±SEM. *p<0.05 vs. AAV8-CAG-NULL.

Figure 19A:
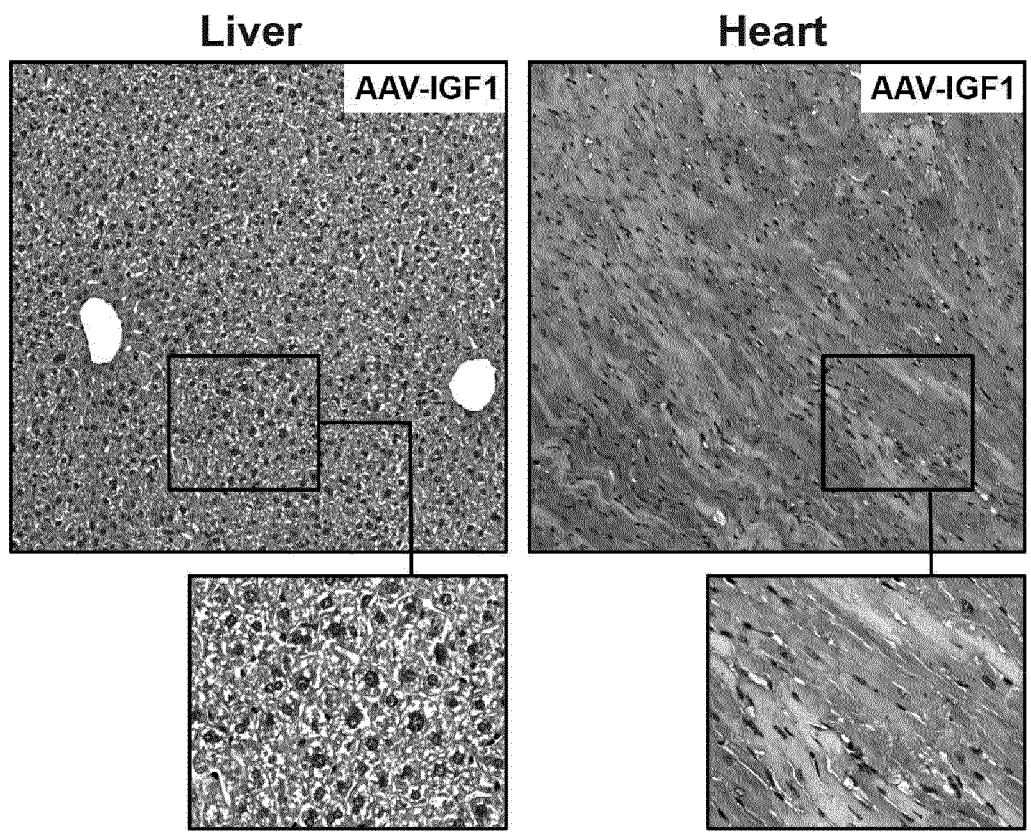
Figure 19B:
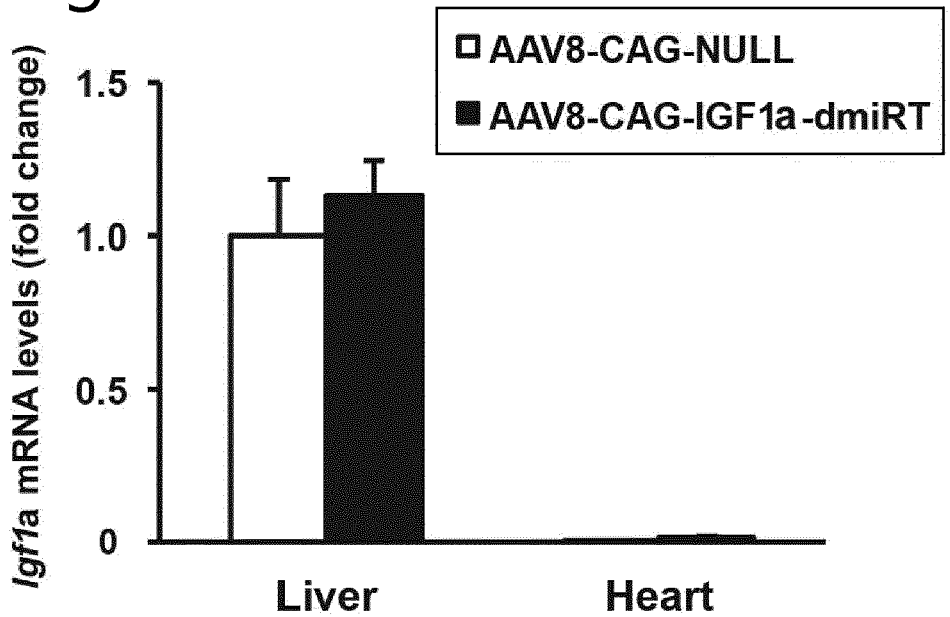

FIG. 19 Liver and heart IGF-1 overproduction is prevented in AAV8-CAG-IGF1a-dmiRT treated mice. (A) No IGF-1$^+$ cells were detected neither in the liver nor in the heart of 28-week-old NOD mice intraductally injected with $1 \times 10^{12}$ vg of AAV8-CAG-IGF-1a-dmiRT (AAV-IGF-1). Original magnification ×400 (insets ×1000). (B) Igf1a gene expression analysis in liver and heart of AAV8-CAG-IGF-1a-dmiRT and AAV8-CAG-NULL-treated mice at 28 weeks of age (n=9-10).

FIG. 20 AAV8-CAG-IGF1a-dmiRT treated mice show preservation of β-cell mass by protection against autoimmune attack. (A) Immunohistochemical analysis of insulin (brown) in pancreas from AAV8-CAG-NULL (AAV-NULL) and AAV8-CAG-IGF-1a-dmiRT (AAV-IGF-1) treated mice at 8 weeks and 28 weeks of age. NG: Normoglycemic HG: Hyperglycemic. (B) β-cell mass quantification. (n=3-5) (C) Insulitis score was quantified in normoglycemic mice at 8 and 28 weeks of age. (D) Fed serum concentration of insulin at 28 weeks of age. ND, Non-Detected. (E-F) Relative gene expression of pro-inflammatory cytokines (E) and antigen presenting molecules (F) in isolated islets from normoglycemic mice at 28 weeks of age (n=4-6). Results are expressed as mean±SEM. *p<0.05 vs. AAV8-CAG-NULL.

FIG. 21. Absence of miR-122a repression in the liver upon intraductal administration of AAV8 vectors bearing miRT-122a sequences. (A) Relative hepatic expression levels of target genes known to be regulated by endogenous miR-122a at 28 weeks of age. Gys1, glycogen synthase 1; AldoA, aldolase A/fructose-biphosphate; Slc7a1, solute carrier family 7; CcngI, cyclin G1. (B) Fed serum cholesterol levels at 28 weeks of age. NG: Normoglycemic. Results are expressed as mean±SEM (n=4-7).

Figure 22:
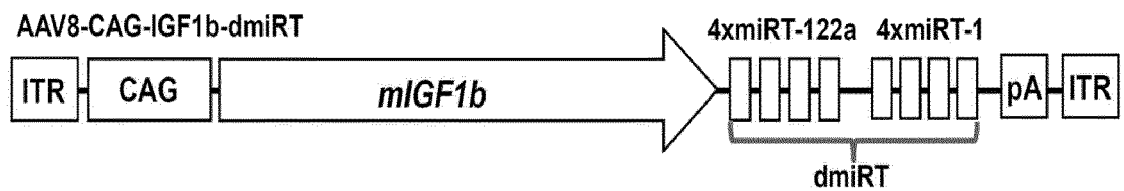

FIG. 22. Schematic representation of the AAV-CAG-IGF-1b-dmiRT expression cassette for the murine isoform IGF-1b. ITR: Inverted Terminal Repeats; CAG: hybrid promoter based on chicken beta-actin promoter and cytomegalovirus enhancer; mIGF-1b: sequence of murine IGF-1b (splicing isoform of pro-Igf-1, also called mechano-growth factor-MGF); miRT-122A: microRNA-122A target sequence (4 copies); miRT-1: microRNA-1 target sequence (4 copies); pA: poly A polyadenylation sequence. The abbreviated form dmiRT refers to microRNA target sequences for both 122A and 1.

FIG. 23. Intraductal delivery of AAV8-CAG-IGF-1b-dmiRT vectors protects NOD mice from autoimmune diabetes. (A) Cumulative diabetes incidence of NOD mice intraductally injected with $1.4 \times 10^{12}$ vg of AAV8-CAG-NULL or AAV8-CAG-IGF1b-dmiRT vectors at 4 weeks of age. (B) Individual glycemic profiles (n=10, AAV8-CAG-NULL; n=17, AAV8-CAG-IGF1b-dmiRT). (C) Immunohistochemical detection of IGF1 (black) (upper panel) in islets, liver and heart at 8 weeks of age; Original magnification ×400 (islets) and ×100 (liver, heart). AAV-NULL: AAV8-CAG-NULL; AAV-IGF-1b: AAV8-CAG-IGF-1b-dmiRT.

(D) Serum IGF-1 circulating levels at 28 weeks of age (n=8-10). Results are expressed as mean±SEM.

EXAMPLES

We developed an AAV8-mediated gene transfer strategy to overexpress IGF-1 specifically in the pancreas of NOD mice. In order to target β-cells as well as to maximize the number of acinar cells that would supply IGF-1 to β-cells, the ubiquitous CAG promoter was selected to drive IGF-1 expression (Otherwise indicated IGF-1 refers to IGF-1a).

Infectivity and Tropism of AAV8 Vectors into NOD Mouse Pancreas

Most studies examining the tropism of AAV vectors have been conducted in adult male individuals from healthy mouse strains (ICR, BALB/c, C57BL/6, etc.). However, the development of a gene therapy strategy for the prevention or treatment of diabetes in the spontaneous model NOD model requires the transfer of therapeutic genes in female individuals. At 4 weeks of age, NOD mice still preserve beta-cell mass, which is free of insulitis. It is from this age onwards that begins the process of infiltration of the islets and massive loss of beta-cells, culminating in the appearance of the disease. Therefore, 4-weeks-old would be a convenient time for the administration of candidate genes in NOD females to preserve beta-cell mass. One such candidate gene would be IGF-1.

Figure 1:
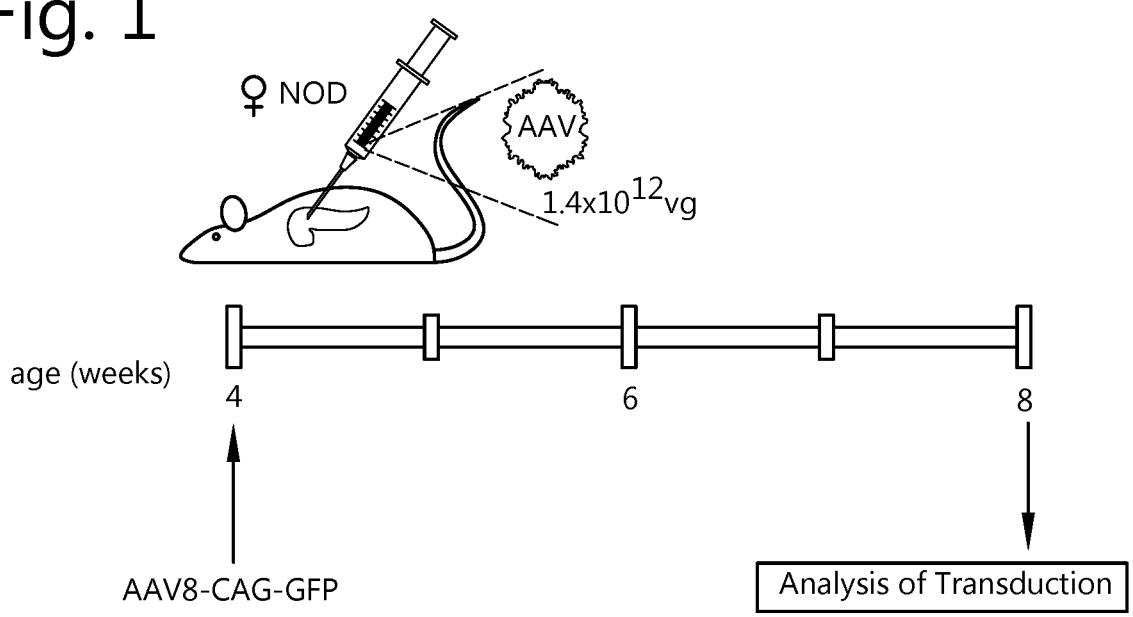
FIG. 1. Experimental design. Intraductal administration of the AAV8-CAG-GFP vector: AAV vector of serotype 8 encoding the green fluorescent protein GFP under the control of the CAG promoter (hybrid cytomegalovirus enhancer/chicken β-actin constitutive promoter).

1. Analysis of AAV8 Vector Transduction Locally Administered to 4-Week-Old Female NOD Mice We used a single-stranded AAV8 vector that overexpressed the green fluorescent protein (GFP) under the control of the ubiquitous promoter CAG (promoter hybrid based on the β-actin promoter of the cytomegalovirus enhancer and chicken) to asses the transduction of pancreatic islets from 4-week-old female NOD mice at a dose of $1.4 \times 10^{12}$ viral genomes (vg) (AAV8-CAG-GFP, viral vector comprising the sequence SEQ ID NO: 32). At one month post-injection animals were killed and tissue transduction was examined (FIG. 1).

1.1. Pancreas Transduction

Figure 2A:
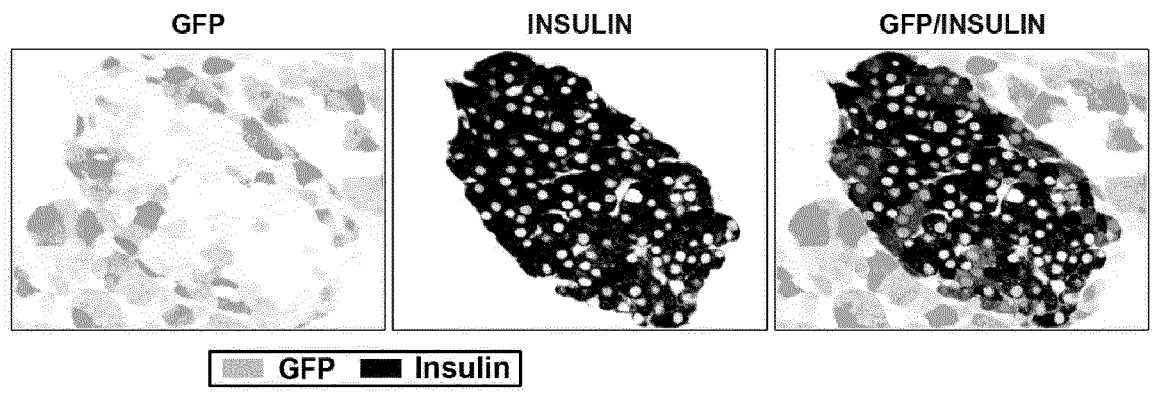
FIG. 2. Pancreas transduction of female NOD mice intraductally administered with the AAV8-CAG-GFP vector. Pancreas immunohistochemistry against GFP (grey) and insulin (black) in samples from mice injected intraductally with $1.4 \times 10^{12}$ vg at the age of 4 weeks and killed 1 month later. (A) Islet β-cell transduction. Original magnification ×400. (B) Exocrine pancreas transduction. Two representative images of the exocrine pancreas immunostained against GFP. Original magnification ×200.
Figure 2B:
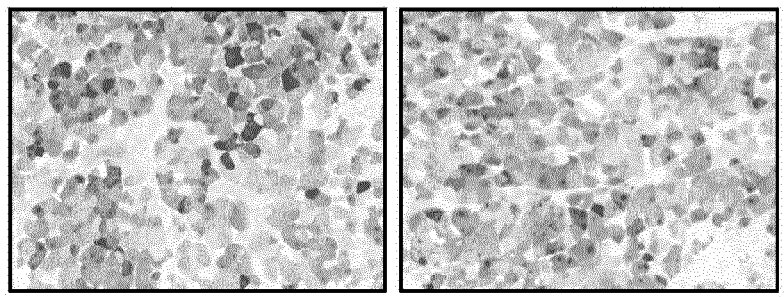

It was observed that female NOD mice locally injected in the pancreas with AAV8-CAG-GFP showed efficient transduction of beta-cells of the islets and a wide distribution of the vector in the exocrine pancreatic tissue (FIG. 2), similar to what had been described in other animal models (Jimenez et al., 2011). Transduction of pancreatic islets was examined by double immunohistochemical staining against GFP and against insulin (FIG. 2A). In addition, it was observed that the dose administered allowed the transduction of mostly the periphery of the islet cells but also cells from the core.

1.2. Transduction of Peripheral Tissues

It has been described that when AAV8 vectors are administered locally by intraductal injection in the pancreas, part of the burden of the administered viral vector is able to reach the systemic circulation and transduce non-pancreatic tissues, mainly the liver and heart (Jimenez et al., 2011). Thus, the use of ubiquitous promoters such as CAG promoter, allows expression of the gene construct carried in the AAV8 vector in the heart and liver of intraductally injected mice.

Figure 3:
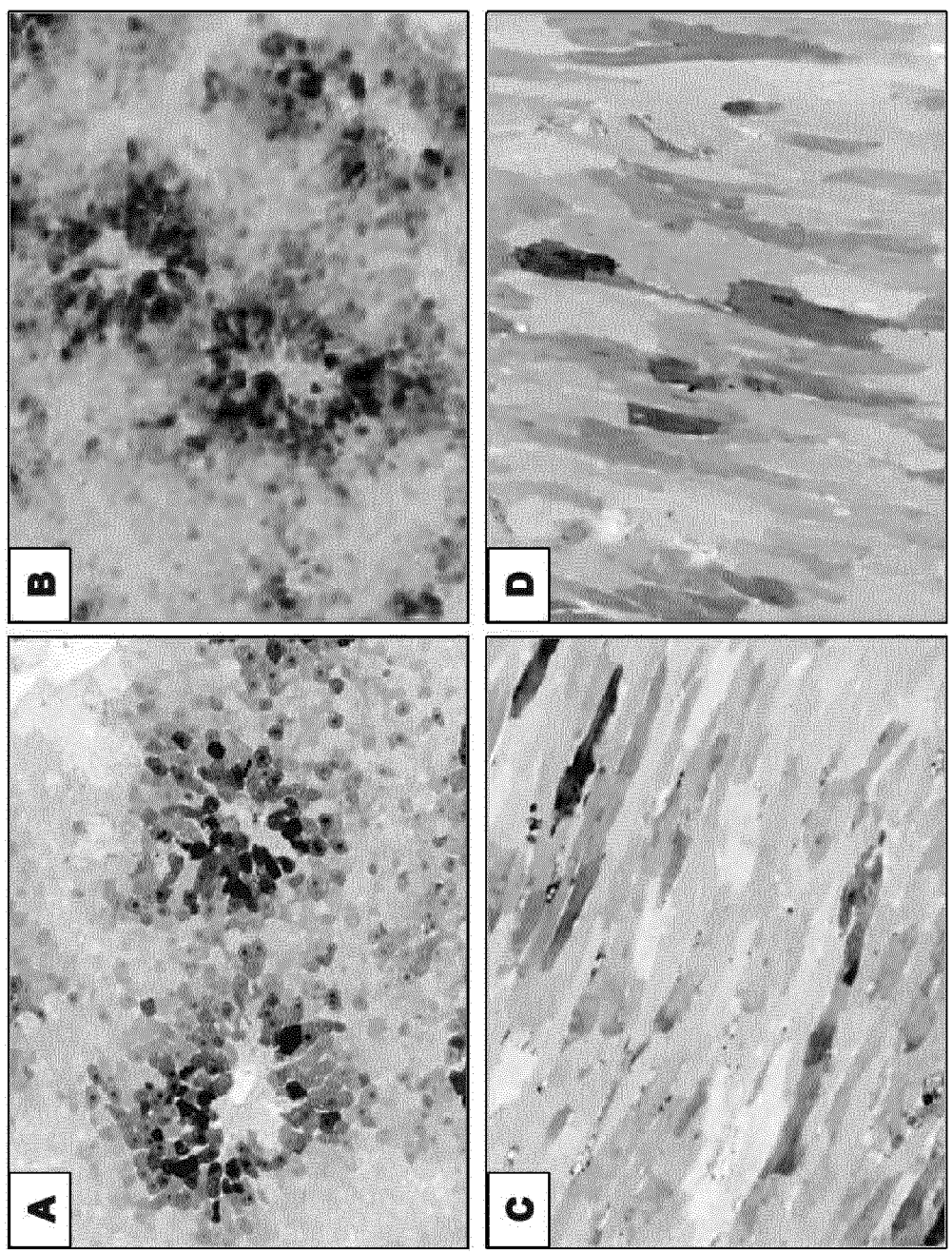
FIG. 3. Liver and heart transduction of female NOD mice intraductally administered with the AAV8-CAG-GFP vector. Samples from mice injected intraductally with $1.4 \times 10^{12}$ vg at the age of 4 weeks and killed 1 month later. (A,B) Liver immunohistochemistry against GFP. Original magnification ×100. (C,D) Heart immunohistochemistry against GFP. Original magnification ×200.

The histological analysis of these tissues in female NOD mice injected with AAV8-CAG-GFP vectors confirmed the expression of green fluorescent protein GFP in liver and heart. Hepatocyte transduction was mostly detected around the central venules of the liver (FIG. 3).

1.3. Modulation of AAV Tropism by Means of microRNA Target Sequences

To preclude transgene expression in liver and heart and restrict AAV8-mediated transgene overexpression to the pancreas, we took advantage of the microRNAs (miRs) regulation network. miRs are small RNA sequences that negatively regulate mRNAs through effects on the stability and translation of mRNA transcripts (Bartel, 2004). Thus, by incorporating target sites for a specific miR (miRTs) into the 3'-UTR of a transgene, its expression is inhibited in cells in which that miR is highly expressed (Brown and Naldini 2009). In this work, the highly expressed liver-specific microRNA-122a (miR-122a) and heart-specific microRNA-1 were selected to modulate AAV tropism.

1.3.1. Analysis of the Expression of microRNA-122a in the Liver of NOD Mice

To validate the incorporation of the target sequence for the microRNA-122a (miRT-122a) into the AAV construct as a strategy to block the expression of the transgene in the liver, the levels of expression of miR-122a were assessed in female NOD mice. This study was conducted in pre-diabetic individuals (normoglycemic) and individuals at the stage of overt diabetes (hyperglycemia) to study whether there were changes in the hepatic expression of miR-122a during the progressive advancement of the disease. In addition, we also analyzed the expression of miR-122a in the pancreas of NOD mice to rule out possible interference of transgene expression in the tissue of interest due to the presence of miRT-122a sequences in the AAV construct.

Figure 4:
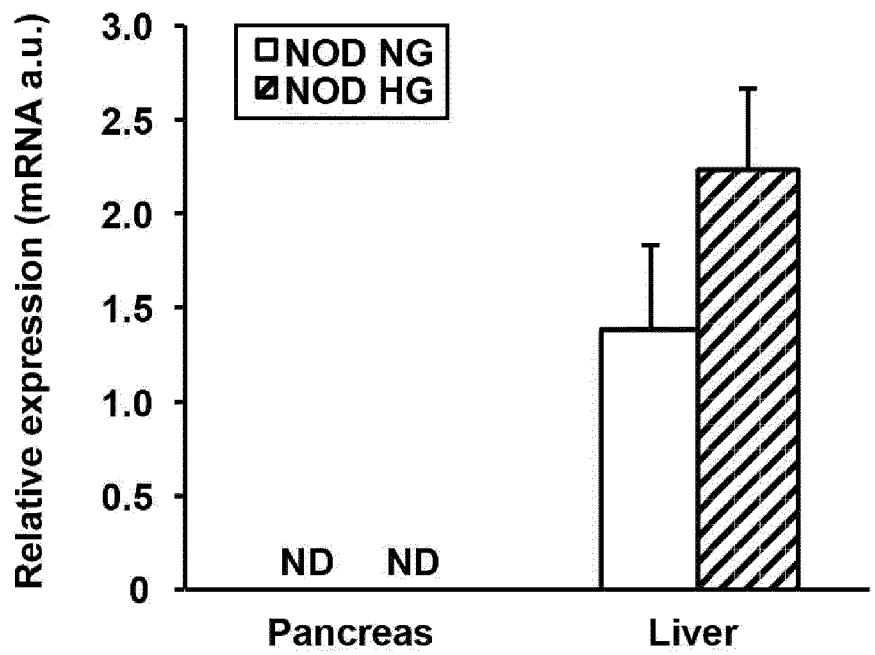
FIG. 4. Expression of microRNA-122a in pancreas and liver. The levels of expression of microRNA-122a (miR-122a) were quantified by qPCR in pancreas and liver samples from female NOD mice. 8-week-old normoglycemic (NG) and 24-week-old hyperglycemic (HG) animals were analyzed. Results are expressed as mean±SEM, n=4-6 animals per group. ND: Non-Detected. a.u.: arbitrary units.

As expected, miR-122a expression was only detected in the liver of NOD animals. In addition, it was observed that the expression levels of miR-122a in the liver were higher in diabetic NOD mice compared with pre-diabetic individuals, although the differences did not reach statistical significance (FIG. 4). This could be due to the role of miR-122a in lipid metabolism in the liver (Esau et al., 2006), which is altered in diabetic mice. In any case, this suggested that even disease progression in NOD mice, the inhibition of the AAV construct in the liver would be sustained, or even increased. However, there was no significant detectable levels of expression of miR-122a in the pancreas, regardless of the stage of diabetic animal.

1.3.2. Analysis of the Expression of microRNA-1 in the Heart of NOD Mice

Figure 5:
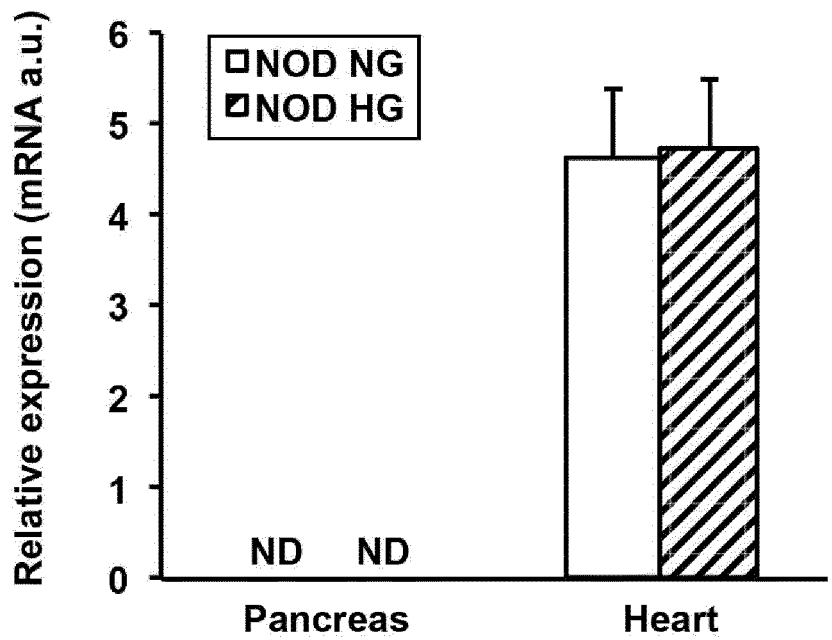
FIG. 5. Expression of microRNA-1 in pancreas and heart. The levels of expression of microRNA-1 (miR-1) were quantified by qPCR in pancreas and heart samples from female NOD mice. 8-week-old normoglycemic (NG) and 24-week-old hyperglycemic (HG) animals were analyzed. Results are expressed as mean±SEM, n=4-6 animals per group. ND: Non-Detected. a.u.: arbitrary units.

Similarly, to validate the use of the target sequence for the microRNA-1 (miRT-1) as a strategy to block the expression of the transgene carried in the AAV vector specifically in the heart, it the levels of expression of miR-1 were assessed in pre-diabetic (normoglycemic) female NOD mice and NOD mice at the phase of overt diabetes (hyperglycemic). In addition, we also analyzed the expression of miR-1 in the pancreas to rule out possible interference of the expression of the transgene in this tissue. The results showed that miR-1 was expressed in the heart of NOD animals at similar levels regardless of the diabetic stage. Regarding the pancreas, expression of miR-1 was not detected for any of the conditions tested (FIG. 5).

Thus, the use of an AAV8 vector intraductally administered to 4-week-old NOD mice would be an appropriate approach to direct the expression of a transgene as IGF-1 in the pancreas of NOD mice. In addition, the incorporation of the target sequences miRT-122a and miRT-1 in the 3'-UTR region of the AAV construct may be an effective strategy to block the expression of the transgene in undesired tissues, such as liver and heart without altering the levels of expression in the pancreas. Thereby, overexpression of IGF-1 locally in the pancreas would be achieved. Moreover, the inhibition of transgene expression provided by the recognition of miRT-122a and miRT-1 in the liver and heart, respectively, would not be altered during diabetes progression in NOD mice.

1.4. Construction of an Adeno-Associated Viral Vector Encoding Murine IGF-1

Figure 6:
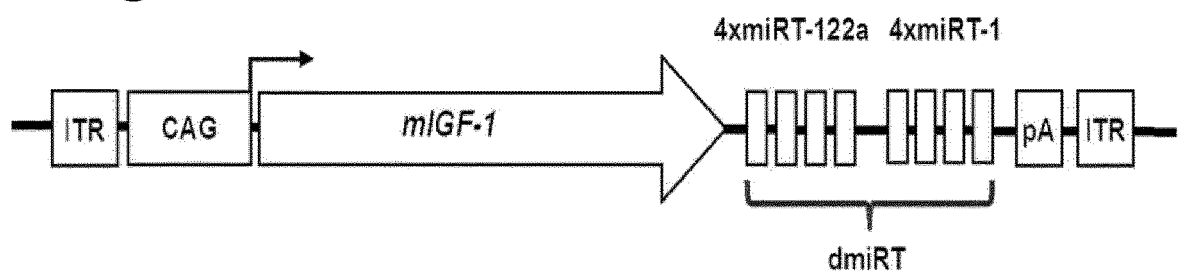
FIG. 6. Schematic diagram of the construct encoding murine IGF-1 protein pAAV-CAG-IGF1-dmiRT. ITR: Inverted Terminal Repeats; CAG: hybrid cytomegalovirus enhancer/chicken β-actin constitutive promoter; mIGF-1: murine sequence of the Igf-1 gene; miRT-122a: target sequence of the microRNA-122a (4 copies); miRT-1: target sequence of the microRNA-1 (4 copies); pA: poly A, polyadenylation signal. The abbreviated form dmiRT refers to both target sequences for microRNA-122a and -1.

A construct for producing AAV8 vectors capable of directing the overexpression of IGF-1 specifically in the pancreas of NOD female individuals was prepared. With the aim of achieving high levels of overexpression of the transgene and transduce the largest possible number of cells in the pancreas, the ubiquitous CAG promoter was used. With the aim of blocking the expression of IGF-1 in undesired tissues such as liver or heart, four copies of the target sequence of the liver-specific miR-122a and four copies of the target sequence of the heart-specific miR-1 totally complementary (pAAV-CAG-IGF-1-4xmiRT122a-4xmiRT1, SEQ ID NO: 30 or SEQ ID NO: 31) were introduced in the region 3'-UTR of the construct. To simplify the nomenclature of the construct, the term dmiRT was used to refer to the presence of four copies of the target sequence for both microRNA-122A and -1 (pAAV-CAG-IGF-1-dmiRT) (FIG. 6).

1.4.1. Checking the Expression of the Construct pAAV-CAG-IGF-1-dmiRT In Vitro and In Vivo.

Before producing the serotype 8 viral vectors AAV8-CAG-IGF-1-dmiRT the in vitro expression of the generated construct pAAV-CAG-IGF-1-dmiRT was verified. To this end, INS-1 cells (from rat insulinoma) and C2C12 cells (mouse myoblasts) were transfected and the levels of IGF-1 were quantified. Furthermore, the expression construct pAAV-CAG-IGF-1-dmiRT was also evaluated in vivo by hydrodynamic administration to ICR mice.

1.4.1.1. Transfection of the Construct pAAV-CAG-IGF-1-dmiRT into INS-1 Cells

Figure 7:
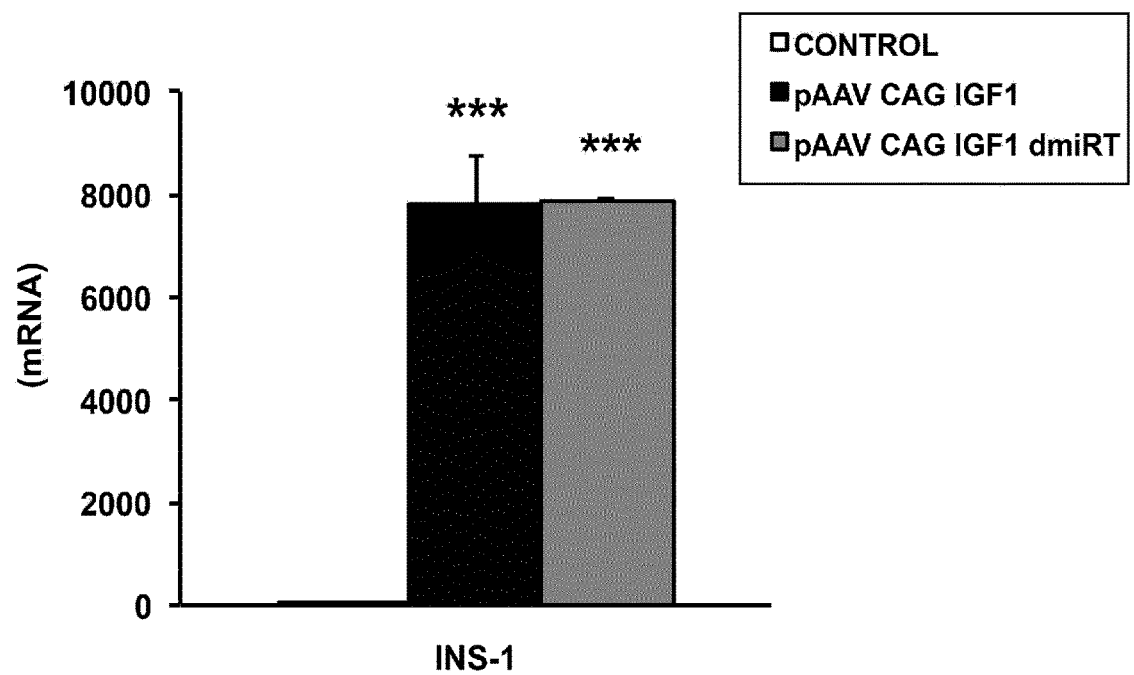
FIG. 7. In vitro testing of the plasmid pAAV-CAG-IGF1-dmiRT expression in INS-1 cells. Igf-1 expression levels 48 h post-transfection. 12-well culture plates were used and each well was transfected with 1 μg of DNA. Control wells were not transfected with any DNA. Values are expressed in arbitrary units normalized for the Rplp0 gene and relative to control group. Results are expressed as mean±SEM, n=3 wells per condition. ***p<0.001 vs. CONTROL.

INS-1 cells were transfected with plasmid pAAV-CAG-IGF-1-dmiRT (SEQ ID NO: 30 or SEQ ID NO: 31) to evaluate whether the generated construct correctly expressed IFG-1. In addition, in order to assess the possible influence of target sequences of microRNAs 122A and 1 in the expression of the construct, INS-1 cells were also transfected with a vector containing the same expression cassette without the target sequences of microRNAs 122A and 1 (pAAV-CAG-IGF-1, SEQ ID NO: 33). At 48 hours post-transfection, the mRNA was isolated from the cells and the levels of IFG-1 quantified by PCR. The result showed a high expression of IGF-1 transcript in transfected cells compared to control cells not transfected, thus verifying the functionality of the generated expression vector. In addition, the levels of overexpression of IGF-1 from construct pAAV-CAG-IGF-1-dmiRT were indistinguishable from the levels obtained with the construct pAAV-CAG-IGF-1 (SEQ ID NO: 33) (FIG. 7). These data indicated that the plasmid was functional in vitro and that the target sequences of microRNAs 122A and 1 did not interfere with the expression of IGF-1 in INS-1 cells.

1.4.1.2. Transfection of the Construct pAAV-CAG-IGF-1-dmiRT into C2C12 Cells: Functionality of the Target Sequence of the microRNA-1

Figure 8:
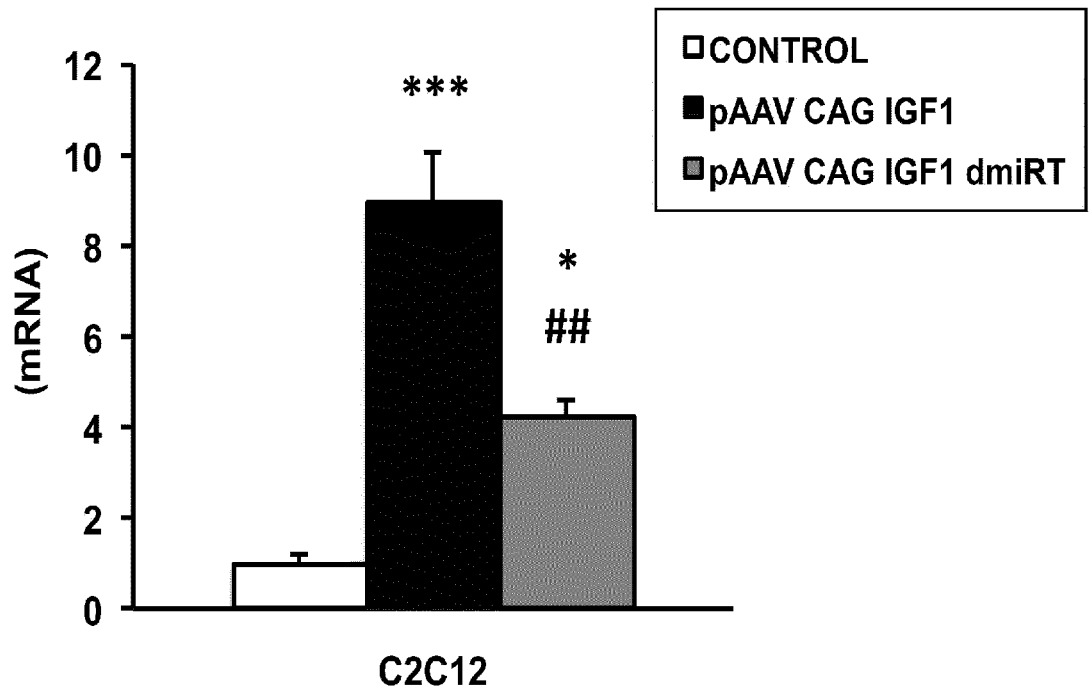
FIG. 8. In vitro testing of the plasmid pAAV-CAG-IGF1-dmiRT expression in C2C12 cells. Igf-1 expression levels 6 days post-transfection and post-induction of the differentiation process of the cells. 6-well culture plates were used and each well was transfected with 4 μg of DNA 6 h before the initiation of the differentiation process. Control wells were not transfected with any DNA. Values are expressed in arbitrary units normalized for the Rplp0 gene and relative to control group. Results are expressed as mean±SEM, n=3 wells per condition. *p<0.05 vs. CONTROL; ***p<0.001 vs. CONTROL; ##p<0.01 vs. pAAV CAG IGF1.

C2C12 cells, an immortalized line of mouse myoblasts, proliferate rapidly under conditions of high concentration of serum, and differentiate and fuse into myotubes in low serum concentration. In order to check the functionality of the target sequence of microRNA-1 in the construct pAAV-CAG-IGF-1-dmiRT, C2C12 cells were transfected and the differentiation process of these cells was induced. To assess the effect of the microRNA target sequence-1 in the construct, cells were also transfected with plasmid pAAV-CAG-IGF-1. After six days of transfection and having induced differentiation to myotubes, mRNA was isolated from the cells and the levels of Igf-1 quantified by PCR. The results showed a marked overexpression of Igf-1 in C2C12 cells transfected with plasmid pAAV-CAG-IGF-1. However, the presence of the target sequence of microRNA-1 in the plasmid construct pAAV-CAG-IGF-1-dmiRT caused a decrease of approximately 50% in the expression of IGF-1 compared to the levels obtained from construct pAAV-CAG-IGF-1 (FIG. 8). These results validate the use of microRNA target sequence-1 to reduce the levels of Igf-1 in muscle cells.

1.4.1.3. Hydrodynamic Administration of the Construct pAAV-CAG-IGF-1-dmiRT in ICR Mice: Functionality of the Target Sequence of the microRNA-122a in Liver.

The cell line mainly used for the in vitro study of liver tissue, cells derived from a hepatocellular carcinoma HepG2, do not express the microRNA-122a. Therefore, to assess the functionality of the target sequence of microRNA-122A, expressed in the liver, and validate the expression construct pAAV-CAG-IGF-1-dmiRT in vivo, an hydrodynamic injection of plasmid in mice ICR was carried out. The hydrodynamic administration through the tail vein (HTV injection) of plasmid DNA is an invaluable tool for gene transfer in mouse. It consists of a fast injection, in about 5 seconds, of a saline solution containing the plasmid DNA in a volume equivalent to 8-10% of body weight of the mouse. ICR male mice of 8 weeks of age were administered by HTV injection with the construct pAAV-CAG-IGF-1-dmiRT. To compare the effect of the microRNA target sequence-122A, animals were also injected with pAAV-CAG-IGF-1 plasmid. The control group was administered with saline solution without any plasmid.

Figure 9:
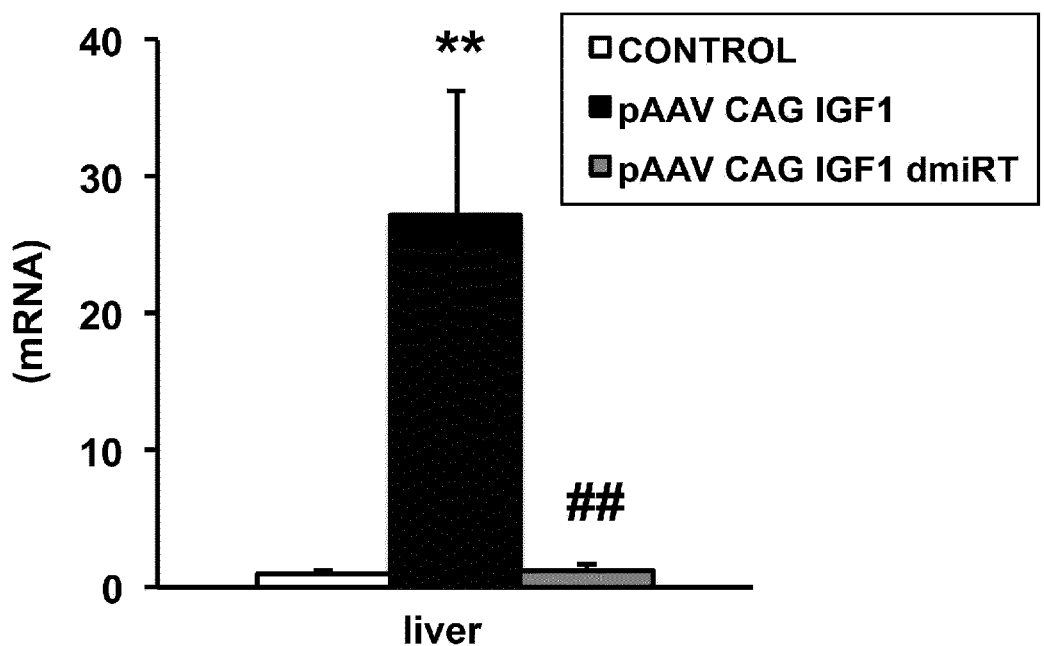
FIG. 9. In vivo testing of the plasmid pAAV-CAG-IGF-1-dmiRT expression by hydrodynamic administration in ICR mice. Igf-1 expression levels in the liver 24 h post-hydrodynamic administration of 20 μg of DNA diluted in saline. Control animals were administered with saline. Values are expressed in arbitrary units normalized for the Rplp0 gene and relative to control group. Results are expressed as mean±SEM, n=3-5 male mice per group. **p<0.01 vs. CONTROL; ##p<0.01 vs. pAAV CAG IGF.

At 24 hours post-administration, the liver was recovered, hepatocytes mRNA was isolated and the levels of Igf-1 were quantified by quantitative PCR. The results showed that the presence of the microRNA-122a target sequence in the construct pAAV-122A-CAG-IGF-1-dmiRT was able to completely block Igf-1 expression in the liver of mice. In contrast, in animals injected with plasmid pAAV-CAG-IGF-1 a marked overexpression of Igf-1 was obtained in this tissue (FIG. 9). These results indicated that the expression vector pAAV-CAG-IGF-1-dmiRT was also functional in vivo and validated the use of the microRNA target sequence-122A to reduce the levels of Igf-1 in liver cells.

1.4.2. Production of Vectors AAV8-CAG-IGF-1-dmiRT for the Gene Transfer in Pancreas of NOD Mice Once validated the expression of the construct pAAV-CAG-IGF-1-dmiRT validated both in vitro and in vivo, the production of vectors AAV of serotype 8 AAV8-CAG-IGF-1-dmiRT was carried out. In addition, to confirm that the target sequences of microRNAs 122A and 1-contained in AAV8-CAG-IGF-1-dmiRT were also functional in the NOD mouse and did not alter the expression in the pancreas, vectors encoding the same expression construct without the dmiRT fragment (AAV8-CAG-IGF-1) were generated. Finally, in order to rule out any effect produced by the administration of a vector AAV8, vectors not encoding any transgene (AAV8-CAG-NUL, vector comprising SEQ ID NO: 34) were also generated (FIG. 10). All-viral vectors AAV8-CAG-IGF-1-dmiRT, AAV8-CAG-IGF and AAV8-CAG-NUL were produced using the system triple transfection in HEK-293 cells as specified in Material and Methods section. Once generated, they were administered to NOD mice to evaluate their infectivity.

1.4.2.1. In Vivo Analysis of Infectivity and Expression of Vectors AAV8-CAG-IGF-1-dmiRT in NOD Mice Female NOD mice of 4 weeks old were intraductal administered with vectors AAV8-CAG-IFGF-1-dmiRT, AAV8-CAG-IGF-1 and AAV8-CAG-NUL at a dose of 1.4× $10^{12}$ vg (vg: viral genomes) per animal to assess their infectivity. One month post-administration, the animals were killed and samples were extracted from the pancreas, liver and heart to quantify the expression of Igf-1 and the presence of viral genomes in these tissues (FIG. 11).

Quantitative PCR analysis of the expression of Igf-1 in pancreas showed a significant increase in Igf-1 mRNA both in animals administered with vectors AAV8-CAG-1IGF1 and in animals with AAV8-CAG-IGF1-dmiRT, compared with the control group injected with the vector AAV8-CAG-NUL. In addition, levels of overexpression in pancreas were similar between the two groups, which corroborated the non-interference of sequences miRT-122a and miRT-1 in the expression of the transgene. However, when measuring the expression of Igf-1 in liver and heart, only increased levels of Igf-1 mRNA were detected in animals injected with the vectors AAV8-CAG-IGF-1. Animals that were administered with the vector containing the target sequences of microRNAs 122A and 1 (AAV8-CAG-IFG-1-dmiRT) showed levels of Igf-1 expression similar to those obtained in animals injected with the vector AAV8-CAG-NUL (FIG. 12).

To confirm that the reduced expression of Igf-1 in liver and in heart of animals injected with the vector AAV8-CAG-IGF-1-dmiRT was not due to a different infectivity of viral preparations AAV8-CAG-IGF-1 and AAV8-CAG-IGF-1-dmiRT, a quantification of viral genomes in these tissues was done. The presence of viral genomes was determined by quantitative PCR, as specified in the Materials and Methods section. The result allowed to observe similar levels of viral genomes present in liver and in heart of the animals injected, regardless of the viral preparation. This indicated that the viral preparations AAV8-CAG-IGF-1-dmiRT, AAV8-CAG-IGF-1 and AAV8-CAG-NUL, administered at the same dose, had a similar infectious power in liver and heart in animals injected intraductally. Therefore, this confirmed that the lower Igf-1 expression observed in these tissues was due to the presence of the target sequences of the microRNA-122A, in liver, and of the microRNA-1 in heart, in the vector AAV8-CAG-IGF-1-dmiRT. In addition, it was observed that the tropism of vectors AAV8 was much higher in the liver, compared with the heart, where a much lower amount of viral genomes per cell was found (FIG. 13).

These results confirmed that the presence of the sequence of recognition of miR-122A, in liver, and miR-1 in heart, in the construct AAV8-CAG-IGF-1-dmiRT, blocked the expression of Igf-1 induced by vector AAV8 in the tissues mentioned. Thus, the vector AAV8-CAG-IGF-1-dmiRT administered intraductal represented an appropriate strategy to direct the overexpression of Igf-1 locally in pancreas of NOD mice.

2. Study of Prevention of Diabetes in NOD Mice Administered with Vector AAV8-CAG-IGF-1-dmiRT To examine whether AAV-mediated specific pancreatic overexpression of Igf1 may prevent the development of autoimmune diabetes, $1\times10^{12}$ vg of AAV8-CAG-IGF-1-dmiRT vectors were intraductally delivered to 4-week-old NOD mice. Control NOD mice received the same dose of non-coding AAV8-CAG-NULL vectors (FIG. 14). Long-term follow-up of blood glucose levels in AAV8-CAG-IGF-1-dmiRT treated mice revealed that whereas 60% of the animals in the control group became diabetic by 28 weeks of age, 75% of the IGF-1-treated mice remained normoglycemic (FIG. 15-16).

2.1. IGF-1 Expression in Animals Administered with AAV8-CAG-IGF-1-dmiRT

One month after intraductal administration of AAV8-CAG-IGF-1-dmiRT vectors IGF-1 overexpression was found in the pancreas of NOD mice. Islets of animals treated with AAV8-CAG-IGF-1-dmiRT vectors showed a clear overexpression of IGF-1 compared to the islets of animals administered with AAV8-CAG-NULL vectors. Immunohistochemical staining against IGF-1 in the pancreas did not allowed to observe transduction of acinar cells possibly due to the rapid secretion of IGF-1. On the other hand, IGF-1 overproduction was not detected in the liver or the heart of animals administered with AAV8-CAG-IGF-1-dmiRT vectors (FIG. 17).

Figure 18C:
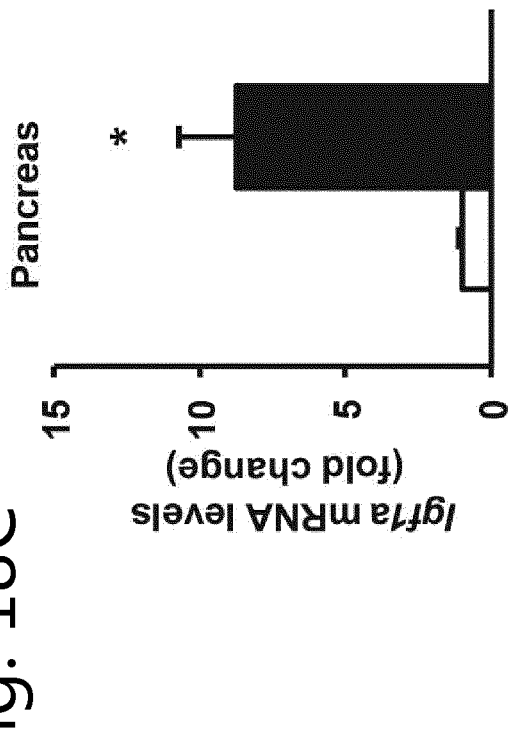
Figure 18B:
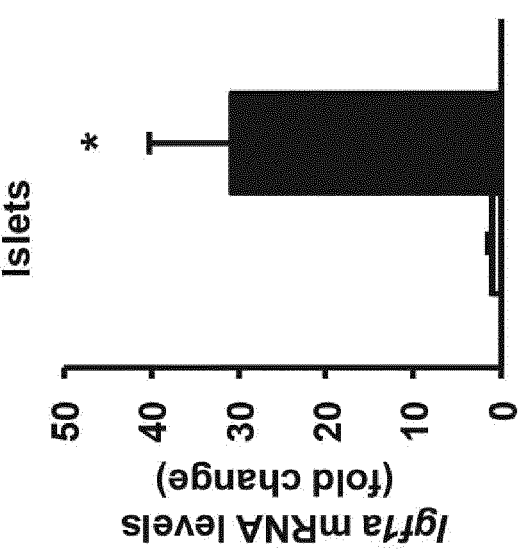
Figure 18D:
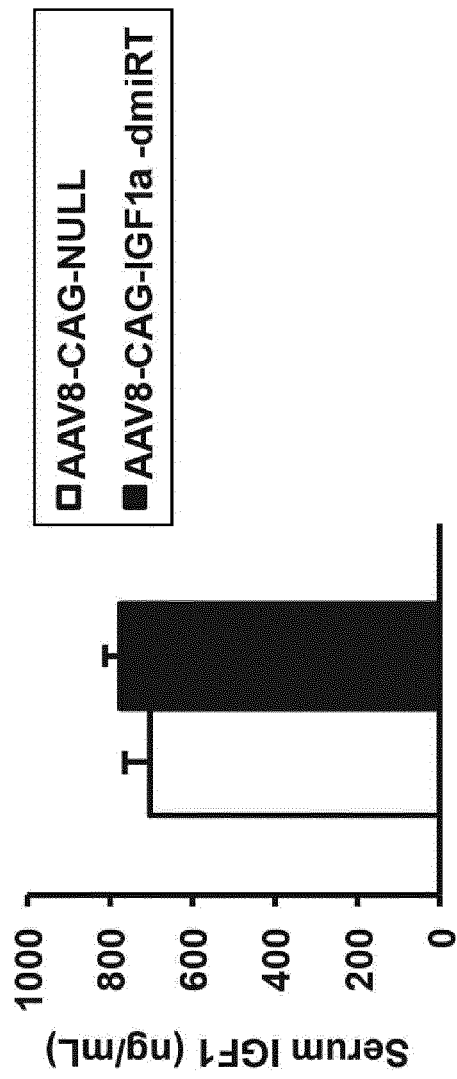

Long-term overproduction of IGF-1 was predominantly detected in beta-cells of the mice receiving AAV8-CAG-IGF-1a-dmiRT vectors but not in the AAV8-CAG-NULL-treated animals (FIG. 18A). Accordingly, at 28 weeks of age, a 30-fold increase in Igf1a mRNA levels was found in islets from AAV8-CAG-IGF-1a-dmiRT-treated mice (FIG. 18B). No IGF-1$^+$ exocrine cells were detected probably due to the rapid secretion of the factor (FIG. 18A). However, a 10-fold increase in Igf1a mRNA levels confirmed IGF1 overexpression in total pancreas of AAV8-CAG-IGF-1a-dmiRT treated mice at 28 weeks of age (FIG. 18C), very similarly to the results reported at 1 month after vector administration (FIG. 12). Consistent with the presence of the dmiRT sequence in the AAV construct, neither IGF-1$^+$ cells nor increased Igf1a mRNA were observed in the liver or the heart of AAV8-CAG-IGF-1a-dmiRT treated mice (FIG. 19). In agreement, no differences in circulating IGF-1 levels were found between groups (FIG. 18D), suggesting that prevention of diabetes was mediated by IGF-1 locally produced in the pancreas.

2.2. AAV8-CAG-IGF-1-dmiRT-Treated Mice Show Preservation of Beta-Cell Mass by Protection Against Autoimmune Attack.

Figure 20B:
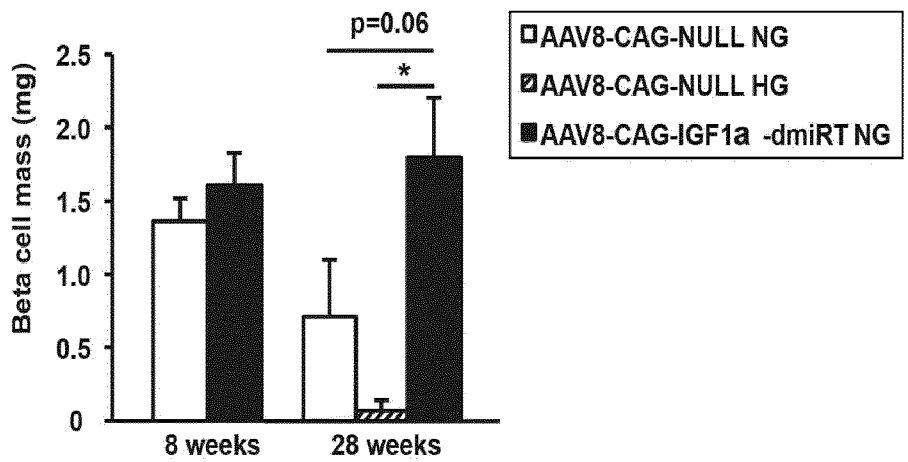
Figure 20C:
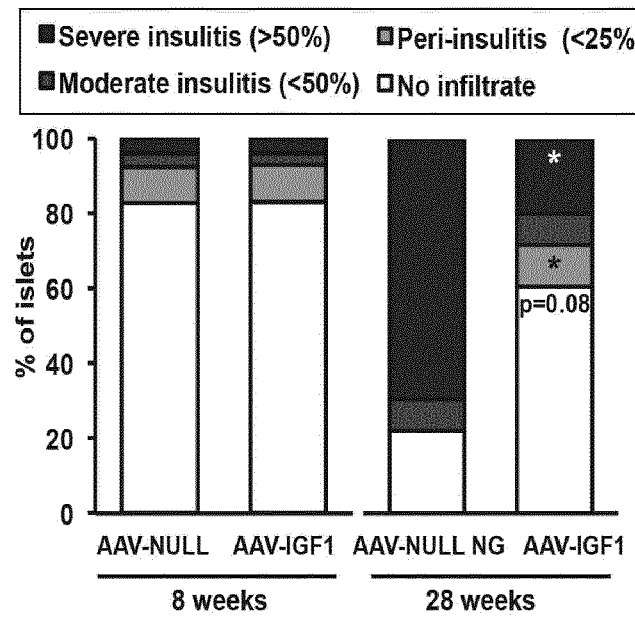
Figure 20D:
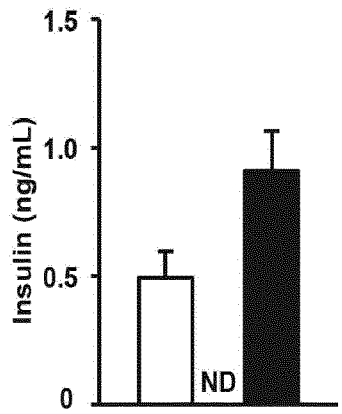
Figure 20E:
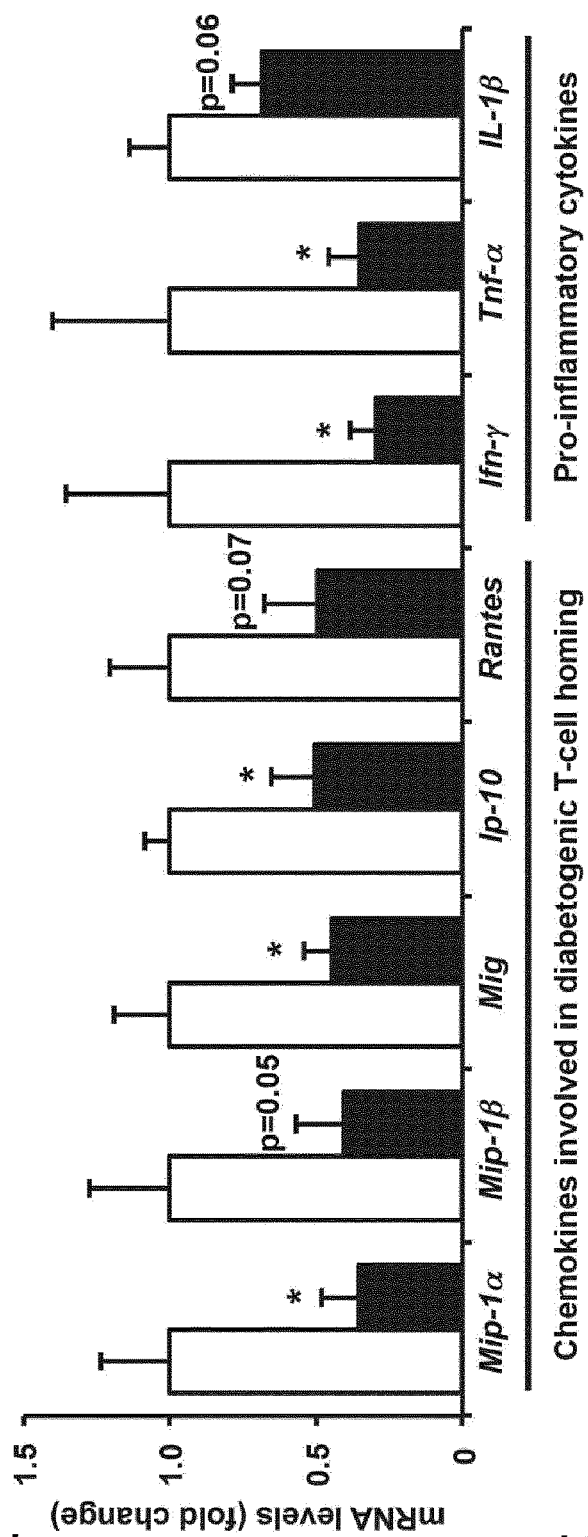
Figure 20F:
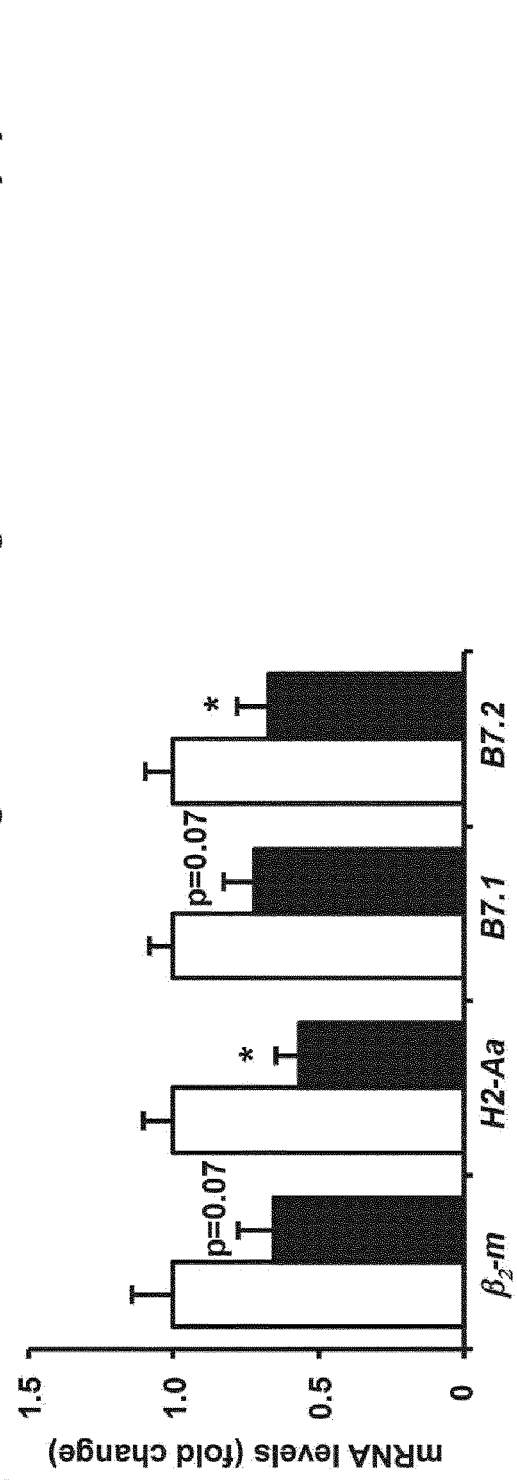

NOD mice treated with AAV8-CAG-IGF-1a-dmiRT vectors were significantly protected against lymphocytic infiltration of the islets and preserved beta-cell mass over time (FIG. 20A-C). Insulitis quantification was not possible in hyperglycemic mice, as beta-cells could barely be detected and the inflammatory infiltrate had disappeared. In agreement with preserved beta-cell mass, normal insulin circulating levels were detected in AAV8-CAG-IGF-1a-dmiRT treated mice at 28 weeks of age (FIG. 20D). Furthermore, islets from AAV8-CAG-IGF-1a-dmiRT mice showed a reduction in the expression of the inflammatory mediators Mip-1alpha, Mip-1 beta, Mig, IP-10 and Rantes as well as in the expression of Ifn-gamma, Tnf-alpha, and Il-1 beta that exert direct cytotoxic effects against beta-cells (FIG. 20E). Additionally, the expression levels of the beta2-microglobulin (62-m), H2-Aa, B7.1 and B7.2 genes, involved in antigen presentation, were also decreased in islets of IGF-1a-treated animals (FIG. 20F).

2.3 Absence of miR-122a Repression in the Liver Upon Intraductal Administration of AAV8 Vectors Bearing miRT-122a Sequences.

Figure 21B:
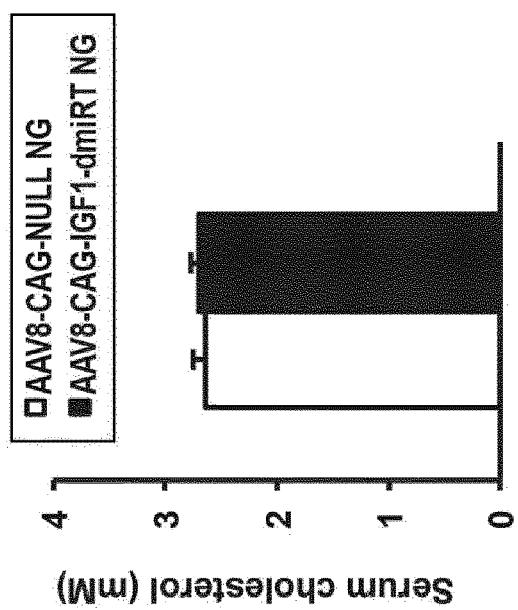
Figure 21A:
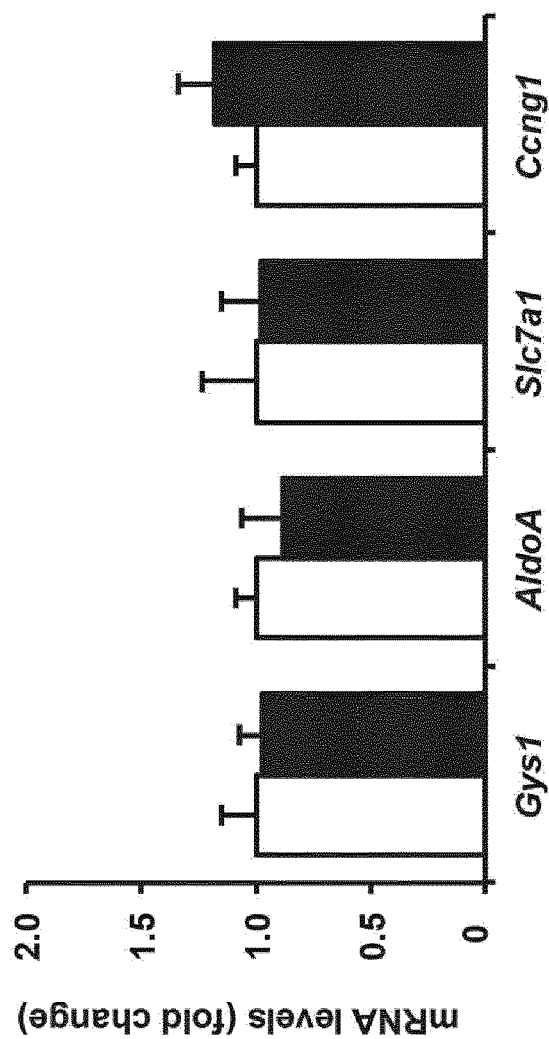

Given that vectors bearing miRTs have been used as competitive inhibitors to repress endogenous miRs, we investigated specific inhibition of miR-122a in the liver of AAV8-CAG-IGF-1-dmiRT treated mice. To exclude diabetes-related alterations, potential miR-122a repression was analyzed in normoglycemic animals. No interference in the expression levels of various miR-122a-regulated genes (Tsai et al 2012) was confirmed in 28-week-old NOD mice treated with AAV8-CAG-IGF-1-dmiRT compared to mice injected with AAV8-CAG-NULL vectors, which do not encode for any target site for miR122a (FIG. 21A). Additionally, serum cholesterol levels, reported to be regulated by miR-122a (Tsai et al 2012), were unchanged in the AAV8-CAG-IGF-1-dmiRT group (FIG. 21B). These results suggest that intraductal administration of AAV8-CAG-IGF-1-dmiRT vectors did not alter microRNA regulation network in the liver.

2.4. Intraductal Delivery of AAV8-CAG-IGF-1b-dmiRT Vector Protects Against Diabetes Development in NOD Mice.

Figure 23A:
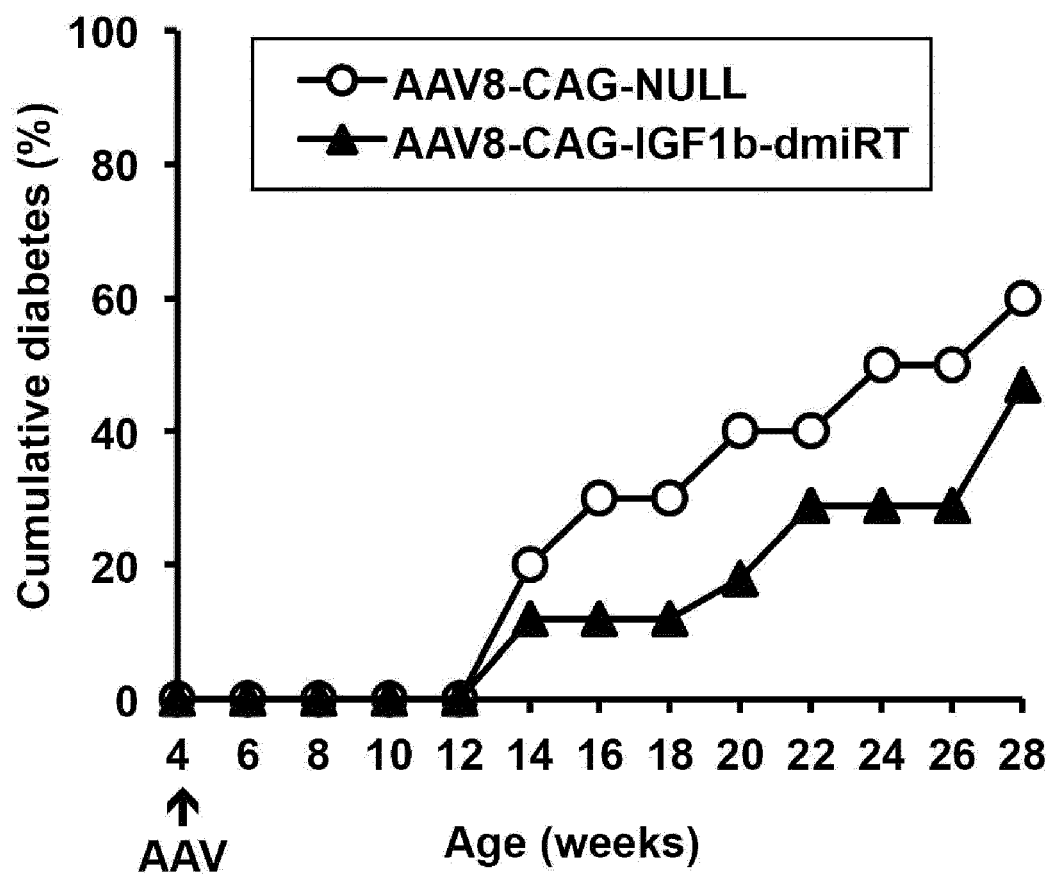
Figure 23B:
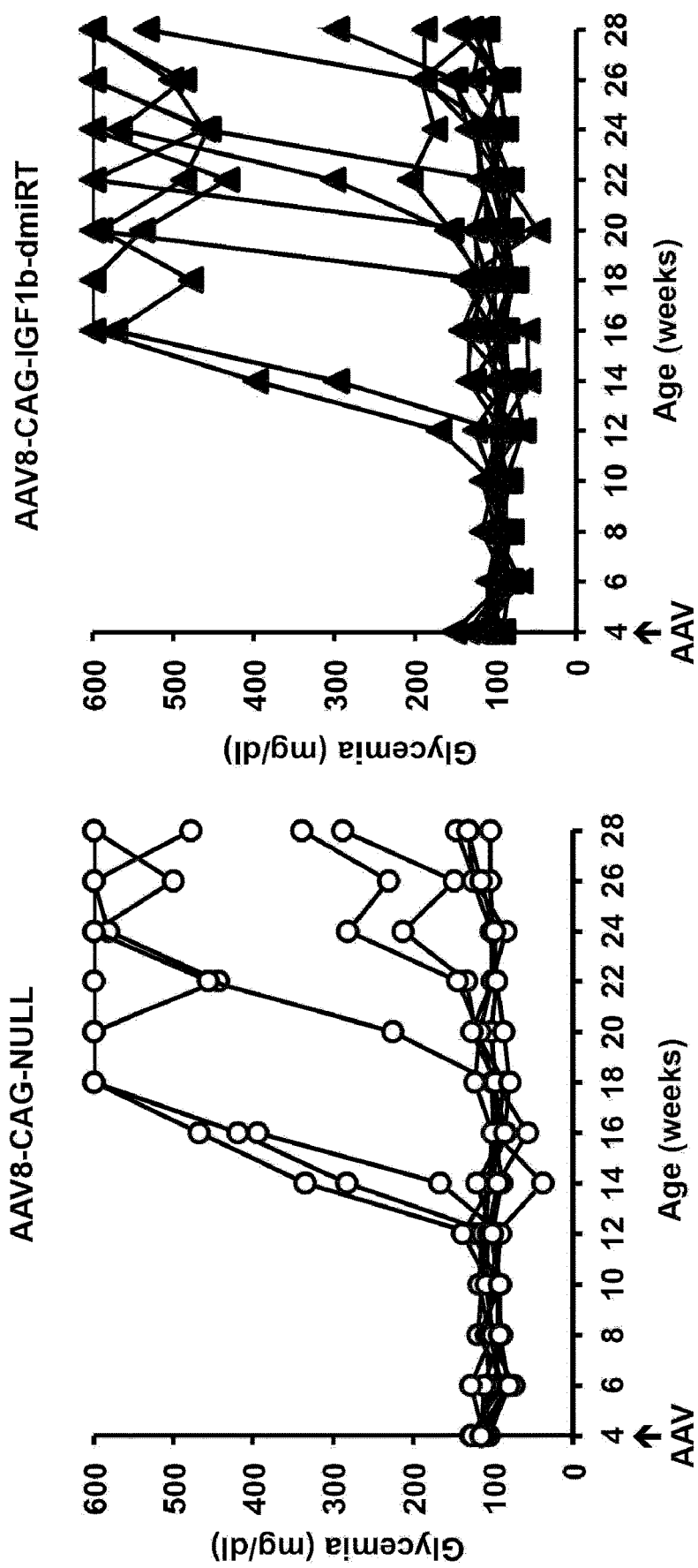
Figure 23C:
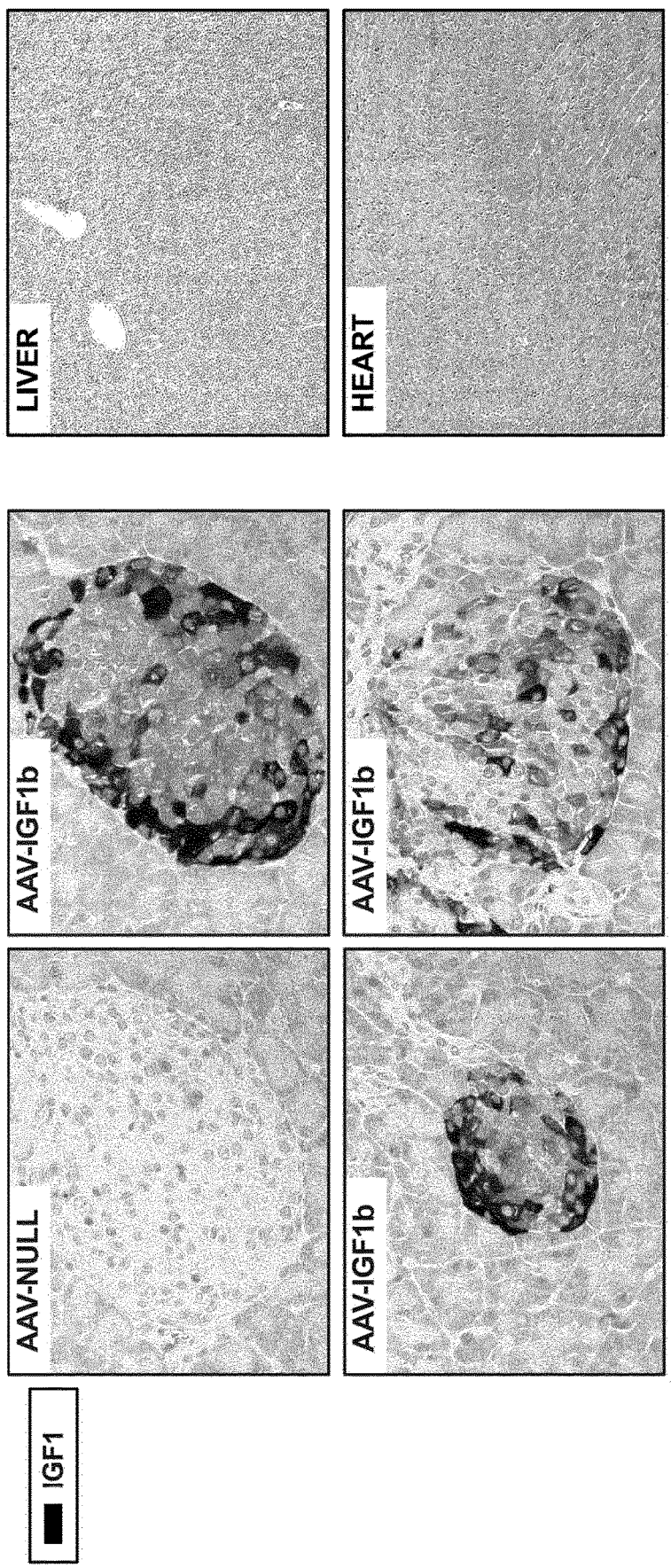
Figure 23D:
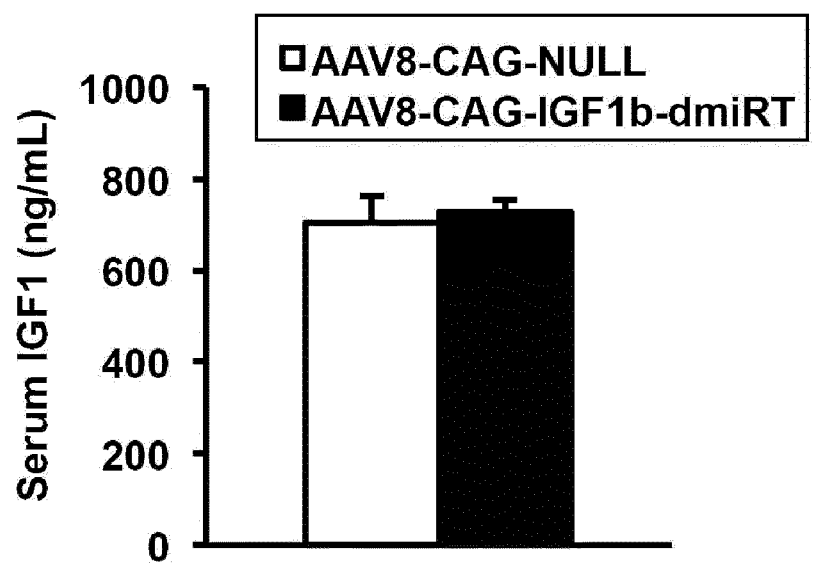

To examine whether AAV-mediated specific pancreatic overexpression of Igf-1b may prevent the development of autoimmune diabetes, $1 \times 10^{12}$ vg of AAV8-CAG-IGF-1b-dmiRT vectors (FIG. 22) were intraductally delivered to 4-week-old NOD mice. Control NOD mice received the same dose of non-coding AAV8-CAG-NULL vectors. Long-term follow-up of blood glucose levels in AAV8-CAG-IGF-1b-dmiRT treated mice revealed that whereas 60% of the animals in the control group became diabetic by 28 weeks of age, 47% of the IGF-1b-treated mice remained normoglycemic (FIG. 23A, B). Overproduction of IGF-1 was predominantly detected in beta-cells of the mice receiving AAV8-CAG-IGF-1b-dmiRT vectors but not in the AAV8-CAG-NULL-treated animals (FIG. 23C). Consistent with the presence of the dmiRT sequence in the AAV construct, no IGF-1$^+$ cells were detected in the liver or the heart of AAV8-CAG-IGF-1b-dmiRT treated mice (FIG. 23C). In agreement, no differences in circulating IGF-1 levels were found between groups (FIG. 23D), suggesting that prevention of diabetes was mediated by IGF-1 locally produced in the pancreas.

3. Materials 3.1. Animals

Female NOD mice were purchased to Charles River Laboratories, Barcelona, Spain. To study the function of the target sequence of microRNA-122a, male ICR mice of 8 weeks old were used (Harlan Teklad, Barcelona, Spain).

Mice were housed in pathogen-free facilities (SER-CBATEG, Centre de Biotecnologia Animal i Teràpia Gènica, Barcelona) under controlled conditions of temperature (22±2° C.) and light (cycles of 12 hours of light and 12 hours of darkness) and fed ad libitum i.e., without restricting access to food, with a standard diet (2019S Teklad Global; Harlan Teklad, Madison, Wis., USA). For sampling, animals were anesthetized using anesthetic inhalators (Isoflurane, IsoFlo®, Abbott Animal Health, Illinois, USA) and were euthanized by beheading. Blood and tissue samples were taken between 9:00 and 11:00 a.m. and immediately frozen with liquid $N_2$ and stored at −80° C. (blood and tissues) and preserved in formaldehyde (tissues). The Ethics Committee in Human and Animal Research and the Autonomous University of Barcelona (UAB) approved all experimental procedures.

3.2. Bacterial Strains

XL2Bue E. coli strains (Stratagene-Agilent Technologies, Santa Clara, Calif., USA) were used to obtain the different plasmid constructs. All plasmids contain the gene for resistance to ampicillin to be selected. The bacterial culture was grown in solid LB media (Miller's LB Broth, Conda, Madrid, Spain) with 2% agar and 50 µg/ml ampicillin.

3.3. Antibodies

The tissue samples were fixed with a buffered solution of 4% formaldehyde, included in paraffin blocks and subsequently, sections of 2-3 microns were obtained to perform incubation with the corresponding antibodies. The antibodies used for the detection of proteins using immunohistochemical techniques are summarized in the following table 1:

TABLE 1

| Antibodies | | | |
|---|---|---|---|
| Antibody | Host | Provider | Ref. |
| Anti-insulin | Guinea Pig | Sigma-Aldrich | I-8510 |
| Anti-IGF-1 | Goat | R&D Systems | AF791 |
| Anti-GFP | Goat | Abeam | ab6673 |
| Anti-IgG of Guinea pig conjugated with Alexa Fluor 568 | Goat | Molecular Probes | A-11075 |
| Anti-IgG goat, byotinylated | Donkey | Santa Cruz | sc-2042 |

3,3-diaminobenzidine (DAB) (Sigma-Aldrich D5637-1G) and counterstaining with Mayer hematoxylin (Merck 109 249) were used for the preparations for light field imaging. For fluorescence images, streptavidin conjugated with Alexa Fluor 488 (Molecular Probes S-11223) was used to amplify the signal of antibody conjugated with biotin.

3.4. Reagents

Molecular biology reagents were obtained from Roche (Roche Diagnostics Corp., IN, USA), Invitrogen Corporation/Life Technologies (San Diego, Calif., USA), Bio-Rad Laboratories (Hercules, Calif., USA), Amersham Biosciences (Piscataway, N.J., USA), Sigma (St. Louis, Mo., USA), Promega Corporation (Madison, Wis., USA), BASF (Barcelona, Spain), Qiagen (Hilden, Germany), QBIOgen/MP Biomedicals (Irvine, Calif., USA) and Fermentas (St. Leon-Rot, Germany). Culture media and antibodies were obtained from PAA (Pasching, Austria) and serum (FBS) from Gibco (Invitrogen, Life Technologies).

3.5. Plasmids

Plasmids used are identified in table 2.

| Plasmids used | | | |
|---|---|---|---|
| Name | Promoter | Gene of interest | PolyA |
| pAAV-CAG-GFP (SEQ ID NO: 32) | CAG | GFP | rabbit β-globin |
| pAAV-CAG-NULL (SEQ ID NO: 34) | CAG | — | rabbit β-globin |
| pAAV-CAG-IGF1-dmiRT (SEQ ID NO: 30 or SEQ ID NO: 31) | CAG | mIGF1 miRT122a miRT1 | rabbit β-globin |

-continued

| Plasmids used | | | |
|---|---|---|---|
| Name | Promoter | Gene of interest | PolyA |
| pAAV-CAG-IGF1 (SEQ ID NO: 33) | CAG | mIGF1 | rabbit β-globin |

The CAG promoter (SEQ ID NO: 52) is a hybrid promoter consisting of the chicken β-actin promoter and the enhancer of Cytomegalovirus and has a ubiquitous expression.

The cloning strategies used for the generation of different plasmids are summarized in the following table 3.

TABLE 3

| cloning strategies used | | |
|---|---|---|
| Name | Cloning strategy | |
| pAAV-CAG-IGF1-dmiRT | vector | pAAV-CAG-GFP-dmiRT-digested with HindIII and NotI. |
| | insert | pAAV-CAG-IGF-1 digested with HindIII and NotI. |
| pAAV-CAG-IGF1 | vector | pAAV-CAG-IGF-1-dmiRT digested with BamHI/KpnI and blunt extremes |

3.6. Methods
3.6.1. Basic DNA Techniques
3.6.1.1. Preparation of Plasmid DNA

To obtain small amounts of plasmid DNA (3-4 μg) minipreparacions (minipreps) were performed according to the alkaline lysis protocol originally described by Bionboim and collaborators (Birnboim and Doly, 1979).

To obtain large amounts of DNA (1-2.5 mg) maxipreparacions (maxipreps) or megapreparacions (megapreps) were performed from 250 or 500 ml of culture medium, respectively. The method is also based on alkaline lysis but in this case, DNA purification was performed by adsorption columns (PureYield™ plasmid MaxiPrep System, Promega Corporation, for maxipreps or EndoFree Plasmid Mega Kit, Qiagen, for the megapreps). The purity and concentration of the obtained DNA was determined by using a Nanodrop device (ND-1000, ThermoCientific).

3.6.1.2. DNA Digestion with Restriction Enzymes

Each restriction enzyme requires specific reaction conditions of pH, ionic strength and temperature. In each case, the instructions of the manufacturer were followed (New England Biolabs, Roche, Promega and Fermentas). In general, DNA was digested with 0.5 units enzyme per 1 μg of DNA in the buffer supplied by the manufacturer for 1-2 hours at the optimum temperature of each enzyme. The reaction product was analyzed on 1-2% agarose gels. When DNA should be digested with two or more restriction enzymes, digestions were carried out jointly if buffers and temperature conditions were compatible. If the enzymes had different requirements, after the first digestion DNA was purified by using the Geneclean® kit (QBIOgene) according to the manufacturer's instructions. DNA was eluted with 30 μL of elution buffer provided by the manufacturer to subsequently perform the second digestion.

3.6.1.3. Dephosphorylation of DNA Fragments

The plasmid DNA, once digested, can be religated. This process can be avoided by removing the phosphate residues at the 5'end of the vector.

For dephosphorylation, one unit of alkaline phosphatase (Shrimp Alkaline phosphatase, Promega) per 1 μg of DNA was used in the commercial buffer 1×. The dephosphorylation reaction was performed for 30 min at 37° C. Subsequently, the enzyme was inactivated at 65° C. for 15 min to avoid any interaction of the phosphatase in the ligation reaction.

3.6.1.4. Generation of DNA Fragments with Blunt Ends

When blunt ends were needed for cloning, the digested DNA fragment was treated with the enzyme Klenow DNA polymerase I (New England Biolabs). The reaction was carried out following the manufacturer's instructions.

3.6.1.5. Generation of Hybrid DNA Molecules: Ligation

The combination of hybrid DNA molecules from different fragments can be made by the action of the enzyme ligase (ligation). The DNA fragments of interest were mixed in various ratios of vector and insert (1:1, 1:5, 1:10) with the enzyme DNA ligase of bacteriophage T4 (New England Biolabs) and the corresponding buffer according to the protocol established by the trading house. The products resulting from the ligation were transformed into competent E. coli cells of the XL2-blue strain (Stratagene-Agilent Technologies, Santa Clara, Calif., USA).

3.6.1.6. Transformation of Competent XL2-Blue E. coli Cells

The plasmid DNA can be introduced into competent bacterial cells via transformation. In this study, the electroporation method was chosen to carry out the transformation of XL2-blue E. coli cells. 40 μl of competent cells ($2 \times 10^{10}$ cells/ml) were thawed on ice until use. 1 μl (approximately 10 ng) of the ligation reaction of DNA or control DNA was added directly to the electrocompetent cells. After incubation on ice for 5 min, cells were electroporated at 2500 V with an electroporador (Bio-Rad). Later, diluted μl LB 200, were sown on LB plates with appropriate antibiotics and were incubated at 37° C. O/N (overnight). The next morning DNA was extracted from recombinant colonies. By using restriction enzymes the presence of the hybrid molecules of DNA was analyzed.

3.6.1.7. DNA Purification from Agarose Gels

Electrophoresis in agarose gel is the standard method used to separate, identify and purify DNA fragments. To separate DNA fragments between 0.2 and 7 kb 1% agarose gels were used. To separate fragments <0.2 kb 2% agarose gels were used. The visualization of the DNA in the gel was achieved by adding low concentrations of the fluorescent dye ethidium bromide (0.5 μg/ml), which is sandwiched between two strands of DNA. DNA was visualized using low wavelength (310 nm) ultraviolet light (UV) using a transiluminator and a camera system (Syngene). 1 kb DNA ladder (Invitrogen) was used as molecular weight marker.

The agarose gels were prepared dissolving agarose in 1×TAE electrophoresis buffer (40 mM Tris-acetate pH 8.3 and 1 mM EDTA) with 0.5 μg/ml of ethidium bromide. DNA samples were loaded in the agarose gel with 1× loading buffer (Fermentas) and ran within 1×TAE electrophoresis buffer at 80 V. In order to obtain and purify DNA fragments of interest from the agarose gel, the GeneJET™ Gel Extraction Kit (Fermentas) was used. The DNA was quantified using a Nanodrop 1000 spectrophotometer (Thermo Fisher Scientific Inc., USA).

3.6.2. Eukaryotic Cells in Culture

3.6.2.1. INS-1 Cells

INS-1 cells (ATCC) are from a rat insulinoma. INS-1 cells were incubated at 37° C., 5% $CO_2$ and medium RPMI-1640 (PAA) (10 mM glucose) with 2 mM glutamine, supplemented with FBS (Fetal Bovine Serum, PAA) at 10% (heat inactivated), 10 mM HEPES, 1 mM sodium pyruvate and 50 μM 2-mercaptoethanol. To perform the maintenance steps, INS-1 cells were trypsinated to cause plate desadhesion, and then cells were plated at different dilutions.

3.6.2.2. C2C12 Cells

C2C12 cell line (ATCC) is from an immortalized line of mouse myoblasts. The maintenance of the cells was conducted in medium DMEM (PAA) with 2 μM glutamine and supplemented with 10% FBS (heat inactivated). To induce their differentiation to myotubes, the same medium was used but supplemented with HS (Horse Serum, PAA) 2% (inactivated by heat) instead of 10% FBS. In both cases they were grown in the incubator at 37° C. and 8.5% $CO_2$.

3.6.2.3. HEK-293 Cells

HEK-293 or 293 cells (ATCC) are human embryonic kidney cells that present the adenoviral gene of Ad5 E1 stably integrated into the genome of cells. These cells were used for the amplification of viral vectors. They were kept in culture medium DMEM (PAA) with 2 mM glutamine, supplemented with 10% FBS (heat inactivated) in an incubator set at 8.5% $CO_2$ and 37° C. When they had a 70% confluence, cells were trypsinated and plated in different dilutions.

3.6.3. DNA Transfection in Cultured Cells

To carry out the analysis of the in vitro expression of the constructs obtained, plasmid transfections were performed in different cell lines (INS-1, C2C12). For this purpose, the technique of transfection with Lipofectamina (Lipofectamine™2000, Invitrogen) was used. The proportion of Lipofectamina/DNA used was 2.5 μl of Lipofectamina (1 mg/ml) to 1 μg DNA in INS-1 cells and 10 μl of Lipofectamina (1 mg/ml) for four μg DNA C2C12 cells. Upon transfection, INS-1 cells and C2C12 were 70-80% confluence. After 4-6 h post-transfection, the medium was changed from INS-1 cells to fresh culture medium. For C2C12 cells, the medium used was differentiation medium DMEM (PAA) with 2 mM glutamine and supplemented with HS (Horse Serum, PAA) 2% (inactivated by heat). The culture of the cells was stopped at 48 h post-transfection, in the case of INS-1 and 6 days post-transfection and induction of differentiation process in the case of C2C12 cells for analyzing the samples.

3.6.4. Production, Purification and Titration of Adeno Associated Viral Vectors

3.6.4.1. Production and Purification

Infective viral particles of AAV8 vectors were generated in HEK-293 cell cultures grown in Roller Bottles (RB) using a triple transfection protocol (Ayuso et al., 2010) which involves the use of three plasmids. This protocol is based on the precipitation of the virus using polyethylene glycol (PEG) and gradient ultracentrifugation with CsCl that eliminates capsids content and lower protein impurities. The co-transfection of each RB (roller bottle) was carried out in 30 ml of calcium phosphate, 150 μg of plasmid DNA of interest (with the ITR sequences and the corresponding expression cassette), together with 150 μg of accessory plasmid rep2/cap8 (expression plasmid coding for the capsid proteins of the virus particles and for proteins necessary for viral replication, Plasmid Factory) and 150 μg of plasmid helper pWEAD (expression plasmid coding for necessary adenoviral proteins; Plasmid Factory).

A total of 10 RB for each vector AAV8-CAG-IGF-1, AAV8-CAG-NULL and AAV8-CAG-IGF-1-dmiRT, and 20 RB for AAV8-CAG-GFP, were used for viral production. 48 h post-transfection, cells were collected and centrifuged at 2500×g for 10 min. The culture medium was stored at 4° C. The cell pellet was reconstituted in TMS (50 mM Tris-HCl, 150 mM NaCl, 2 mM $MgCl_2$, pH 8.0) and was sonicated to lyse the cells and release the virus from the inside. The lysate was centrifuged for 30 min at 2500×g and the supernatant of this centrifugation was added to the culture medium previously stored at 4° C. Then the viral particles were precipitated by an incubation of 15 hours in PEG 8000 8% (Sigma) at 4° C. After that, vectors were precipitated by centrifugation at 4000×g for 30 min. This new precipitate, which contained viral vectors from the culture medium and from the cells, were reconstituted in TMS treated with benzonase (Merck) for 1 h at 37° C. and then centrifuged for 10 min at 10000×g. The resulting supernatant was loaded into 37.5 ml tubes Ultra clear (Beckman) containing a CsCl discontinuous gradient of density 1.5 (5 ml) and 1.3 g/ml (10 ml). Then, they were centrifuged for 17 h at 27000 rpm in a SW28 rotor (Beckman). The virus bands were collected using 18 G needles and were transferred to Ultra clear tubes of 12.5 ml. The remaining of the 12.5 ml was filled with CsCl to 1.379 g/ml to generate a continuous gradient. These tubes were centrifuged at 38000 rpm in a SW40Ti rotor (Beckman) for 48 h. Finally, the bands corresponding to the full virus were collected and dialyzed through a 10 kDa membrane (Slide-A-Lyzer Dialysis Products, Pierce) and then filtered through 0.22 μm filters (Millipore).

3.6.4.2. Titration of Viral Genomes

The AAV8 viral genomes were determined by quantitative PCR (qPCR) adapting the protocol described by AAV2 and AAV8 Reference Standard Material (Lock et al., 2010) to vectors used in this study. Quantification of each vector was made in parallel with a reference vector of known concentration to ensure the validity of results. As a standard curve a linearized plasmid was used and quantified by measuring the absorbance at 260 nm. To ensure that the title of the viral vector will not be overestimated due to the presence in the final viral preparation of remaining DNA plasmids from the transfection, a DNAse treatment was performed prior to quantification. Only encapsidated genomes are resistant to digestion with DNase. 5 μl of each preparation of the viral vector in 5 μl of DNAse buffer 10× (130 mM Tris-HCl, 50 mM $MgCl_2$, 1.2 mM $CaCl_2$, pH 7.5), 1 μl of DNAse (10 U/mL) and 36 μl: Milli-Q water. The digestion was incubated 60 min at 37° C. After digestion of the samples, they were diluted to obtain an amplification value within the range of standard curve. Each TaqMan qPCR reaction contained in a final volume of 10 µl: TaqMan LightCycler® 480 Probe Master 5 µl, Primer forward (10 µM) 0.2 µl, Primer reverse (10 µM) 0.2 µl, probe (10 µM) 0.1 µl, H$_2$O Milli-Q 2 µl, diluted vector 2.5 µl. The reaction involved an initial incubation for 10 min at 95° C. (activation of the polymerase and denaturation of viral capsids, allowing the release of genomes) followed by 40 cycles of 30 s at 95° C. (denaturation) and 30 s at 60° C. (alignment and elongation). The primers used in the quantification of viral genomes of AAV hybridized to the common zone of the poly A (β-globin intron):

```
Forward:
                                            (SEQ ID NO: 38)
5' CTT GAG CAT CTG ACT TCT GGC TAA T 3'

Reverse:
                                            (SEQ ID NO: 39)
5' GGA GAG GAG GAA AAA TCT GGC TAG 3'

Probe:
                                            (SEQ ID NO: 40)
5' CCG AGT GAG AGA CAC AAA AAA TTC CAA CAC 3'
```

The viral title was the result of the median of three quantification performed on different days as identified in table 4.

TABLE 4

| viral titres | |
|---|---|
| Viral vector | Titre (vg/ml) |
| AAV8-CAG-GFP | 8.7 × 10$^{13}$ |
| AAV8-CAG-NULL | 1.4 × 10$^{13}$ |
| AAV8-CAG-IGF-1 | 9.8 × 10$^{13}$ |
| AAV8-CAG-IGF-1-dmiRT | 1.3 × 10$^{14}$ |

3.6.4.3. Quantification of Viral Particles by Silver Staining

The analysis of the viral preparations by protein electrophoresis SDS-PAGE and subsequent staining with silver nitrate allows quantification of the viral capsids, which compared with the value of viral genomes obtained by qPCR allows to calculate the percentage of empty capsids in each preparation (ratio: viral particles/viral genomes). Moreover, this method allows display on the gel the degree of contamination of nonviral protein that could affect the transduction efficiency in vivo. The appropriate volumes of the vector of interest, of the vector reference (control also used in the quantification by qPCR) and of different dilutions of K208 vector (of known concentration and used as a standard curve) were mixed with the buffer 4× Novex® Tris-Glycine LDS Sample Buffer (Invitrogen) and 10× NuPAGE Sample Reducing Agent (Invitrogen) to a final volume of 20 µl. After 5 minutes of boiling, samples were loaded on a gel 10% Bis-Tris Gel 1.5 mm 15 well (Invitrogen) and ran to 120 V for 2 h. Proteins of the gel were fixed with a mixture of Milli-Q H$_2$O/ethanol/acetic acid. Then the gel was sensitized with a mixture of Na$_2$S$_2$O$_3$/sodium acetate/ethanol/H$_2$O Milli-Q. Finally, the gel was stained with silver nitrate and the bands were revealed using a mixture of Na$_2$CO$_3$/Formaldehyde/Milli-Q H$_2$O. The title of viral particles was obtained by densitometry. From the intensity of the VP3 of each dilution of vector K208 a standard curve was generated to quantify viral particles of different preparations.

3.6.4.4. Determination of Viral Genomes in Tissues by qPCR

The final value of the number of viral genomes that have transduced a given cell is also representative of the transgene copy number per cell. The determination of viral genomes was obtained from the comparison of 20 ng of genomic DNA extracted from various tissues of mice with a calibration curve generated from linearized plasmid serial dilutions.

3.6.4.4.1. Generation of the Calibration Curve

The calibration curve was generated with linearized plasmid DNA pAAV-CAG-GFP-WPRE. Therefore, knowing the concentration of the plasmid and the number of base pairs of the construct (7772 bp) the number of copies of transgene per µl was obtained. This plasmid DNA was serially diluted so as to achieve a calibration curve of logarithmic dilutions $10^7$:$10^6$:$10^5$:$10^4$:$10^3$:$10^2$ copies of the transgene/µl.

3.6.4.4.2. Quantification of the Number of Copies of the Transgene by qPCR

Once the calibration curve generated and samples diluted, a qPCR was performed for calculating the number of copies of the transgene. Each qPCR reaction (TaqMan LightCycler® 480 Probe Master, Roche) was performed in 20 µl final volume: TaqMan LightCycler® 480 Probe Master 10 µl, Primer forward (10 µM) 1 µl, Primer reverse (10 µM) 1 µl, probe (10 µM) 0.2 µl, H$_2$O Milli-Q 6.8 µl, diluted vector 1 µl. The reaction involved an initial denaturation for 10 min at 95° C. and 45 cycles of 10 s at 95° C., alignment (30 s at 60° C.) and elongation (1 s at 72° C.). The oligonucleotides used are the following:

```
Forward:
                                            (SEQ ID NO: 41)
5' CTT GAG CAT CTG ACT TCT GGC TAA T 3'

Reverse:
                                            (SEQ ID NO: 42)
5' GGA GAG GAG GAA AAA TCT GGC TAG 3'

Probe:
                                            (SEQ ID NO: 43)
5' CCG AGT GAG AGA CAC AAA AAA TTC CAA CAC 3'.
```

The values obtained in the qPCR relative to the calibration curve, provided the number of copies of the transgene that was initially in 20 ng of total genomic DNA. Knowing that in mice, 20 ng of genomic DNA correspond to 3115.26 diploid cells, the number of copies of the transgene per diploid cell was obtained.

TABLE 5

| TaqMan reaction | |
|---|---|
| TaqMan Reaction | Volume |
| TaqMan LightCycler ® 480 Probe Mast | 10 µl |
| Primer forward (10 µM) | 1 µl |
| Primer reverse (10 µM) | 1 µl |
| Sonda (10 µM) | 0.2 µl |
| H$_2$O Milli-Q | 6.8 µl |
| Vector dilution | 1 µl |

3.6.4.5. In Vivo Injection of the Viral Vectors 3.6.4.5.1. Retrograde Administration Through Pancreatic Biliary Duct The retrograde injection via pancreatic biliary duct was conducted following the protocol described by Loiler and collaborators (Loiler et al., 2005) with minor modifications. The animals were anesthetized by an intraperitonial injection of ketamine (100 mg/kg) and xylacine (10 mg/kg). Once the zone shaved and an incision of 2-3 cm done, the abdomen was opening through an incision through the alba line, putting an abdominal separator. The bile duct was identified. Liver lobes were separated and the bile duct was clamped in the bifurcation of the hepatic tryad to prevent the spread of viral vector to the liver. Later, a 30 G needle was introduced through the Vater papilla and retrograly followed through biliary duct. The needle was fixed clamping the duct at the point of the intestine to secure its position and prevent the escape of viral vectors in the intestine. Slowly, a total volume of 100 µl was injected with the corresponding dose of viral vectors. 1 min after injection, the clip which fixed the needle was pulled from and a drop of surgical veterinary adhesive Histoacryl (Braun, TS1050044FP) was applied at the entry point of the needle. Approximately 2 min later the clip of the biliar duct was pulled from and the abdominal wall and skin were sutured. The mice were left to recover from anesthesia on a heating mantle to prevent heat loss.

3.6.4.5.2. Hydrodynamic Administration

The hydrodynamic administration via tail vein was performed as previously described (Liu et al., 1999). The DNA plasmid was diluted in saline volume (ml) equal to ~10% of the average body weight (g) of the animals and it was manually injected through the tail lateral vein in less than 5 seconds. Before injection, the animals were exposed to infrared light under a 250 W (Philips) for a few minutes to dilate blood vessels and facilitate the visualization and access to the vein of the tail. The animals were placed in a plastic restrainer (Harvard Apparatus) to immobilize them and to facilitate the injection. 30 G needles (BD) were used. In general, the mice tolerated well the hydrodynamic injections. Immediately after injection the mice normally remained motionless and showed forced breath that persisted for a few minutes, reaction which is caused by the nature of the injection. Apart from these immediate effects due to the hydrodynamic injection, the animals did not suffer known consequences during treatment.

3.6.4.6. Isolation of Pancreatic Islets

The pancreatic islets were extracted from pancreas digestion and subsequent isolation of pancreatic islets. In order to digest the pancreas, mice were sacrificed, the abdominal cavity was exposed and 3 ml of a solution of Liberase (Roche, 0104 mg/ml medium without serum M199 (Gibco-Life Technologies 10012-037)) was perfused to the pancreas via the common biliar duct. During perfusion, circulation through the Vatter ampoule was blocked by placing a clamp. Once perfused, the pancreas were isolated from the animal remained in a tube in gel before being digested at 37° C. for 19 min. To stop digestion and dilute the Liberase solution, 35 ml of cold medium M199 with 10% serum (Biowest S0250-500) were added and the tube stirred for 30 s to completely disintegrate the tissue. Then, two washes with 30 ml and 10 ml respectively of M199 medium supplemented with serum were done. Then, the solution of disintegrated tissue was filtered (450 mm PGI 34-1800-09) and collected into a new tube. The filtrate with 20 ml of medium with serum was centrifuged (Eppendorf 5810R rotor A-4-62) at 200-230×g for 5 min at 4° C. The supernatant was discarded and after carefully removing all traces of the medium, the pellet was resuspended in 13 ml of Histopaque-1077 (Sigma 10771) and M199 medium without serum was added to a volume of 25 ml avoiding mixing the two phases. Then it was centrifuged (Eppendorf 5810R) at 1000×g for 24 min at 4° C. to obtain the pancreatic islets at the interface between the medium and the Histopaque and thus, they were collected with the pipette. Once isolated, the islets were washed twice with 40 ml of medium with serum and centrifuged at 1400 rpm, 2.5 min at room temperature. In the final wash the pellet with islets was resuspended in 15 ml of M199 medium. In this step, and to help their identification under the microscope, the islets were stained by adding a solution of 200 µl Dithizone to the medium (for 10 ml volume: 30 mg Dithizone (Fluka 43820), 9 ml absolute EtOH, 150 µl $NH_4OH$ and 850 µl $H_2O$). After 5 min of incubation, islets were transferred to a petri dish to be caught under the binocular microscope.

Once islets recovered, they were centrifuged at 300×g, 5 min and 4° C. to remove the remains of medium, and were processed to RNA extraction.

3.6.5. Analysis of the mRNA Expression by qPCR 3.6.5.1. Total RNA Extraction

The tissue samples to obtain total RNA were obtained from freshly sacrificed animals and were quickly frozen in liquid nitrogen. Frozen tissues were homogenized (Polytron® MICCRA D-KIT-9 Prozess ART & Labortechnik GmbH & Co. KG, Mullheim, Germany) in 1 ml solution TriPure Isolation Reagent (Roche, 11667), and following the protocol of RNA purification in column RNeasy Mini Kit de QIAGEN (Cat. No. 74104, QIAGEN, Invitrogen), total RNA was obtained. All samples were treated with DNaseI purification columns (RNase-Free DNase Set supplied with the columns, Qiagen) and after removing the enzyme with the buffer supplied by the manufactured, the RNA was eluted in 30 µl of distilled water free of RNases (DEPC). Finally, the concentration of RNA obtained was determined using a device Nanodrop (ND-1000, ThermoCientific).

3.6.5.2. RNA Extraction from Pancreatic Islets

The obtention of RNA from pancreatic islets was performed by adding 1 ml of the solution TriPure Isolation Reagent (Roche, 11667) to resuspend the islets and following the commercial protocol of RNA purification in column RNeasy Micro Kit by QIAGEN (Cat. No. 74004, QIAGEN, Invitrogen). The RNA was finally eluted in a volume of 14 µl of water free of RNases. The concentration and purity of the obtained RNA was determined using a device Nanodrop (ND-1000, ThermoCientific).

3.6.5.3. cDNA Synthesis

One µg of total RNA was retrotranscripted to cDNA using the Transcriptor First Strand cDNA Synthesis Kit (Roche) following the manufacturer's instructions. Oligo-dT and random hexamer oligonucleotides were used as primers in the reaction with the presence of RNA inhibitor.

3.6.5.4. Quantitative PCR

The qPCR was done in LightCycler® 480 (Roche) using LightCycler® 480 SYBR Green I Master (Roche). The following table 6 shows the different primers of mouse (m) or rat (r) used in qPCR:

TABLE 6 primers used in qPCR

| Gene | Forward sequence (5'-3') | Reverse sequence (5'-3') |
|---|---|---|
| mIGF-1a | TGGATGCTCTTCAGTTCGTGT | CAACACTCATCCACAATGCCT |
| mCcl3 (Mip-1α) | GCAACCAAGTCTTCTCAGCG | AGCAAAGGCTGCTGGTTTCA |
| mCcl4 (Mip-1β) | CCATGAAGCTCTGCGTGTCT | GAGAAACAGCAGGAAGTGGGA |
| mCxcl9 (MIG) | CGAGGCACGATCCACTACAA | AGTCCGGATCTAGGCAGGTT |
| mCxcl10 (IP-10) | CCAAGTGCTGCCGTCATTTT | AGCTTCCCTATGGCCCTCAT |
| mCcl5 (RANTES) | GTGCCCACGTCAAGGAGTATT | CCCACTTCTTCTCTGGGTTGG |
| mCCL2 (MCP-1) | ATGCAGTTAACGCCCCACTC | GCTTCTTTGGGACACCTGCT |
| mIFN-γ | AGACAATCAGGCCATCAGCA | TGGACCTGTGGGTTGTTGAC |
| mTNF-α | TCTTCTCATTCCTGCTTGTGG | GGTCTGGGCCATAGAACTGA |
| mIL-1β | TGCCACCTTTTGACAGTGATG | TGATGTGCTGCTGCGAGATT |
| mH2-Aa | CTCTGATTCTGGGGGTCCT | ACCATAGGTGCCTACGTGGT |
| mβ2-microglobulin | CCGGAGAATGGGAAGC | GTAGACGGTCTTGGGC |
| mCD80 (B7.1) | ATACGACTCGCAACCACACC | GAATCCTGCCCCAAAGAGCA |
| mCD86 (B7.2) | GCTTCAGTTACTGTGGCCCT | TGTCAGCGTTACTATCCCGC |
| mSlc7a1 | AAA CAC CCG TAA TCG CCA CT | GGC TGG TAC CGT AAG ACC AA |
| mCcng1 | TGA CTG CAA GAT TAC GGG ACT | CCC AAG ATG CTT CGC CTG TA |
| mGys1 | CCG CTA ACT CTA CCG GTC AC | CCC CAT TCA TCC CCT GTC AC |
| mAldoA | GCG TTC GCT CCT TAG TCC TT | AAT GCA GGG ATT CAC ACG GT |
| mRplp0 | TCCCACCTTGTCTCCAGTCT | ACTGGTCTAGGACCCGAGAAG |
| rRplp0 | GATGCCCAGGGAAGACAG | CACAATGAAGCATTTTGGGTAG |

(identified as SEQ ID NO: 53-92)

Each qPCR reaction contained 20 μl of total volume: SYBR Green LightCycler® 480 Probe Master 10 μl, Primer forward (10 μM) 0.4 μl, Primer reverse (10 μM) 0.4 μl, H$_2$O Milli-Q 7.2 μl, cDNA (dil. 1/10) 2 μl. The reaction consisted of 5 min at 95° C. for initial denaturation and 45 cycles of four phases: denaturation (10 s at 95° C.), alignment (10 s at 60° C.), elongation (10 s at 72° C.) and 30 s at 60° C. Before cooling the reaction to 4° C., it was kept 5 s at 95 C and 1 min at 65° C. to determine the melting temperature. The method delta-delta-Ct (2-ΔΔCt) described by Livak (Livak and Schmittgen 2001) was used to quantify the relative expression of genes of interest.

3.6.6. Analysis of miRNA Expression by qPCR 3.6.6.1. miRNA Extraction from Tissues Tissues were mechanically disintegrated with a polytron (Polytron® MICCRA-KIT D-9, ART Prozess & Labortechnik GmbH & Co. KG, Mullheim, Germany) with a lysis solution following the manufacturer's instructions of the commercial kit miRVana™ miRNA Isolation Kit (Ambion by Life Technologies, Madrid, Spain).

3.6.6.2. cDNA Synthesis

The obtained miRNA were diluted to a concentration of 5 ng/μl, from which 2 μl were retrotranscripted into cDNA using miRCURY LNA™ Universal RT microRNA PCR-Universal cDNA synthesis kit II (Exiqon, Vedbaek, Denmark) following manufacturer's instructions.

3.6.6.3. Quantitative PCR

Differently to the aforementioned quantitative PCR mRNA method, for the miRNA, ExilLENT SYBR® Green Master mix (Exiqon, Vedbaek, Denmark) was used following the manufacturer's instructions. Each qPCR reaction contained 10 mL total volume: PCR Master mix 5 μl, Primer mix 1 μl, cDNA (dil. 1/80) 4 μl. The results of Ct were processed as explained in section 7.4, but in this case a different housekeeping gene, the U6, was used.

3.6.7. Determination of Serum Parameters

Serum was obtained from blood samples obtained from the tail vein, or after the decapitation of mice in studies to final time. In both cases, blood was collected in heparine tubes and was kept for 1 h at 4° C. Later, it was centrifuged for 10 min at 4° C. 12000×g to obtain the serum, which was kept frozen at −80° C. until the time of the determination of different parameters.

3.6.7.1. Glucose

Serum glucose levels were determined from a drop of blood (5 μl) from the tail of mice, through the system Glucometer Elite™ (Bayer Leverkusen, Germany). An animal was considered as diabetic, with two consecutive measurements of a glycemia ≥250 mg/dl.

3.6.7.2. Insulin

The circulating insulin levels were determined from 100 μl of serum by radioimmunoassay (RIA) using the Rat Insulin kit (Millipore) following the manufacturer's instructions. Mouse Insulin has a cross-reactivity of 100% compared to the one of rat.

3.6.7.3. IGF-1

Circulating IGF-1 levels were determined from 10 μl of serum using a commercial ELISA kit for mouse/rat IGF-1 (AC-18F1, Novozymes, Denmark) and following the manufacturer instructions. The detection limit of the kit is 63 ng/ml.

3.6.7.4. Cholesterol

Total cholesterol in serum was quantified spectrophotometrically using an enzymatic assay kit (Horiba-ABX, Montpellier, France) and determined by Pentra 400 Analyzer (Horiba-ABX).

3.6.8. Immunohistochemical Analysis of the Tissues

Tissues were fixed with a buffered solution of formalin 10% for 24 h at 4° C., they were included in paraffin blocks (inclusor type Histokinette) and sections were obtained (2-3 μm) with the help of a microtome (RM2135, Leica Biosystems, Barcelona). Subsequently, tissue sections were deparaffined (2 washes with xylol 10 min, 2 washes with 100% ethanol 5 min and 2 washes with 96% ethanol 5 min) and proceeded to the stain. The sections were incubated O/N at 4° C. with primary antibodies (see section 3.3.), three washes of 5 min with PBS were done, and then incubated with the corresponding secondary antibody (see section 3.3) for 1 h at room temperature. For fluorescence immunohistochemistry, sections were subsequently incubated with streptavidin conjugated with fluorophores. For immunohistochemistry in light field, they were revealed with diaminobenzidine (DAB) (see section 3.3.). The images were obtained with an Eclipse 90i microscope (Nikon Instruments Inc., Tokyo, Japan). The program Nis Elements Advanced Research 2:20 was used to quantify the marked areas.

3.6.9. Determination of Beta-Cell Mass

Beta cell mass was calculated by multiplying the total weight of the pancreas by the percentage of the beta cell area. The beta cell area of the pancreas was calculated from three sections separated 200 μm and immunostaining against insulin by dividing the area of all insulin positive cells in each section between the total area of the corresponding section.

3.6.10. Determination of the Degree of Insulitis

The incidence and severity of insulitis was analyzed in 3 pancreatic paraffin sections, each separately 100-150 microns and immunostained against insulin. The degree of insulitis (lymphocyte infiltration) in the pancreatic islets was determined according to the following classification criteria: no infiltration (0%), periinsulitis (mononuclear cells surrounding ducts and islets, but without major infiltration of the architecture of the islet, <25%); moderate insulitis (mononuclear cell infiltrate <50% of the surface of the islet); severe insulitis (>50% of the area of the islet infiltrated by lymphocytes and/or loss of islet architecture).

3.6.11. Statistical Analysis

Results were expressed as mean±standard error of the mean (SEM). Comparison of the results was performed using the Student t test of impaired data or through the table ANOVA of two factors. The differences were considered statistically significant with $*/^\#p<0.05$, $/^{\#\#}p<0.01$ and $*/^{\#\#\#}p<0.001$.

TABLE 7 list of SEQ ID Nos identified in the sequence listing

| SEQ ID NO | Type of sequence |
|---|---|
| 1 | Murine nucleic acid coding for IGF-1a (SEQ ID NO: 28) |
| 2 | Murine nucleic acid coding for IGF-1b (SEQ ID NO: 29) |
| 3 | Human nucleic acid coding for IGF-1a (SEQ ID NO: 23) |
| 4 | Human nucleic acid coding for IGF-1b (SEQ ID NO: 24) |
| 5 | Human nucleic acid coding for IGF-1c/MGF (SEQ ID NO: 25) |
| 6 | Human nucleic acid coding for IGF-1c/MGF (SEQ ID NO: 26) |
| 7 | Human nucleic acid (SEQ ID NO: 27) |
| 8-22 | Nucleic acid sequences target for a given miRNA |
| 23 | Human protein IGF-1a (isoform 2) |
| 24 | Human protein IGF-1b (isoform 3) |
| 25 | Human protein IGF-1c/MGF (isoform 1) |
| 26 | Human protein IGF-1c/MGF (isoform 4) |
| 27 | Human protein IGF-1 (isoform XI) |
| 28 | Murine protein IGF-1a (isoform 5) |
| 29 | Murine protein IGF-1b |
| 30 | pAAV-CAG-preproIGF-1a-doble-miRT122a-miRT1 (SEQ ID NO: 28) |
| 31 | pAAV-CAG-preproIGF-1b-doble-miRT122a-miRT1 (SEQ ID NO: 29) |
| 32 | pAAV-CAG-GFP |
| 33 | pAAV-CAG-IGF-1 |
| 34 | pAAV-CAG-NULL |
| 35-43 | primers |
| 44 | Murine protein IGF-1b/MGF (variant 1) |
| 45 | Murine protein IGF-1 (variant 2) |
| 46 | Murine protein IGF-1b/MGF (variant 3) |
| 47 | Murine protein IGF-1a (variant 4) |
| 48 | Murine nucleic acid coding for IGF-1b/MGF (SEQ ID NO: 44) |
| 49 | Murine nucleic acid coding for IGF-1 (SEQ ID NO: 45) |
| 50 | Murine nucleic acid coding for IGF-1b (SEQ ID NO: 46) |
| 51 | Murine nucleic acid coding for IGF-1a (SEQ ID NO: 47) |
| 52 | CAG promoter |
| 53-92 | primers |
| 93-95 | Nucleic acid sequences target for a given miRNA |
| 96 | Expression cassette of SEQ ID NO: 30 |
| 97 | Viral vector of SEQ ID NO: 30 |
| 98 | Expression cassette of SEQ ID NO: 31 |
| 99 | Viral vector of SEQ ID NO: 31 |

BIBLIOGRAPHIC REFERENCES

Agudo, J., Ayuso, E., Jimenez, V., Salavert, A., Casellas, A., Tafuro, S., Haurigot, V., Ruberte, J., Segovia, J. C., Bueren, J., et al. (2008). IGF-I mediates regeneration of endocrine pancreas by increasing beta cell replication through cell cycle protein modulation in mice. Diabetologia 51, 1862-1872.

Alexopoulou, A. N., Couchman, J. R., and Whiteford, J. R. (2008). The CMV early enhancer/chicken beta actin (CAG) promoter can be used to drive transgene expression during the differentiation of murine embryonic stem cells into vascular progenitors. BMC Cell Biol. 9, 2.

Altschul, S. F., Madden, T. L., Schäffer, A. A., Zhang, J., Zhang, Z., Miller, W., and Lipman, D. J. (1997). Gapped BLAST and PSI-BLAST: a new generation of protein database search programs. Nucleic Acids Res. 25, 3389-3402.

American Diabetes Association (2010). Diagnosis and Classification of Diabetes Mellitus, Diabetes Care, vol. 33, Suppl. S62-69.

American Diabetes Association (2014). Diagnosis and classification of diabetes mellitus. Diabetes Care 37 Suppl 1, S81-S90.

Anguela, X. M., Tafuro, S., Roca, C., Callejas, D., Agudo, J., Obach, M., Ribera, A., Ruzo, A., Mann, C. J., Casellas, A., et al. (2013). Nonviral-mediated hepatic expression of IGF-I increases Treg levels and suppresses autoimmune diabetes in mice. Diabetes 62, 551-560.

Ayuso, E., Mingozzi, F., and Bosch, F. (2010). Production, purification and characterization of adeno-associated vectors. Curr. Gene Ther. 10, 423-436.

Bartel, D. P. (2004). MicroRNAs: genomics, biogenesis, mechanism, and function. Cell 116, 281-297.

Bergerot, I., Fabien, N., Maguer, V., and Thivolet, C. (1995). Insulin-like growth factor-1 (IGF-1) protects NOD mice from insulitis and diabetes. Clin. Exp. Immunol. 102, 335-340.

Bergerot, I., Fabien, N., and Thivolet, C. (1996). Effects of insulin like growth factor-1 and insulin on effector T cells generating autoimmune diabetes. Diabetes Metab. 22, 235-239.

Birnboim, H. C., and Doly, J. (1979). A rapid alkaline extraction procedure for screening recombinant plasmid DNA. Nucleic Acids Res. 7, 1513-1523.

Brown, B. D., and Naldini, L. (2009). Exploiting and antagonizing microRNA regulation for therapeutic and experimental applications. Nat. Rev. Genet. 10, 578-585.

Carter, P. J., and Samulski, R. J. (2000). Adeno-associated viral vectors as gene delivery vehicles. Int. J. Mol. Med. 6, 17-27.

Casellas, A., Salavert, A., Agudo, J., Ayuso, E., Jimenez, V., Moya, M., Muñoz, S., Franckhauser, S., and Bosch, F. (2006). Expression of IGF-I in pancreatic islets prevents lymphocytic infiltration and protects mice from type 1 diabetes. Diabetes 55, 3246-3255.

Cheetham, T. D., Holly, J. M., Clayton, K., Cwyfan-Hughes, S., and Dunger, D. B. (1995). The effects of repeated daily recombinant human insulin-like growth factor I administration in adolescents with type 1 diabetes. Diabet. Med. 12, 885-892.

Chen, S., Ding, J., Bekeredjian, R., Yang, B., Shohet, R. V, Johnston, S. A., . . . Grayburn, P. A. (2006). Efficient gene delivery to pancreatic islets with ultrasonic microbubble destruction technology. Proceedings of the National Academy of Sciences of the United States of America, 103(22), 8469-74.

Ebert, M. S., Neilson, J. R., and Sharp, P. A. (2007). MicroRNA sponges: competitive inhibitors of small RNAs in mammalian cells. Nat. Methods 4, 721-726.

Esau, C., Davis, S., Murray, S. F., Yu, X. X., Pandey, S. K., Pear, M., Watts, L., Booten, S. L., Graham, M., McKay, R., et al. (2006). miR-122 regulation of lipid metabolism revealed by in vivo antisense targeting. Cell Metab. 3, 87-98.

Gao, G., Vandenberghe, L. H., Alvira, M. R., Lu, Y., Calcedo, R., Zhou, X., and Wilson, J. M. (2004). Clades of Adeno-associated viruses are widely disseminated in human tissues. J. Virol. 78, 6381-6388.

Geisler, A., Jungmann, A., Kurreck, J., Poller, W., Katus, H. A., Vetter, R., . . . Müller, O. J. (2011). microRNA122-regulated transgene expression increases specificity of cardiac gene transfer upon intravenous delivery of AAV9 vectors. Gene Therapy, 18(2), 199-209.

George, M., Ayuso, E., Casellas, A., Costa, C., Devedjian, J. C., and Bosch, F. (2002). Beta cell expression of IGF-I leads to recovery from type 1 diabetes. J. Clin. Invest. 109, 1153-1163.

Hendrick, L. M., Harewood, G. C., Patchett, S. E., and Murray, F. E. (2011). Utilization of resource leveling to optimize ERCP efficiency. Ir. J. Med. Sci. 180, 143-148.

Hill, D. J., and Hogg, J. (1992). Expression of insulin-like growth factors (IGFs) and their binding proteins (IGF BPs) during pancreatic development in rat, and modulation of IGF actions on rat islet DNA synthesis by IGF BPs. Adv. Exp. Med. Biol. 321, 113-120; discussion 121-122.

Jabri, N., Schalch, D. S., Schwartz, S. L., Fischer, J. S., Kipnes, M. S., Radnik, B. J., Turman, N. J., Marcsisin, V. S., and Guler, H. P. (1994). Adverse effects of recombinant human insulin-like growth factor I in obese insulin-resistant type II diabetic patients. Diabetes 43, 369-374.

Jimenez, V., Ayuso, E., Mallol, C., Agudo, J., Casellas, A., Obach, M., Muñoz, S., Salavert, A., and Bosch, F. (2011). In vivo genetic engineering of murine pancreatic beta cells mediated by single-stranded adeno-associated viral vectors of serotypes 6, 8 and 9. Diabetologia 54, 1075-1086.

Jimenez, V., Muñoz, S., Casana, E., Mallol, C., Elias, I., Jambrina, C., Ribera, A., Ferre, T., Franckhauser, S., and Bosch, F. (2013). In vivo adeno-associated viral vector-mediated genetic engineering of white and brown adipose tissue in adult mice. Diabetes 62, 4012-4022.

Kaino, Y., Hirai, H., Ito, T., and Kida, K. (1996). Insulin-like growth factor I (IGF-I) delays the onset of diabetes in non-obese diabetic (NOD) mice. Diabetes Res. Clin. Pract. 34, 7-11.

Kang, W. J., Cho, Y. L., Chae, J. R., Lee, J. D., Ali, B. A., Al-Khedhairy, A. A., . . . Kim, S. (2012). Dual optical biosensors for imaging microRNA-1 during myogenesis. Biomaterials, 33(27), 6430-7.

Kulkarni, R. N., Holzenberger, M., Shih, D. Q., Ozcan, U., Stoffel, M., Magnuson, M. A., and Kahn, C. R. (2002). beta-cell-specific deletion of the Igf1 receptor leads to hyperinsulinemia and glucose intolerance but does not alter beta-cell mass. Nat. Genet. 31, 111-115.

Liu, F., Song, Y., and Liu, D. (1999). Hydrodynamics-based transfection in animals by systemic administration of plasmid DNA. Gene Ther. 6, 1258-1266.

Livak, K. J., and Schmittgen, T. D. (2001). Analysis of relative gene expression data using real-time quantitative PCR and the 2(-Delta Delta C(T)) Method. Methods 25, 402-408.

Lock, M., McGorray, S., Auricchio, A., Ayuso, E., Beecham, E. J., Blouin-Tavel, V., Bosch, F., Bose, M., Byrne, B. J., Caton, T., et al. (2010). Characterization of a recombinant adeno-associated virus type 2 Reference Standard Material. Hum. Gene Ther. 21, 1273-1285.

Loiler, S. A., Tang, Q., Clarke, T., Campbell-Thompson, M. L., Chiodo, V., Hauswirth, W., Cruz, P., Perret-Gentil, M., Atkinson, M. A., Ramiya, V. K., et al. (2005). Localized gene expression following administration of adeno-associated viral vectors via pancreatic ducts. Mol. Ther. 12, 519-527.

Lu, Y., Herrera, P. L., Guo, Y., Sun, D., Tang, Z., LeRoith, D., and Liu, J.-L. (2004). Pancreatic-specific inactivation of IGF-I gene causes enlarged pancreatic islets and significant resistance to diabetes. Diabetes 53, 3131-3141.

Mingozzi F, High K A. Therapeutic in vivo gene transfer for genetic disease using AAV: progress and challenges. Nat Rev Genet. 2011 May; 12(5):341-55.

Pescovitz, M. D., Greenbaum, C. J., Bundy, B., Becker, D. J., Gitelman, S. E., Goland, R., Gottlieb, P. A., Marks, J. B., Moran, A., Raskin, P., et al. (2014). B-lymphocyte depletion with rituximab and β-cell function: two-year results. Diabetes Care 37, 453-459.

Rehman, K. K., Wang, Z., Bottino, R., Balamurugan, A. N., Trucco, M., Li, J., . . . Robbins, P. D. (2005). Efficient gene delivery to human and rodent islets with double-stranded (ds) AAV-based vectors. Gene Therapy, 12(17), 1313-23.

Savage, M. O., Camacho-Hübner, C., and Dunger, D. B. (2004). Therapeutic applications of the insulin-like growth factors. Growth Horm. IGF Res. 14, 301-308.

Sherry, N., Hagopian, W., Ludvigsson, J., Jain, S. M., Wahlen, J., Ferry, R. J., Bode, B., Aronoff, S., Holland, C., Carlin, D., et al. (2011). Teplizumab for treatment of type 1 diabetes (Protégé study): 1-year results from a randomised, placebo-controlled trial. Lancet 378, 487-497.

Smith, T. J. (2010). Insulin-like growth factor-I regulation of immune function: a potential therapeutic target in autoimmune diseases? Pharmacol. Rev. 62, 199-236.

Tsai, W.-C., Hsu, S.-D., Hsu, C.-S., Lai, T.-C., Chen, S.-J., Shen, R., Huang, Y., Chen, H.-C., Lee, C.-H., Tsai, T.-F., et al. (2012). MicroRNA-122 plays a critical role in liver homeostasis and hepatocarcinogenesis. J. Clin. Invest. 122, 2884-2897.

The invention claimed is:

1. An adeno-associated viral expression vector comprising a gene construct comprising:
(a) a nucleotide sequence encoding the Insulin-like growth factor 1 (IGF-1) of a mammal; and
(b) at least one target sequence of the microRNA-122a and at least one target sequence of the microRNA-1, wherein the sequences (a) and (b) are operationally linked to a ubiquitous promoter, wherein the vector comprises a sequence selected from SEQ ID NO: 30 and SEQ ID NO: 31.

* * * * *

SEQUENCE LISTING

```
<160> NUMBER OF SEQ ID NOS: 99

<210> SEQ ID NO 1
<211> LENGTH: 6987
<212> TYPE: DNA
<213> ORGANISM: Mus musculus

<400> SEQUENCE: 1
acaatggaaa tgagtggctt cccttggggg aaaaagacgg actccaactc ccagctgtgc        60
aatttactca ttgtttaaat ggacaaaagg cagtttaccc aggctcagag catacctgcc       120
tgggtgtcca aatgtaacta gatgctttca caaaccccac ccacaaaaca acacctgttc       180
ttaagtcctc agttttgtgt tcacctcggc ctcatagtac ccactctgac ctgctgtgta       240
aacgacccgg acctaccaaa atgaccgcac ctgcaataaa gatacacatc atgtcgtctt       300
cacacctctt ctacctggcg ctctgcttgc tcaccttcac cagctccacc acagctggac       360
cagagaccct ttgcggggct gagctggtgg atgctcttca gttcgtgtgt ggaccgaggg       420
gcttttactt caacaagccc acaggctatg gctccagcat tcggagggca cctcagacag       480
gcattgtgga tgagtgttgc ttccggagct gtgatctgag gagactggag atgtactgtg       540
ccccactgaa gcctacaaaa gcagcccgct ctatccgtgc ccagcgccac actgacatgc       600
ccaagactca gaaggaagta catttgaaga acacaagtag aggaagtgca ggaaacaaga       660
cctacagaat gtaggaggag cctcccacgg agcagaaaat gccacatcac cgcaggatcc       720
tttgctgctt gagcaacctg caaacatcg aaacacctac caaataacaa taataagtcc       780
aataacatta caaagatggg catttcccc aatgaaatat acaagtaaac attccaacat       840 cgtcttagg agtgtttgtt taaaaagctt tgcaccttgc aaaagtggtc ctggcgtggg       900
tagattgctg ttggtccttt atcaataaca ttctatagag aaaaaaaata tatatataac       960
tatatctcct agtccctgcc tctaaagagc cgaaaatgca tggatgttgt agagatccag      1020
ttgctctaag tttctctctg aattttggct gctgaagcca ttcatttagc aactgtgtag      1080
aggtggttta tgaatggttc ccttatcttc acctcttccc acgtagctca agctgcttgt      1140
tttacagagt ctaatcatct tgtctagctg cattagacac acccttttcct aacacttgta     1200 tttgttgaat ttggcctcct taagagcaat agcaaataag tagtcaagtg gcctaccaag      1260
ttttaacgta cctgactcca tctgtggcat ttgtaccaaa tataagttga atgcatttat      1320
tttagacaca aagctttatt tttttttgaca ttgtgtttca agaaaaaaaa tagaataaca     1380
ataactacaa ctttgaggcc aatcattttt aggtgtgtgt ttgaagcata gaacgtctct      1440
taaactctca atggtttctt caaatgataa gttagtatgt aacctaagta tagcagtttc      1500 tctcttttt attttttcc atatagagca ctatgtaaag ttagtatatc aataatacag        1560
gaaatatcaa acagtatgta aaactctgtt gttgttgttt tttagtacaa tggtgctatt      1620
ttgtagtttg ttatatgaaa gaatctagtc aacacagtaa aaggagaaag caaagcaaaa      1680
acaacaaacg aaagcctgga gcctaagatg acaaaacgag gaagggaact gaaaaaaaaa      1740
```

-continued

```
atccttcctc ttgggagatg caaaggcctc cccaattatg ccttccaaga agaacttaag    1800
atatagagtc cattaagacg cacttacttg tcaagtccag agaggaagct atggagtggg    1860
aaaagcaaga ggctagggat ttgggagtcc tggtttcttt ttaatcactg aagaagtaag    1920
tatttgcaac ctgggtcaca caaactcacc accctgtgac ctcagtcaaa tcactccacc    1980
tctcggtgcc tcagttttcc tcatctgcaa aatgggggca atatgtcatc tacctacctc    2040
aaaggggtgg tatgaagatt aaaaagtaga ccttcagatt tttgttctgg gtttccagga    2100
gggtgcaaca tcagaaccct tgaattgcta ggatgcaagg aattctgtaa ataacccact    2160
aacaatgtag ctccaaggat cattcatctg tcactgggat gccaccacaa tatccaagtt    2220
cttattggtg aagctgtgca actaattagt gacaagctaa ggactcagtc tccccagcat    2280
gtcacacggc aggagacatt tgatttgcag ttttatttaa cttctgcatt tgagcttatg    2340
actataaaga ctagtgaaaa aagggagag aggagaaaga agatccttgc caagtaaagg    2400
gtaattaatt attattccat ttatccactc tcattaaagg gtaattaatt attccatgta    2460
tccactctca ttaatccttc cagtcactta gtatctagaa ataactctaa cattgtcaat    2520
gagactctac tcagtttgcc aaacacaatt ctccttcccc atagcatatg aaaaaaaggc    2580
gctgacattc ttaaattttg aaatagtatc tattacaatc acaggttgct gtagcagatg    2640
tagtcttgcc cttgtttgta catgcatgta ttttttttt aattttatga aaatgtgcta    2700
gcaagaattg ctacttgagg ggcaaaattc ttccttctca agcctgaggt tctccctagt    2760
gtctgcttag aaggaaggat ccagcttcct ggaaatgtgt tggatgcatt caactgggca    2820
ttgctaacca aaaacattta gaaaaatgtt ctctatgtat atagcaagat tgtctccctc    2880
ttttaaaaac aaaatccaat attcacatct tattacctac aaccttgatt ctctattgca    2940
agcttcctta atattcttat aaaatgtatt aagaaaaaca aaaaggacac ctttagctct    3000
ccttccgcca ggttgcctct agaatctctg gggaaatgca gaaggtgctg ttgagtaaag    3060
ccctcagaag gattggattt aggaacatca ggcacgctgt acatcccctg attactgtag    3120
aaatgtaaat ggaataagag gtcagctgac catccacctg cttccccaga aggatacagg    3180
gaaaagttag gccctcacac accctgggtg acacttctga cttctagttc ttgttcacag    3240
tgtgtacttt ttcaaattgg taattcccag aaaaacacat aggtggcctt ctccagatct    3300
gtgggcttcc tgccatggtt ggatttggtg attccaagtg tctatcacat atttgtgtca    3360
cttaattcta tccacagtca gaaattcttt caatgaggaa agtttaaata tgcaatcctt    3420
tatccaatac ctaattctct ccaactgcat cataaatcaa gtaataaaaa ttaattgtac    3480
taattaatca taataatgta ccattgtact tttaaatgaa tgaacactgc aagacaaatc    3540
tatgtaaact ctgaaaagta actgatcatt atatggtgaa tcaaaatgac tcaagattga    3600
tagaaaggga catttaaaat tttacaactc aaaattttgt agactttgct atggaggtaa    3660
attgttttag tgcctagaga tggagcggtt ttaataaatt tacaaagaa ctataaagat    3720 aggtaggaag gaattttcat ttgataggat tgttgctgat ttacttactc aatacctagg    3780
tcaaatgttg atcctattct ccaaagacta tcaagtgctt gaacattgta agatgagtct    3840
gctccactga aaatgtaata catctctcca ttataatcta ttttcctggg gtaaaaaaat    3900 cctttttta aatatccacc tacatatacc taccctacat gtgcatttgc acatgcgtgc    3960
atacgctcat gcgccccacc ccacacacac ctattcaccc taagactaag aagaaatcat    4020
ttctttgaaa gtcttatctt tcaaaaaagg cagcggtgcc ccttgagact ccttctcctt    4080
ctttgaatgt caatgtgaaa tgtggcatgt ctgtgtacat gaaaccatct cataccctat    4140
```

```
ggctccaggg tttctttatg gtttgtgcac ttgggaggat gcgcagaaga caggatgcag    4200
cctgttttgc tttccccttt actgtttggc cagctacgcc aatgtggtgc tattgtttct    4260
ttaagaaagt acttgactaa aaaaaaagaa aaaagaaaaa aaagaaaaga aaaagaaaaa    4320
agaaaaaaaa agaaagcata gacctatttt tttaaagtct gaaaacaaca gttctatagt    4380
agatggctta ctgagatagc attagatcta gccaccaccc tagccaccac ctttcaacta    4440
tgtgtcactc acaagtagaa tattgttcac caagttgtga gtttgggggt tcagagacaa    4500
aggatggaaa agttttaaag ttagatggct caatcatttc attggctctc aaatttaaca    4560
aaattggcaa tacttcaccc aatctgaagt gttggtcaat aacttgaact gggggcaaaa    4620
ataacttcag gcaaatggca gaagaaaata attaacttac ttcttgcttt ttttgttgat    4680
tgtttggttt cctgttgatt tttggttttg gttttgctgt gggtgggtga gtacatgtgt    4740
gtaagtacgt gtgtgtgtgt gtgtgtgtgt gtgtgtgtgt gtgttccact caaaaacaaa    4800
tactcagaaa gtggagaaaa tacaacgatt ttaagagcat agacttacct actactagaa    4860
ccagcttctg tcacatcctc tggagaaggc actgatttct tgttttgtag aggttgctct    4920
tccatcagtg acctgaaaga gtgaccagtc tcctagagta gacatggatc tcattaggag    4980
aagacagaag tatttcctta tgaattgggc ttatctactg acaaagaaag ggaagagttt    5040
atgagaagtt attgaagaag atggctaaca gtctgtgaag attttgttct ggttttttt    5100 gttgttgttg ttgttgggtt tgggttttga tttttttttt tttttttta ctttatacaa    5160 tctttatgaa tggaaatctt aatgctcaaa aagacttggt cttttttct ctttcgtaac    5220 agaatggaag atgacaaact cacatagact cttttctaggc tggctagcaa aggtgtggtt    5280
tgacttattt gaatcagacc atttttaaatg ttcctctcta ttttaatca taaaaggctg    5340 tcataattta ttagcgtagg cccttttttgg cacttctcaa atgaatgagc attcccattc    5400
aaagcatggc tttccccatg gttccaaaac atgaatgatt aatattaagg aattatttac    5460
ttcaaaatac agtagaagtg tgagtctctg ttcccattcc ccacaaagat cattaagtcc    5520
tgaatcgggg gcgggggtgg ggcgcctgga tactaaggga attttttttgt tgcttgtttt    5580 ttgttttcaa tgctagtgct taatcctata gtatacagat ttgcttcttg ctattgtgat    5640
attctgtaag actttcctgt taggtattag aaattgatac ataaataccct tttttgtgtg    5700 gtttctattt aaaaggaaag agataagact gtctgaacct taaattcgta aggcacatga    5760
taaagagatc acattaaata acaagccata tctggttcaa tcctttcttt cttatcatt    5820 taaggaaaac ttgcccagat aagacagagg cccaggggac ttttgaaact ctctttgttc    5880
cgccaattca ttttggctgg tgatggtttt tccccagtgt ctgcctcaga atctttaga    5940 ggctggccag actaaagact gtcttttaaa acacatttca catggttcct cttaatgaat    6000
gattacactt atgtagaaca tgattttttt ttctctccac ttatttttt tttccccatc    6060 attgataagg gttcttaagg agaagaattc attaacaaaa ctcaagaaag cgtacaaaaa    6120
aaaaattcta aatgtcactg cccaattgaa atacgagcta aaatggaaat actttctcct    6180
acttaaaacc cagactgaat caccttcaaa atgacctttc acaatctttc caatttgcct    6240
ttgtttaaac tgtctgggcc taaaagcaag cattattcat tttctcttgc ccaaagtgaa    6300
cttgtgtaaa gtaggaaaat taaagaaaac tgctagaaat cccttccaac cagtggctga    6360
cccctctcac tagctcacag caaagtctcc tctgttgatc tatcacctag tctcatttcg    6420
tttgaatatt tacattgtac ctactgctaa acacttggca ggaggctcca tccatatctc    6480
```

| | |
|---|---|
| ctatcggtgt ctctgtatcc ttaaaccttg caaacatcat acagtgtata ttaagtttac | 6540 |
| aggaaagctc caaatagcat atcagacctg gtctctcttt gttaaagatt taaggagcta | 6600 |
| tgggaatctg gattacaacg cacattttgc ttcatttatt tttatcacac tttaaaggcc | 6660 |
| aagggtgatg attaacttac agacactgaa ttgatttccc tactgaaacc tgaaagtaat | 6720 |
| atttggtcat tcattgtatg tgttttacac aaaaaaaaca tcttctatca aattactcct | 6780 |
| gattgtattt gaagtggtta ttcaattcat ttatggcaga gcaatatctg tcctaatgac | 6840 |
| tcttataaaa tgtaactaac tgaatcatta tcttacattt actgtttagt aagcatattt | 6900 |
| tgaaattgta tggctagagt gtcataataa aatggtatat ctttctttag taattacatt | 6960 |
| aaaattaatc atgtttgatt aactggt | 6987 |

<210> SEQ ID NO 2
<211> LENGTH: 1536
<212> TYPE: DNA
<213> ORGANISM: Mus musculus

<400> SEQUENCE: 2

| | |
|---|---|
| gacttcttga agataaagat acacatcatg tcgtcttcac acctcttcta cctggcgctc | 60 |
| tgcttgctca cctcaccag ctccaccaca gctggaccag agacccttg cggggctgag | 120 |
| ctggtggatg ctcttcagtt cgtgtgtgga ccgaggggct tttacttcaa caagcccaca | 180 |
| ggctatggct ccagcattcg gagggcacct cagacaggca ttgtggatga gtgttgcttc | 240 |
| cggagctgtg atctgaggag actggagatg tactgtgccc cactgaagcc tacaaaagca | 300 |
| gcccgctcta tccgtgccca cgccacact gacatgccca agactcagaa gtccccgtcc | 360 |
| ctatcgacaa acaagaaaac gaagctgcaa aggagaagga aggaagtac atttgaagaa | 420 |
| cacaagtaga ggaagtgcag gaaacaagac ctacagaatg taggaggagc ctcccacgga | 480 |
| gcagaaaatg ccacatcacc gcaggatcct ttgctgcttg agcaacctgc aaaacatcga | 540 |
| aacacctacc aaataacaat aataagtcca ataacattac aaagatgggc atttccccca | 600 |
| atgaaatata caagtaaaca ttccaacatc gtctttagga gtgtttgttt aaaaagcttt | 660 |
| gcaccttgca aaagtggtcc tggcgtgggt agattgctgt tgatcccttta tcaataacat | 720 |
| tctatagaga aaaaaatata tatatataac tatatctcct agtccctgcc tctaaagagc | 780 |
| cgaaaatgca tggatgttgt agagatccag ttgctctaag tttctctctg aattttggct | 840 |
| gctgaagcca ttcatttagc aactgtgtag aggtggttta tgaatggttc ccttatcttc | 900 |
| acctcttccc acgtagctca agctgcttgt tttacagagt ctaatcatct tgtctagctc | 960 |
| cattagacac acccttttcct aacacttgta tttgttgaat ttggcctcct taagagcaat | 1020 |
| agcaaataag tagtcaagtg gcctaccaag ttttaacgta cctgactcca tctgtggcat | 1080 |
| ttgtaccaaa tataagttga atgcatttat tttagacaca aagcttatt tttttgaca | 1140 |
| ttgtgttca agaaaaaaaa tagaataaca ataactacaa ctttgaggcc aatcattttt | 1200 |
| aggtgtgtgt ttgaagcata gaacgtctct taaactctca atggttcctt caaatgataa | 1260 |
| gttagtatgt aacctaagta tagcagtttc tctcttttt attttttcc atatagagca | 1320 |
| ctatgtaaag ttagtatatc aataatacag gaaatatcaa acagtatgta aaactctgtt | 1380 |
| gttgttgttt tttagtacaa tggtgctatt ttgtagtttg ttatatgaaa gaatctagtc | 1440 |
| aacacagtaa aaggagaaag caaagcaaaa acaacaaacg aaagcctgga gcctaagatg | 1500 |
| acaaaacgag gaagggaact gaaaaaaaaa aaaaaa | 1536 |

<210> SEQ ID NO 3
<211> LENGTH: 7204
<212> TYPE: DNA
<213> ORGANISM: Homo sapiens

<400> SEQUENCE: 3

| | | | | | | |
|---|---|---|---|---|---|---|
| gcatacctgc | ctgggtgtcc | aaatgtaact | agatgctttc | acaaacccca | cccacaaagc | 60 |
| agcacatgtt | tttaagactt | cagttttcta | ttcacatcgg | cctcataata | cccaccctga | 120 |
| cctgctgtaa | aagacctgga | acaaacaaaa | atgattacac | ctacagtgaa | gatgcacacc | 180 |
| atgtcctcct | cgcatctctt | ctacctggcg | ctgtgcctgc | tcaccttcac | cagctctgcc | 240 |
| acggctggac | cggagacgct | ctgcggggct | gagctggtgg | atgctcttca | gttcgtgtgt | 300 |
| ggagacaggg | gcttttattt | caacaagccc | acagggtatg | gctccagcag | tcggagggcg | 360 |
| cctcagacag | gcatcgtgga | tgagtgctgc | ttccggagct | gtgatctaag | gaggctggag | 420 |
| atgtattgcg | caccccctcaa | gcctgccaag | tcagctcgct | ctgtccgtgc | ccagcgccac | 480 |
| accgacatgc | ccaagaccca | gaaggaagta | catttgaaga | cgcaagtag | agggagtgca | 540 |
| ggaaacaaga | actacaggat | gtaggaagac | cctcctgagg | agtgaagagt | gacatgccac | 600 |
| cgcaggatcc | tttgctctgc | acgagttacc | tgttaaactt | tggaacacct | accaaaaaat | 660 |
| aagtttgata | acatttaaaa | gatgggcgtt | tcccccaatg | aaatacacaa | gtaaacattc | 720 |
| caacattgtc | tttaggagtg | atttgcacct | tgcaaaaatg | gtcctggagt | tggtagattg | 780 |
| ctgttgatct | tttatcaata | atgttctata | gaaaagaaaa | aaaaaatata | tatatatata | 840 |
| tatcttagtc | cctgcctctc | aagagccaca | aatgcatggg | tgttgtatag | atccagttgc | 900 |
| actaaattcc | tctctgaatc | ttggctgctg | gagccattca | ttcagcaacc | ttgtctaagt | 960 |
| ggtttatgaa | ttgtttcctt | atttgcactt | ctttctacac | aactcgggct | gtttgtttta | 1020 |
| cagtgtctga | taatcttgtt | agtctatacc | caccacctcc | cttcataacc | tttatatttg | 1080 |
| ccgaatttgg | cctcctcaaa | agcagcagca | agtcgtcaag | aagcacacca | attctaaccc | 1140 |
| acaagattcc | atctgtggca | tttgtaccaa | atataagttg | gatgcatttt | attttagaca | 1200 |
| caaagcttta | ttttccaca | tcatgcttac | aaaaaagaat | aatgcaaata | gttgcaactt | 1260 |
| tgaggccaat | cattttagg | catatgtttt | aaacatagaa | agtttcttca | actcaaaaga | 1320 |
| gttccttcaa | atgatgagtt | aatgtgcaac | ctaattagta | actttcctct | tttattttt | 1380 |
| tccatataga | gcactatgta | aatttagcat | atcaattata | caggatatat | caaacagtat | 1440 |
| gtaaaactct | gttttttagt | ataatggtgc | tattttgtag | tttgttatat | gaaagagtct | 1500 |
| ggccaaaacg | gtaatacgtg | aaagcaaaac | aataggggaa | gcctggagcc | aaagatgaca | 1560 |
| caaggggaag | ggtactgaaa | acaccatcca | tttgggaaag | aaggcaaagt | cccccccagtt | 1620 |
| atgccttcca | agaggaactt | cagacacaaa | agtccactga | tgcaaattgg | actggcgagt | 1680 |
| ccagagagga | aactgtggaa | tggaaaaagc | agaaggctag | gaattttagc | agtcctggtt | 1740 |
| tctttttctc | atggaagaaa | tgaacatctg | ccagctgtgt | catggactca | ccactgtgtg | 1800 |
| accttgggca | agtcacttca | cctctctgtg | cctcagtttc | ctcatctgca | aaatgggggc | 1860 |
| aatatgtcat | ctacctacct | caaaggggtg | gtataaggtt | taaaaagata | aagattcaga | 1920 |
| ttttttttac | cctgggttgc | tgtaagggtg | caacatcagg | gcgcttgagt | tgctgagatg | 1980 |
| caaggaattc | tataaataac | ccattcatag | catagctaga | gattggtgaa | ttgaatgctc | 2040 |
| ctgcatctc | agttccttgtc | agtgaagcta | tccaataac | tggccaacta | gttgttaaaa | 2100 |
| gctaacagct | caatctctta | aaacactttt | caaaatatgt | gggaagcatt | tgattttcaa | 2160 |

```
tttgattttg aattctgcat ttggttttat gaatacaaag ataagtgaaa agagagaaag    2220
gaaaagaaaa aggagaaaaa caaagagatt tctaccagtg aaagggaat taattactct    2280 ttgttagcac tcactgactc ttctatgcag ttactacata tctagtaaaa cctcgtttaa    2340
tactataaat aatattctat tcattttgaa aaacacaatg attccttctt ttctaggcaa    2400
tataaggaaa gtgatccaaa atttgaaata ttaaaataat atctaataaa aagtcacaaa    2460
gttatcttct ttaacaaact ttactcttat tcttagctgt atatacattt ttttaaaagt    2520
ttgttaaaat atgcttgact agagtttcca gttgaaaggc aaaaacttcc atcacaacaa    2580
gaaatttccc atgcctgctc agaagggtag cccctagctc tctgtgaatg tgttttatcc    2640
attcaactga aaattggtat caagaaagtc cactggttag tgtactagtc catcatagcc    2700
tagaaaatga tccctatctg cagatcaaga ttttctcatt agaacaatga attatccagc    2760
attcagatct ttctagtcac cttagaactt tttggttaaa agtacccagg cttgattatt    2820
tcatgcaaat tctatatttt acattcttgg aaagtctata tgaaaaacaa aaataacatc    2880
ttcagttttt ctcccactgg gtcacctcaa ggatcagagg ccaggaaaaa aaaaaaaaag    2940
actccctgga tctctgaata tatgcaaaaa gaaggcccca tttagtggag ccagcaatcc    3000
tgttcagtca acaagtattt taactctcag tccaacatta tttgaattga gcacctcaag    3060
catgcttagc aatgttctaa tcactatgga cagatgtaaa agaaactata catcattttt    3120
gccctctgcc tgttttccag acatacaggt tctgtggaat aagatactgg actcctcttc    3180
ccaagatggc acttcttttt atttcttgtc cccagtgtgt acctttaaa attattccct    3240 ctcaacaaaa ctttataggc agtcttctgc agacttaacg tgttttctgt catagttaga    3300
tgtgataatt ctaagagtgt ctatgactta ttttccttcac ttaattctat ccacagtcaa    3360
aaatccccca aggaggaaag ctgaaagatg cactgccata ttatctttct taactttttc    3420
caacacataa tcctctccaa ctggattata ataaattga aataactca ttataccaat    3480 tcactatttt attttttaat gaattaaaac tagaaaacaa attgatgcaa accctggaag    3540
tcagttgatt actatatact acagcagaat gactcagatt tcatagaaag gagcaaccaa    3600
aatgtcacaa cccaaaactt tacaagcttt gcttcagaat tagattgctt tataattctt    3660
gaatgaggca atttcaagat atttgtaaaa gaacagtaaa cattggtaag aatgagcttt    3720
caactcatag gcttatttcc aatttaattg accatactgg atacttaggt caaatttctg    3780
ttctctcttc cccaaataat attaaagtat tatttgaact ttttaagatg aggcagttcc    3840
cctgaaaaag ttaatgcagc tctccatcag aatccactct tctagggata tgaaaatctc    3900
ttaacaccca ccctacatac acagacacac acacacacac acacacacac acacacacac    3960
acattcaccc taaggatcca atggaatact gaaaagaaat cacttccttg aaaattttat    4020
taaaaaacaa acaaacaaac aaaaagcctg tccaccctg agaatccttc ctctccttgg    4080
aacgtcaatg tttgtgtaga tgaaaccatc tcatgctctg tggctccagg gtttctgtta    4140 ctatttatg cacttgggag aaggcttaga ataaagatg tagcacattt tgctttccca    4200
tttattgttt ggccagctat gccaatgtgg tgctattgtt tctttaagaa agtacttgac    4260
taaaaaaaaa agaaaaaaag aaaaaaaaga aagcatagac atattttttt aaagtataaa    4320
aacaacaatt ctatagatag atggcttaat aaaatagcat taggtctatc tagccaccac    4380 caccttttcaa cttttttatca ctcacaagta gtgtactgtt caccaaattg tgaatttggg    4440
ggtgcagggg caggagttgg aaattttta agttagaag gctccattgt tttgttggct    4500
ctcaaactta gcaaaattag caatatatta tccaatcttc tgaacttgat caagagcatg    4560
```

```
gagaataaac gcgggaaaaa agatcttata ggcaaataga agaatttaaa agataagtaa    4620
gttccttatt gattttttgtg cactctgctc taaaacagat attcagcaag tggagaaaat    4680
aagaacaaag agaaaaaata catagattta cctgcaaaaa atagcttctg ccaaatcccc    4740
cttgggtatt ctttggcatt tactggttta tagaagacat tctcccttca cccagacatc    4800
tcaaagagca gtagctctca tgaaaagcaa tcactgatct catttgggaa atgttggaaa    4860
gtatttcctt atgagatggg ggttatctac tgataaagaa agaatttatg agaaattgtt    4920
gaaagagatg gctaacaatc tgtgaagatt ttttgtttct tgttttgtt ttttttttt    4980 ttttacttta tacagtcttt atgaatttct taatgttcaa aatgacttgg ttcttttctt    5040
ctttttttat atcagaatga ggaataataa gttaaaccca catagactct ttaaaactat    5100
aggctagata gaaatgtatg tttgacttgt tgaagctata atcagactat ttaaaatgtt    5160
ttgctatttt taatcttaaa agattgtgct aatttattag agcagaacct gtttggctct    5220
cctcagaaga aagaatcttt ccattcaaat cacatggctt tccaccaata ttttcaaaag    5280
ataaatctga tttatgcaat ggcatcattt attttaaaac agaagaattg tgaaagttta    5340
tgcccctccc ttgcaaagac cataaagtcc agatctggta gggggggcaac aacaaaagga    5400 aaatgttgtt gattcttggt tttggatttt gttttgtttt caatgctagt gtttaatcct    5460
gtagtacata tttgcttatt gctatttaa tatttataa gaccttcctg ttaggtatta    5520
gaaagtgata catagatatc tttttgtgt aatttctatt taaaaagag agaagactgt    5580 cagaagcttt aagtgcatat ggtacaggat aaagatatca atttaaataa ccaattccta    5640
tctggaacaa tgcttttgtt ttttaaagaa acctctcaca gataagacag aggcccaggg    5700
gatttttgaa gctgtctta ttctgccccc atcccaaccc agcccttatt attttagtat    5760
ctgcctcaga attttataga gggctgacca agctgaaact ctagaattaa aggaacctca    5820
ctgaaaacat atatttcacg tgttccctct tttttttttt cctttttgtg agatggggtc    5880
tcgcactgtc ccccaggctg gagtgcagtg gcatgatctc ggctcactgc aacctccacc    5940
tcctgggttt aagcgattct cctgcctcag cctcctgagt agctgggatt acaggcaccc    6000
accactatgc ccggctaatt ttttggattt ttaatagaga cggggtttta ccatgttggc    6060
caggttggtc tcaaactcct gaccttgtga tttgcccgcc tcagcctccc aaattgctgg    6120
gattacaggc atgagccacc acaccctgcc catgtgttcc ctcttaatgt atgattacat    6180
ggatcttaaa catgatcctt ctctcctcat tcttcaacta tctttgatgg ggtcttttcaa    6240 ggggaaaaaa atccaagctt ttttaaagta aaaaaaaaaa aagagaggac acaaaaccaa    6300
atgttactgc tcaactgaaa tatgagttaa gatggagaca gagttctcc taataaccgg    6360 agctgaatta ccttcactt tcaaaaacat gaccttccac aatccttaga atctgccttt    6420
ttttatatta ctgaggccta aaagtaaaca ttactcattt tattttgccc aaaatgcact    6480
gatgtaaagt aggaaaaata aaaacagagc tctaaaatcc ctttcaagcc acccattgac    6540
cccactcacc aactcatagc aaagtcactt ctgttaatcc cttaatctga ttttgtttgg    6600
atatttatct tgtacccgct gctaaacaca ctgcaggagg gactctgaaa cctcaagctg    6660
tctacttaca tcttttatct gtgtctgtgt atcatgaaaa tgtctattca aaatatcaaa    6720
acctttcaaa tatcacgcag cttatattca gtttacataa aggcccccaaa taccatgtca    6780 gatcttttg gtaaaagagt taatgaacta tgagaattgg gattacatca tgtatttgc    6840 ctcatgtatt tttatcacac ttataggcca agtgtgataa ataaacttac agacactgaa    6900
```

```
ttaatttccc ctgctacttt gaaaccagaa ataatgact ggccattcgt tacatctgtc      6960
ttagttgaaa agcatatttt ttattaaatt aattctgatt gtatttgaaa ttattattca      7020
attcacttat ggcagaggaa tatcaatcct aatgacttct aaaaatgtaa ctaattgaat      7080
cattatctta catttactgt ttaataagca tattttgaaa atgtatggct agagtgtcat      7140
aataaaatgg tatatctttc tttagtaatt acattaaaat tagtcatgtt tgattaatta      7200
gttc                                                                  7204

<210> SEQ ID NO 4
<211> LENGTH: 949
<212> TYPE: DNA
<213> ORGANISM: Homo sapiens

<400> SEQUENCE: 4
ttttgtagat aaatgtgagg attttctcta aatccctctt ctgtttgcta aatctcactg        60
tcactgctaa attcagagca gatagagcct gcgcaatgga ataaagtcct caaaattgaa       120
atgtgacatt gctctcaaca tctcccatct ctctggattt cttttttgctt cattattcct      180 gctaaccaat tcattttcag actttgtact tcagaagcaa tgggaaaaat cagcagtctt       240
ccaacccaat tatttaagtg ctgcttttgt gatttcttga aggtgaagat gcacaccatg       300
tcctcctcgc atctcttcta cctggcgctg tgcctgctca ccttcaccag ctctgccacg       360
gctggaccgg agacgctctg cggggctgag ctggtggatg ctcttcagtt cgtgtgtgga       420
gacaggggct tttatttcaa caagcccaca gggtatggct ccagcagtcg gagggcgcct       480
cagacaggca tcgtggatga gtgctgcttc cggagctgtg atctaaggag gctggagatg       540
tattgcgcac ccctcaagcc tgccaagtca gctcgctctg tccgtgccca gcgccacacc       600
gacatgccca gacccagaa gtatcagccc ccatctacca acaagaacac gaagtctcag       660
agaaggaaag gttggccaaa gacacatcca ggaggggaac agaaggaggg gacagaagca       720
agtctgcaga tcagaggaaa gaagaaagag cagaggaggg agattggaag tagaaatgct       780
gaatgcagag gcaaaaaagg aaaatgaagg acaggaggat taaacagaca gaggcaagga       840
tgatgagaga ggagcagaca gcaagaatga aaagcagaaa atacaataga ggaaatgaag       900
aaaagtaggc ctgctggagc tagatgatga tgtgatggaa atagaagta                   949

<210> SEQ ID NO 5
<211> LENGTH: 7370
<212> TYPE: DNA
<213> ORGANISM: Homo sapiens

<400> SEQUENCE: 5
ttttgtagat aaatgtgagg attttctcta aatccctctt ctgtttgcta aatctcactg        60
tcactgctaa attcagagca gatagagcct gcgcaatgga ataaagtcct caaaattgaa       120
atgtgacatt gctctcaaca tctcccatct ctctggattt cttttttgctt cattattcct      180 gctaaccaat tcattttcag actttgtact tcagaagcaa tgggaaaaat cagcagtctt       240
ccaacccaat tatttaagtg ctgcttttgt gatttcttga aggtgaagat gcacaccatg       300
tcctcctcgc atctcttcta cctggcgctg tgcctgctca ccttcaccag ctctgccacg       360
gctggaccgg agacgctctg cggggctgag ctggtggatg ctcttcagtt cgtgtgtgga       420
gacaggggct tttatttcaa caagcccaca gggtatggct ccagcagtcg gagggcgcct       480
cagacaggca tcgtggatga gtgctgcttc cggagctgtg atctaaggag gctggagatg       540
tattgcgcac ccctcaagcc tgccaagtca gctcgctctg tccgtgccca gcgccacacc       600
```

```
gacatgccca agacccagaa gtatcagccc ccatctacca acaagaacac gaagtctcag      660
agaaggaaag gaagtacatt tgaagaacgc aagtagaggg agtgcaggaa acaagaacta      720
caggatgtag gaagaccctc ctgaggagtg aagagtgaca tgccaccgca ggatcctttg      780
ctctgcacga gttacctgtt aaactttgga cacctacca aaaataagt ttgataacat        840 ttaaaagatg ggcgtttccc ccaatgaaat acacaagtaa acattccaac attgtcttta     900
ggagtgattt gcaccttgca aaaatggtcc tggagttggt agattgctgt tgatctttta     960
tcaataatgt tctatagaaa agaaaaaaaa aatatatata tatatatatc ttagtccctg     1020
cctctcaaga gccacaaatg catgggtgtt gtatagatcc agttgcacta aattcctctc     1080
tgaatcttgg ctgctggagc cattcattca gcaaccttgt ctaagtggtt tatgaattgt     1140
ttccttattt gcacttcttt ctacacaact cgggctgttt gttttacagt gtctgataat     1200
cttgttagtc tatacccacc acctcccttc ataacctta tatttgccga atttggcctc      1260
ctcaaaagca gcagcaagtc gtcaagaagc acaccaattc taacccacaa gattccatct     1320
gtggcatttg taccaaatat aagttggatg cattttattt tagacacaaa gctttatttt     1380
tccacatcat gcttacaaaa aagaataatg caaatagttg caactttgag gccaatcatt     1440
tttaggcata tgttttaaac atagaaagtt tcttcaactc aaaagagttc cttcaaatga     1500
tgagttaatg tgcaacctaa ttagtaactt tcctcttttt atttttttcca tatagagcac    1560 tatgtaaatt tagcatatca attatacagg atatatcaaa cagtatgtaa aactctgttt     1620
tttagtataa tggtgctatt ttgtagtttg ttatatgaaa gagtctggcc aaaacggtaa     1680
tacgtgaaag caaacaata ggggaagcct ggagccaaag atgacacaag gggaagggta      1740
ctgaaaacac catccatttg ggaaagaagg caaagtcccc ccagttatgc cttccaagag     1800
gaacttcaga cacaaaagtc cactgatgca aattggactg gcgagtccag agaggaaact     1860
gtggaatgga aaagcagaa ggctaggaat tttagcagtc ctggtttctt tttctcatgg      1920
aagaaatgaa catctgccag ctgtgtcatg gactcaccac tgtgtgacct tgggcaagtc     1980
acttcacctc tctgtgcctc agtttcctca tctgcaaaat gggggcaata tgtcatctac     2040
ctacctcaaa ggggtggtat aaggtttaaa aagataaaga ttcagatttt ttttaccctg     2100
ggttgctgta agggtgcaac atcagggcgc ttgagttgct gagatgcaag gaattctata     2160
aataacccat tcatagcata gctagagatt ggtgaattga atgctcctga catctcagtt     2220
cttgtcagtg aagctatcca aataactggc caactagttg ttaaaagcta acagctcaat     2280
ctcttaaaac acttttcaaa atatgtggga agcatttgat tttcaatttg attttgaatt     2340
ctgcatttgg ttttatgaat acaaagataa gtgaaaagag agaaggaaa agaaaaagga     2400 gaaaacaaa gagatttcta ccagtgaaag gggaattaat tactctttgt tagcactcac      2460
tgactcttct atgcagttac tacatatcta gtaaaacctc gtttaatact ataaataata     2520
ttctattcat tttgaaaaac acaatgattc cttcttttct aggcaatata aggaaagtga     2580
tccaaaattt gaaatattaa aataatatct aataaaaagt cacaaagtta tcttctttaa     2640
caaactttac tcttattctt agctgtatat acatttttt aaaagtttgt taaaatatgc      2700
ttgactagag tttccagttg aaaggcaaaa acttccatca caacaagaaa tttcccatgc     2760
ctgctcagaa gggtagcccc tagctctctg tgaatgtgtt ttatccattc aactgaaaat     2820
tggtatcaag aaagtccact ggttagtgta ctagtccatc atagcctaga aaatgatccc     2880
tatctgcaga tcaagatttt ctcattagaa caatgaatta tccagcattc agatctttct     2940
```

```
agtcacccta gaactttttg gttaaaagta cccaggcttg attatttcat gcaaattcta    3000
tattttacat tcttggaaag tctatatgaa aaacaaaaat aacatcttca gtttttctcc    3060
cactgggtca cctcaaggat cagaggccag gaaaaaaaaa aaaagactc cctggatctc     3120 tgaatatatg caaaagaag gccccattta gtggagccag caatcctgtt cagtcaacaa     3180
gtattttaac tctcagtcca acattatttg aattgagcac ctcaagcatg cttagcaatg    3240
ttctaatcac tatggacaga tgtaaaagaa actatacatc attttgccc tctgcctgtt     3300 ttccagacat acaggttctg tggaataaga tactggactc ctcttcccaa gatggcactt    3360 cttttattt cttgtcccca gtgtgtacct tttaaaatta tccctctca acaaaacttt      3420 ataggcagtc ttctgcagac ttaacgtgtt ttctgtcata gttagatgtg ataattctaa    3480
gagtgtctat gacttatttc cttcacttaa ttctatccac agtcaaaaat cccccaagga    3540
ggaaagctga agatgcact gccatattat ctttcttaac ttttccaac acataatcct      3600 ctccaactgg attataaata aattgaaaat aactcattat accaattcac tattttattt    3660
tttaatgaat taaaactaga aaacaaattg atgcaaaccc tggaagtcag ttgattacta    3720
tatactacag cagaatgact cagatttcat agaaaggagc aaccaaaatg tcacaaccca    3780
aaactttaca agctttgctt cagaattaga ttgctttata attcttgaat gaggcaattt    3840
caagatattt gtaaaagaac agtaaacatt ggtaagaatg agcttcaac tcataggctt     3900 atttccaatt taattgacca tactggatac ttaggtcaaa tttctgttct ctcttcccca    3960
aataatatta aagtattatt tgaactttt aagatgaggc agttcccctg aaaaagttaa     4020
tgcagctctc catcagaatc cactcttcta gggatatgaa aatctcttaa cacccaccct    4080
acatacacag acacacacac acacacacac acacacacac acacacacat tcaccctaag    4140
gatccaatgg aatactgaaa agaaatcact tccttgaaaa ttttattaaa aaacaaacaa    4200
acaaacaaaa agcctgtcca cccttgagaa tccttcctct ccttggaacg tcaatgtttg    4260
tgtagatgaa accatctcat gctctgtggc tccagggttt ctgttactat tttatgcact    4320
tgggagaagg cttagaataa aagatgtagc acattttgct ttcccattta ttgtttggcc    4380
agctatgcca atgtggtgct attgtttctt taagaaagta cttgactaaa aaaaaaagaa    4440 aaaagaaaa aaagaaaagc atagacatat tttttaaag tataaaaaca acaattctat      4500
agatagatgg cttaataaaa tagcattagg tctatctagc caccaccacc tttcaacttt    4560
ttatcactca caagtagtgt actgttcacc aaattgtgaa tttggggtg caggggcagg     4620 agttggaaat tttttaaagt tagaaggctc cattgttttg ttggctctca aacttagcaa    4680
aattagcaat atattatcca atcttctgaa cttgatcaag agcatggaga ataaacgcgg    4740
gaaaaaagat cttataggca aatagaagaa tttaaaagat aagtaagttc cttattgatt    4800
tttgtgcact ctgctctaaa acagatattc agcaagtgga gaaaataaga acaaagagaa    4860
aaaatacata gatttacctg caaaaaatag cttctgccaa atccccttg ggtattcttt     4920 ggcatttact ggtttataga agacattctc ccttcaccca gacatctcaa agagcagtag    4980
ctctcatgaa aagcaatcac tgatctcatt tgggaaatgt tggaaagtat tccttatga     5040 gatgggggtt atctactgat aaagaaagaa tttatgagaa attgttgaaa gagatggcta    5100
acaatctgtg aagattttt gtttcttgtt tttgttttt ttttttttt actttataca       5160 gtctttatga atttcttaat gttcaaaatg acttggttct tttcttcttt ttttatatca    5220
gaatgaggaa taataagtta aacccacata gactctttaa aactataggc tagatagaaa    5280
tgtatgtttg acttgttgaa gctataatca gactatttaa aatgttttgc tatttttaat    5340
```

```
cttaaaagat tgtgctaatt tattagagca gaacctgttt ggctctcctc agaagaaaga      5400
atctttccat tcaaatcaca tggctttcca ccaatatttt caaaagataa atctgattta      5460
tgcaatggca tcatttattt taaaacagaa gaattgtgaa agtttatgcc cctcccttgc      5520
aaagaccata aagtccagat ctggtagggg ggcaacaaca aaaggaaaat gttgttgatt      5580
cttggttttg gattttgttt tgttttcaat gctagtgttt aatcctgtag tacatatttg      5640
cttattgcta ttttaatatt ttataagacc ttcctgttag gtattagaaa gtgatacata      5700
gatatctttt ttgtgtaatt tctatttaaa aaagagagaa gactgtcaga agctttaagt      5760
gcatatggta caggataaag atatcaattt aaataaccaa ttcctatctg gaacaatgct      5820 tttgttttt aaagaaacct ctcacagata agacagaggc ccaggggatt tttgaagctg       5880
tctttattct gccccccatcc caacccagcc cttattattt tagtatctgc ctcagaattt      5940
tatagagggc tgaccaagct gaaactctag aattaaagga acctcactga aaacatatat      6000
ttcacgtgtt ccctcttttt ttttttcctt tttgtgagat ggggtctcgc actgtccccc      6060
aggctggagt gcagtggcat gatctcggct cactgcaacc tccacctcct gggtttaagc      6120
gattctcctg cctcagcctc ctgagtagct gggattacag gcaccacca ctatgccgg       6180 ctaatttttt ggattttta tagagacggg gttttaccat gttggccagg ttggtctcaa       6240
actcctgacc ttgtgatttg cccgcctcag cctcccaaat tgctgggatt acaggcatga      6300
gccaccacac cctgcccatg tgttccctct taatgtatga ttacatggat cttaaacatg      6360
atccttctct cctcattctt caactatctt tgatggggtc tttcaagggg aaaaaaatcc      6420 aagcttttt aaagtaaaaa aaaaaaaga gaggacacaa aaccaaatgt tactgctcaa        6480
ctgaaatatg agttaagatg gagacagagt ttctcctaat aaccggagct gaattacctt      6540
tcactttcaa aaacatgacc ttccacaatc cttagaatct gccttttttt atattactga      6600
ggcctaaaag taaacattac tcatttatt ttgcccaaaa tgcactgatg taaagtagga       6660
aaaataaaaa cagagctcta aaatcccttt caagccaccc attgacccca ctcaccaact      6720
catagcaaag tcacttctgt taatccctta atctgatttt gtttggatat ttatcttgta      6780
cccgctgcta aacacactgc aggagggact ctgaaacctc aagctgtcta cttacatctt      6840
ttatctgtgt ctgtgtatca tgaaaatgtc tattcaaaat atcaaaacct tcaaatatc      6900 acgcagctta tattcagttt acataaaggc cccaaatacc atgtcagatc tttttggtaa      6960
aagagttaat gaactatgag aattgggatt acatcatgta ttttgcctca tgtattttta      7020
tcacacttat aggccaagtg tgataaataa acttacagac actgaattaa tttcccctgc      7080
tactttgaaa ccagaaaata atgactggcc attcgttaca tctgtcttag ttgaaaagca      7140 tatttttat taaattaatt ctgattgtat ttgaaattat tattcaattc acttatggca       7200
gaggaatatc aatcctaatg acttctaaaa atgtaactaa ttgaatcatt atcttacatt      7260
tactgtttaa taagcatatt ttgaaaatgt atggctagag tgtcataata aaatggtata      7320
tctttcttta gtaattacat taaaattagt catgtttgat taattagttc                 7370
```

<210> SEQ ID NO 6
<211> LENGTH: 7321
<212> TYPE: DNA
<213> ORGANISM: Homo sapiens

<400> SEQUENCE: 6

```
ttttgtagat aaatgtgagg attttctcta atccctctt ctgtttgcta aatctcactg        60
```

-continued

```
tcactgctaa attcagagca gatagagcct gcgcaatgga ataaagtcct caaaattgaa      120
atgtgacatt gctctcaaca tctcccatct ctctggattt cttttttgctt cattattcct     180 gctaaccaat tcattttcag actttgtact tcagaagcaa tgggaaaaat cagcagtctt     240
ccaacccaat tatttaagtg ctgcttttgt gatttcttga aggtgaagat gcacaccatg     300
tcctcctcgc atctcttcta cctggcgctg tgcctgctca ccttcaccag ctctgccacg     360
gctggaccgg agacgctctg cggggctgag ctggtggatg ctcttcagtt cgtgtgtgga     420
gacaggggct tttatttcaa caagcccaca gggtatggct ccagcagtcg agggcgcct      480 cagacaggca tcgtggatga gtgctgcttc cggagctgtg atctaaggag gctggagatg     540
tattgcgcac ccctcaagcc tgccaagtca gctcgctctg tccgtgccca gcgccacacc    600
gacatgccca agacccagaa ggaagtacat ttgaagaacg caagtagagg gagtgcagga     660
aacaagaact acaggatgta ggaagaccct cctgaggagt gaagagtgac atgccaccgc     720
aggatccttt gctctgcacg agttacctgt taaactttgg aacacctacc aaaaaataag     780
tttgataaca tttaaaagat gggcgtttcc cccaatgaaa tacacaagta acattccaa      840 cattgtcttt aggagtgatt tgcaccttgc aaaaatggtc ctggagttgg tagattgctg     900
ttgatctttt atcaataatg ttctatagaa aagaaaaaaa aaatatatat atatatatat     960
cttagtccct gcctctcaag agccacaaat gcatgggtgt tgtatagatc cagttgcact    1020
aaattcctct ctgaatcttg gctgctggag ccattcattc agcaaccttg tctaagtggt    1080
ttatgaattg tttccttatt tgcacttctt tctacacaac tcgggctgtt tgttttacag    1140
tgtctgataa tcttgttagt ctatacccac cacctccctt cataaccttt atatttgccg    1200
aatttggcct cctcaaaagc agcagcaagt cgtcaagaag cacaccaatt ctaacccaca    1260
agattccatc tgtggcattt gtaccaaata taagttggat gcattttatt ttagacacaa    1320
agctttattt ttccacatca tgcttacaaa aagaataat gcaaatagtt gcaactttga     1380
ggccaatcat ttttaggcat atgtttttaaa catagaaagt ttcttcaact caaaagagtt    1440
ccttcaaatg atgagttaat gtgcaaccta attagtaact ttcctctttt tattttttcc    1500
atatagagca ctatgtaaat ttagcatatc aattatacag gatatatcaa acagtatgta    1560
aaactctgtt ttttagtata atggtgctat tttgtagttt gttatatgaa agagtctggc    1620
caaaacggta atacgtgaaa gcaaacaat aggggaagcc tggagccaaa gatgacacaa     1680
ggggaagggt actgaaaaca ccatccattt gggaagaag gcaaagtccc cccagttatg     1740
ccttccaaga ggaacttcag acacaaaagt ccactgatgc aaattggact ggcgagtcca    1800
gagaggaaac tgtggaatgg aaaaagcaga aggctaggaa ttttagcagt cctggtttct    1860
ttttctcatg gaagaaatga acatctgcca gctgtgtcat ggactcacca ctgtgtgacc    1920
ttgggcaagt cacttcacct ctctgtgcct cagtttcctc atctgcaaaa tgggggcaat    1980
atgtcatcta cctacctcaa aggggtggta taaggtttaa aaagataaag attcagattt    2040
tttttaccct gggttgctgt aagggtgcaa catcagggcg cttgagttgc tgagatgcaa    2100
ggaattctat aaataaccca ttcatagcat agctagagat tggtgaattg aatgctcctg    2160
acatctcagt tcttgtcagt gaagctatcc aaataactgg ccaactagtt gttaaaagct    2220
aacagctcaa tctcttaaaa cacttttcaa aatatgtggg aagcatttga ttttcaattt    2280
gattttgaat tctgcatttg gttttatgaa tacaaagata agtgaaaaga gagaaaggaa    2340
aagaaaaagg agaaaaacaa agagatttct accagtgaaa ggggaattaa ttactctttg    2400
ttagcactca ctgactcttc tatgcagtta ctacatatct agtaaaacct cgtttaatac    2460
```

```
tataaataat attctattca ttttgaaaaa cacaatgatt ccttcttttc taggcaatat    2520
aaggaaagtg atccaaaatt tgaaatatta aataatatc taataaaaag tcacaaagtt     2580
atcttcttta acaaacttta ctcttattct tagctgtata tacatttttt taaaagtttg    2640
ttaaaatatg cttgactaga gtttccagtt gaaaggcaaa acttccatc acaacaagaa     2700 atttcccatg cctgctcaga agggtagccc ctagctctct gtgaatgtgt tttatccatt    2760
caactgaaaa ttggtatcaa gaaagtccac tggttagtgt actagtccat catagcctag    2820
aaaatgatcc ctatctgcag atcaagattt tctcattaga acaatgaatt atccagcatt    2880
cagatctttc tagtcacctt agaactttt ggttaaaagt acccaggctt gattatttca     2940
tgcaaattct atattttaca ttcttggaaa gtctatatga aaacaaaaa taacatcttc     3000 agtttttctc ccactgggtc acctcaagga tcagaggcca ggaaaaaaaa aaaaagact    3060 ccctggatct ctgaatatat gcaaaagaa ggccccattt agtggagcca gcaatcctgt    3120
tcagtcaaca agtattttaa ctctcagtcc aacattattt gaattgagca cctcaagcat    3180
gcttagcaat gttctaatca ctatggacag atgtaaaaga aactatacat cattttgcc    3240 ctctgcctgt tttccagaca tacaggttct gtggaataag atactggact cctcttccca    3300
agatggcact tctttttatt tcttgtcccc agtgtgtacc ttttaaaatt attccctctc    3360
aacaaaactt tataggcagt cttctgcaga cttaacgtgt tttctgtcat agttagatgt    3420
gataattcta agagtgtcta tgacttattt ccttcactta attctatcca cagtcaaaaa    3480
tcccccaagg aggaaagctg aaagatgcac tgccatatta tctttcttaa ctttttccaa    3540
cacataatcc tctccaactg gattataaat aaattgaaaa taactcatta taccaattca    3600
ctattttatt ttttaatgaa ttaaaactag aaaacaaatt gatgcaaacc ctggaagtca    3660
gttgattact atatactaca gcagaatgac tcagatttca tagaaaggag caaccaaaat    3720
gtcacaaccc aaaactttac aagctttgct tcagaattag attgctttat aattcttgaa    3780
tgaggcaatt tcaagatatt tgtaaaagaa cagtaaacat tggtaagaat gagctttcaa    3840
ctcataggct tatttccaat ttaattgacc atactggata cttaggtcaa atttctgttc    3900
tctcttcccc aaataatatt aaagtattat ttgaactttt taagatgagg cagttcccct    3960
gaaaaagtta atgcagctct ccatcagaat ccactcttct agggatatga aaatctctta    4020
acacccaccc tacatacaca gacacacaca cacacacaca cacacacaca cacacacaca    4080
ttcaccctaa ggatccaatg gaatactgaa aagaaatcac ttccttgaaa attttattaa    4140
aaaacaaaca aacaaacaaa aagcctgtcc acccttgaga atccttcctc tccttggaac    4200
gtcaatgttt gtgtagatga aaccatctca tgctctgtgg ctccagggtt tctgttacta    4260
ttttatgcac ttgggagaag gcttagaata aaagatgtag cacattttgc tttcccattt    4320
attgtttggc cagctatgcc aatgtggtgc tattgtttct ttaagaaagt acttgactaa    4380
aaaaaaaaga aaaaagaaa aaaagaaag catagacata tttttttaaa gtataaaaac     4440
aacaattcta tagatagatg gcttaataaa atagcattag gtctatctag ccaccaccac    4500 cttttcaactt tttatcactc acaagtagtg tactgttcac caaattgtga atttgggggt    4560
gcaggggcag gagttggaaa ttttttaaag ttagaaggct ccattgtttt gttggctctc    4620
aaacttagca aaattagcaa tatattatcc aatcttctga acttgatcaa gagcatggag    4680
aataaacgcg ggaaaaaaga tcttataggc aaatagaaga atttaaaaga taagtaagtt    4740
ccttattgat ttttgtgcac tctgctctaa aacagatatt cagcaagtgg agaaaataag    4800
```

```
aacaaagaga aaaaatacat agatttacct gcaaaaaata gcttctgcca aatcccccctt    4860 gggtattctt tggcatttac tggtttatag aagacattct cccttcaccc agacatctca    4920
aagagcagta gctctcatga aaagcaatca ctgatctcat ttgggaaatg ttggaaagta    4980
tttccttatg agatgggggt tatctactga taaagaaaga atttatgaga aattgttgaa    5040
agagatggct aacaatctgt gaagattttt tgtttcttgt ttttgttttt ttttttttt     5100 tactttatac agtctttatg aatttcttaa tgttcaaaat gacttggttc ttttcttctt    5160
tttttatatc agaatgagga ataataagtt aaacccacat agactcttta aaactatagg    5220
ctagatagaa atgtatgttt gacttgttga agctataatc agactattta aaatgttttg    5280 ctattttttaa tcttaaaaga ttgtgctaat ttattagagc agaacctgtt tggctctcct   5340
cagaagaaag aatctttcca ttcaaatcac atggctttcc accaatattt tcaaaagata    5400
aatctgattt atgcaatggc atcatttatt ttaaaacaga agaattgtga agtttatgc     5460 ccctcccttg caaagaccat aaagtccaga tctggtaggg gggcaacaac aaaaggaaaa    5520
tgttgttgat tcttggtttt ggattttgtt ttgttttcaa tgctagtgtt taatcctgta    5580
gtacatattt gcttattgct atttaatat tttataagac cttcctgtta ggtattagaa     5640
agtgatacat agatatcttt tttgtgtaat ttctatttaa aaaagagaga agactgtcag    5700
aagctttaag tgcatatggt acaggataaa gatatcaatt taaataacca attcctatct    5760
ggaacaatgc ttttgttttt taaagaaacc tctcacagat aagacagagg cccaggggat    5820
ttttgaagct gtcttttattc tgccccatc ccaacccagc ccttattatt ttagtatctg    5880
cctcagaatt ttatagaggg ctgaccaagc tgaaactcta gaattaaagg aacctcactg    5940
aaaacatata tttcacgtgt tccctctttt ttttttttcct ttttgtgaga tggggtctcg   6000
cactgtcccc caggctggag tgcagtggca tgatctcggc tcactgcaac ctccacctcc    6060
tgggtttaag cgattctcct gcctcagcct cctgagtagc tgggattaca ggcacccacc    6120
actatgcccg gctaatttttt tggattttta atagagacgg ggtttacca tgttggccag    6180 gttggtctca aactcctgac cttgtgattt gcccgcctca gcctcccaaa ttgctgggat    6240
tacaggcatg agccaccaca ccctgcccat gtgttccctc ttaatgtatg attacatgga    6300
tcttaaacat gatccttctc tcctcattct tcaactatct ttgatggggt cttcaaggg     6360 gaaaaaaatc caagcttttt taaagtaaaa aaaaaaaag agaggacaca aaaccaaatg    6420
ttactgctca actgaaatat gagttaagat ggagacagag tttctcctaa taaccggagc    6480
tgaattacct ttcactttca aaaacatgac cttccacaat ccttagaatc tgcctttttt    6540
tatattactg aggcctaaaa gtaaacatta ctcattttat tttgcccaaa atgcactgat    6600
gtaaagtagg aaaaataaaa acagagctct aaaatcccctt tcaagccacc cattgaccccc   6660 actcaccaac tcatagcaaa gtcacttctg ttaatccctt aatctgattt tgtttggata    6720
tttatcttgt acccgctgct aaacacactg caggagggac tctgaaacct caagctgtct    6780
acttacatct tttatctgtg tctgtgtatc atgaaaatgt ctattcaaaa tatcaaaacc    6840
tttcaaatat cacgcagctt atattcagtt tacataaagg ccccaaatac catgtcagat    6900 cttttttggta aaagagttaa tgaactatga gaattgggat tacatcatgt attttgcctc   6960
atgtattttt atcacactta taggccaagt gtgataaata aacttacaga cactgaatta    7020
atttcccctg ctactttgaa accagaaaat aatgactggc cattcgttac atctgtctta    7080
gttgaaaagc atatttttta ttaaattaat tctgattgta tttgaaatta ttattcaatt    7140
cacttatggc agaggaatat caatcctaat gacttctaaa aatgtaacta attgaatcat    7200
```

```
tatcttacat ttactgttta ataagcatat tttgaaaatg tatggctaga gtgtcataat    7260
aaaatggtat atctttcttt agtaattaca ttaaaattag tcatgtttga ttaattagtt    7320
c                                                                    7321

<210> SEQ ID NO 7
<211> LENGTH: 877
<212> TYPE: DNA
<213> ORGANISM: Homo sapiens

<400> SEQUENCE: 7
ttctattcac atcggcctca taatacccac cctgacctgc tgtaaaagac ctggaacaaa     60
caaaaatgat tacacctaca gtgaagatgc acaccatgtc ctcctcgcat ctcttctacc    120
tggcgctgtg cctgctcacc ttcaccagct ctgccacggc tggaccggag acgtctgcg     180 gggctgagct ggtggatgct cttcagttcg tgtgtggaga caggggcttt tatttcaaca    240
agcccacagg gtatggctcc agcagtcgga gggcgcctca gacaggcatc gtggatgagt    300
gctgcttccg gagctgtgat ctaaggaggc tggagatgta ttgcgcaccc ctcaagcctg    360
ccaagtcagc tcgctctgtc cgtgcccagc gccacaccga catgcccaag acccagaagt    420
atcagccccc atctaccaac aagaacacga gtctcagag aaggaaaggt tggccaaaga     480
cacatccagg aggggaacag aaggagggga cagaagcaag tctgcagatc agaggaaaga    540
agaaagagca gaggagggag attggaagta gaaatgctga atgcagaggc aaaaaggaa     600 aatgaaggac aggaggatta acagacaga ggcaaggatg atgagagagg agcagacagc     660
aagaatgaaa agcagaaaat acaatagagg aaatgaagaa aagtaggcct gctggagcta    720
gatgatgatg tgatggaaat agaagtaacc ttttagagaa tctcgctaag aaacatggag    780
aaaacggaaa agaaaaatgt aatgccctag aaagcgcaaa gaaagacagt ggcaaaaatg    840
aaaaaaaaaa ataaaaatta taaagaggc aaaaaaa                              877

<210> SEQ ID NO 8
<211> LENGTH: 22
<212> TYPE: DNA
<213> ORGANISM: Artificial
<220> FEATURE:
<223> OTHER INFORMATION: target sequence for microRNA 122a (miRBase
      database accession number MI0000442)

<400> SEQUENCE: 8
caaacaccat tgtcacactc ca                                              22

<210> SEQ ID NO 9
<211> LENGTH: 21
<212> TYPE: DNA
<213> ORGANISM: Artificial
<220> FEATURE:
<223> OTHER INFORMATION: target sequence for microRNA 152 (MI0000462)

<400> SEQUENCE: 9
agtcacgtac tgtcttgaac c                                               21

<210> SEQ ID NO 10
<211> LENGTH: 23
<212> TYPE: DNA
<213> ORGANISM: Artificial
<220> FEATURE:
<223> OTHER INFORMATION: sequence target microRNA 199a-5p (MI0000242)

<400> SEQUENCE: 10
```
gggtcacaag tctgatggac aag                                             23

<210> SEQ ID NO 11
<211> LENGTH: 22
<212> TYPE: DNA
<213> ORGANISM: Artificial
<220> FEATURE:
<223> OTHER INFORMATION: sequence target for microRNA 99a-3p (MI0000101)

<400> SEQUENCE: 11
tgtcatcaga cgtgtaacca at                                              22

<210> SEQ ID NO 12
<211> LENGTH: 21
<212> TYPE: DNA
<213> ORGANISM: Artificial
<220> FEATURE:
<223> OTHER INFORMATION: target sequence for microRNA 215 (MI0000291)

<400> SEQUENCE: 12
tactggatac ttaactgtct g                                               21

<210> SEQ ID NO 13
<211> LENGTH: 21
<212> TYPE: DNA
<213> ORGANISM: Artificial
<220> FEATURE:
<223> OTHER INFORMATION: target sequence for microRNA 192 (MI0000234)

<400> SEQUENCE: 13
ggctgtcaat tcataggtca g                                               21

<210> SEQ ID NO 14
<211> LENGTH: 22
<212> TYPE: DNA
<213> ORGANISM: Artificial
<220> FEATURE:
<223> OTHER INFORMATION: target sequence for microRNA 194 (MI0000488)

<400> SEQUENCE: 14
acattgtcgt tgaggtacac ct                                              22

<210> SEQ ID NO 15
<211> LENGTH: 22
<212> TYPE: DNA
<213> ORGANISM: Artificial
<220> FEATURE:
<223> OTHER INFORMATION: target sequence for microRNA 1 (MI0000651)

<400> SEQUENCE: 15
ttacatactt ctttacattc ca                                              22

<210> SEQ ID NO 16
<211> LENGTH: 22
<212> TYPE: DNA
<213> ORGANISM: Artificial
<220> FEATURE:
<223> OTHER INFORMATION: target sequence for microRNA 148 (MI0000253)

<400> SEQUENCE: 16
agtcacgtga tgtcttgaaa ca                                              22

<210> SEQ ID NO 17
<211> LENGTH: 22
<212> TYPE: DNA

```
<213> ORGANISM: Artificial
<220> FEATURE:
<223> OTHER INFORMATION: target sequence for microRNA 133a (MI0000450)

<400> SEQUENCE: 17
aaaccagggg aagttggtcg ac                                              22

<210> SEQ ID NO 18
<211> LENGTH: 22
<212> TYPE: DNA
<213> ORGANISM: Artificial
<220> FEATURE:
<223> OTHER INFORMATION: target sequence microRNA 206 (MI0000490)

<400> SEQUENCE: 18
accttacatt ccttcacaca cc                                              22

<210> SEQ ID NO 19
<211> LENGTH: 20
<212> TYPE: DNA
<213> ORGANISM: Artificial
<220> FEATURE:
<223> OTHER INFORMATION: target sequence for microRNA 124 (MI0000443)

<400> SEQUENCE: 19
attccgtgcg ccacttacgg                                                 20

<210> SEQ ID NO 20
<211> LENGTH: 24
<212> TYPE: DNA
<213> ORGANISM: Artificial
<220> FEATURE:
<223> OTHER INFORMATION: target sequence for microRNA 125 (MI0000469)

<400> SEQUENCE: 20
agggactctg ggaaattgga cact                                            24

<210> SEQ ID NO 21
<211> LENGTH: 22
<212> TYPE: DNA
<213> ORGANISM: Artificial
<220> FEATURE:
<223> OTHER INFORMATION: target sequence for microRNA 216 (MI0000292)

<400> SEQUENCE: 21
attagagtcg accgttgaca ct                                              22

<210> SEQ ID NO 22
<211> LENGTH: 22
<212> TYPE: DNA
<213> ORGANISM: Artificial
<220> FEATURE:
<223> OTHER INFORMATION: target sequence for microRNA 130 (MI0000448)

<400> SEQUENCE: 22
gtcacgttac aattttcccg ta                                              22

<210> SEQ ID NO 23
<211> LENGTH: 137
<212> TYPE: PRT
<213> ORGANISM: Homo sapiens

<400> SEQUENCE: 23

Met Ile Thr Pro Thr Val Lys Met His Thr Met Ser Ser Ser His Leu
1               5                   10                  15
```

```
Phe Tyr Leu Ala Leu Cys Leu Leu Thr Phe Thr Ser Ser Ala Thr Ala
            20                  25                  30

Gly Pro Glu Thr Leu Cys Gly Ala Glu Leu Val Asp Ala Leu Gln Phe
        35                  40                  45

Val Cys Gly Asp Arg Gly Phe Tyr Phe Asn Lys Pro Thr Gly Tyr Gly
 50                  55                  60

Ser Ser Ser Arg Arg Ala Pro Gln Thr Gly Ile Val Asp Glu Cys Cys
 65                  70                  75                  80

Phe Arg Ser Cys Asp Leu Arg Arg Leu Glu Met Tyr Cys Ala Pro Leu
                85                  90                  95

Lys Pro Ala Lys Ser Ala Arg Ser Val Arg Ala Gln Arg His Thr Asp
            100                 105                 110

Met Pro Lys Thr Gln Lys Glu Val His Leu Lys Asn Ala Ser Arg Gly
            115                 120                 125

Ser Ala Gly Asn Lys Asn Tyr Arg Met
            130                 135
```

<210> SEQ ID NO 24
<211> LENGTH: 195
<212> TYPE: PRT
<213> ORGANISM: Homo sapiens

<400> SEQUENCE: 24

```
Met Gly Lys Ile Ser Ser Leu Pro Thr Gln Leu Phe Lys Cys Cys Phe
 1               5                  10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
 65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
            115                 120                 125

Met Pro Lys Thr Gln Lys Tyr Gln Pro Pro Ser Thr Asn Lys Asn Thr
            130                 135                 140

Lys Ser Gln Arg Arg Lys Gly Trp Pro Lys Thr His Pro Gly Gly Glu
145                 150                 155                 160

Gln Lys Glu Gly Thr Glu Ala Ser Leu Gln Ile Arg Gly Lys Lys Lys
                165                 170                 175

Glu Gln Arg Arg Glu Ile Gly Ser Arg Asn Ala Glu Cys Arg Gly Lys
            180                 185                 190

Lys Gly Lys
        195
```

<210> SEQ ID NO 25
<211> LENGTH: 158
<212> TYPE: PRT
<213> ORGANISM: Homo sapiens

<400> SEQUENCE: 25

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser His Leu
            20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
            115                 120                 125

Met Pro Lys Thr Gln Lys Tyr Gln Pro Pro Ser Thr Asn Lys Asn Thr
        130                 135                 140

Lys Ser Gln Arg Arg Lys Gly Ser Thr Phe Glu Glu Arg Lys
145                 150                 155

<210> SEQ ID NO 26
<211> LENGTH: 153
<212> TYPE: PRT
<213> ORGANISM: Homo sapiens

<400> SEQUENCE: 26

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser His Leu
            20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
            115                 120                 125

Met Pro Lys Thr Gln Lys Glu Val His Leu Lys Asn Ala Ser Arg Gly
        130                 135                 140

Ser Ala Gly Asn Lys Asn Tyr Arg Met
145                 150

<210> SEQ ID NO 27
<211> LENGTH: 179
<212> TYPE: PRT
<213> ORGANISM: Homo sapiens

<400> SEQUENCE: 27

Met Ile Thr Pro Thr Val Lys Met His Thr Met Ser Ser His Leu
1               5                   10                  15

-continued

```
Phe Tyr Leu Ala Leu Cys Leu Leu Thr Phe Thr Ser Ser Ala Thr Ala
             20                  25                  30

Gly Pro Glu Thr Leu Cys Gly Ala Glu Leu Val Asp Ala Leu Gln Phe
         35                  40                  45

Val Cys Gly Asp Arg Gly Phe Tyr Phe Asn Lys Pro Thr Gly Tyr Gly
 50                  55                  60

Ser Ser Arg Arg Ala Pro Gln Thr Gly Ile Val Asp Glu Cys Cys
 65                  70                  75                  80

Phe Arg Ser Cys Asp Leu Arg Arg Leu Glu Met Tyr Cys Ala Pro Leu
                 85                  90                  95

Lys Pro Ala Lys Ser Ala Arg Ser Val Arg Ala Gln Arg His Thr Asp
            100                 105                 110

Met Pro Lys Thr Gln Lys Tyr Gln Pro Pro Ser Thr Asn Lys Asn Thr
            115                 120                 125

Lys Ser Gln Arg Arg Lys Gly Trp Pro Lys Thr His Pro Gly Gly Glu
        130                 135                 140

Gln Lys Glu Gly Thr Glu Ala Ser Leu Gln Ile Arg Gly Lys Lys Lys
145                 150                 155                 160

Glu Gln Arg Arg Glu Ile Gly Ser Arg Asn Ala Glu Cys Arg Gly Lys
                165                 170                 175

Lys Gly Lys

<210> SEQ ID NO 28
<211> LENGTH: 137
<212> TYPE: PRT
<213> ORGANISM: Mus musculus

<400> SEQUENCE: 28

Met Thr Ala Pro Ala Ile Lys Ile His Ile Met Ser Ser His Leu
 1               5                  10                  15

Phe Tyr Leu Ala Leu Cys Leu Leu Thr Phe Thr Ser Ser Thr Thr Ala
             20                  25                  30

Gly Pro Glu Thr Leu Cys Gly Ala Glu Leu Val Asp Ala Leu Gln Phe
         35                  40                  45

Val Cys Gly Pro Arg Gly Phe Tyr Phe Asn Lys Pro Thr Gly Tyr Gly
 50                  55                  60

Ser Ser Ile Arg Arg Ala Pro Gln Thr Gly Ile Val Asp Glu Cys Cys
 65                  70                  75                  80

Phe Arg Ser Cys Asp Leu Arg Arg Leu Glu Met Tyr Cys Ala Pro Leu
                 85                  90                  95

Lys Pro Thr Lys Ala Ala Arg Ser Ile Arg Ala Gln Arg His Thr Asp
            100                 105                 110

Met Pro Lys Thr Gln Lys Glu Val His Leu Lys Asn Thr Ser Arg Gly
            115                 120                 125

Ser Ala Gly Asn Lys Thr Tyr Arg Met
        130                 135

<210> SEQ ID NO 29
<211> LENGTH: 133
<212> TYPE: PRT
<213> ORGANISM: Mus musculus

<400> SEQUENCE: 29

Met Ser Ser Ser His Leu Phe Tyr Leu Ala Leu Cys Leu Leu Thr Phe
 1               5                  10                  15

Thr Ser Ser Thr Thr Ala Gly Pro Glu Thr Leu Cys Gly Ala Glu Leu
```

```
            20                  25                  30
Val Asp Ala Leu Gln Phe Val Cys Gly Pro Arg Gly Phe Tyr Phe Asn
         35                  40                  45

Lys Pro Thr Gly Tyr Gly Ser Ser Ile Arg Arg Ala Pro Gln Thr Gly
     50                  55                  60

Ile Val Asp Glu Cys Cys Phe Arg Ser Cys Asp Leu Arg Arg Leu Glu
 65                  70                  75                  80

Met Tyr Cys Ala Pro Leu Lys Pro Thr Lys Ala Arg Ser Ile Arg
                 85                  90                  95

Ala Gln Arg His Thr Asp Met Pro Lys Thr Gln Lys Ser Pro Ser Leu
             100                 105                 110

Ser Thr Asn Lys Lys Thr Lys Leu Gln Arg Arg Arg Lys Gly Ser Thr
         115                 120                 125

Phe Glu Glu His Lys
     130

<210> SEQ ID NO 30
<211> LENGTH: 7264
<212> TYPE: DNA
<213> ORGANISM: Artificial
<220> FEATURE:
<223> OTHER INFORMATION: polynucleotide herewith called
      pAAV-CAG-preproIGF1a-doble mirT122a-mirT1, expressing in pancreas
      murine preproIGF-1 isoform 5 (with NCBI accesion
      number NP_001104746).

<400> SEQUENCE: 30
cactgaggcc cagctgcgcg ctcgctcgct cactgaggcc gcccgggcaa agcccgggcg      60
tcgggcgacc tttggtcgcc cggcctcagt gagcgagcga gcgcgcagag agggagtggc     120
caactccatc actaggggtt ccttgtagtt aatgattaac cgccatgct  acttatctac     180 tcgacattga ttattgacta gttattaata gtaatcaatt acggggtcat tagttcatag     240
cccatatatg gagttccgcg ttacataact tacggtaaat ggcccgcctg gctgaccgcc     300
caacgacccc cgcccattga cgtcaataat gacgtatgtt cccatagtaa cgccaatagg     360
gactttccat tgacgtcaat gggtggagta tttacggtaa actgcccact ggcagtaca     420 tcaagtgtat catatgccaa gtacgccccc tattgacgtc aatgacggta aatggcccgc     480
ctggcattat gcccagtaca tgaccttatg ggactttcct acttggcagt acatctacgt     540
attagtcatc gctattacca tggtcgaggt gagccccacg ttctgcttca ctctccccat     600 ctccccccc tccccacccc caattttgta tttatttatt ttttaattat tttgtgcagc      660 gatggggcg gggggggg ggggcgcgc gccaggcggg gcggggcggg gcgaggggcg         720
gggcggggcg aggcggagag gtgcggcggc agccaatcag agcggcgcgc tccgaaagtt     780
tccttttatg gcgaggcggc ggcggcggcg gccctataaa aagcgaagcg cgcggcgggc     840
gggagtcgct gcgttgcctt cgccccgtgc cccgctccgc gccgcctcgc gccgcccgcc     900
ccggctctga ctgaccgcgt tactcccaca ggtgagcggg cggacggcc  cttctcctcc     960 gggctgtaat tagcgcttgg tttaatgacg gcttgtttct tttctgtggc tgcgtgaaag    1020
ccttgagggg ctccgggagg gccctttgtg cgggggagc ggctcggggg gtgcgtgcgt     1080
gtgtgtgtgc gtggggagcg ccgcgtgcgg ctccgcgctg cccggcggct gtgagcgctg    1140
cgggcgcggc gcggggcttt gtgcgctccg cagtgtgcgc gaggggagcg cggccggggg    1200
cggtgccccg cggtgcgggg ggctgcgagg ggaacaaagg ctgcgtgcgg ggtgtgtgcg    1260
tgggggggtg agcagggggt gtgggcgcgt cggtcgggct gcaaccccc  ctgcacccc     1320
```

```
ctccccgagt tgctgagcac ggcccggctt cgggtgcggg gctccgtacg gggcgtggcg    1380
cggggctcgc cgtgccgggc ggggggtggc ggcaggtggg ggtgccgggc ggggcggggc    1440
cgcctcgggc cggggagggc tcggggagg ggcgcggcgg ccccggagc gccggcggct     1500 gtcgaggcgc ggcgagccgc agccattgcc ttttatggta atcgtgcgag agggcgcagg    1560
gacttccttt gtcccaaatc tgtgcggagc cgaaatctgg gaggcgccgc cgcacccct    1620 ctagcgggcg cggggcgaag cggtgcggcg ccggcaggaa ggaaatgggc ggggagggcc    1680
ttcgtgcgtc gccgcgccgc cgtccccttc tccctctcca gcctcggggc tgtccgcggg    1740
gggacggctg ccttcggggg ggacggggca gggcggggtt cggcttctgg cgtgtgaccg    1800
gcggctctag agcctctgct aaccatgttc atgccttctt cttttccta cagctcctgg    1860 gcaacgtgct ggttattgtg ctgtctcatc attttggcaa agaattgatt aattcgagcg    1920
aacgcgtcga gtcgctcggt acgatttaaa ttgaattggc ctcgagcgca agcttgatat    1980
cgaattccgt agatgctttc acaaacccca cccacaaaac aacacatgtt cttaagtcct    2040
cagttttgtg ttcacctcgg cctcatagta cccactctga cctgctgtgt aaacgacccg    2100
gacctaccaa aatgaccgca cctgcaataa agatacacat catgtcgtct tcacacctct    2160
tctacctggc gctctgcttg ctcaccttca ccagctccac cacagctgga ccagagaccc    2220
tttgcggggc tgagctggtg gatgctcttc agttcgtgtg tggaccgagg ggcttttact    2280
tcaacaagcc cacaggctat ggctccagca ttcggagggc acctcagaca ggcattgtgg    2340
atgagtgttg cttccggagc tgtgatctga ggagactgga gatgtactgt gccccactga    2400
agcctacaaa agcagcccgc tctatccgtg cccagcgcca cactgacatg cccaagactc    2460
agaaggaagt acatttgaag aacacaagta gaggaagtgc aggaaacaag acctacagaa    2520
tgtaggagga gcctcccacg gagcagaaaa tgccacatca ccgcaggatc cactagttct    2580
agagcggccg ctaattctag atcgcgaaca aacaccattg tcacactcca gtatacacaa    2640
acaccattgt cacactccag atatcacaaa caccattgtc acactccaag gcgaacaaac    2700
accattgtca cactccaagg ctattctaga tcgcgaatta catacttctt tacattccag    2760
tatacattac atacttcttt acattccaga tatcattaca tacttcttta cattccaagg    2820
cgaattacat acttctttac attccaaggc tacctgaggc ccgggggtac ctcttaatta    2880
actggcctca tgggccttcc gctcactgcc cgctttccag tcgggaaacc tgtcgtgcca    2940
gtcaggtgca ggctgcctat cagaaggtgg tggctggtgt ggccaatgcc ctggctcaca    3000
aataccactg agatcttttt ccctctgcca aaaattatgg ggacatcatg aagcccttg    3060 agcatctgac ttctggctaa taaaggaaat ttattttcat tgcaatagtg tgttggaatt    3120
ttttgtgtct ctcactcgga aggacatatg ggagggcaaa tcatttaaaa catcagaatg    3180
agtatttggt ttagagtttg gcaacatatg cccatatgct ggctgccatg aacaaaggtt    3240
ggctataaag aggtcatcag tatatgaaac agccccctgc tgtccattcc ttattccata    3300
gaaaagcctt gacttgaggt tagatttttt ttatattttg ttttgtgtta tttttttctt    3360
taacatccct aaaattttcc ttacatgttt tactagccag attttcctc ctctcctgac     3420 tactcccagt catagctgtc cctcttctct tatggagatc cctcgacctg cagcccaagc    3480
tgtagataag tagcatggcg ggttaatcat taactacaag gaaccctag tgatggagtt     3540 ggccactccc tctctgcgcg ctcgctcgct cactgaggcc gggcgaccaa aggtcgcccg    3600
acgcccgggc tttgcccggg cggcctcagt gagcgagcga gcgcgcagct ggcgtaatag    3660
```

```
cagtgagcga gcgagcgcgc agctgcatta atgaatcggc caacgcgcgg ggagaggcgg    3720
tttgcgtatt gggcgctctt ccgcttcctc gctcactgac tcgctgcgct cggtcgttcg    3780
gctgcggcga gcggtatcag ctcactcaaa ggcggtaata cggttatcca cagaatcagg    3840
ggataacgca ggaaagaaca tgtgagcaaa aggccagcaa aaggccagga accgtaaaaa    3900
ggccgcgttg ctggcgtttt tccataggct ccgcccccct gacgagcatc acaaaaatcg    3960
acgctcaagt cagaggtggc gaaacccgac aggactataa agataccagg cgtttccccc    4020
tggaagctcc ctcgtgcgct ctcctgttcc gaccctgccg cttaccggat acctgtccgc    4080
ctttctccct tcgggaagcg tggcgctttc tcatagctca cgctgtaggt atctcagttc    4140
ggtgtaggtc gttcgctcca agctgggctg tgtgcacgaa ccccccgttc agcccgaccg    4200
ctgcgcctta tccggtaact atcgtcttga gtccaacccg gtaagacacg acttatcgcc    4260
actggcagca gccactggta acaggattag cagagcgagg tatgtaggcg gtgctacaga    4320
gttcttgaag tggtggccta actacggcta cactagaaga acagtatttg gtatctgcgc    4380
tctgctgaag ccagttacct tcggaaaaag agttggtagc tcttgatccg gcaaacaaac    4440
caccgctggt agcggtggtt tttttgtttg caagcagcag attacgcgca gaaaaaaagg    4500
atctcaagaa gatcctttga tcttttctac ggggtctgac gctcagtgga acgaaaactc    4560
acgttaaggg attttggtca tgagattatc aaaaaggatc ttcacctaga tccttttaaa    4620
ttaaaaatga agttttaaat caatctaaag tatatatgag taaacttggt ctgacagtta    4680
ccaatgctta atcagtgagg cacctatctc agcgatctgt ctatttcgtt catccatagt    4740
tgcctgactc cccgtcgtgt agataactac gatacgggag ggcttaccat ctggccccag    4800
tgctgcaatg ataccgcgag acccacgctc accggctcca gatttatcag caataaacca    4860
gccagccgga agggccgagc gcagaagtgg tcctgcaact ttatccgcct ccatccagtc    4920
tattaattgt tgccgggaag ctagagtaag tagttcgcca gttaatagtt tgcgcaacgt    4980
tgttgccatt gctacaggca tcgtggtgtc acgctcgtcg tttggtatgg cttcattcag    5040
ctccggttcc caacgatcaa ggcgagttac atgatccccc atgttgtgca aaaaagcggt    5100
tagctccttc ggtcctccga tcgttgtcag aagtaagttg gccgcagtgt tatcactcat    5160
ggttatggca gcactgcata attctcttac tgtcatgcca tccgtaagat gcttttctgt    5220
gactggtgag tactcaacca agtcattctg agaatagtgt atgcggcgac cgagttgctc    5280
ttgcccggcg tcaatacggg ataataccgc gccacatagc agaactttaa aagtgctcat    5340
cattggaaaa cgttcttcgg ggcgaaaact ctcaaggatc ttaccgctgt tgagatccag    5400
ttcgatgtaa cccactcgtg cacccaactg atcttcagca tcttttactt tcaccagcgt    5460
ttctgggtga gcaaaaacag gaaggcaaaa tgccgcaaaa aagggaataa gggcgacacg    5520
gaaatgttga atactcatac tcttcctttt tcaatattat tgaagcattt atcagggtta    5580
ttgtctcatg agcggataca tatttgaatg tatttagaaa aataaacaaa taggggttcc    5640
gcgcacattt ccccgaaaag tgccacctga cgtctaagaa accattatta tcatgacatt    5700
aacctataaa aataggcgta tcacgaggcc ctttcgtctc gcgcgtttcg gtgatgacgg    5760
tgaaaacctc tgacacatgc agctcccgga cggtcaca gcttgtctgt aagcggatgc    5820
cgggagcaga caagcccgtc agggcgcgtc agcgggtgtt ggcgggtgtc ggggctggct    5880
taactatgcg gcatcagagc agattgtact gagagtgcac catatgcggt gtgaaatacc    5940
gcacagatgc gtaaggagaa ataccgcat caggcgattc caacatccaa taatcatac    6000
aggcaaggca aagaattagc aaaattaagc aataaagcct cagagcataa agctaaatcg    6060
```

```
gttgtaccaa aaacattatg accctgtaat acttttgcgg gagaagcctt tatttcaacg    6120
caaggataaa aattttttaga accctcatat attttaaatg caatgcctga gtaatgtgta    6180
ggtaaagatt caaacgggtg agaaaggccg agacagtca aatcaccatc aatatgatat     6240
tcaaccgttc tagctgataa attcatgccg gagagggtag ctattttga gaggtctcta     6300 caaaggctat caggtcattg cctgagagtc tggagcaaac aagagaatcg atgaacggta    6360
atcgtaaaac tagcatgtca atcatatgta ccccggttga taatcagaaa agccccaaaa    6420
acaggaagat tgtataagca aatatttaaa ttgtaagcgt taatattttg ttaaaattcg    6480
cgttaaattt ttgttaaatc agctcatttt ttaaccaata ggccgaaatc ggcaaaatcc    6540
cttataaatc aaaagaatag accgagatag ggttgagtgt tgttccagtt tggaacaaga    6600
gtccactatt aaagaacgtg gactccaacg tcaaagggcg aaaaaccgtc tatcagggcg    6660
atggcccact acgtgaacca tcaccctaat caagtttttt ggggtcgagg tgccgtaaag    6720
cactaaatcg gaaccctaaa gggagccccc gatttagagc ttgacgggga aagccggcga    6780
acgtggcgag aaaggaaggg aagaaagcga aggagcggg cgctagggcg ctggcaagtg    6840
tagcggtcac gctgcgcgta accaccacac ccgccgcgct taatgcgccg ctacagggcg    6900
cgtactatgg ttgctttgac gagcacgtat aacgtgcttt cctcgttaga atcagagcgg    6960
gagctaaaca ggaggccgat taaagggatt ttagacagga acggtacgcc agaatcctga    7020
gaagtgtttt tataatcagt gaggccaccg agtaaaagag tctgtccatc acgcaaatta    7080
accgttgtcg caatacttct ttgattagta ataacatcac ttgcctgagt agaagaactc    7140
aaactatcgg ccttgctggt aatatccaga acaatattac cgccagccat tgcaacggaa    7200
tcgccattcg ccattcaggc tgcgcaactg ttgggaaggg cgatcggtgc gggcctcttc    7260
gcta                                                                 7264
```

<210> SEQ ID NO 31
<211> LENGTH: 7200
<212> TYPE: DNA
<213> ORGANISM: Artificial
<220> FEATURE:
<223> OTHER INFORMATION: polynucleotide herewith called
      pAAV-CAG-preproIGF1b-doble mirT122a-mirT1, expressing in pancreas
      murine preproIGF1 with NCBI accesion number l'NCBI AAH12409.

<400> SEQUENCE: 31

```
cactgaggcc cagctgcgcg ctcgctcgct cactgaggcc gcccgggcaa agcccgggcg      60
tcgggcgacc tttggtcgcc cggcctcagt gagcgagcga gcgcgcagag agggagtggc     120
caactccatc actagggggtt ccttgtagtt aatgattaac ccgccatgct acttatctac    180
tcgacattga ttattgacta gttattaata gtaatcaatt acgggtcat tagttcatag     240 cccatatatg gagttccgcg ttacataact tacggtaaat ggcccgcctg gctgaccgcc    300
caacgacccc cgcccattga cgtcaataat gacgtatgtt cccatagtaa cgccaatagg    360
gactttccat tgacgtcaat gggtggagta tttacggtaa actgcccact tggcagtaca    420
tcaagtgtat catatgccaa gtacgccccc tattgacgtc aatgacggta aatggcccgc    480
ctggcattat gcccagtaca tgaccttatg gactttcct acttggcagt acatctacgt    540
attagtcatc gctattacca tggtcgaggt gagccccacg ttctgcttca ctctccccat    600
ctcccccccc tcccccaccccc caattttgta tttatttatt ttttaattat tttgtgcagc    660
gatgggggcg ggggggggggg ggggcgcgc gccaggcggg gcgggcggg gcgaggggcg     720
```

```
gggcggggcg aggcggagag gtgcggcggc agccaatcag agcggcgcgc tccgaaagtt    780
tccttttatg gcgaggcggc ggcggcggcg gccctataaa aagcgaagcg cgcggcgggc    840
gggagtcgct gcgttgcctt cgccccgtgc cccgctccgc gccgcctcgc gccgcccgcc    900
ccggctctga ctgaccgcgt tactcccaca ggtgagcggg cgggacggcc cttctcctcc    960
gggctgtaat tagcgcttgg tttaatgacg gcttgtttct tttctgtggc tgcgtgaaag   1020
ccttgagggg ctccgggagg gcccttttgtg cgggggggagc ggctcggggg gtgcgtgcgt   1080
gtgtgtgtgc gtggggagcg ccgcgtgcgg ctccgcgctg cccggcggct gtgagcgctg   1140
cgggcgcggc gcggggcttt gtgcgctccg cagtgtgcgc gaggggagcg cggccggggg   1200
cggtgccccg cggtgcgggg ggctgcgagg ggaacaaagg ctgcgtgcgg ggtgtgtgcg   1260
tgggggggtg agcaggggt gtgggcgcgt cggtcgggct gcaacccccc ctgcacccccc   1320
ctccccgagt tgctgagcac ggcccggctt cgggtgcggg gctccgtacg gggcgtggcg   1380
cggggctcgc cgtgccgggc gggggtggc ggcaggtggg ggtgccgggc ggggcggggc   1440
cgcctcgggc cggggagggc tcgggggagg ggcgcggcgg ccccccggagc gccggcggct   1500
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcaccccct   1620
ctagcgggcg cggggcgaag cggtgcggcg ccggcaggaa ggaaatgggc ggggagggcc   1680
ttcgtgcgtc gccgcgccgc cgtcccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt cttttttccta cagctcctgg   1860
gcaacgtgct ggttattgtg ctgtctcatc attttggcaa agaattgatt aattcgagcg   1920
aacgcgtcga gtcgctcggt acgatttaaa ttgaattggc ctcgagcgca agcttgagct   1980
agctcgatat cgtcgaccca cgcgtccgga cttcttgaag ataaagatac acatcatgtc   2040
gtcttcacac ctcttctacc tggcgctctg cttgctcacc ttcaccagct ccaccacagc   2100
tggaccagag acccttgcg gggctgagct ggtggatgct cttcagttcg tgtgtggacc   2160
gagggggcttt tacttcaaca agcccacagg ctatggctcc agcattcgga gggcacctca   2220
gacaggcatt gtggatgagt gttgcttccg gagctgtgat ctgaggagac tggagatgta   2280
ctgtgcccca ctgaagccta caaaagcagc ccgctctatc cgtgcccagc gccacactga   2340
catgcccaag actcagaagt ccccgtccct atcgacaaac aagaaaacga agctgcaaag   2400
gagaaggaaa ggaagtacat ttgaagaaca caagtagagg aagtgcagga aacaagacct   2460
acagaatgta ggaggagcct cccacggagc agaaaatgcc acatcaccgc aggatccgcg   2520
cggccgctaa ttctagatcg cgaacaaaca ccattgtcac actccagtat acacaaacac   2580
cattgtcaca ctccagatat cacaaacacc attgtcacac tccaaggcga acaaacacca   2640
ttgtcacact ccaaggctat tctagatcgc gaattacata cttctttaca ttccagtata   2700
cattacatac ttctttacat tccagatatc attacatact tctttacatt ccaaggcgaa   2760
ttacatactt ctttacattc caaggctacc tgaggcccgg gggtacctct taattaactg   2820
gcctcatggg ccttccgctc actgcccgct ttccagtcgg gaaacctgtc gtgccagtca   2880
ggtgcaggct gcctatcaga aggtggtggc tggtgtggcc aatgccctgg ctcacaaata   2940
ccactgagat cttttttccct ctgccaaaaa ttatggggac atcatgaagc ccttgagca   3000
tctgacttct ggctaataaa ggaaatttat tttcattgca atagtgtgtt ggaatttttt   3060
gtgtctctca ctcggaagga catatgggag ggcaaatcat ttaaaacatc agaatgagta   3120
```

```
tttggtttag agtttggcaa catatgccca tatgctggct gccatgaaca aaggttggct    3180
ataaagaggt catcagtata tgaaacagcc ccctgctgtc cattccttat tccatagaaa    3240
agccttgact tgaggttaga tttttttat atttttgtttt gtgttatttt tttctttaac    3300
atccctaaaa ttttccttac atgttttact agccagattt ttcctcctct cctgactact    3360
cccagtcata gctgtccctc ttctcttatg gagatccctc gacctgcagc caagctgta     3420 gataagtagc atggcgggtt aatcattaac tacaaggaac ccctagtgat ggagttggcc    3480
actccctctc tgcgcgctcg ctcgctcact gaggccgggc gaccaaaggt cgcccgacgc    3540
ccgggctttg cccgggcggc ctcagtgagc gagcgagcgc gcagctggcg taatagcagt    3600
gagcgagcga gcgcgcagct gcattaatga atcggccaac gcgcggggag aggcggtttg    3660
cgtattgggc gctcttccgc ttcctcgctc actgactcgc tgcgctcggt cgttcggctg    3720
cggcgagcgg tatcagctca ctcaaaggcg gtaatacggt tatccacaga atcaggggat    3780
aacgcaggaa agaacatgtg agcaaaaggc cagcaaaagg ccaggaaccg taaaaaggcc    3840
gcgttgctgg cgtttttcca taggctccgc cccctgacg agcatcacaa aaatcgacgc     3900
tcaagtcaga ggtggcgaaa cccgacagga ctataaagat accaggcgtt tccccctgga    3960
agctccctcg tgcgctctcc tgttccgacc ctgccgctta ccggatacct gtccgccttt    4020
ctcccttcgg gaagcgtggc gctttctcat agctcacgct gtaggtatct cagttcggtg    4080
taggtcgttc gctccaagct gggctgtgtg cacgaacccc ccgttcagcc cgaccgctgc    4140
gccttatccg gtaactatcg tcttgagtcc aacccggtaa gacacgactt atcgccactg    4200
gcagcagcca ctggtaacag gattagcaga gcgaggtatg taggcggtgc tacagagttc    4260
ttgaagtggt ggcctaacta cggctacact agaagaacag tatttggtat ctgcgctctg    4320
ctgaagccag ttaccttcgg aaaaagagtt ggtagctctt gatccggcaa acaaaccacc    4380
gctggtagcg gtggttttt tgtttgcaag cagcagatta cgcgcagaaa aaaggatct     4440 caagaagatc ctttgatctt ttctacgggg tctgacgctc agtggaacga aaactcacgt    4500
taagggattt tggtcatgag attatcaaaa aggatcttca cctagatcct tttaaattaa    4560
aaatgaagtt ttaaatcaat ctaaagtata tatgagtaaa cttggtctga cagttaccaa    4620
tgcttaatca gtgaggcacc tatctcagcg atctgtctat ttcgttcatc catagttgcc    4680
tgactccccg tcgtgtagat aactacgata cgggagggct taccatctgg ccccagtgct    4740
gcaatgatac cgcgagaccc acgctcaccg gctccagatt tatcagcaat aaaccagcca    4800
gccgaagggc cgagcgcag aagtggtcct gcaactttat ccgcctccat ccagtctatt     4860
aattgttgcc gggaagctag agtaagtagt tcgccagtta atagtttgcg caacgttgtt    4920
gccattgcta caggcatcgt ggtgtcacgc tcgtcgtttg gtatggcttc attcagctcc    4980
ggttcccaac gatcaaggcg agttacatga tcccccatgt tgtgcaaaaa agcggttagc    5040
tccttcggtc ctccgatcgt tgtcagaagt aagttggccg cagtgttatc actcatggtt    5100
atggcagcac tgcataattc tcttactgtc atgccatccg taagatgctt ttctgtgact    5160
ggtgagtact caaccaagtc attctgagaa tagtgtatgc ggcgaccgag ttgctcttgc    5220
ccggcgtcaa tacgggataa taccgcgcca catagcagaa ctttaaaagt gctcatcatt    5280
ggaaaacgtt cttcggggcg aaaactctca aggatcttac cgctgttgag atccagttcg    5340
atgtaaccca ctcgtgcacc caactgatct tcagcatctt ttactttcac cagcgtttct    5400
gggtgagcaa aaacaggaag gcaaaatgcc gcaaaaaagg gaataagggc gacacggaaa    5460
```

```
tgttgaatac tcatactctt ccttttcaa tattattgaa gcatttatca gggttattgt    5520
ctcatgagcg gatacatatt tgaatgtatt tagaaaaata aacaaatagg ggttccgcgc    5580
acatttcccc gaaaagtgcc acctgacgtc taagaaacca ttattatcat gacattaacc    5640
tataaaaata ggcgtatcac gaggcccttt cgtctcgcgc gtttcggtga tgacggtgaa    5700
aacctctgac acatgcagct cccggagacg gtcacagctt gtctgtaagc ggatgccggg    5760
agcagacaag cccgtcaggg cgcgtcagcg ggtgttggcg ggtgtcgggg ctggcttaac    5820
tatgcggcat cagagcagat tgtactgaga gtgcaccata tgcggtgtga ataccgcac     5880 agatgcgtaa ggagaaaata ccgcatcagg cgattccaac atccaataaa tcatacaggc    5940
aaggcaaaga attagcaaaa ttaagcaata aagcctcaga gcataaagct aaatcggttg    6000
taccaaaaac attatgaccc tgtaatactt tgcgggaga agcctttatt tcaacgcaag     6060
gataaaaatt tttagaaccc tcatatattt taaatgcaat gcctgagtaa tgtgtaggta    6120
aagattcaaa cgggtgagaa aggccggaga cagtcaaatc accatcaata tgatattcaa    6180
ccgttctagc tgataaattc atgccggaga gggtagctat ttttgagagg tctctacaaa    6240
ggctatcagg tcattgcctg agagtctgga gcaaacaaga gaatcgatga acggtaatcg    6300
taaaactagc atgtcaatca tatgtacccc ggttgataat cagaaaagcc ccaaaaacag    6360
gaagattgta taagcaaata tttaaattgt aagcgttaat attttgttaa aattcgcgtt    6420
aaatttttgt taaatcagct cattttttaa ccaataggcc gaaatcggca aaatccctta    6480
taaatcaaaa gaatagaccg agatagggtt gagtgttgtt ccagtttgga caagagtcc     6540 actattaaag aacgtggact ccaacgtcaa agggcgaaaa accgtctatc agggcgatgg    6600
cccactacgt gaaccatcac cctaatcaag ttttttgggg tcgaggtgcc gtaaagcact    6660
aaatcggaac cctaaaggga gcccccgatt tagagcttga cggggaaagc cggcgaacgt    6720
ggcgagaaag gaagggaaga agcgaaagg agcgggcgct agggcgctgg caagtgtagc    6780
ggtcacgctg cgcgtaacca ccacacccgc cgcgcttaat gcgccgctac agggcgcgta    6840
ctatggttgc tttgacgagc acgtataacg tgctttcctc gttagaatca gagcgggagc    6900
taaacaggag gccgattaaa gggatttag acaggaacgg tacgccagaa tcctgagaag    6960 tgttttata atcagtgagg ccaccgagta aaagagtctg tccatcacgc aaattaaccg    7020
ttgtcgcaat acttctttga ttagtaataa catcacttgc ctgagtagaa gaactcaaac    7080
tatcggcctt gctggtaata tccagaacaa tattaccgcc agccattgca acggaatcgc    7140
cattcgccat tcaggctgcg caactgttgg gaagggcgat cggtgcgggc ctcttcgcta    7200
```

<210> SEQ ID NO 32
<211> LENGTH: 7127
<212> TYPE: DNA
<213> ORGANISM: Artificial
<220> FEATURE:
<223> OTHER INFORMATION: polynucleotide for expressing in pancreas green
      fluorescent protein (GFP)

<400> SEQUENCE: 32

```
tcaggtgcag gctgcctatc agaaggtggt ggctggtgtg gccaatgccc tggctcacaa     60
ataccactga gatctttttc cctctgccaa aaattatggg gacatcatga agccccttga    120
gcatctgact tctggctaat aaaggaaatt tatttcatt gcaatagtgt gttggaattt    180
tttgtgtctc tcactcggaa ggacatatgg gagggcaaat catttaaaac atcagaatga    240
gtatttggtt tagagtttgg caacatatgc ccatatgctg gctgccatga acaaaggttg    300
```

```
gctataaaga ggtcatcagt atatgaaaca gcccctgct gtccattcct tattccatag     360
aaaagccttg acttgaggtt agatttttt tatatttgt tttgtgttat tttttctttt      420
aacatcccta aaattttcct tacatgtttt actagccaga ttttcctcc tctcctgact     480 actcccagtc atagctgtcc ctcttctctt atggagatcc ctcgacctgc agcccaagct    540
gtagataagt agcatggcgg gttaatcatt aactacaagg aacccctagt gatggagttg    600
gccactccct ctctgcgcgc tcgctcgctc actgaggccg ggcgaccaaa ggtcgcccga    660
cgcccgggct ttgcccgggc ggcctcagtg agcgagcgag cgcgcagctg gcgtaatagc    720
gaagaggccc gcaccgatcg cccttcccaa cagttgcgca gcctgaatgg cgaatgcgca    780
ttccgttgca atggctggcg gtaatattgt tctggatatt accagcaagg ccgatagttt    840
gagttcttct actcaggcaa gtgatgttat tactaatcaa agaagtattg cgacaacggt    900
taatttgcgt gatggacaga ctcttttact cggtggcctc actgattata aaaacacttc    960
tcaggattct ggcgtaccgt tcctgtctaa atccctta atcggcctcc tgtttagctc     1020
ccgctctgat tctaacgagg aaagcacgtt atacgtgctc gtcaaagcaa ccatagtacg   1080
cgccctgtag cggcgcatta agcgcggcgg gtgtggtggt tacgcgcagc gtgaccgcta   1140
cacttgccag cgccctagcg cccgctcctt tcgctttctt cccttccttt ctcgccacgt   1200
tcgccggctt tccccgtcaa gctctaaatc gggggctccc tttagggttc cgatttagtg   1260
ctttacggca cctcgacccc aaaaaacttg attagggtga tggttcacgt agtgggccat   1320
cgccctgata cacggttttt cgccctttga cgttggagtc cacgttcttt aatagtggac   1380
tcttgttcca aactggaaca acactcaacc ctatctcggt ctattctttt gatttataag   1440
ggattttgcc gatttcggcc tattggttaa aaaatgagct gatttaacaa aaatttaacg   1500
cgaattttaa caaaatatta acgcttacaa tttaaatatt tgcttataca atcttcctgt   1560
ttttggggct tttctgatta tcaaccgggg tacatatgat tgacatgcta gttttacgat   1620
taccgttcat cgattctctt gtttgctcca gactctcagg caatgacctg atagcctttg   1680
tagagacctc tcaaaaatag ctaccctctc cggcatgaat ttatcagcta aacggttga    1740 atatcatatt gatggtgatt tgactgtctc cggcctttct cacccgtttg aatctttacc   1800
tacacattac tcaggcattg catttaaaat atatgagggt tctaaaaatt tttatccttg   1860
cgttgaaata aaggcttctc ccgcaaaagt attacagggt cataatgttt ttggtacaac   1920
cgatttagct ttatgctctg aggctttatt gcttaatttt gctaattctt tgccttgcct   1980
gtatgattta ttggatgttg gaatcgcctg atgcggtatt ttctccttac gcatctgtgc   2040
ggtatttcac accgcatatg gtgcactctc agtacaatct gctctgatgc cgcatagtta   2100
agccagcccc gacacccgcc aacacccgct gacgcgccct gacgggcttg tctgctcccg   2160
gcatccgctt acagacaagc tgtgaccgtc tccgggagct gcatgtgtca gaggttttca   2220
ccgtcatcac cgaaacgcgc gagacgaaag ggcctcgtga tacgcctatt tttataggtt   2280
aatgtcatga taataatggt ttcttagacg tcaggtggca cttttcgggg aaatgtgcgc   2340
ggaaccccta tttgtttatt tttctaaata cattcaaata tgtatccgct catgagacaa   2400
taaccctgat aaatgcttca ataatattga aaaggaaga gtatgagtat tcaacatttc    2460
cgtgtcgccc ttattccctt ttttgcggca ttttgccttc ctgtttttgc tcacccagaa   2520
acgctggtga agtaaaaga tgctgaagat cagttgggtg cacgagtggg ttacatcgaa    2580
ctggatctca acagcggtaa gatccttgag agttttcgcc ccgaagaacg ttttccaatg   2640
atgagcactt ttaaagttct gctatgtggc gcggtattat cccgtattga cgccgggcaa   2700
```

```
gagcaactcg gtcgccgcat acactattct cagaatgact tggttgagta ctcaccagtc   2760
acagaaaagc atcttacgga tggcatgaca gtaagagaat tatgcagtgc tgccataacc   2820
atgagtgata acactgcggc caacttactt ctgacaacga tcggaggacc gaaggagcta   2880
accgcttttt tgcacaacat gggggatcat gtaactcgcc ttgatcgttg ggaaccggag   2940
ctgaatgaag ccataccaaa cgacgagcgt gacaccacga tgcctgtagc aatggcaaca   3000
acgttgcgca aactattaac tggcgaacta cttactctag cttcccggca acaattaata   3060
gactggatgg aggcggataa agttgcagga ccacttctgc gctcggccct tccggctggc   3120
tggtttattg ctgataaatc tggagccggt gagcgtgggt ctcgcggtat cattgcagca   3180
ctggggccag atggtaagcc ctcccgtatc gtagttatct acacgacggg gagtcaggca   3240
actatggatg aacgaaatag acagatcgct gagataggtg cctcactgat taagcattgg   3300
taactgtcag accaagttta ctcatatata ctttagattg atttaaaact tcattttaa    3360 tttaaaagga tctaggtgaa gatcctttt gataatctca tgaccaaaat cccttaacgt    3420
gagttttcgt tccactgagc gtcagacccc gtagaaaaga tcaaggatc ttcttgagat    3480 ccttttttc tgcgcgtaat ctgctgcttg caaacaaaaa aaccaccgct accagcggtg    3540
gtttgtttgc cggatcaaga gctaccaact cttttccga aggtaactgg cttcagcaga    3600
gcgcagatac caaatactgt tcttctagtg tagccgtagt taggccacca cttcaagaac    3660
tctgtagcac cgcctacata cctcgctctg ctaatcctgt taccagtggc tgctgccagt    3720
ggcgataagt cgtgtcttac cgggttggac tcaagacgat agttaccgga taaggcgcag    3780
cggtcgggct gaacggggggg ttcgtgcaca cagcccagct tggagcgaac gacctacacc    3840
gaactgagat acctacagcg tgagctatga gaaagcgcca cgcttcccga agggagaaag    3900
gcggacaggt atccggtaag cggcagggtc ggaacaggag agcgcacgag ggagcttcca    3960
gggggaaacg cctggtatct ttatagtcct gtcgggtttc gccacctctg acttgagcgt    4020 cgattttgt gatgctcgtc agggggcgg agcctatgga aaaacgccag caacgcggcc     4080
tttttacggt tcctggcctt tgctggcct tttgctcaca tgttctttcc tgcgttatcc    4140
cctgattctg tggataaccg tattaccgcc tttgagtgag ctgataccgc tcgccgcagc    4200
cgaacgaccg agcgcagcga gtcagtgagc gaggaagcgg aagagcgccc aatacgcaaa    4260
ccgcctctcc ccgcgcgttg gccgattcat taatgcagct gcgcgctcgc tcgctcactg    4320
aggcccagct gcgcgctcgc tcgctcactg aggccgcccg gcaaagccc gggcgtcggg     4380 cgacctttgg tcgcccggcc tcagtgagcg agcgagcgcg cagagaggga gtggccaact    4440
ccatcactag gggttccttg tagttaatga ttaacccgcc atgctactta tctactcgac    4500
attgattatt gactagttat taatagtaat caattacggg gtcattagtt catagcccat    4560
atatggagtt ccgcgttaca aacttacgg taaatggccc gcctggctga ccgcccaacg     4620 accccgccc attgacgtca ataatgacgt atgttcccat agtaacgcca atagggactt     4680
tccattgacg tcaatgggtg gagtattac ggtaaactgc ccacttggca gtacatcaag     4740
tgtatcatat gccaagtacg ccccctattg acgtcaatga cggtaaatgg cccgcctggc    4800
attatgccca gtacatgacc ttatgggact ttcctacttg gcagtacatc tacgtattag    4860
tcatcgctat taccatggtc gaggtgagcc ccacgttctg cttcactctc cccatctccc    4920 cccctcccc accccaatt ttgtatttat tattttttta attattttgt gcagcgatgg      4980 gggcggggggg gggggggggg cgcgcgccag gcggggcggg gcggggcgag gggcggggcg   5040
```

```
gggcgaggcg gagaggtgcg gcggcagcca atcagagcgg cgcgctccga aagtttcctt    5100
ttatggcgag gcggcggcgg cggcggccct ataaaaagcg aagcgcgcgg cgggcgggag    5160
tcgctgcgtt gccttcgccc cgtgccccgc tccgcgccgc ctcgcgccgc ccgccccggc    5220
tctgactgac cgcgttactc ccacaggtga gcgggcggga cggcccttct cctccgggct    5280
gtaattagcg cttggtttaa tgacggcttg tttcttttct gtggctgcgt gaaagccttg    5340
aggggctccg ggagggccct ttgtgcgggg ggagcggctc ggggggtgcg tgcgtgtgtg    5400
tgtgcgtggg gagcgccgcg tgcggctccg cgctgcccgg cggctgtgag cgctgcgggc    5460
gcggcgcggg gctttgtgcg ctccgcagtg tgcgcgaggg gagcgcggcc ggggcggtg     5520 ccccgcggtg cgggggctg cgagggggaac aaaggctgcg tgcggggtgt gtgcgtgggg    5580
gggtgagcag gggtgtggg cgcgtcggtc gggctgcaac ccccctgca ccccctccc      5640 cgagttgctg agcacggccc ggcttcgggt gcgggctcc gtacggggcg tggcgcgggg    5700
ctcgccgtgc cgggcggggg gtggcggcag gtggggtgc cggcggggc ggggccgcct     5760 cgggccgggg agggctcggg ggaggggcgc ggcggccccc ggagcgccgg cggctgtcga   5820
ggcgcggcga gccgcagcca ttgccttta tggtaatcgt gcgagagggc cagggactt     5880 cctttgtccc aaatctgtgc ggagccgaaa tctgggaggc gccgccgcac ccctctagc    5940 gggcgcgggg cgaagcggtg cggcgccggc aggaaggaaa tgggcgggga gggccttcgt   6000
gcgtcgccgc gccgccgtcc ccttctccct tccagcctc ggggctgtcc gcggggggac    6060
ggctgccttc gggggggacg gggcagggcg gggttcggct tctggcgtgt gaccggcggc   6120
tctagagcct ctgctaacca tgttcatgcc ttcttctttt tcctacagct cctgggcaac    6180
gtgctggtta ttgtgctgtc tcatcatttt ggcaaagaat tgattaattc gagcgaacgc    6240
gtcgagtcgc tcggtacgat ttaaattgaa ttggcctcga gcgcaagctt gagctagcgc    6300
taccggtcgc caccatggtg agcaagggcg aggagctgtt caccggggtg gtgcccatcc    6360
tggtcgagct ggacggcgac gtaaacggcc acaagttcag cgtgtccggc gagggcgagg    6420
gcgatgccac ctacggcaag ctgaccctga agttcatctg caccaccggc aagctgcccg    6480
tgccctggcc caccctcgtg accaccctga cctacggcgt gcagtgcttc agccgctacc    6540
ccgaccacat gaagcagcac gacttcttca gtccgccat gcccgaaggc tacgtccagg    6600
agcgcaccat cttcttcaag gacgacggca actacaagac ccgcgccgag gtgaagttcg    6660
agggcgacac cctggtgaac cgcatcgagc tgaagggcat cgacttcaag gaggacggca    6720
acatcctggg gcacaagctg gagtacaact acaacagcca caacgtctat atcatggccg    6780
acaagcagaa gaacggcatc aaggtgaact tcaagatccg ccacaacatc gaggacggca    6840
gcgtgcagct cgccgaccac taccagcaga acacccccat cggcgacggc cccgtgctgc    6900
tgcccgacaa ccactacctg agcacccagt ccgccctgag caaagacccc aacgagaagc    6960
gcgatcacat ggtcctgctg gagttcgtga ccgccgccgg gatcactctc ggcatggacg    7020
agctgtacaa gtccggactc agatctcgag ctcaagcttc gaattctgca gtcgacggta    7080
ccgcgggccc gggatccacc ggatctagat aactgatccg cgcggcc                  7127
```

<210> SEQ ID NO 33
<211> LENGTH: 6964
<212> TYPE: DNA
<213> ORGANISM: Artificial
<220> FEATURE:
<223> OTHER INFORMATION: polynucleotide for expression of murine preproIGF1

```
<400> SEQUENCE: 33
ctcttaatta actggcctca tgggccttcc gctcactgcc cgctttccag tcgggaaacc      60
tgtcgtgcca gtcaggtgca ggctgcctat cagaaggtgg tggctggtgt ggccaatgcc     120
ctggctcaca ataccactg agatcttttt ccctctgcca aaattatgg ggacatcatg       180 aagccccttg agcatctgac ttctggctaa taaaggaaat ttattttcat tgcaatagtg     240
tgttggaatt ttttgtgtct ctcactcgga aggacatatg ggagggcaaa tcatttaaaa     300
catcagaatg agtatttggt ttagagtttg gcaacatatg cccatatgct ggctgccatg     360
aacaaaggtt ggctataaag aggtcatcag tatatgaaac agcccctgc tgtccattcc      420 ttattccata gaaaagcctt gacttgaggt tagattttt ttatattttg ttttgtgtta      480 ttttttctt taacatccct aaaattttcc ttacatgttt tactagccag attttcctc      540 ctctcctgac tactcccagt catagctgtc cctcttctct tatggagatc cctcgacctg     600
cagcccaagc tgtagataag tagcatggcg ggttaatcat taactacaag gaacccctag     660
tgatggagtt ggccactccc tctctgcgcg ctcgctcgct cactgaggcc gggcgaccaa     720
aggtcgcccg acgcccgggc tttgcccggg cggcctcagt gagcgagcga gcgcgcagct     780
ggcgtaatag cagtgagcga gcgagcgcgc agctgcatta atgaatcggc caacgcgcgg     840
ggagaggcgg tttgcgtatt gggcgctctt ccgcttcctc gctcactgac tcgctgcgct     900
cggtcgttcg gctgcggcga gcggtatcag ctcactcaaa ggcggtaata cggttatcca     960
cagaatcagg ggataacgca ggaaagaaca tgtgagcaaa aggccagcaa aaggccagga    1020
accgtaaaaa ggccgcgttg ctggcgtttt tccataggct ccgccccct gacgagcatc     1080 acaaaaatcg acgctcaagt cagaggtggc gaaacccgac aggactataa agataccagg    1140
cgtttccccc tggaagctcc ctcgtgcgct ctcctgttcc gaccctgccg cttaccggat    1200
acctgtccgc ctttctccct tcgggaagcg tggcgctttc tcatagctca cgctgtaggt    1260
atctcagttc ggtgtaggtc gttcgctcca agctgggctg tgtgcacgaa ccccccgttc    1320
agcccgaccg ctgcgcctta tccggtaact atcgtcttga gtccaacccg gtaagacacg    1380
acttatcgcc actggcagca gccactggta acaggattag cagagcgagg tatgtaggcg    1440
gtgctacaga gttcttgaag tggtggccta actacggcta cactagaaga acagtatttg    1500
gtatctgcgc tctgctgaag ccagttacct tcggaaaaag agttggtagc tcttgatccg    1560
gcaaacaaac caccgctggt agcggtggtt ttttgtttg caagcagcag attacgcgca     1620
gaaaaaaagg atctcaagaa gatcctttga tcttttctac ggggtctgac gctcagtgga    1680
acgaaaactc acgttaaggg attttggtca tgagattatc aaaaaggatc ttcacctaga    1740
tccttttaaa ttaaaaatga agttttaaat caatctaaag tatatatgag taaacttggt    1800
ctgacagtta ccaatgctta atcagtgagg cacctatctc agcgatctgt ctatttcgtt    1860
catccatagt tgcctgactc cccgtcgtgt agataactac gatacgggag gcttaccat     1920 ctggccccag tgctgcaatg ataccgcgag acccacgctc accggctcca gatttatcag    1980
caataaacca gccagccgga agggccgagc gcagaagtgg tcctgcaact ttatccgcct    2040
ccatccagtc tattaattgt tgccgggaag ctagagtaag tagttcgcca gttaatagtt    2100
tgcgcaacgt tgttgccatt gctacaggca tcgtggtgtc acgctcgtcg tttggtatgg    2160
cttcattcag ctccggttcc caacgatcaa ggcgagttac atgatccccc atgttgtgca    2220
aaaaagcggt tagctccttc ggtcctccga tcgttgtcag aagtaagttg gccgcagtgt    2280
tatcactcat ggttatggca gcactgcata attctcttac tgtcatgcca tccgtaagat    2340
```

```
gcttttctgt gactggtgag tactcaacca agtcattctg agaatagtgt atgcggcgac    2400
cgagttgctc ttgcccggcg tcaatacggg ataataccgc gccacatagc agaactttaa    2460
aagtgctcat cattggaaaa cgttcttcgg ggcgaaaact ctcaaggatc ttaccgctgt    2520
tgagatccag ttcgatgtaa cccactcgtg cacccaactg atcttcagca tcttttactt    2580
tcaccagcgt ttctgggtga gcaaaaacag gaaggcaaaa tgccgcaaaa aagggaataa    2640
gggcgacacg gaaatgttga atactcatac tcttcctttt tcaatattat tgaagcattt    2700
atcagggtta ttgtctcatg agcggataca tatttgaatg tatttagaaa aataaacaaa    2760
taggggttcc gcgcacattt ccccgaaaag tgccacctga cgtctaagaa accattatta    2820
tcatgacatt aacctataaa aataggcgta tcacgaggcc ctttcgtctc gcgcgtttcg    2880
gtgatgacgg tgaaaacctc tgacacatgc agctcccgga cggtcaca gcttgtctgt     2940 aagcggatgc cgggagcaga caagcccgtc agggcgcgtc agcgggtgtt ggcgggtgtc    3000
ggggctggct taactatgcg gcatcagagc agattgtact gagagtgcac catatgcggt    3060
gtgaaatacc gcacagatgc gtaaggagaa ataccgcat caggcgattc caacatccaa     3120
taaatcatac aggcaaggca agaattagc aaaattaagc aataaagcct cagagcataa     3180
agctaaatcg gttgtaccaa aaacattatg accctgtaat acttttgcgg gagaagcctt    3240
tatttcaacg caaggataaa aattttttaga accctcatat attttaaatg caatgcctga   3300
gtaatgtgta ggtaaagatt caaacggtg agaaaggccg gagacagtca atcaccatc      3360 aatatgatat tcaaccgttc tagctgataa attcatgccg gagagggtag ctatttttga    3420
gaggtctcta caaaggctat caggtcattg cctgagagtc tggagcaaac aagagaatcg    3480
atgaacggta atcgtaaaac tagcatgtca atcatatgta ccccggttga taatcagaaa    3540 agcccccaaaa acaggaagat tgtataagca aatatttaaa ttgtaagcgt taatattttg   3600
ttaaaattcg cgttaaattt ttgttaaatc agctcatttt ttaaccaata ggccgaaatc    3660
ggcaaaatcc cttataaatc aaaagaatag accgagatag ggttgagtgt tgttccagtt    3720
tggaacaaga gtccactatt aaagaacgtg gactccaacg tcaaagggcg aaaaaccgtc    3780
tatcagggcg atggcccact acgtgaacca tcacctaat caagttttt ggggtcgagg      3840 tgccgtaaag cactaaatcg gaaccctaaa gggagccccc gatttagagc ttgacgggga    3900
aagccggcga acgtggcgag aaaggaaggg aagaaagcga aaggagcggg cgctagggcg    3960
ctggcaagtg tagcggtcac gctgcgcgta accaccacac ccgccgcgct taatgcgccg    4020
ctacagggcg cgtactatgg ttgctttgac gagcacgtat aacgtgcttt cctcgttaga    4080
atcagagcgg gagctaaaca ggaggccgat taaagggatt ttagacagga acggtacgcc    4140
agaatcctga gaagtgtttt tataatcagt gaggccaccg agtaaaagag tctgtccatc    4200
acgcaaatta accgttgtcg caatacttct ttgattagta ataacatcac ttgcctgagt    4260
agaagaactc aaactatcgg ccttgctggt aatatccaga acaatattac cgccagccat    4320
tgcaacggaa tcgccattcg ccattcaggc tgcgcaactg ttgggaaggg cgatcggtgc    4380
gggcctcttc gctacactga gcccagctg cgcgctcgct cgctcactga ggccgcccgg     4440
gcaaagcccg ggcgtcgggc gacctttggt cgcccggcct cagtgagcga gcgagcgcgc    4500
agagagggag tggccaactc catcactagg ggttccttgt agttaatgat taacccgcca    4560
tgctacttat ctactcgaca ttgattattg actagttatt aatagtaatc aattacgggg    4620
tcattagttc atagcccata tatggagttc cgcgttacat aacttacggt aaatggcccg    4680
```

```
cctggctgac cgcccaacga cccccgccca ttgacgtcaa taatgacgta tgttcccata    4740
gtaacgccaa tagggacttt ccattgacgt caatgggtgg agtatttacg gtaaactgcc    4800
cacttggcag tacatcaagt gtatcatatg ccaagtacgc ccctattga cgtcaatgac     4860
ggtaaatggc ccgcctggca ttatgcccag tacatgacct tatgggactt tcctacttgg    4920
cagtacatct acgtattagt catcgctatt accatggtcg aggtgagccc cacgttctgc    4980
ttcactctcc ccatctcccc ccctcccca ccccaattt tgtatttatt tattttttaa     5040
ttattttgtg cagcgatggg ggcggggggg gggggggggc gcgcgccagg cggggcgggg    5100
cggggcgagg ggcggggcgg ggcgaggcgg agaggtgcgg cggcagccaa tcagagcggc    5160
gcgctccgaa agtttccttt tatggcgagg cggcggcggc ggcggccta taaaaagcga    5220
agcgcgcggc gggcgggagt cgctgcgttg ccttcgcccc gtgccccgct ccgcccgcc    5280
tcgcgccgcc cgccccggct ctgactgacc gcgttactcc cacaggtgag cgggcgggac    5340
ggcccttctc ctccgggctg taattagcgc ttggtttaat gacggcttgt ttcttttctg    5400
tggctgcgtg aaagccttga ggggctccgg gaggcccctt tgtgcgggg gagcggctcg     5460
gggggtgcgt gcgtgtgtgt gtgcgtgggg agcgccgcgt gcggctccgc gctgcccggc    5520
ggctgtgagc gctgcgggcg cggcgcgggg ctttgtgcgc tccgcagtgt gcgcgagggg    5580
agcgcggccg ggggcggtgc cccgcggtgc gggggctgc gagggggaaca aaggctgcgt    5640
gcggggtgtg tgcgtgggg ggtgagcagg gggtgtgggc gcgtcggtcg ggctgcaacc    5700
cccctgcac cccctcccc gagttgctga gcacggcccg gcttcgggtg cggggctccg     5760
tacggggcgt ggcgcgggc tcgccgtgcc gggcgggggg tggcggcagg tgggggtgcc    5820
gggcggggcg gggccgcctc gggccgggga gggctcgggg gaggggcgcg gcggccccg    5880
gagcgccggc ggctgtcgag gcgcggcgag ccgcagccat tgccttttat ggtaatcgtg    5940
cgagagggcg cagggacttc ctttgtccca aatctgtgcg gagccgaaat ctgggaggcg    6000
ccgccgcacc ccctctagcg ggcgcggggc gaagcggtgc ggcgccggca ggaaggaaat    6060
gggcggggag ggccttcgtg cgtcgccgcg ccgccgtccc cttctccctc tccagcctcg    6120
gggctgtccg cggggggacg gctgccttcg gggggacgg ggcagggcgg ggttcggctt    6180
ctggcgtgtg accggcggct ctagagcctc tgctaaccat gttcatgcct tcttcttttt    6240
cctacagctc ctgggcaacg tgctggttat tgtgctgtct catcattttg gcaaagaatt    6300
gattaattcg agcgaacgcg tcgagtcgct cggtacgatt taaattgaat tggcctcgag    6360
cgcaagcttg atatcgaatt ccgtagatgc tttcacaaac cccacccaca aaacaacaca    6420
tgttcttaag tcctcagttt tgtgttcacc tcggcctcat agtacccact ctgacctgct    6480
gtgtaaacga cccggaccta ccaaaatgac cgcacctgca ataaagatac acatcatgtc    6540
gtcttcacac ctcttctacc tggcgctctg cttgctcacc ttcaccagct ccaccacagc    6600
tggaccagag acccttgcg gggctgagct ggtggatgct cttcagttcg tgtgtggacc    6660
gagggcttt tacttcaaca agcccacagg ctatggctcc agcattcgga gggcacctca    6720
gacaggcatt gtggatgagt gttgcttccg gagctgtgat ctgaggagac tggagatgta    6780
ctgtgcccca ctgaagccta caaaagcagc ccgctctatc cgtgcccagc ccacactga    6840
catgcccaag actcagaagg aagtacattt gaagaacaca agtagaggaa gtgcaggaaa    6900
caagacctac agaatgtagg aggagcctcc cacggagcag aaaatgccac atcaccgcag    6960
gatc                                                                 6964
```

<210> SEQ ID NO 34
<211> LENGTH: 6321
<212> TYPE: DNA
<213> ORGANISM: Artificial
<220> FEATURE:
<223> OTHER INFORMATION: polynucleotide containing adenoassociated virus genome elements without any transgene

<400> SEQUENCE: 34

| | | | | | |
|---|---|---|---|---|---|
| aattcgagct | cggtacccgg | gaatcaattc | actcctcagg | tgcaggctgc | ctatcagaag | 60 |
| gtggtggctg | gtgtggccaa | tgccctggct | cacaaatacc | actgagatct | tttccctct | 120 |
| gccaaaaatt | atggggacat | catgaagccc | cttgagcatc | tgacttctgg | ctaataaagg | 180 |
| aaatttattt | tcattgcaat | agtgtgttgg | aattttttgt | gtctctcact | cggaaggaca | 240 |
| tatgggaggg | caaatcattt | aaaacatcag | aatgagtatt | tggtttagag | tttggcaaca | 300 |
| tatgcccata | tgctggctgc | catgaacaaa | ggttggctat | aaagaggtca | tcagtatatg | 360 |
| aaacagcccc | tgctgtcca | ttccttattc | catagaaaag | ccttgacttg | aggttagatt | 420 |
| tttttatat | tttgttttgt | gttatttttt | tctttaacat | ccctaaaatt | ttccttacat | 480 |
| gttttactag | ccagattttt | cctcctctcc | tgactactcc | cagtcatagc | tgtccctctt | 540 |
| ctcttatgga | gatccctcga | cctgcagccc | aagctgtaga | taagtagcat | ggcgggttaa | 600 |
| tcattaacta | caaggaaccc | ctagtgatgg | agttggccac | tccctctctg | cgcgctcgct | 660 |
| cgctcactga | ggccgcccgg | gctttgcccg | ggcggcctca | gtgagcgagc | gagcgcgcag | 720 |
| ctgcattaat | gaatcggcca | acgcgcgggg | agaggcggtt | tgcgtattgg | gcgctcttcc | 780 |
| gcttcctcgc | tcactgactc | gctgcgctcg | gtcgttcggc | tgcggcgagc | ggtatcagct | 840 |
| cactcaaagg | cggtaatacg | gttatccaca | gaatcagggg | ataacgcagg | aaagaacatg | 900 |
| tgagcaaaag | gccagcaaaa | ggccaggaac | cgtaaaaagg | ccgcgttgct | ggcgtttttc | 960 |
| cataggctcc | gccccctga | cgagcatcac | aaaaatcgac | gctcaagtca | gaggtggcga | 1020 |
| aacccgacag | gactataaag | ataccaggcg | tttccccctg | gaagctccct | cgtgcgctct | 1080 |
| cctgttccga | ccctgccgct | taccggatac | ctgtccgcct | ttctcccttc | gggaagcgtg | 1140 |
| gcgctttctc | atagctcacg | ctgtaggtat | ctcagttcgg | tgtaggtcgt | tcgctccaag | 1200 |
| ctgggctgtg | tgcacgaacc | ccccgttcag | cccgaccgct | gcgccttatc | cggtaactat | 1260 |
| cgtcttgagt | ccaacccggt | aagacacgac | ttatcgccac | tggcagcagc | cactggtaac | 1320 |
| aggattagca | gagcgaggta | tgtaggcggt | gctacagagt | tcttgaagtg | gtggcctaac | 1380 |
| tacggctaca | ctagaagaac | agtatttggt | atctgcgctc | tgctgaagcc | agttaccttc | 1440 |
| ggaaaaagag | ttggtagctc | ttgatccggc | aaacaaacca | ccgctggtag | cggtggtttt | 1500 |
| tttgtttgca | agcagcagat | tacgcgcaga | aaaaaaggat | ctcaagaaga | tcctttgatc | 1560 |
| ttttctacgg | ggtctgacgc | tcagtggaac | gaaaactcac | gttaagggat | tttggtcatg | 1620 |
| agattatcaa | aaaggatctt | cacctagatc | cttttaaatt | aaaaatgaag | ttttaaatca | 1680 |
| atctaaagta | tatatgagta | aacttggtct | gacagttacc | aatgcttaat | cagtgaggca | 1740 |
| cctatctcag | cgatctgtct | atttcgttca | tccatagttg | cctgactccc | cgtcgtgtag | 1800 |
| ataactacga | tacgggaggg | cttaccatct | ggccccagtg | ctgcaatgat | accgcgagac | 1860 |
| ccacgctcac | cggctccaga | tttatcagca | ataaaccagc | cagccggaag | ggccgagcgc | 1920 |
| agaagtggtc | ctgcaacttt | atccgcctcc | atccagtcta | ttaattgttg | ccgggaagct | 1980 |
| agagtaagta | gttcgccagt | taatagtttg | cgcaacgttg | ttgccattgc | tacaggcatc | 2040 |
| gtggtgtcac | gctcgtcgtt | tggtatggct | tcattcagct | ccggttccca | acgatcaagg | 2100 |

```
cgagttacat gatcccccat gttgtgcaaa aaagcggtta gctccttcgg tcctccgatc    2160
gttgtcagaa gtaagttggc cgcagtgtta tcactcatgg ttatggcagc actgcataat    2220
tctcttactg tcatgccatc cgtaagatgc ttttctgtga ctggtgagta ctcaaccaag    2280
tcattctgag aatagtgtat gcggcgaccg agttgctctt gcccggcgtc aatacgggat    2340
aataccgcgc cacatagcag aactttaaaa gtgctcatca ttggaaaacg ttcttcgggg    2400
cgaaaactct caaggatctt accgctgttg agatccagtt cgatgtaacc cactcgtgca    2460
cccaactgat cttcagcatc ttttactttc accagcgttt ctgggtgagc aaaaacagga    2520
aggcaaaatg ccgcaaaaaa gggaataagg gcgacacgga aatgttgaat actcatactc    2580
ttcctttttc aatattattg aagcatttat cagggttatt gtctcatgag cggatacata    2640
tttgaatgta tttagaaaaa taaacaaata ggggttccgc gcacatttcc ccgaaaagtg    2700
ccacctgacg tctaagaaac cattattatc atgacattaa cctataaaaa taggcgtatc    2760
acgaggccct ttcgtctcgc gcgtttcggt gatgacggtg aaaacctctg acacatgcag    2820
ctcccggaga cggtcacagc ttgtctgtaa gcggatgccg ggagcagaca agcccgtcag    2880
ggcgcgtcag cgggtgttgg cgggtgtcgg gctggctta actatgcggc atcagagcag    2940
attgtactga gagtgcacca tatgcggtgt gaaataccgc acagatgcgt aaggagaaaa    3000
taccgcatca ggcgattcca acatccaata aatcatacag gcaaggcaaa gaattagcaa    3060
aattaagcaa taaagcctca gagcataaag ctaaatcggt tgtaccaaaa acattatgac    3120
cctgtaatac ttttgcggga gaagccttta tttcaacgca aggataaaaa ttttttagaac    3180
cctcatatat tttaaatgca atgcctgagt aatgtgtagg taaagattca acgggtgag    3240
aaaggccgga gacagtcaaa tcaccatcaa tatgatattc aaccgttcta gctgataaat    3300
tcatgccgga gagggtagct attttttgaga ggtctctaca aaggctatca ggtcattgcc    3360
tgagagtctg gagcaaacaa gagaatcgat gaacggtaat cgtaaaacta gcatgtcaat    3420
catatgtacc ccggttgata atcagaaaag ccccaaaaac aggaagattg tataagcaaa    3480
tatttaaatt gtaagcgtta atattttgtt aaaattcgcg ttaaattttt gttaaatcag    3540
ctcattttt aaccaatagg ccgaaatcgg caaaatccct tataaatcaa agaatagac     3600
cgagataggg ttgagtgttg ttccagtttg gaacaagagt ccactattaa agaacgtgga    3660
ctccaacgtc aaagggcgaa aaaccgtcta tcagggcgat ggcccactac gtgaaccatc    3720
accctaatca agttttttgg ggtcgaggtg ccgtaaagca ctaaatcgga acccctaaagg    3780
gagccccga tttagagctt gacggggaaa gccggcgaac gtggcgagaa aggaagggaa    3840
gaaagcgaaa ggagcgggcg ctagggcgct ggcaagtgta gcggtcacgc tgcgcgtaac    3900
caccacaccc gccgcgctta atgcgccgct acagggcgcg tactatggtt gctttgacga    3960
gcacgtataa cgtgctttcc tcgttagaat cagagcggga gctaaacagg aggccgatta    4020
aagggatttt agacaggaac ggtacgccag aatcctgaga agtgttttta taatcagtga    4080
ggccaccgag taaaagagtc tgtccatcac gcaaattaac cgttgtcgca atacttcttt    4140
gattagtaat aacatcactt gcctgagtag aagaactcaa actatcggcc ttgctggtaa    4200
tatccagaac aatattaccg ccagccattg caacggaatc gccattcgcc attcaggctg    4260
cgcaactgtt gggaagggcg atcggtgcgg gcctcttcgc tattacgcca gctgcgcgct    4320
cgctcgctca ctgaggccgc ccgggcaaag cccgggcgtc gggcgacctt tggtcgcccg    4380
gcctcagtga gcgagcgagc gcgcagagag ggagtggcca actccatcac tagggggttcc    4440
```

-continued

```
ttgtagttaa tgattaaccc gccatgctac ttatctactc gacattgatt attgactagt    4500
tattaatagt aatcaattac ggggtcatta gttcatagcc catatatgga gttccgcgtt    4560
acataactta cggtaaatgg cccgcctggc tgaccgccca acgacccccg cccattgacg    4620
tcaataatga cgtatgttcc catagtaacg ccaataggga cttttccattg acgtcaatgg    4680
gtggagtatt tacggtaaac tgcccacttg gcagtacatc aagtgtatca tatgccaagt    4740
acgccccta ttgacgtcaa tgacggtaaa tggcccgcct ggcattatgc ccagtacatg    4800
accttatggg actttcctac ttggcagtac atctacgtat tagtcatcgc tattaccatg    4860
gtcgaggtga gccccacgtt ctgcttcact ctccccatct ccccccctc cccaccccca    4920
attttgtatt tatttatttt ttaattattt tgtgcagcga tgggggcggg gggggggggg    4980
gggcgcgcgc caggcggggc ggggcgggc gaggggcggg gcggggcgag gcggagaggt    5040
gcggcggcag ccaatcagag cggcgcgctc cgaaagtttc cttttatggc gaggcggcgg    5100
cggcggcggc cctataaaaa gcgaagcgcg cggcgggcgg gagtcgctgc gttgccttcg    5160
ccccgtgccc cgctccgccg ccgcctcgcg ccgcccgccc cggctctgac tgaccgcgtt    5220
actcccacag gtgagcgggc gggacggccc ttctcctccg ggctgtaatt agcgcttggt    5280
ttaatgacgg cttgtttctt ttctgtggct gcgtgaaagc cttgagggc tccgggaggg    5340
cccttttgtgc ggggggagcg gctcgggggg tgcgtgcgtg tgtgtgtgcg tggggagcgc    5400
cgcgtgcggc tccgcgctgc ccggcggctg tgagcgctgc gggcgcggcg cggggctttg    5460
tgcgctccgc agtgtgcgcg aggggagcgc ggccgggggc ggtgccccgc ggtgcggggg    5520
gggctgcgag gggaacaaag gctgcgtgcg gggtgtgtgc gtgggggggt gagcagggg    5580
tgtgggcgcg tcggtcgggc tgcaaccccc cctgcacccc cctccccgag ttgctgagca    5640
cggcccggct tcgggtgcgg ggctccgtac ggggcgtggc gcggggctcg ccgtgccggg    5700
cgggggtgg cggcaggtgg gggtgccggg cggggcgggg ccgcctcggg ccggggaggg    5760
ctcgggggag gggcgcggcg gcccccggag cgccggcggc tgtcgaggcg cggcgagccg    5820
cagccattgc cttttatggt aatcgtgcga gagggcgcag ggacttcctt tgtcccaaat    5880
ctgtgcggag ccgaaatctg ggaggcgccg ccgcaccccc tctagcgggc gcggggcgaa    5940
gcggtgcggc gccggcagga aggaaatggg cggggagggc cttcgtgcgt cgccgcgccg    6000
ccgtcccctt ctccctctcc agcctcgggg ctgtccgcgg ggggacggct gccttcgggg    6060
gggacgggc agggcggggt tcggcttctg gcgtgtgacc ggcggctcta gagcctctgc    6120
taaccatgtt catgccttct tctttttcct acagctcctg gcaacgtgc tggttattgt    6180
gctgtctcat catttggca aagaattgat taattcgagc gaacgcgtcg agtcgctcgg    6240
tacgatttaa attgaattgg cctcgagcgc aagcttgagc tagctcgata tcggcctagg    6300
ctggatccgc gcggccgcaa g                                              6321
```

<210> SEQ ID NO 35
<211> LENGTH: 20
<212> TYPE: DNA
<213> ORGANISM: Artificial
<220> FEATURE:
<223> OTHER INFORMATION: Forward primer

<400> SEQUENCE: 35
tggatgctct tcagttcgtg                                                20

<210> SEQ ID NO 36
<211> LENGTH: 20

```
<212> TYPE: DNA
<213> ORGANISM: Artificial
<220> FEATURE:
<223> OTHER INFORMATION: Reverse primer

<400> SEQUENCE: 36
gagggtggct gttagccata                                                 20

<210> SEQ ID NO 37
<211> LENGTH: 20
<212> TYPE: DNA
<213> ORGANISM: Artificial
<220> FEATURE:
<223> OTHER INFORMATION: Reverse primer

<400> SEQUENCE: 37
gcaacactca tccacaatgc                                                 20

<210> SEQ ID NO 38
<211> LENGTH: 25
<212> TYPE: DNA
<213> ORGANISM: Artificial
<220> FEATURE:
<223> OTHER INFORMATION: Forward primer

<400> SEQUENCE: 38
cttgagcatc tgacttctgg ctaat                                           25

<210> SEQ ID NO 39
<211> LENGTH: 24
<212> TYPE: DNA
<213> ORGANISM: Artificial
<220> FEATURE:
<223> OTHER INFORMATION: Reverse primer

<400> SEQUENCE: 39
ggagaggagg aaaaatctgg ctag                                            24

<210> SEQ ID NO 40
<211> LENGTH: 30
<212> TYPE: DNA
<213> ORGANISM: Artificial
<220> FEATURE:
<223> OTHER INFORMATION: Probe

<400> SEQUENCE: 40
ccgagtgaga gacacaaaaa attccaacac                                      30

<210> SEQ ID NO 41
<211> LENGTH: 30
<212> TYPE: DNA
<213> ORGANISM: Artificial
<220> FEATURE:
<223> OTHER INFORMATION: Forward primer

<400> SEQUENCE: 41
ccgagtgaga gacacaaaaa attccaacac                                      30

<210> SEQ ID NO 42
<211> LENGTH: 30
<212> TYPE: DNA
<213> ORGANISM: Artificial
<220> FEATURE:
<223> OTHER INFORMATION: Reverse primer

<400> SEQUENCE: 42
```
ccgagtgaga gacacaaaaa attccaacac                                    30

<210> SEQ ID NO 43
<211> LENGTH: 30
<212> TYPE: DNA
<213> ORGANISM: Artificial
<220> FEATURE:
<223> OTHER INFORMATION: Probe

<400> SEQUENCE: 43
ccgagtgaga gacacaaaaa attccaacac                                    30

<210> SEQ ID NO 44
<211> LENGTH: 159
<212> TYPE: PRT
<213> ORGANISM: Mus musculus

<400> SEQUENCE: 44

Met Gly Lys Ile Ser Ser Leu Pro Thr Gln Leu Phe Lys Ile Cys Leu
1               5                   10                  15

Cys Asp Phe Leu Lys Ile Lys Ile His Ile Met Ser Ser Ser His Leu
            20                  25                  30

Phe Tyr Leu Ala Leu Cys Leu Leu Thr Phe Thr Ser Ser Thr Thr Ala
        35                  40                  45

Gly Pro Glu Thr Leu Cys Gly Ala Glu Leu Val Asp Ala Leu Gln Phe
    50                  55                  60

Val Cys Gly Pro Arg Gly Phe Tyr Phe Asn Lys Pro Thr Gly Tyr Gly
65                  70                  75                  80

Ser Ser Ile Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Thr Lys Ala Ala Arg Ser Ile Arg Ala Gln Arg His Thr Asp
        115                 120                 125

Met Pro Lys Thr Gln Lys Ser Pro Ser Leu Ser Thr Asn Lys Lys Thr
    130                 135                 140

Lys Leu Gln Arg Arg Lys Gly Ser Thr Phe Glu Glu His Lys
145                 150                 155

<210> SEQ ID NO 45
<211> LENGTH: 165
<212> TYPE: PRT
<213> ORGANISM: Mus musculus

<400> SEQUENCE: 45

Met Thr Ala Pro Ala Ile Lys Ile His Ile Met Ser Ser Ser His Leu
1               5                   10                  15

Phe Tyr Leu Ala Leu Cys Leu Leu Thr Phe Thr Ser Ser Thr Thr Ala
            20                  25                  30

Gly Pro Glu Thr Leu Cys Gly Ala Glu Leu Val Asp Ala Leu Gln Phe
        35                  40                  45

Val Cys Gly Pro Arg Gly Phe Tyr Phe Asn Lys Pro Thr Gly Tyr Gly
    50                  55                  60

Ser Ser Ile Arg Arg Ala Pro Gln Thr Gly Ile Val Asp Glu Cys Cys
65                  70                  75                  80

Phe Arg Ser Cys Asp Leu Arg Arg Leu Glu Met Tyr Cys Ala Pro Leu
                85                  90                  95

Lys Pro Thr Lys Ala Ala Arg Ser Ile Arg Ala Gln Arg His Thr Asp

-continued

```
                100                 105                 110
Met Pro Lys Thr Gln Lys Ser Pro Ser Leu Ser Thr Asn Lys Lys Thr
            115                 120                 125

Lys Leu Gln Arg Arg Lys Gly Glu Pro Lys Thr His Pro Glu Gly
        130                 135                 140

Glu Gln Glu Glu Val Thr Glu Ala Thr Arg Lys Ile Arg Gly Pro Arg
145                 150                 155                 160

Glu Lys Arg Leu Gly
            165

<210> SEQ ID NO 46
<211> LENGTH: 143
<212> TYPE: PRT
<213> ORGANISM: Mus musculus

<400> SEQUENCE: 46

Met Thr Ala Pro Ala Ile Lys Ile His Ile Met Ser Ser Ser His Leu
1               5                   10                  15

Phe Tyr Leu Ala Leu Cys Leu Leu Thr Phe Thr Ser Ser Thr Thr Ala
            20                  25                  30

Gly Pro Glu Thr Leu Cys Gly Ala Glu Leu Val Asp Ala Leu Gln Phe
        35                  40                  45

Val Cys Gly Pro Arg Gly Phe Tyr Phe Asn Lys Pro Thr Gly Tyr Gly
50                  55                  60

Ser Ser Ile Arg Arg Ala Pro Gln Thr Gly Ile Val Asp Glu Cys Cys
65                  70                  75                  80

Phe Arg Ser Cys Asp Leu Arg Arg Leu Glu Met Tyr Cys Ala Pro Leu
                85                  90                  95

Lys Pro Thr Lys Ala Ala Arg Ser Ile Arg Ala Gln Arg His Thr Asp
            100                 105                 110

Met Pro Lys Thr Gln Lys Ser Pro Ser Leu Ser Thr Asn Lys Lys Thr
        115                 120                 125

Lys Leu Gln Arg Arg Arg Lys Gly Ser Thr Phe Glu Glu His Lys
    130                 135                 140

<210> SEQ ID NO 47
<211> LENGTH: 153
<212> TYPE: PRT
<213> ORGANISM: Mus musculus

<400> SEQUENCE: 47

Met Gly Lys Ile Ser Ser Leu Pro Thr Gln Leu Phe Lys Ile Cys Leu
1               5                   10                  15

Cys Asp Phe Leu Lys Ile Lys Ile His Ile Met Ser Ser Ser His Leu
            20                  25                  30

Phe Tyr Leu Ala Leu Cys Leu Leu Thr Phe Thr Ser Ser Thr Thr Ala
        35                  40                  45

Gly Pro Glu Thr Leu Cys Gly Ala Glu Leu Val Asp Ala Leu Gln Phe
    50                  55                  60

Val Cys Gly Pro Arg Gly Phe Tyr Phe Asn Lys Pro Thr Gly Tyr Gly
65                  70                  75                  80

Ser Ser Ile Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Thr Lys Ala Ala Arg Ser Ile Arg Ala Gln Arg His Thr Asp
```

```
                115                 120                 125
Met Pro Lys Thr Gln Lys Glu Val His Leu Lys Asn Thr Ser Arg Gly
            130                 135                 140

Ser Ala Gly Asn Lys Thr Tyr Arg Met
145                 150

<210> SEQ ID NO 48
<211> LENGTH: 7121
<212> TYPE: DNA
<213> ORGANISM: Mus musculus

<400> SEQUENCE: 48
```

| | | | | | |
|---|---|---|---|---|---|
| gataactttg | ccagaagagg | gagagagaga | gaaggcgaat | gttcccccag | ctgtttcctg | 60 |
| tctacagtgt | ctgtgttttg | tagataaatg | tgaggatttt | ctctaaatcc | ctcttctgct | 120 |
| tgctaaatct | cactgtcact | gctaaattca | gagcagatag | agcctgcgca | atggaataaa | 180 |
| gtcctcaaaa | ttgaaatgtg | acattgctct | aacatctccc | atctctctgg | atttcttttt | 240 |
| cgcctcatta | tccctgccca | ccaattcatt | tccagacttt | gtacttcaga | agcgatgggg | 300 |
| aaaatcagca | gccttccaac | tcaattattt | aagatctgcc | tctgtgactt | cttgaagata | 360 |
| aagatacaca | tcatgtcgtc | ttcacacctc | ttctacctgg | cgctctgctt | gctcaccttc | 420 |
| accagctcca | ccacagctgg | accagagacc | ctttgcgggg | ctgagctggt | ggatgctctt | 480 |
| cagttcgtgt | gtggaccgag | gggcttttac | ttcaacaagc | ccacaggcta | tggctccagc | 540 |
| attcggaggg | cacctcagac | aggcattgtg | gatgagtgtt | gcttccggag | ctgtgatctg | 600 |
| aggagactgg | agatgtactg | tgccccactg | aagcctacaa | agcagcccg | ctctatccgt | 660 |
| gcccagcgcc | acactgacat | gcccaagact | cagaagtccc | cgtccctatc | gacaaacaag | 720 |
| aaaacgaagc | tgcaaaggag | aaggaaagga | agtacatttg | aagaacacaa | gtagaggaag | 780 |
| tgcaggaaac | aagacctaca | gaatgtagga | ggagcctccc | acggagcaga | aaatgccaca | 840 |
| tcaccgcagg | atcctttgct | gcttgagcaa | cctgcaaaac | atcgaaacac | ctaccaaata | 900 |
| acaataataa | gtccaataac | attacaaaga | tgggcatttc | ccccaatgaa | atatacaagt | 960 |
| aaacattcca | acatcgtctt | taggagtgtt | tgtttaaaaa | gctttgcacc | ttgcaaaagt | 1020 |
| ggtcctggcg | tgggtagatt | gctgttggtc | ctttatcaat | aacattctat | agagaaaaaa | 1080 |
| aatatatata | taactatatc | tcctagtccc | tgcctctaaa | gagccgaaaa | tgcatggatg | 1140 |
| ttgtagagat | ccagttgctc | taagtttctc | tctgaatttt | ggctgctgaa | gccattcatt | 1200 |
| tagcaactgt | gtagaggtgg | tttatgaatg | gttcccttat | cttcacctct | tcccacgtag | 1260 |
| ctcaagctgc | ttgttttaca | gagtctaatc | atcttgtcta | gctgcattag | acacacccttt | 1320 |
| tcctaacact | tgtatttgtt | gaatttggcc | tccttaagag | caatagcaaa | taagtagtca | 1380 |
| agtggcctac | caagttttaa | cgtacctgac | tccatctgtg | gcatttgtac | caaatataag | 1440 |
| ttgaatgcat | ttatttaga | cacaaagctt | tatttttttt | gacattgtgt | tcaagaaaa | 1500 |
| aaaatagaat | aacaataact | acaactttga | ggccaatcat | ttttaggtgt | gtgtttgaag | 1560 |
| catagaacgt | ctcttaaact | ctcaatggtt | tcttcaaatg | ataagttagt | atgtaaccta | 1620 |
| agtatagcag | tttctctctt | tttattttt | tccatatag | agcactatgt | aaagttagta | 1680 |
| tatcaataat | acaggaaata | tcaaacagta | tgtaaaactc | tgttgttgtt | gttttttagt | 1740 |
| acaatggtgc | tattttgtag | tttgttatat | gaaagaatct | agtcaacaca | gtaaaaggag | 1800 |
| aaagcaaagc | aaaaacaaca | aacgaaagcc | tggagcctaa | gatgacaaaa | cgaggaaggg | 1860 |
| aactgaaaaa | aaaaatcctt | cctcttggga | gatgcaaagg | cctccccaat | tatgccttcc | 1920 |

```
aagaagaact taagatatag agtccattaa gacgcactta cttgtcaagt ccagagagga   1980
agctatggag tgggaaaagc aagaggctag ggatttggga gtcctggttt cttttaatc    2040 actgaagaag taagtatttg caacctgggt cacacaaact caccaccctg tgacctcagt   2100
caaatcactc cacctctcgg tgcctcagtt ttcctcatct gcaaatgggg gcaatatgt    2160 catctaccta cctcaaaggg gtggtatgaa gattaaaaag tagaccttca gattttgtt    2220 ctgggtttcc aggagggtgc aacatcagaa cccttgaatt gctaggatgc aaggaattct   2280
gtaaataacc cactaacaat gtagctccaa ggatcattca tctgtcactg ggatgccacc   2340
acaatatcca agttcttatt ggtgaagctg tgcaactaat tagtgacaag ctaaggactc   2400
agtctcccca gcatgtcaca cggcaggaga catttgattt gcagttttat ttaacttctg   2460
catttgagct tatgactata aagactagtg aaaagaaggg agagaggaga aagaagatcc   2520
ttgccaagta aagggtaatt aattattatt ccatttatcc actctcatta aagggtaatt   2580
aattattcca tgtatccact ctcattaatc cttccagtca cttagtatct agaaataact   2640
ctaacattgt caatgagact ctactcagtt tgccaaacac aattctcctt ccccatagca   2700
tatgaaaaaa aggcgctgac attcttaaat tttgaaatag tatctattac aatcacaggt   2760
tgctgtagca gatgtagtct tgcccttgtt tgtacatgca tgtatttttt ttttaatttt   2820
atgaaaatgt gctagcaaga attgctactt gaggggcaaa attcttcctt ctcaagcctg   2880
aggttctccc tagtgtctgc ttagaaggaa ggatccagct tcctggaaat gtgttggatg   2940
cattcaactg ggcattgcta accaaaaaca tttagaaaaa tgttctctat gtatatagca   3000
agattgtctc cctcttttaa aaacaaaatc caatattcac atcttattac ctacaacctt   3060
gattctctat tgcaagcttc cttaatattc ttataaaatg tattaagaaa acaaaaagg    3120 acacctttag ctctccttcc gccaggttgc ctctagaatc tctggggaaa tgcagaaggt   3180
gctgttgagt aaagccctca gaaggattgg atttaggaac atcaggcacg ctgtacatcc   3240
cctgattact gtagaaatgt aaatggaata agaggtcagc tgaccatcca cctgcttccc   3300
cagaaggata cagggaaaag ttaggccctc acacaccctg ggtgacactt ctgacttcta   3360
gttcttgttc acagtgtgta cttttttcaaa ttggtaattc ccagaaaaac acataggtgg  3420
ccttctccag atctgtgggc ttcctgccat ggttggattt ggtgattcca agtgtctatc   3480
acatattttg ttcacttaat tctatccaca gtcagaaatt ctttcaatga ggaaagttta   3540
aatatgcaat cctttatcca atacctaatt ctctccaact gcatcataaa tcaagtaata   3600
aaaattaatt gtactaatta atcataataa tgtaccattg tacttttaaa tgaatgaaca   3660
ctgcaagaca aatctatgta aactctgaaa agtaactgat cattatatgg tgaatcaaaa   3720
tgactcaaga ttgatagaaa gggacattta aaattttaca actcaaaatt ttgtagactt   3780
tgctatggag gtaaattgtt ttagtgccta gagatggagc ggttttaata aatttacaaa   3840
agaactataa agataggtag gaaggaattt tcatttgata ggattgttgc tgatttactt   3900
actcaatacc taggtcaaat gttgatccta ttctccaaag actatcaagt gcttgaacat   3960
tgtaagatga gtctgctcca ctgaaaatgt aatacatctc tccattataa tctatttccc   4020
tggggtaaaa aaatccttttt tttaaatatc cacctacata tacctaccct acatgtgcat   4080
ttgcacatgc gtgcatacgc tcatgcgccc caccccacac acacctattc accctaagac   4140
taagaagaaa tcatttcttt gaaagtctta tctttcaaaa aaggcagcgg tgccccttga   4200
gactccttct ccttctttga atgtcaatgt gaaatgtggc atgtctgtgt acatgaaacc   4260
```

-continued

```
atctcatacc ctatggctcc agggtttctt tatggtttgt gcacttggga ggatgcgcag    4320
aagacaggat gcagcctgtt ttgctttccc ctttactgtt tggccagcta cgccaatgtg    4380
gtgctattgt ttcttttaaga aagtacttga ctaaaaaaaa agaaaaaaag aaaaaaagaa    4440
aagaaaaaga aaaagaaaa aaaagaaag catagaccta ttttttttaaa gtctgaaaac    4500 aacagttcta tagtagatgg cttactgaga tagcattaga tctagccacc accctagcca    4560
ccacctttca actatgtgtc actcacaagt agaatattgt tcaccaagtt gtgagtttgg    4620
gggttcagag acaaaggatg gaaaagttt aaagttagat ggctcaatca tttcattggc    4680
tctcaaattt aacaaaattg gcaatacttc acccaatctg aagtgttggt caataacttg    4740
aactgggggc aaaaataact tcaggcaaat ggcagaagaa aataattaac ttacttcttg    4800 cttttttgt tgattgttg gtttcctgtt gattttggt tttggttttg ctgtgggtgg    4860
gtgagtacat gtgtgtaagt acgtgtgtgt gtgtgtgtgt gtgtgtgtgt gtgtgtgttc    4920
cactcaaaaa caaatactca gaaagtggag aaaatacaac gatttaaga gcatagactt    4980 acctactact agaaccagct tctgtcacat cctctggaga aggcactgat ttcttgtttt    5040
gtagaggttg ctcttccatc agtgacctga aagagtgacc agtctcctag agtagacatg    5100
gatctcatta ggagaagaca gaagtatttc cttatgaatt gggcttatct actgacaaag    5160
aaagggaaga gtttatgaga agttattgaa gaagatggct aacagtctgt gaagattttg    5220
ttctggtttt ttttgttgtt gttgttgttg ggtttgggtt ttgattttt ttttttttt    5280 tttactttat acaatcttta tgaatggaaa tcttaatgct caaaaagact tggtctttt    5340 ttctcttttcg taacagaatg gaagatgaca aactcacata gactcttttct aggctggcta    5400 gcaaaggtgt ggtttgactt atttgaatca gaccatttta aatgttcctc tctattttta    5460
atcataaaag gctgtcataa tttattagcg taggcccttt ttggcacttc tcaaatgaat    5520
gagcattccc attcaaagca tggctttccc catggttcca aaacatgaat gattaatatt    5580
aaggaattat ttacttcaaa atacagtaga agtgtgagtc tctgttccca ttccccacaa    5640
agatcattaa gtcctgaatc ggggggcggg gtggggcgcc tggatactaa gggaattttt    5700
ttgttgcttg ttttttgttt tcaatgctag tgcttaatcc tatagtatac agatttgctt    5760
cttgctattg tgatattctg taagactttc ctgttaggta ttagaaattg atacataaat    5820 acctttttg tgtggtttct atttaaaagg aaagagataa gactgtctga acctaaatt    5880 cgtaaggcac atgataaaga gatcacatta ataacaagc catatctggt tcaatccttt    5940
ctttcttatc attttaagga aaacttgccc agataagaca gaggcccagg ggactttga    6000 aactctcttt gttccgccaa ttcatttgg ctggtgatgg ttttttcccca gtgtctgcct    6060 cagaatcttt tagaggctgg ccagactaaa gactgtcttt taaaacacat ttcacatggt    6120
tcctcttaat gaatgattac acttatgtag aacatgattt tttttctct ccacttattt    6180 ttttttccc catcattgat aagggttctt aaggagaaga attcattaac aaaactcaag    6240
aaagcgtaca aaaaaaaat tctaaatgtc actgcccaat tgaaatacga gctaaaatgg    6300
aaatactttc tcctacttaa aacccagact gaatcacctt caaaatgacc tttcacaatc    6360
tttccaattt gcctttgttt aaactgtctg ggcctaaaag caagcattat tcattttctc    6420
ttgcccaaag tgaacttgtg taaagtagga aaattaaaag aaactgctag aaatcccttc    6480
caaccagtgg ctgacccctc tcactagctc acagcaaagt ctcctctgtt gatctatcac    6540
ctagtctcat ttcgtttgaa tatttacatt gtacctactg ctaaacactt ggcaggaggc    6600
tccatccata tctcctatcg gtgtctctgt atccttaaac cttgcaaaca tcatacagtg    6660
```

| | |
|---|---|
| tatattaagt ttacaggaaa gctccaaata gcatatcaga cctggtctct ctttgttaaa | 6720 |
| gatttaagga gctatgggaa tctggattac aacgcacatt ttgcttcatt tatttttatc | 6780 |
| acactttaaa ggccaagggt gatgattaac ttacagacac tgaattgatt tccctactga | 6840 |
| aacctgaaag taatatttgg tcattcattg tatgtgtttt acacaaaaaa aacatcttct | 6900 |
| atcaaattac tcctgattgt atttgaagtg gttattcaat tcatttatgg cagagcaata | 6960 |
| tctgtcctaa tgactcttat aaaatgtaac taactgaatc attatcttac atttactgtt | 7020 |
| tagtaagcat attttgaaat tgtatggcta gagtgtcata ataaaatggt atatctttct | 7080 |
| ttagtaatta cattaaaatt aatcatgttt gattaactgg t | 7121 |

<210> SEQ ID NO 49
<211> LENGTH: 1087
<212> TYPE: DNA
<213> ORGANISM: Mus musculus

<400> SEQUENCE: 49

| | |
|---|---|
| acaatggaaa tgagtggctt cccttggggg aaaaagacgg actccaactc ccagctgtgc | 60 |
| aatttactca ttgtttaaat ggacaaaagg cagtttaccc aggctcagag catacctgcc | 120 |
| tgggtgtcca aatgtaacta gatgctttca caaaccccac ccacaaaaca cacctgttc | 180 |
| ttaagtcctc agttttgtgt tcacctcggc ctcatagtac ccactctgac ctgctgtgta | 240 |
| aacgacccgg acctaccaaa atgaccgcac ctgcaataaa gatacacatc atgtcgtctt | 300 |
| cacacctctt ctacctggcg ctctgcttgc tcaccttcac cagctccacc acagctggac | 360 |
| cagagaccct ttgcggggct gagctggtgg atgctcttca gttcgtgtgt ggaccgaggg | 420 |
| gcttttactt caacaagccc acaggctatg gctccagcat tcggagggca cctcagacag | 480 |
| gcattgtgga tgagtgttgc ttccggagct gtgatctgag gagactggag atgtactgtg | 540 |
| ccccactgaa gcctacaaaa gcagcccgct ctatccgtgc ccagcgccac actgacatgc | 600 |
| ccaagactca gaagtccccg tccctatcga caaacaagaa aacgaagctg caaaggagaa | 660 |
| ggaaaggtga gccaaagaca cacccagaag gggaacagga ggaggtaacg gaggcaactc | 720 |
| ggaaaatcag aggtcccaga gaaaaaagac tgggctagga actgtgagca agcaggcaaa | 780 |
| gagggacatg cgggaacagg gatgaaggac gtgcgggaac agggatgaag aaggagcaga | 840 |
| caggagccca ggaaagccgc agaggagctg aagcaaggca gtcctcacta agctagataa | 900 |
| tgtctgtgac ggaagtaaga aagtcctcct ctgggatacg gcacttacac atgggaagaa | 960 |
| tggtacgggg aagtgtaaca cctcagaaag tgacaagtga ccaggatgga acatcaacaa | 1020 |
| caataacaac cattaaaaac atgccaccaa gaccttccct ccccttctta aaaatataaa | 1080 |
| tcagagt | 1087 |

<210> SEQ ID NO 50
<211> LENGTH: 7039
<212> TYPE: DNA
<213> ORGANISM: Mus musculus

<400> SEQUENCE: 50

| | |
|---|---|
| acaatggaaa tgagtggctt cccttggggg aaaaagacgg actccaactc ccagctgtgc | 60 |
| aatttactca ttgtttaaat ggacaaaagg cagtttaccc aggctcagag catacctgcc | 120 |
| tgggtgtcca aatgtaacta gatgctttca caaaccccac ccacaaaaca cacctgttc | 180 |
| ttaagtcctc agttttgtgt tcacctcggc ctcatagtac ccactctgac ctgctgtgta | 240 |

```
aacgacccgg acctaccaaa atgaccgcac ctgcaataaa gatacacatc atgtcgtctt    300
cacacctctt ctacctggcg ctctgcttgc tcaccttcac cagctccacc acagctggac    360
cagagaccct tgcggggct gagctggtgg atgctcttca gttcgtgtgt ggaccgaggg     420
gcttttactt caacaagccc acaggctatg gctccagcat tcggagggca cctcagacag    480
gcattgtgga tgagtgttgc ttccggagct gtgatctgag gagactggag atgtactgtg    540
ccccactgaa gcctacaaaa gcagcccgct ctatccgtgc ccagcgccac actgacatgc    600
ccaagactca gaagtccccg tccctatcga caaacaagaa aacgaagctg caaaggagaa    660
ggaaaggaag tacatttgaa gaacacaagt agaggaagtg caggaaacaa gacctacaga    720
atgtaggagg agcctcccac ggagcagaaa atgccacatc accgcaggat cctttgctgc    780
ttgagcaacc tgcaaaacat cgaaacacct accaaataac aataataagt ccaataacat    840
tacaaagatg ggcatttccc ccaatgaaat atacaagtaa acattccaac atcgtcttta    900
ggagtgtttg tttaaaaagc tttgcacctt gcaaagtggg tcctggcgtg ggtagattgc    960
tgttggtcct ttatcaataa cattctatag agaaaaaaaa tatatatata actatatctc   1020
ctagtccctg cctctaaaga gccgaaaatg catggatgtt gtagagatcc agttgctcta   1080
agtttctctc tgaattttgg ctgctgaagc cattcattta gcaactgtgt agaggtggtt   1140
tatgaatggt tcccttatct tcacctcttc ccacgtagct caagctgctt gttttacaga   1200
gtctaatcat cttgtctagc tgcattagac acacccttc ctaacacttg tatttgttga   1260
atttggcctc cttaagagca atagcaaata agtagtcaag tggcctacca agttttaacg   1320
tacctgactc catctgtggc atttgtacca aatataagtt gaatgcattt attttagaca   1380
caaagcttta tttttttga cattgtgttt caagaaaaaa aatagaataa caataactac    1440
aactttgagg ccaatcattt ttaggtgtgt gtttgaagca tagaacgtct cttaaactct    1500
caatggtttc ttcaaatgat aagttagtat gtaacctaag tatagcagtt tctctctttt   1560 ttatttttt ccatatagag cactatgtaa agttagtata tcaataatac aggaaatatc    1620
aaacagtatg taaaactctg ttgttgttgt tttttagtac aatggtgcta ttttgtagtt   1680
tgttatatga agaatctag tcaacacagt aaaaggagaa agcaaagcaa aaacaacaaa    1740
cgaaagcctg gagcctaaga tgacaaaacg aggaagggaa ctgaaaaaaa aaatccttcc    1800
tcttgggaga tgcaaaggcc tccccaatta tgccttccaa gaagaactta agatatagag    1860
tccattaaga cgcacttact tgtcaagtcc agagaggaag ctatggagtg ggaaaagcaa    1920
gaggctaggg atttgggagt cctggttct ttttaatcac tgaagaagta agtatttgca    1980
acctgggtca cacaaactca ccaccctgtg acctcagtca aatcactcca cctctcggtg   2040
cctcagtttt cctcatctgc aaaatggggg caatatgtca tctacctacc tcaaaggggt   2100
ggtatgaaga ttaaaaagta gaccttcaga ttttttgttct gggtttccag gagggtgcaa   2160
catcagaacc cttgaattgc taggatgcaa ggaattctgt aaataaccca ctaacaatgt    2220
agctccaagg atcattcatc tgtcactggg atgccaccac aatatccaag ttcttattgg    2280
tgaagctgtg caactaatta gtgacaagct aaggactcag tctccccagc atgtcacacg    2340
gcaggagaca tttgatttgc agttttattt aacttctgca tttgagctta tgactataaa    2400
gactagtgaa aagaagggag agaggagaaa gaagatcctt gccaagtaaa gggtaattaa    2460
ttattattcc atttatccac tctcattaaa gggtaattaa ttattccatg tatccactct    2520
cattaatcct tccagtcact tagtatctag aaataactct aacattgtca atgagactct    2580
actcagtttg ccaaacacaa ttctccttcc ccatagcata tgaaaaaaag gcgctgacat    2640
```

```
tcttaaattt tgaaatagta tctattacaa tcacaggttg ctgtagcaga tgtagtcttg    2700
cccttgtttg tacatgcatg tattttttt ttaattttat gaaaatgtgc tagcaagaat    2760
tgctacttga ggggcaaaat tcttccttct caagcctgag gttctcccta gtgtctgctt    2820
agaaggaagg atccagcttc ctggaaatgt gttggatgca ttcaactggg cattgctaac    2880
caaaaacatt tagaaaaatg ttctctatgt atatagcaag attgtctccc tcttttaaaa    2940
acaaaatcca atattcacat cttattacct acaaccttga ttctctattg caagcttcct    3000
taatattctt ataaaatgta ttaagaaaaa caaaaaggac acctttagct ctccttccgc    3060
caggttgcct ctagaatctc tggggaaatg cagaaggtgc tgttgagtaa agccctcaga    3120
aggattggat ttaggaacat caggcacgct gtacatcccc tgattactgt agaaatgtaa    3180
atggaataag aggtcagctg accatccacc tgcttcccca gaaggataca gggaaaagtt    3240
aggccctcac acaccctggg tgacacttct gacttctagt tcttgttcac agtgtgtact    3300
ttttcaaatt ggtaattccc agaaaaacac ataggtggcc ttctccagat ctgtgggctt    3360
cctgccatgg ttggatttgg tgattccaag tgtctatcac atattttgtt cacttaattc    3420
tatccacagt cagaaattct ttcaatgagg aaagtttaaa tatgcaatcc tttatccaat    3480
acctaattct ctccaactgc atcataaatc aagtaataaa aattaattgt actaattaat    3540
cataataatg taccattgta cttttaaatg aatgaacact gcaagacaaa tctatgtaaa    3600
ctctgaaaag taactgatca ttatatggtg aatcaaaatg actcaagatt gatagaaagg    3660
gacatttaaa attttacaac tcaaaatttt gtagactttg ctatggaggt aaattgtttt    3720
agtgcctaga gatggagcgg ttttaataaa tttacaaaag aactataaag ataggtagga    3780
aggaattttc atttgatagg attgttgctg atttacttac tcaataccta ggtcaaaatgt    3840 tgatcctatt ctccaaagac tatcaagtgc ttgaacattg taagatgagt ctgctccact    3900
gaaaatgtaa tacatctctc cattataatc tattttcctg gggtaaaaaa atcctttttt    3960
taaatatcca cctacatata cctaccctac atgtgcattt gcacatgcgt gcatacgctc    4020
atgcgcccca ccccacacac acctattcac cctaagacta agaagaaatc atttctttga    4080
aagtcttatc tttcaaaaaa ggcagcggtg ccccttgaga ctccttctcc ttctttgaat    4140
gtcaatgtga aatgtggcat gtctgtgtac atgaaaccat ctcataccct atggctccag    4200 ggtttctta tggtttgtgc acttgggagg atgcgcagaa gacaggatgc agcctgtttt    4260
gctttcccct ttactgtttg gccagctacg ccaatgtggt gctattgttt ctttaagaaa    4320
gtacttgact aaaaaaaaag aaaaaaagaa aaaagaaaa gaaaagaaa aagaaaaaa    4380 aaagaaagca tagacctatt ttttaaagt ctgaaaacaa cagttctata gtagatggct    4440
tactgagata gcattagatc tagccaccac cctagccacc acctttcaac tatgtgtcac    4500
tcacaagtag aatattgttc accaagttgt gagtttgggg gttcagagac aaaggatgga    4560
aaagttttaa agttagatgg ctcaatcatt tcattggctc tcaaatttaa caaaattggc    4620
aatacttcac ccaatctgaa gtgttggtca ataacttgaa ctgggggcaa aaataacttc    4680
aggcaaatgg cagaagaaaa taattaactt acttcttgct ttttttgttg attgtttggt    4740
ttcctgttga ttttttggttt tggttttgct gtgggtgggt gagtacatgt gtgtaagtac    4800
gtgtgtgtgt gtgtgtgtgt gtgtgtgtgt gtgtgttcca ctcaaaaaca aatactcaga    4860
aagtggagaa aatacaacga ttttaagagc atagacttac ctactactag aaccagcttc    4920
tgtcacatcc tctggagaag gcactgattt cttgtttgt agaggttgct cttccatcag    4980
```

| | | | | |
|---|---|---|---|---|
| tgacctgaaa | gagtgaccag | tctcctagag | tagacatgga | tctcattagg agaagacaga | 5040 |
| agtatttcct | tatgaattgg | gcttatctac | tgacaaagaa | agggaagagt ttatgagaag | 5100 |
| ttattgaaga | agatggctaa | cagtctgtga | agattttgtt | ctggtttttt ttgttgttgt | 5160 |
| tgttgttggg | tttgggtttt | gattttttt | tttttttttt | tactttatac aatctttatg | 5220 |
| aatggaaatc | ttaatgctca | aaaagacttg | gtcttttttt | ctctttcgta acagaatgga | 5280 |
| agatgacaaa | ctcacataga | ctctttctag | gctggctagc | aaaggtgtgg tttgacttat | 5340 |
| ttgaatcaga | ccatttttaaa | tgttcctctc | tattttttaat | cataaaaggc tgtcataatt | 5400 |
| tattagcgta | ggccctttt | ggcacttctc | aaatgaatga | gcattcccat tcaaagcatg | 5460 |
| gctttcccca | tggttccaaa | acatgaatga | ttaatattaa | ggaattattt acttcaaaat | 5520 |
| acagtagaag | tgtgagtctc | tgttcccatt | ccccacaaag | atcattaagt cctgaatcgg | 5580 |
| gggcggggggt | ggggcgcctg | gatactaagg | gaatttttt | gttgcttgtt ttttgttttc | 5640 |
| aatgctagtg | cttaatccta | tagtatacag | atttgcttct | tgctattgtg atattctgta | 5700 |
| agactttcct | gttaggtatt | agaaattgat | acataaatac | cttttttgtg tggtttctat | 5760 |
| ttaaaggaa | agagataaga | ctgtctgaac | cttaaattcg | taaggcacat gataaagaga | 5820 |
| tcacattaaa | taacaagcca | tatctggttc | aatccttttct | ttcttatcat tttaaggaaa | 5880 |
| acttgcccag | ataagacaga | ggcccagggg | actttgaaa | ctctctttgt tccgccaatt | 5940 |
| catttttggct | ggtgatggtt | ttccccagt | gtctgcctca | gaatctttta gaggctggcc | 6000 |
| agactaaaga | ctgtcttta | aaacacattt | cacatggttc | ctcttaatga atgattacac | 6060 |
| ttatgtagaa | catgattttt | tttctctcc | acttattttt | tttttcccca tcattgataa | 6120 |
| gggttcttaa | ggagaagaat | tcattaacaa | aactcaagaa | agcgtacaaa aaaaaaattc | 6180 |
| taaatgtcac | tgcccaattg | aaatacgagc | taaaatggaa | atactttctc ctacttaaaa | 6240 |
| cccagactga | atcaccttca | aaatgacctt | tcacaatctt | tccaatttgc ctttgtttaa | 6300 |
| actgtctggg | cctaaaagca | agcattattc | attttctctt | gcccaaagtg aacttgtgta | 6360 |
| aagtaggaaa | attaaaagaa | actgctagaa | atcccttcca | accagtggct gaccctctc | 6420 |
| actagctcac | agcaaagtct | cctctgttga | tctatcacct | agtctcattt cgtttgaata | 6480 |
| tttacattgt | acctactgct | aaacacttgg | caggaggctc | catccatatc tcctatcggt | 6540 |
| gtctctgtat | ccttaaacct | tgcaaacatc | atacagtgta | tattaagttt acaggaaagc | 6600 |
| tccaaatagc | atatcagacc | tggtctctct | ttgttaaaga | tttaaggagc tatgggaatc | 6660 |
| tggattacaa | cgcacatttt | gcttcattta | tttttatcac | actttaaagg ccaagggtga | 6720 |
| tgattaactt | acagacactg | aattgatttc | cctactgaaa | cctgaaagta atatttggtc | 6780 |
| attcattgta | tgtgttttac | acaaaaaaaa | catcttctat | caaattactc ctgattgtat | 6840 |
| ttgaagtggt | tattcaattc | atttatggca | gagcaatatc | tgtcctaatg actcttataa | 6900 |
| aatgtaacta | actgaatcat | tatcttacat | ttactgttta | gtaagcatat tttgaaattg | 6960 |
| tatggctaga | gtgtcataat | aaaatggtat | atctttcttt | agtaattaca ttaaaattaa | 7020 |
| tcatgtttga | ttaactggt | | | | 7039 |

<210> SEQ ID NO 51
<211> LENGTH: 7069
<212> TYPE: DNA
<213> ORGANISM: Mus musculus

<400> SEQUENCE: 51
gataactttg ccagaagagg gagagagaga gaaggcgaat gttcccccag ctgtttcctg    60

```
tctacagtgt ctgtgttttg tagataaatg tgaggatttt ctctaaatcc ctcttctgct    120
tgctaaatct cactgtcact gctaaattca gagcagatag agcctgcgca atggaataaa    180
gtcctcaaaa ttgaaatgtg acattgctct aacatctccc atctctctgg atttcttttt    240
cgcctcatta tccctgccca ccaattcatt tccagacttt gtacttcaga agcgatgggg    300
aaaatcagca gccttccaac tcaattattt aagatctgcc tctgtgactt cttgaagata    360
aagatacaca tcatgtcgtc ttcacacctc ttctacctgg cgctctgctt gctcaccttc    420
accagctcca ccacagctgg accagagacc ctttgcgggg ctgagctggt ggatgctctt    480
cagttcgtgt gtggaccgag gggcttttac ttcaacaagc ccacaggcta tggctccagc    540
attcggaggg cacctcagac aggcattgtg gatgagtgtt gcttccggag ctgtgatctg    600
aggagactgg agatgtactg tgccccactg aagcctacaa agcagcccg ctctatccgt    660 gcccagcgcc acactgacat gcccaagact cagaaggaag tacatttgaa gaacacaagt    720
agaggaagtg caggaaacaa gacctacaga atgtaggagg agcctcccac ggagcagaaa    780
atgccacatc accgcaggat cctttgctgc ttgagcaacc tgcaaaacat cgaaacacct    840
accaaataac aataataagt ccaataacat tacaaagatg gcatttccc ccaatgaaat     900 atacaagtaa acattccaac atcgtcttta ggagtgtttg tttaaaaagc tttgcacctt    960 gcaaagtgg tcctggcgtg ggtagattgc tgttggtcct ttatcaataa cattctatag     1020
agaaaaaaaa tatatatata actatatctc ctagtccctg cctctaaaga gccgaaaatg    1080
catggatgtt gtagagatcc agttgctcta agtttctctc tgaattttgg ctgctgaagc    1140
cattcattta gcaactgtgt agaggtggtt tatgaatggt tcccttatct tcacctcttc    1200
ccacgtagct caagctgctt gttttacaga gtctaatcat cttgtctagc tgcattagac    1260 acacccttc ctaacacttg tatttgttga atttggcctc cttaagagca atagcaaata    1320
agtagtcaag tggcctacca agttttaacg tacctgactc catctgtggc atttgtacca    1380
aatataagtt gaatgcattt attttagaca caaagcttta ttttttttga cattgtgttt    1440
caagaaaaaa aatagaataa caataactac aactttgagg ccaatcattt ttaggtgtgt    1500
gtttgaagca tagaacgtct cttaaactct caatggtttc ttcaaatgat aagttagtat    1560
gtaacctaag tatagcagtt tctctctttt ttattttttt ccatatagag cactatgtaa    1620
agttagtata tcaataatac aggaaatatc aaacagtatg taaaactctg ttgttgttgt    1680
tttttagtac aatggtgcta ttttgtagtt tgttatatga agaatctag tcaacacagt     1740 aaaaggagaa agcaaagcaa aaacaacaaa cgaaagcctg gagcctaaga tgacaaaacg    1800
aggaagggaa ctgaaaaaaa aaatccttcc tcttgggaga tgcaaaggcc tccccaatta    1860
tgccttccaa gaagaactta agatatagag tccattaaga cgcacttact tgtcaagtcc    1920
agagaggaag ctatggagtg ggaaaagcaa gaggctaggg atttgggagt cctggtttct    1980
ttttaatcac tgaagaagta agtatttgca acctgggtca cacaaactca ccaccctgtg    2040
acctcagtca aatcactcca cctctcggtg cctcagtttt cctcatctgc aaaatggggg    2100
caatatgtca tctacctacc tcaaaggggt ggtatgaaga ttaaaaagta gaccttcaga    2160 ttttgttct gggtttccag gagggtgcaa catcagaacc cttgaattgc taggatgcaa     2220
ggaattctgt aaataaccca ctaacaatgt agctccaagg atcattcatc tgtcactggg    2280
atgccaccac aatatccaag ttcttattgg tgaagctgtg caactaatta gtgacaagct    2340
aaggactcag tctccccagc atgtcacacg gcaggagaca tttgatttgc agttttattt    2400
```

```
aacttctgca tttgagctta tgactataaa gactagtgaa agaagggag agaggagaaa    2460
gaagatcctt gccaagtaaa gggtaattaa ttattattcc atttatccac tctcattaaa    2520
gggtaattaa ttattccatg tatccactct cattaatcct tccagtcact tagtatctag    2580
aaataactct aacattgtca atgagactct actcagtttg ccaaacacaa ttctccttcc    2640
ccatagcata tgaaaaaaag gcgctgacat tcttaaattt tgaaatagta tctattacaa    2700
tcacaggttg ctgtagcaga tgtagtcttg cccttgtttg tacatgcatg tattttttt    2760
ttaattttat gaaaatgtgc tagcaagaat tgctacttga ggggcaaaat tcttccttct    2820
caagcctgag gttctcccta gtgtctgctt agaaggaagg atccagcttc ctggaaatgt    2880
gttggatgca ttcaactggg cattgctaac caaaaacatt tagaaaatg ttctctatgt    2940
atatagcaag attgtctccc tcttttaaaa acaaaatcca atattcacat cttattacct    3000
acaaccttga ttctctattg caagcttcct taatattctt ataaaatgta ttaagaaaaa    3060
caaaaaggac acctttagct ctccttccgc caggttgcct ctagaatctc tggggaaatg    3120
cagaaggtgc tgttgagtaa agccctcaga aggattggat ttaggaacat caggcacgct    3180
gtacatcccc tgattactgt agaaatgtaa atggaataag aggtcagctg accatccacc    3240
tgcttcccca gaaggataca gggaaaagtt aggccctcac acaccctggg tgacacttct    3300
gacttctagt tcttgttcac agtgtgtact ttttcaaatt ggtaattccc agaaaaacac    3360
ataggtggcc ttctccagat ctgtgggctt cctgccatgg ttggatttgg tgattccaag    3420
tgtctatcac atattttgtt cacttaattc tatccacagt cagaaattct ttcaatgagg    3480
aaagtttaaa tatgcaatcc tttatccaat acctaattct ctccaactgc atcataaatc    3540
aagtaataaa aattaattgt actaattaat cataataatg taccattgta cttttaaatg    3600
aatgaacact gcaagacaaa tctatgtaaa ctctgaaaag taactgatca ttatatggtg    3660
aatcaaaatg actcaagatt gatagaaagg acatttaaa attttacaac tcaaaatttt    3720
gtagactttg ctatggaggt aaattgtttt agtgcctaga gatggagcgg ttttaataaa    3780
tttacaaaag aactataaag ataggtagga aggaattttc atttgatagg attgttgctg    3840
atttacttac tcaataccta ggtcaaatgt tgatcctatt ctccaaagac tatcaagtgc    3900
ttgaacattg taagatgagt ctgctccact gaaaatgtaa tacatctctc cattataatc    3960
tattttcctg gggtaaaaaa atccttttt taaatatcca cctacatata cctaccctac    4020
atgtgcattt gcacatgcgt gcatacgctc atgcgcccca ccccacacac acctattcac    4080
cctaagacta agaagaaatc atttctttga aagtcttatc tttcaaaaaa ggcagcggtg    4140
ccccttgaga ctccttctcc ttctttgaat gtcaatgtga aatgtggcat gtctgtgtac    4200
atgaaaccat ctcatacccc atggctccag ggtttcttta tggtttgtgc acttgggagg    4260
atgcgcagaa gacaggatgc agcctgtttt gctttcccct ttactgtttg gccagctacg    4320
ccaatgtggt gctattgttt ctttaagaaa gtacttgact aaaaaaaaag aaaaaaagaa    4380
aaaagaaaa gaaaaagaaa aagaaaaaa aagaaagca tagacctatt tttttaaagt    4440
ctgaaaacaa cagttctata gtagatggct tactgagata gcattagatc tagccaccac    4500
cctagccacc acctttcaac tatgtgtcac tcacaagtag aatattgttc accaagttgt    4560
gagtttgggg gttcagagac aaaggatgga aaagttttaa agttagatgg ctcaatcatt    4620
tcattggctc tcaaatttaa caaaattggc aatacttcac ccaatctgaa gtgttggtca    4680
ataacttgaa ctgggggcaa aaataacttc aggcaaatgg cagaagaaaa taattaactt    4740
acttcttgct ttttttgttg attgtttggt ttcctgttga tttttggttt tggttttgct    4800
```

-continued

```
gtgggtgggt gagtacatgt gtgtaagtac gtgtgtgtgt gtgtgtgtgt gtgtgtgtgt    4860
gtgtgttcca ctcaaaaaca aatactcaga aagtggagaa aatacaacga ttttaagagc    4920
atagacttac ctactactag aaccagcttc tgtcacatcc tctggagaag gcactgattt    4980
cttgttttgt agaggttgct cttccatcag tgacctgaaa gagtgaccag tctcctagag    5040
tagacatgga tctcattagg agaagacaga agtatttcct tatgaattgg cttatctac     5100 tgacaaagaa agggaagagt ttatgagaag ttattgaaga agatggctaa cagtctgtga    5160 agatttgtt  ctggtttttt ttgttgttgt tgttgttggg tttgggtttt gatttttttt    5220 ttttttttt  tactttatac aatctttatg aatggaaatc ttaatgctca aaaagacttg    5280 gtctttttt  ctctttcgta acagaatgga agatgacaaa ctcacataga ctctttctag    5340
gctggctagc aaaggtgtgg tttgacttat ttgaatcaga ccattttaaa tgttcctctc    5400
tatttttaat cataaaaggc tgtcataatt tattagcgta ggcccttttt ggcacttctc    5460
aaatgaatga gcattcccat tcaaagcatg gctttcccca tggttccaaa acatgaatga    5520
ttaatattaa ggaattattt acttcaaaat acagtagaag tgtgagtctc tgttcccatt    5580
ccccacaaag atcattaagt cctgaatcgg gggcggggt  ggggcgcctg gatactaagg    5640 gaatttttt  gttgcttgtt ttttgttttc aatgctagtg cttaatccta tagtatacag    5700
atttgcttct tgctattgtg atattctgta agactttcct gttaggtatt agaaattgat    5760
acataaatac cttttttgtg tggtttctat ttaaaggaa  agagataaga ctgtctgaac    5820
cttaaattcg taaggcacat gataaagaga tcacattaaa taacaagcca tatctggttc    5880
aatcctttct ttcttatcat tttaaggaaa acttgcccag ataagacaga ggcccagggg    5940
acttttgaaa ctctctttgt tccgccaatt cattttggct ggtgatggtt tttcccagt     6000 gtctgcctca gaatctttta gaggctggcc agactaaaga ctgtctttta aaacacattt    6060
cacatggttc ctcttaatga atgattcac  ttatgtagaa catgattttt ttttctctcc    6120 acttatttt  tttttcccca tcattgataa gggttcttaa ggagaagaat tcattaacaa    6180
aactcaagaa agcgtacaaa aaaaaaattc taaatgtcac tgcccaattg aaatacgagc    6240
taaaatggaa atactttctc ctacttaaaa cccagactga atcaccttca aaatgacctt    6300
tcacaatctt tccaatttgc ctttgtttaa actgtctggg cctaaaagca agcattattc    6360
attttctctt gcccaaagtg aacttgtgta agtaggaaa  attaaaagaa actgctagaa    6420
atcccttcca accagtggct gaccctctc  actagctcac agcaaagtct cctctgttga    6480
tctatcacct agtctcattt cgtttgaata tttacattgt acctactgct aaacacttgg    6540
caggaggctc catccatatc tcctatcggt gtctctgtat ccttaaacct tgcaaacatc    6600
atacagtgta tattaagttt acaggaaagc tccaaatagc atatcagacc tggtctctct    6660
ttgttaaaga tttaaggagc tatgggaatc tggattacaa cgcacatttt gcttcattta    6720
tttttatcac actttaaagg ccaagggtga tgattaactt acagacactg aattgatttc    6780
cctactgaaa cctgaaagta atatttggtc attcattgta tgtgttttac acaaaaaaaa    6840
catcttctat caaattactc ctgattgtat ttgaagtggt tattcaattc atttatggca    6900
gagcaatatc tgtcctaatg actcttataa aatgtaacta actgaatcat tatcttacat    6960
ttactgttta gtaagcatat tttgaaattg tatggctaga gtgtcataat aaaatggtat    7020
atctttcttt agtaattaca ttaaaattaa tcatgtttga ttaactggt              7069
```

<210> SEQ ID NO 52

<211> LENGTH: 1649
<212> TYPE: DNA
<213> ORGANISM: Artificial
<220> FEATURE:
<223> OTHER INFORMATION: CAG promoter

<400> SEQUENCE: 52

```
tctactcgac attgattatt gactagttat taatagtaat caattacggg gtcattagtt      60
catagcccat atatggagtt ccgcgttaca taacttacgg taaatggccc gcctggctga     120
ccgcccaacg accccgccc attgacgtca ataatgacgt atgttcccat agtaacgcca      180
atagggactt tccattgacg tcaatgggtg gagtatttac ggtaaactgc ccacttggca     240
gtacatcaag tgtatcatat gccaagtacg cccctattg acgtcaatga cggtaaatgg      300
cccgcctggc attatgccca gtacatgacc ttatgggact ttcctacttg gcagtacatc     360
tacgtattag tcatcgctat taccatggtc gaggtgagcc cacgttctg cttcactctc      420
cccatctccc cccctccc acccccaatt ttgtatttat ttattttta attattttgt        480
gcagcgatgg gggcggggg ggggggggg cgcgcgccag gcggggcggg gcggggcgag       540
gggcggggcg gggcgaggcg gagaggtgcg gcggcagcca atcagagcgg cgcgctccga     600
aagtttcctt ttatggcgag gcggcggcgg cggcggccct ataaaaagcg aagcgcgcgg     660
cgggcgggag tcgctgcgtt gccttcgccc cgtgccccgc tccgcgccgc ctcgcgccgc     720
ccgccccggc tctgactgac cgcgttactc ccacaggtga gcgggcggga cggcccttct     780
cctccgggct gtaattagcg cttggtttaa tgacggcttg tttcttttct gtggctgcgt     840
gaaagccttg aggggctccg ggagggccct ttgtgcgggg ggagcggctc gggggtgcg      900
tgcgtgtgtg tgtgcgtggg gagcgccgcg tgcggctccg cgctgcccgg cggctgtgag     960
cgctgcgggc gcggcgcggg gctttgtgcg ctccgcagtg tgcgcgaggg gagcgcggcc    1020
ggggcggtg cccgcggtg cggggggctg cgagggaac aaaggctgcg tgcggggtgt      1080
gtgcgtgggg gggtgagcag ggggtgtggg cgcgtcggtc gggctgcaac cccccctgca    1140
cccccctccc cgagttgctg agcacggccc ggcttcgggt gcgggctcc gtacggggcg     1200
tggcgcgggg ctcgccgtgc cgggcggggg gtggcggcag gtggggtgc cgggcggggc     1260
ggggccgcct cgggccgggg agggctcggg ggaggggcgc ggcggccccc ggagcgccgg    1320
cggctgtcga ggcgcggcga gccgcagcca ttgcctttta tggtaatcgt gcgagagggc    1380
gcagggactt cctttgtccc aaatctgtgc ggagccgaaa tctgggaggc gccgccgcac    1440
ccctctagc gggcgcgggg cgaagcggtg cggcgccggc aggaaggaaa tgggcgggga    1500
gggccttcgt gcgtcgccgc gccgccgtcc ccttctccct ctccagcctc ggggctgtcc     1560
gcggggggac ggctgccttc ggggggacg gggcagggcg gggttcggct tctggcgtgt     1620
gaccggcggc tctagagcct ctgctaacc                                     1649
```

<210> SEQ ID NO 53
<211> LENGTH: 21
<212> TYPE: DNA
<213> ORGANISM: Artificial
<220> FEATURE:
<223> OTHER INFORMATION: Primer: mIGF-1a forward sequence

<400> SEQUENCE: 53

```
tggatgctct tcagttcgtg t                                                21
```

<210> SEQ ID NO 54
<211> LENGTH: 21

```
<212> TYPE: DNA
<213> ORGANISM: Artificial
<220> FEATURE:
<223> OTHER INFORMATION: Primer: mIGF-1a, reverse sequence

<400> SEQUENCE: 54
caacactcat ccacaatgcc t                                               21

<210> SEQ ID NO 55
<211> LENGTH: 20
<212> TYPE: DNA
<213> ORGANISM: Artificial
<220> FEATURE:
<223> OTHER INFORMATION: Primer: mCcl3 (Mip-1alpha), forward sequence

<400> SEQUENCE: 55
gcaaccaagt cttctcagcg                                                 20

<210> SEQ ID NO 56
<211> LENGTH: 20
<212> TYPE: DNA
<213> ORGANISM: Artificial
<220> FEATURE:
<223> OTHER INFORMATION: Primer: mCcl3 (Mip-1alpha), reverse sequence

<400> SEQUENCE: 56
agcaaaggct gctggtttca                                                 20

<210> SEQ ID NO 57
<211> LENGTH: 20
<212> TYPE: DNA
<213> ORGANISM: Artificial
<220> FEATURE:
<223> OTHER INFORMATION: Primer: mCcl4 (Mip-1beta), forward sequence

<400> SEQUENCE: 57
ccatgaagct ctgcgtgtct                                                 20

<210> SEQ ID NO 58
<211> LENGTH: 21
<212> TYPE: DNA
<213> ORGANISM: Artificial
<220> FEATURE:
<223> OTHER INFORMATION: Primer: mCcl4 (Mip-1beta), reverse sequence

<400> SEQUENCE: 58
gagaaacagc aggaagtggg a                                               21

<210> SEQ ID NO 59
<211> LENGTH: 20
<212> TYPE: DNA
<213> ORGANISM: Artificial
<220> FEATURE:
<223> OTHER INFORMATION: Primer: mCxcl9 (MIG), forward sequence

<400> SEQUENCE: 59
cgaggcacga tccactacaa                                                 20

<210> SEQ ID NO 60
<211> LENGTH: 20
<212> TYPE: DNA
<213> ORGANISM: Artificial
<220> FEATURE:
<223> OTHER INFORMATION: Primer: mCxcl9 (MIG), reverse sequence

<400> SEQUENCE: 60
```
agtccggatc taggcaggtt                                          20

<210> SEQ ID NO 61
<211> LENGTH: 20
<212> TYPE: DNA
<213> ORGANISM: Artificial
<220> FEATURE:
<223> OTHER INFORMATION: Primer: mCxcl10 (IP-10), forward sequence

<400> SEQUENCE: 61
ccaagtgctg ccgtcatttt                                          20

<210> SEQ ID NO 62
<211> LENGTH: 20
<212> TYPE: DNA
<213> ORGANISM: Artificial
<220> FEATURE:
<223> OTHER INFORMATION: Primer: mCxcl10 (IP-10), reverse sequence

<400> SEQUENCE: 62
agcttcccta tggccctcat                                          20

<210> SEQ ID NO 63
<211> LENGTH: 21
<212> TYPE: DNA
<213> ORGANISM: Artificial
<220> FEATURE:
<223> OTHER INFORMATION: Primer: mCcl5 (RANTES), forward sequence

<400> SEQUENCE: 63
gtgcccacgt caaggagtat t                                        21

<210> SEQ ID NO 64
<211> LENGTH: 21
<212> TYPE: DNA
<213> ORGANISM: Artificial
<220> FEATURE:
<223> OTHER INFORMATION: Primer: mCcl5 (RANTES), reverse sequence

<400> SEQUENCE: 64
cccacttctt ctctgggttg g                                        21

<210> SEQ ID NO 65
<211> LENGTH: 20
<212> TYPE: DNA
<213> ORGANISM: Artificial
<220> FEATURE:
<223> OTHER INFORMATION: Primer: mCCL2 (MCP-1), forward sequence

<400> SEQUENCE: 65
atgcagttaa cgccccactc                                          20

<210> SEQ ID NO 66
<211> LENGTH: 20
<212> TYPE: DNA
<213> ORGANISM: Artificial
<220> FEATURE:
<223> OTHER INFORMATION: Primer: mCCL2 (MCP-1), reverse sequence

<400> SEQUENCE: 66
gcttctttgg gacacctgct                                          20

<210> SEQ ID NO 67
<211> LENGTH: 20
<212> TYPE: DNA
<213> ORGANISM: Artificial

```
<220> FEATURE:
<223> OTHER INFORMATION: Primer: mIFN-gamma, forward sequence

<400> SEQUENCE: 67
agacaatcag gccatcagca                                                 20

<210> SEQ ID NO 68
<211> LENGTH: 20
<212> TYPE: DNA
<213> ORGANISM: Artificial
<220> FEATURE:
<223> OTHER INFORMATION: Primer: mIFNgamma, reverse sequence

<400> SEQUENCE: 68
tggacctgtg ggttgttgac                                                 20

<210> SEQ ID NO 69
<211> LENGTH: 21
<212> TYPE: DNA
<213> ORGANISM: Artificial
<220> FEATURE:
<223> OTHER INFORMATION: Primer: mTNFalpha, forward sequence

<400> SEQUENCE: 69
tcttctcatt cctgcttgtg g                                               21

<210> SEQ ID NO 70
<211> LENGTH: 20
<212> TYPE: DNA
<213> ORGANISM: Artificial
<220> FEATURE:
<223> OTHER INFORMATION: Primer: mTNFalpha, reverse sequence

<400> SEQUENCE: 70
ggtctgggcc atagaactga                                                 20

<210> SEQ ID NO 71
<211> LENGTH: 21
<212> TYPE: DNA
<213> ORGANISM: Artificial
<220> FEATURE:
<223> OTHER INFORMATION: Primer: mIL-1beta, forward sequence

<400> SEQUENCE: 71
tgccaccttt tgacagtgat g                                               21

<210> SEQ ID NO 72
<211> LENGTH: 20
<212> TYPE: DNA
<213> ORGANISM: Artificial
<220> FEATURE:
<223> OTHER INFORMATION: Primer: mIL-1beta, reverse sequence

<400> SEQUENCE: 72
tgatgtgctg ctgcgagatt                                                 20

<210> SEQ ID NO 73
<211> LENGTH: 19
<212> TYPE: DNA
<213> ORGANISM: Artificial
<220> FEATURE:
<223> OTHER INFORMATION: Primer: mH2-Aa, forward sequence

<400> SEQUENCE: 73
ctctgattct gggggtcct                                                  19
```

<210> SEQ ID NO 74
<211> LENGTH: 20
<212> TYPE: DNA
<213> ORGANISM: Artificial
<220> FEATURE:
<223> OTHER INFORMATION: Primer: mH2Aa, reverse sequence

<400> SEQUENCE: 74
accataggtg cctacgtggt                                               20

<210> SEQ ID NO 75
<211> LENGTH: 16
<212> TYPE: DNA
<213> ORGANISM: Artificial
<220> FEATURE:
<223> OTHER INFORMATION: Primer: mbeta2-microglobulin, forward sequence

<400> SEQUENCE: 75
ccggagaatg ggaagc                                                   16

<210> SEQ ID NO 76
<211> LENGTH: 16
<212> TYPE: DNA
<213> ORGANISM: Artificial
<220> FEATURE:
<223> OTHER INFORMATION: Primer: mbeta2-microglobulin, reverse sequence

<400> SEQUENCE: 76
gtagacggtc ttgggc                                                   16

<210> SEQ ID NO 77
<211> LENGTH: 20
<212> TYPE: DNA
<213> ORGANISM: Artificial
<220> FEATURE:
<223> OTHER INFORMATION: Primer: mCD80 (B 7.1), forward sequence

<400> SEQUENCE: 77
atacgactcg caaccacacc                                               20

<210> SEQ ID NO 78
<211> LENGTH: 20
<212> TYPE: DNA
<213> ORGANISM: Artificial
<220> FEATURE:
<223> OTHER INFORMATION: Primer: mCD80 (B 7.1), reverse sequence

<400> SEQUENCE: 78
gaatcctgcc ccaaagagca                                               20

<210> SEQ ID NO 79
<211> LENGTH: 20
<212> TYPE: DNA
<213> ORGANISM: Artificial
<220> FEATURE:
<223> OTHER INFORMATION: Primer: mCD86 (B 7.2), forward sequence

<400> SEQUENCE: 79
gcttcagtta ctgtggccct                                               20

<210> SEQ ID NO 80
<211> LENGTH: 20
<212> TYPE: DNA
<213> ORGANISM: Artificial
<220> FEATURE:
<223> OTHER INFORMATION: Primer: mCD86 (B 7.2), reverse sequence

<400> SEQUENCE: 80
tgtcagcgtt actatcccgc                                            20

<210> SEQ ID NO 81
<211> LENGTH: 20
<212> TYPE: DNA
<213> ORGANISM: Artificial
<220> FEATURE:
<223> OTHER INFORMATION: Primer, mSlc7a1, forward sequence

<400> SEQUENCE: 81
aaacacccgt aatcgccact                                            20

<210> SEQ ID NO 82
<211> LENGTH: 20
<212> TYPE: DNA
<213> ORGANISM: Artificial
<220> FEATURE:
<223> OTHER INFORMATION: Primer: mSlc7a1, reverse sequence

<400> SEQUENCE: 82
ggctggtacc gtaagaccaa                                            20

<210> SEQ ID NO 83
<211> LENGTH: 21
<212> TYPE: DNA
<213> ORGANISM: Artificial
<220> FEATURE:
<223> OTHER INFORMATION: Primer: mCcng1, forward sequence

<400> SEQUENCE: 83
tgactgcaag attacgggac t                                          21

<210> SEQ ID NO 84
<211> LENGTH: 20
<212> TYPE: DNA
<213> ORGANISM: Artificial
<220> FEATURE:
<223> OTHER INFORMATION: Primer, mCcng1, reverse sequence

<400> SEQUENCE: 84
cccaagatgc ttcgcctgta                                            20

<210> SEQ ID NO 85
<211> LENGTH: 20
<212> TYPE: DNA
<213> ORGANISM: Artificial
<220> FEATURE:
<223> OTHER INFORMATION: Primer: mGys1, forward sequence

<400> SEQUENCE: 85
ccgctaactc taccggtcac                                            20

<210> SEQ ID NO 86
<211> LENGTH: 20
<212> TYPE: DNA
<213> ORGANISM: Artificial
<220> FEATURE:
<223> OTHER INFORMATION: Primer: mGys1, reverse sequence

<400> SEQUENCE: 86
ccccattcat ccnctgtcac                                            20

<210> SEQ ID NO 87

<210> SEQ ID NO 87
<211> LENGTH: 20
<212> TYPE: DNA
<213> ORGANISM: Artificial
<220> FEATURE:
<223> OTHER INFORMATION: Primer: mAldoA, forward sequence

<400> SEQUENCE: 87
gcgttcgctc cttagtcctt                                              20

<210> SEQ ID NO 88
<211> LENGTH: 20
<212> TYPE: DNA
<213> ORGANISM: Artificial
<220> FEATURE:
<223> OTHER INFORMATION: Primer: mAldoA, reverse sequence

<400> SEQUENCE: 88
aatgcaggga ttcacacggt                                              20

<210> SEQ ID NO 89
<211> LENGTH: 20
<212> TYPE: DNA
<213> ORGANISM: Artificial
<220> FEATURE:
<223> OTHER INFORMATION: Primer: mRplp0, forward sequence

<400> SEQUENCE: 89
tcccaccttg tctccagtct                                              20

<210> SEQ ID NO 90
<211> LENGTH: 42
<212> TYPE: DNA
<213> ORGANISM: Artificial
<220> FEATURE:
<223> OTHER INFORMATION: Primer: mRplp0, reverse sequence

<400> SEQUENCE: 90
actggtctag gacccgagaa actggtctag gacccgagaa gg                     42

<210> SEQ ID NO 91
<211> LENGTH: 18
<212> TYPE: DNA
<213> ORGANISM: Artificial
<220> FEATURE:
<223> OTHER INFORMATION: Primer: rRplp0, forward sequence

<400> SEQUENCE: 91
gatgcccagg gaagacag                                                18

<210> SEQ ID NO 92
<211> LENGTH: 22
<212> TYPE: DNA
<213> ORGANISM: Artificial
<220> FEATURE:
<223> OTHER INFORMATION: Primer: rRplp0, reverse sequence

<400> SEQUENCE: 92
cacaatgaag cattttgggt ag                                           22

<210> SEQ ID NO 93
<211> LENGTH: 22
<212> TYPE: DNA
<213> ORGANISM: Artificial
<220> FEATURE:
<223> OTHER INFORMATION: target sequence of miRNA199A-3p

<400> SEQUENCE: 93

-continued

```
tgtcatcaga cgtgtaacca at                                          22

<210> SEQ ID NO 94
<211> LENGTH: 22
<212> TYPE: DNA
<213> ORGANISM: Artificial
<220> FEATURE:
<223> OTHER INFORMATION: Target sequence of miRNA208

<400> SEQUENCE: 94
tattctgctc gtttttcgaa ca                                          22

<210> SEQ ID NO 95
<211> LENGTH: 21
<212> TYPE: DNA
<213> ORGANISM: Artificial
<220> FEATURE:
<223> OTHER INFORMATION: target sequence of miRNA101

<400> SEQUENCE: 95
atgtcatgac actattgact t                                           21

<210> SEQ ID NO 96
<211> LENGTH: 3281
<212> TYPE: DNA
<213> ORGANISM: Artificial
<220> FEATURE:
<223> OTHER INFORMATION: expression cassette present in SEQ ID NO:30

<400> SEQUENCE: 96
ctcgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtcgagg tgagccccac gttctgcttc actctcccca    420
tctccccccc ctccccaccc ccaattttgt atttatttat tttttaatta ttttgtgcag    480 cgatggggc ggggggggggg ggggggcgcg cgccaggcgg ggcggggcgg ggcgagggc     540 ggggcgggc gaggcggaga ggtgcggcgg cagccaatca gagcggcgcg ctccgaaagt     600 ttcctttat ggcgaggcgg cggcggcggc ggccctataa aaagcgaagc gcgcggcggg     660
cgggagtcgc tgcgttgcct tcgccccgtg ccccgctccg cgccgcctcg cgccgcccgc    720
cccggctctg actgaccgcg ttactcccac aggtgagcgg gcgggacggc ccttctcctc    780
cgggctgtaa ttagcgcttg gtttaatgac ggcttgtttc ttttctgtgg ctgcgtgaaa    840
gccttgaggg gctccgggag ggccctttgt gcggggggag cggctcgggg ggtgcgtgcg    900
tgtgtgtgtg cgtggggagc gccgcgtgcg gctccgcgct gcccggcggc tgtgagcgct    960
gcgggcgcgg cgcggggctt tgtgcgctcc gcagtgtgcg cgaggggagc gcggccgggg   1020
gcggtgcccc gcggtgcggg gggctgcgag gggaacaaag gctgcgtgcg gggtgtgtgc   1080
gtgggggggt gagcaggggg tgtgggcgcg tcggtcgggc tgcaaccccc cctgcacccc   1140
cctccccgag ttgctgagca cggcccggct tcgggtgcgg ggctccgtac ggggcgtggc   1200
gcggggctcg ccgtgccggg cgggggtgg cggcaggtgg gggtgccggg cggggcgggg   1260
```

```
ccgcctcggg ccggggaggg ctcggggggag gggcgcggcg gcccccggag cgccggcggc   1320
tgtcgaggcg cggcgagccg cagccattgc ctttatggt aatcgtgcga gagggcgcag    1380
ggacttcctt tgtcccaaat ctgtgcggag ccgaaatctg ggaggcgccg ccgcaccccc   1440
tctagcgggc gcggggcgaa gcggtgcggc gccggcagga aggaaatggg cggggagggc   1500
cttcgtgcgt cgccgcgccg ccgtcccctt ctccctctcc agcctcgggg ctgtccgcgg   1560
ggggacggct gccttcgggg gggacggggc agggcgggt tcggcttctg gcgtgtgacc    1620
ggcggctcta gagcctctgc taaccatgtt catgccttct tcttttcct acagctcctg    1680 ggcaacgtgc tggttattgt gctgtctcat catttggca aagaattgat taattcgagc    1740
gaacgcgtcg agtcgctcgg tacgatttaa attgaattgg cctcgagcgc aagcttgata   1800
tcgaattccg tagatgcttt cacaaacccc acccacaaaa caacacatgt tcttaagtcc   1860
tcagttttgt gttcacctcg gcctcatagt acccactctg acctgctgtg taaacgaccc   1920
ggacctacca aaatgaccgc acctgcaata aagatacaca tcatgtcgtc ttcacacctc   1980
ttctacctgg cgctctgctt gctcaccttc accagctcca ccacagctgg accagagacc   2040
ctttgcgggg ctgagctggt ggatgctctt cagttcgtgt gtggaccgag gggcttttac    2100
ttcaacaagc ccacaggcta tggctccagc attcggaggg cacctcagac aggcattgtg    2160
gatgagtgtt gcttccggag ctgtgatctg aggagactgg agatgtactg tgccccactg    2220
aagcctacaa aagcagcccg ctctatccgt gcccagcgcc acactgacat gcccaagact    2280
cagaaggaag tacatttgaa gaacacaagt agaggaagtg caggaaacaa gacctacaga    2340
atgtaggagg agcctcccac ggagcagaaa atgccacatc accgcaggat ccactagttc    2400
tagagcggcc gctaattcta gatcgcgaac aaacaccatt gtcacactcc agtatacaca    2460
aacaccattg tcacactcca gatatcacaa acaccattgt cacactccaa ggcgaacaaa    2520
caccattgtc acactccaag gctattctag atcgcgaatt acatacttct ttacattcca    2580
gtatacatta catacttctt tacattccag atatcattac atacttcttt acattccaag    2640
gcgaattaca tacttcttta cattccaagg ctacctgagg cccggggta cctcttaatt     2700 aactggcctc atgggccttc cgctcactgc ccgctttcca gtcgggaaac ctgtcgtgcc    2760
agtcaggtgc aggctgccta tcagaaggtg gtggctggtg tggccaatgc cctggctcac    2820
aaataccact gagatctttt tccctctgcc aaaaattatg gggacatcat gaagcccctt    2880
gagcatctga cttctggcta taaaggaaa tttatttca ttgcaatagt gtgttggaat      2940
tttttgtgtc tctcactcgg aaggacatat gggagggcaa atcatttaaa acatcagaat    3000
gagtatttgg tttagagttt ggcaacatat gcccatatgc tggctgccat gaacaaaggt    3060
tggctataaa gaggtcatca gtatatgaaa cagccccctg ctgtccattc cttattccat    3120
agaaaagcct tgacttgagg ttagattttt tttatatttt gttttgtgtt attttttct     3180 ttaacatccc taaaattttc cttacatgtt ttactagcca gatttttcct cctctcctga    3240
ctactcccag tcatagctgt ccctcttctc ttatggagat c                        3281
```

<210> SEQ ID NO 97
<211> LENGTH: 3650
<212> TYPE: DNA
<213> ORGANISM: Artificial
<220> FEATURE:
<223> OTHER INFORMATION: Viral vector present in SEQ ID NO:30

<400> SEQUENCE: 97

```
actgaggccc agctgcgcgc tcgctcgctc actgaggccg cccgggcaaa gcccgggcgt    60
```

-continued

```
cgggcgacct tggtcgccc ggcctcagtg agcgagcgag cgcgcagaga gggagtggcc      120
aactccatca ctaggggttc cttgtagtta atgattaacc cgccatgcta cttatctact    180
cgacattgat tattgactag ttattaatag taatcaatta cggggtcatt agttcatagc    240
ccatatatgg agttccgcgt tacataactt acggtaaatg gcccgcctgg ctgaccgccc    300
aacgaccccc gcccattgac gtcaataatg acgtatgttc ccatagtaac gccaataggg    360
actttccatt gacgtcaatg ggtggagtat ttacggtaaa ctgcccactt ggcagtacat    420
caagtgtatc atatgccaag tacgccccct attgacgtca atgacggtaa atggcccgcc    480
tggcattatg cccagtacat gaccttatgg actttcctac ttggcagta catctacgta     540
ttagtcatcg ctattaccat ggtcgaggtg agccccacgt tctgcttcac tctccccatc    600
tccccccct ccccacccc aattttgtat ttatttattt tttaattatt ttgtgcagcg      660
atggggcgg ggggggggg gggcgcgcg ccaggcgggg cggggcgggg cgaggggcgg       720
ggcggggcga ggcggagagg tgcggcggca gccaatcaga gcggcgcgct ccgaaagttt    780
cctttatgg cgaggcggcg gcggcggcgg ccctataaaa agcgaagcgc gcggcgggcg     840
ggagtcgctg cgttgccttc gccccgtgcc ccgctccgcg ccgcctcgcg ccgcccgccc    900
cggctctgac tgaccgcgtt actcccacag gtgagcgggc gggacggccc ttctcctccg    960
ggctgtaatt agcgcttggt ttaatgacgg cttgtttctt ttctgtggct gcgtgaaagc    1020
cttgaggggc tccgggaggg ccctttgtgc ggggggagcg gctcgggggg tgcgtgcgtg   1080
tgtgtgtgcg tggggagcgc cgcgtgcggc tccgcgctgc ccggcggctg tgagcgctgc   1140
gggcgcggcg cggggctttg tgcgctccgc agtgtgcgcg aggggagcgc ggccggggc     1200
ggtgccccgc ggtgcggggg gctgcgaggg gaacaaaggc tgcgtgcggg gtgtgtgcgt   1260
gggggggtga gcaggggtg tgggcgcgtc ggtcgggctg caacccccc tgcaccccc      1320
tccccgagtt gctgagcacg gcccggcttc gggtgcgggg ctccgtacgg ggcgtggcgc   1380
ggggctcgcc gtgccgggcg gggggtggcg gcaggtgggg gtgccgggcg gggcgggggcc  1440
gcctcgggcc ggggagggct cggggagggg gcgcggcggc ccccggagcg ccggcggctg   1500
tcgaggcgcg gcgagccgca gccattgcct tttatggtaa tcgtgcgaga gggcgcaggg   1560
acttcctttg tcccaaatct gtgcggagcc gaaatctggg aggcgccgcc gcaccccctc   1620
tagcgggcgc ggggcgaagc ggtgcggcgc cggcaggaag gaaatgggcg gggagggcct   1680
tcgtgcgtcg ccgcgccgcc gtccccttct ccctctccag cctcggggct gtccgcgggg   1740
ggacggctgc cttcgggggg gacggggcag ggcggggttc ggcttctggc gtgtgaccgg   1800
cggctctaga gcctctgcta accatgttca tgccttcttc tttttcctac agctcctggg   1860
caacgtgctg gttattgtgc tgtctcatca ttttggcaaa gaattgatta attcgagcga   1920
acgcgtcgag tcgctcggta cgatttaaat tgaattggcc tcgagcgcaa gcttgatatc   1980
gaattccgta gatgctttca caaacccac ccacaaaaca acacatgttc ttaagtcctc    2040
agttttgtgt tcacctcggc ctcatagtac ccactctgac ctgctgtgta aacgacccgg   2100
acctaccaaa atgaccgcac ctgcaataaa gatacacatc atgtcgtctt cacacctctt   2160
ctacctggcg ctctgcttgc tcaccttcac cagctccacc acagctggac cagagaccct   2220
ttgcggggct gagctggtgg atgctcttca gttcgtgtgt ggaccgaggg gcttttactt   2280
caacaagccc acaggctatg gctccagcat tcggagggca cctcagacag gcattgtgga   2340
tgagtgttgc ttccggagct gtgatctgag gagactggag atgtactgtg ccccactgaa   2400
```

| | |
|---|---|
| gcctacaaaa gcagcccgct ctatccgtgc ccagcgccac actgacatgc ccaagactca | 2460 |
| gaaggaagta catttgaaga acacaagtag aggaagtgca ggaaacaaga cctacagaat | 2520 |
| gtaggaggag cctcccacgg agcagaaaat gccacatcac cgcaggatcc actagttcta | 2580 |
| gagcggccgc taattctaga tcgcgaacaa acaccattgt cacactccag tatacacaaa | 2640 |
| caccattgtc acactccaga tatcacaaac accattgtca cactccaagg cgaacaaaca | 2700 |
| ccattgtcac actccaaggc tattctagat cgcgaattac atacttcttt acattccagt | 2760 |
| atacattaca tacttcttta cattccagat atcattacat acttctttac attccaaggc | 2820 |
| gaattacata cttctttaca ttccaaggct acctgaggcc cggggtacc tcttaattaa | 2880 |
| ctggcctcat gggccttccg ctcactgccc gctttccagt cgggaaacct gtcgtgccag | 2940 |
| tcaggtgcag gctgcctatc agaaggtggt ggctggtgtg gccaatgccc tggctcacaa | 3000 |
| ataccactga gatctttttc cctctgccaa aaattatggg gacatcatga agccccttga | 3060 |
| gcatctgact tctggctaat aaaggaaatt tattttcatt gcaatagtgt gttggaattt | 3120 |
| tttgtgtctc tcactcggaa ggacatatgg gagggcaaat catttaaaac atcagaatga | 3180 |
| gtatttggtt tagagtttgg caacatatgc ccatatgctg gctgccatga acaaaggttg | 3240 |
| gctataaaga ggtcatcagt atatgaaaca gcccctgct gtccattcct tattccatag | 3300 |
| aaaagccttg acttgaggtt agatttttt tatattttgt tttgtgttat tttttctttt | 3360 |
| aacatcccta aaatttcct tacatgtttt actagccaga ttttcctcc tctcctgact | 3420 |
| actcccagtc atagctgtcc ctcttctctt atggagatcc ctcgacctgc agcccaagct | 3480 |
| gtagataagt agcatggcgg gttaatcatt aactacaagg aacccctagt gatggagttg | 3540 |
| gccactccct ctctgcgcgc tcgctcgctc actgaggccg ggcgaccaaa ggtcgcccga | 3600 |
| cgcccgggct tgcccgggc ggcctcagtg agcgagcgag cgcgcagctg | 3650 |

<210> SEQ ID NO 98
<211> LENGTH: 3217
<212> TYPE: DNA
<213> ORGANISM: Artificial
<220> FEATURE:
<223> OTHER INFORMATION: Experssion cassette present in SEQ ID NO:31

<400> SEQUENCE: 98

| | |
|---|---|
| ctcgacattg attattgact agttattaat agtaatcaat tacggggtca ttagttcata | 60 |
| gcccatatat ggagttccgc gttacataac ttacggtaaa tggcccgcct ggctgaccgc | 120 |
| ccaacgaccc ccgcccattg acgtcaataa tgacgtatgt tcccatagta acgccaatag | 180 |
| ggactttcca ttgacgtcaa tgggtggagt atttacggta aactgcccac ttggcagtac | 240 |
| atcaagtgta tcatatgcca agtacgcccc ctattgacgt caatgacggt aaatggcccg | 300 |
| cctggcatta tgcccagtac atgaccttat gggactttcc tacttggcag tacatctacg | 360 |
| tattagtcat cgctattacc atggtcgagg tgagccccac gttctgcttc actctcccca | 420 |
| tctccccccc ctccccaccc ccaattttgt atttatttat tttttaatta tttttgtgcag | 480 |
| cgatggggc gggggggggg gggggcgcg cgccaggcgg ggcggggcgg ggcgaggggc | 540 |
| ggggcgggc gaggcggaga ggtgcggcgg cagccaatca gagcggcgcg ctccgaaagt | 600 |
| ttccttttat ggcgaggcgg cggcggcggc ggccctataa aaagcgaagc gcgcggcggg | 660 |
| cgggagtcgc tgcgttgcct tcgccccgtg ccccgctccg cgccgcctcg cgccgcccgc | 720 |
| cccggctctg actgaccgcg ttactcccac aggtgagcgg gcgggacggc ccttctcctc | 780 |
| cgggctgtaa ttagcgcttg gtttaatgac ggcttgtttc ttttctgtgg ctgcgtgaaa | 840 |

```
gccttgaggg gctccgggag ggccctttgt gcgggggggag cggctcgggg ggtgcgtgcg        900
tgtgtgtgtg cgtggggagc gccgcgtgcg gctccgcgct gcccggcggc tgtgagcgct        960
gcgggcgcgg cgcggggctt tgtgcgctcc gcagtgtgcg cgaggggagc gcggccgggg       1020
gcggtgcccc gcggtgcggg gggctgcgag gggaacaaag gctgcgtgcg gggtgtgtgc       1080
gtggggggt gagcagggg tgtgggcgcg tcggtcgggc tgcaaccccc cctgcacccc         1140
cctccccgag ttgctgagca cggcccggct tcggtgcgg ggctccgtac ggggcgtggc        1200
gcggggctcg ccgtgccggg cgggggtgg cggcaggtgg gggtgccggg cggggcgggg        1260
ccgcctcggg ccggggaggg ctcggggag gggcgcggcg gccccggag cgccggcggc         1320
tgtcgaggcg cggcgagccg cagccattgc cttttatggt aatcgtgcga gagggcgcag       1380
ggacttcctt tgtcccaaat ctgtgcgag ccgaaatctg ggaggcgccg ccgcacccc         1440
tctagcgggc gcggggcgaa gcggtgcggc gccggcagga aggaaatggg cggggagggc       1500
cttcgtgcgt cgccgcgccg ccgtcccctt ctccctctcc agcctcgggg ctgtccgcgg       1560
ggggacggct gccttcgggg gggacggggc agggcggggt tcggcttctg gcgtgtgacc       1620
ggcggctcta gagcctctgc taaccatgtt catgccttct tctttttcct acagctcctg       1680
ggcaacgtgc tggttattgt gctgtctcat cattttggca aagaattgat taattcgagc       1740
gaacgcgtcg agtcgctcgg tacgatttaa attgaattgg cctcgagcgc aagcttgagc       1800
tagctcgata tcgtcgaccc acgcgtccgg acttcttgaa gataaagata cacatcatgt       1860
cgtcttcaca cctcttctac ctggcgctct gcttgctcac cttcaccagc tccaccacag       1920
ctggaccaga gacccttgc gggctgagc tggtggatgc tcttcagttc gtgtgtggac         1980
cgagggctt ttacttcaac aagcccacag gctatggctc cagcattcgg agggcacctc        2040
agacaggcat tgtggatgag tgttgcttcc ggagctgtga tctgaggaga ctggagatgt       2100
actgtgcccc actgaagcct acaaaagcag cccgctctat ccgtgcccag cgccacactg       2160
acatgcccaa gactcagaag tccccgtccc tatcgacaaa caagaaaacg aagctgcaaa       2220
ggagaaggaa aggaagtaca tttgaagaac acaagtagag gaagtgcagg aaacaagacc       2280
tacagaatgt aggaggagcc tcccacggag cagaaaatgc cacatcaccg caggatccgc       2340
gcggccgcta attctagatc gcgaacaaac accattgtca cactccagta tacacaaaca       2400
ccattgtcac actccagata tcacaaacac cattgtcaca ctccaaggcg aacaaacacc       2460
attgtcacac tccaaggcta ttctagatcg cgaattacat acttctttac attccagtat       2520
acattacata cttctttaca ttccagatat cattacatac ttctttacat tccaaggcga       2580
attacatact tctttacatt ccaaggctac ctgaggcccg ggggtacctc ttaattaact       2640
ggcctcatgg gccttccgct cactgcccgc tttccagtcg ggaaacctgt cgtgccagtc       2700
aggtgcaggc tgcctatcag aaggtggtgg ctggtgtggc caatgccctg gctcacaaat       2760
accactgaga tctttttccc tctgccaaaa attatgggga catcatgaag ccccttgagc       2820
atctgacttc tggctaataa aggaaattta ttttcattgc aatagtgtgt tggaattttt       2880
tgtgtctctc actcggaagg acatatggga gggcaaatca tttaaaacat cagaatgagt       2940
atttggttta gagtttggca acatatgccc atatgctggc tgccatgaac aaaggttggc       3000
tataaagagg tcatcagtat atgaaacagc cccctgctgt ccattcctta ttccatagaa       3060
aagccttgac ttgaggttag attttttta tattttgttt tgtgttattt ttttcttttaa      3120
catccctaaa attttcctta catgttttac tagccagatt tttcctcctc tcctgactac       3180
```
tcccagtcat agctgtccct cttctcttat ggagatc                        3217

<210> SEQ ID NO 99
<211> LENGTH: 3586
<212> TYPE: DNA
<213> ORGANISM: Artificial
<220> FEATURE:
<223> OTHER INFORMATION: Viral vector present in SEQ ID NO: 31

<400> SEQUENCE: 99

```
actgaggccc agctgcgcgc tcgctcgctc actgaggccg cccgggcaaa gcccgggcgt      60
cgggcgacct ttggtcgccc ggcctcagtg agcgagcgag cgcgcagaga gggagtggcc     120
aactccatca ctaggggttc cttgtagtta atgattaacc cgccatgcta cttatctact     180
cgacattgat tattgactag ttattaatag taatcaatta cggggtcatt agttcatagc     240
ccatatatgg agttccgcgt tacataactt acggtaaatg gcccgcctgg ctgaccgccc     300
aacgaccccc gcccattgac gtcaataatg acgtatgttc ccatagtaac gccaataggg     360
actttccatt gacgtcaatg ggtggagtat ttacggtaaa ctgcccactt ggcagtacat     420
caagtgtatc atatgccaag tacgccccct attgacgtca atgacggtaa atggcccgcc     480
tggcattatg cccagtacat gaccttatgg actttcctta cttggcagta catctacgta     540
ttagtcatcg ctattaccat ggtcgaggtg agccccacgt tctgcttcac tctccccatc     600
tccccccccct cccacccccc aattttgtat ttatttattt tttaattatt ttgtgcagcg     660
atggggggcgg ggggggggg gggcgcgcg ccaggcgggg cggggcgggg cgaggggcgg     720
ggcggggcga ggcggagagg tgcggcggca gccaatcaga gcggcgcgct ccgaaagttt     780
cctttatgg cgaggcggcg gcggcggcgg ccctataaaa agcgaagcgc gcggcgggcg     840
ggagtcgctg cgttgccttc gccccgtgcc ccgctccgcg ccgcctcgcg ccgcccgccc     900
cggctctgac tgaccgcgtt actcccacag gtgagcgggc gggacggccc ttctcctccg     960
ggctgtaatt agcgcttggt ttaatgacgg cttgtttctt ttctgtggct gcgtgaaagc    1020
cttgagggc tccgggaggg cccctttgtgc ggggggagcg gctcggggg tgcgtgcgtg    1080
tgtgtgtgcg tggggagcgc cgcgtgcggc tccgcgctgc ccggcggctg tgagcgctgc    1140
gggcgcggcg cggggctttg tgcgctccgc agtgtgcgcg aggggagcgc ggccggggc    1200
ggtgccccgc ggtgcggggg gctgcgaggg gaacaaaggc tgcgtgcggg gtgtgtgcgt    1260
ggggggtga gcagggggtg tgggcgcgtc ggtcgggctg caacccccc tgcacccccc    1320
tcccccgagtt gctgagcacg gcccggcttc gggtgcgggg ctccgtacgg ggcgtggcgc    1380
ggggctcgcc gtgccgggcg gggggtggcg gcaggtgggg gtgccgggcg gggcggggcc    1440
gcctcgggcc ggggagggct cggggagggg gcgcggcggc ccccggagcg ccggcggctg    1500
tcgaggcgcg gcgagccgca gccattgcct tttatggtaa tcgtgcgaga gggcgcaggg    1560
acttcctttg tcccaaatct gtgcggagcc gaaatctggg aggcgccgcc gcacccctc    1620
tagcgggcgc ggggcgaagc ggtgcggcgc cggcaggaag gaaatgggcg gggagggcct    1680
tcgtgcgtcg ccgcgccgcc gtcccccttct ccctctccag cctcggggct gtccgcgggg    1740
ggacggctgc cttcggggggg gacggggcag ggcggggttc ggcttctggc gtgtgaccgg    1800
cggctctaga gcctctgcta accatgttca tgccttcttc ttttttcctac agctcctggg    1860
caacgtgctg gttattgtgc tgtctcatca ttttggcaaa gaattgatta attcgagcga    1920
acgcgtcgag tcgctcggta cgatttaaat tgaattggcc tcgagcgcaa gcttgagcta    1980
gctcgatatc gtcgacccac gcgtccggac ttcttgaaga taaagataca catcatgtcg    2040
```

```
tcttcacacc tcttctacct ggcgctctgc ttgctcacct tcaccagctc caccacagct    2100
ggaccagaga cccttttgcgg ggctgagctg gtggatgctc ttcagttcgt gtgtggaccg    2160
aggggctttt acttcaacaa gcccacaggc tatggctcca gcattcggag ggcacctcag    2220
acaggcattg tggatgagtg ttgcttccgg agctgtgatc tgaggagact ggagatgtac    2280
tgtgccccac tgaagcctac aaaagcagcc cgctctatcc gtgcccagcg ccacactgac    2340
atgcccaaga ctcagaagtc cccgtcccta tcgacaaaca agaaaacgaa gctgcaaagg    2400
agaaggaaag gaagtacatt tgaagaacac aagtagagga agtgcaggaa acaagaccta    2460
cagaatgtag gaggagcctc ccacggagca gaaaatgcca catcaccgca ggatccgcgc    2520
ggccgctaat tctagatcgc gaacaaacac cattgtcaca ctccagtata cacaaacacc    2580
attgtcacac tccagatatc acaaacacca ttgtcacact ccaaggcgaa caaacaccat    2640
tgtcacactc caaggctatt ctagatcgcg aattacatac ttctttacat tccagtatac    2700
attacatact tctttacatt ccagatatca ttacatactt ctttacattc caaggcgaat    2760
tacatacttc tttacattcc aaggctacct gaggcccggg ggtacctctt aattaactgg    2820
cctcatgggc cttccgctca ctgcccgctt tccagtcggg aaacctgtcg tgccagtcag    2880
gtgcaggctg cctatcagaa ggtggtggct ggtgtggcca atgccctggc tcacaaatac    2940
cactgagatc ttttttccctc tgccaaaaat tatggggaca tcatgaagcc ccttgagcat    3000
ctgacttctg gctaataaag gaaatttatt ttcattgcaa tagtgtgttg gaattttttg    3060
tgtctctcac tcggaaggac atatgggagg gcaaatcatt taaaacatca gaatgagtat    3120
ttggtttaga gtttggcaac atatgcccat atgctggctg ccatgaacaa aggttggcta    3180
taaagaggtc atcagtatat gaaacagccc cctgctgtcc attccttatt ccatagaaaa    3240
gccttgactt gaggttagat ttttttttata ttttgttttg tgttattttt ttctttaaca    3300
tccctaaaat tttccttaca tgttttacta gccagatttt tcctcctctc ctgactactc    3360
ccagtcatag ctgtccctct tctcttatgg agatccctcg acctgcagcc caagctgtag    3420
ataagtagca tggcgggtta atcattaact acaaggaacc cctagtgatg gagttggcca    3480
ctccctctct gcgcgctcgc tcgctcactg aggccgggcg accaaaggtc gcccgacgcc    3540
cgggctttgc ccgggcggcc tcagtgagcg agcgagcgcg cagctg                   3586
```